United States Patent
Ellingsworth et al.

(10) Patent No.: US 12,324,831 B2
(45) Date of Patent: *Jun. 10, 2025

(54) **ISOLATED POLYPEPTIDE OF THE TOXIN A AND TOXIN B PROTEINS OF *C. DIFFICILE* AND USES THEREOF**

(71) Applicants: Valneva Austria GmbH, Vienna (AT); Valneva USA, Inc., Gaithersburg, MD (US)

(72) Inventors: Larry R. Ellingsworth, Rockville, MD (US); David Flyer, Olney, MD (US); Jing-Hui Tian, Germantown, MD (US); Steven R. Fuhrmann, Germantown, MD (US); Stefanie Kluepfel-Stahl, Bethesda, MD (US); Gregory M. Glenn, Gaithersburg, MD (US); Kerstin Westritschnig, Vienna (AT)

(73) Assignees: Valneva Austria GmbH, Vienna (AT); Valneva USA, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/930,742

(22) Filed: Sep. 9, 2022

(65) Prior Publication Data

US 2023/0173052 A1    Jun. 8, 2023

Related U.S. Application Data

(60) Continuation of application No. 17/406,765, filed on Aug. 19, 2021, now Pat. No. 11,478,540, which is a continuation of application No. 17/061,891, filed on Oct. 2, 2020, now Pat. No. 11,357,844, which is a continuation of application No. 16/295,031, filed on Mar. 7, 2019, now Pat. No. 10,821,166, which is a continuation of application No. 15/421,808, filed on Feb. 1, 2017, now Pat. No. 10,357,557, which is a division of application No. 14/342,565, filed as application No. PCT/EP2011/065304 on Sep. 5, 2011, now Pat. No. 9,598,472.

(51) Int. Cl.
| | |
|---|---|
| A61K 39/08 | (2006.01) |
| C07K 14/33 | (2006.01) |
| C07K 16/12 | (2006.01) |
| A61K 39/00 | (2006.01) |

(52) U.S. Cl.
CPC ............ *A61K 39/08* (2013.01); *C07K 14/33* (2013.01); *C07K 16/1282* (2013.01); *A61K 2039/53* (2013.01); *A61K 2039/55505* (2013.01); *A61K 2039/55544* (2013.01); *A61K 2039/575* (2013.01); *C07K 2317/76* (2013.01); *C07K 2319/00* (2013.01); *C07K 2319/40* (2013.01); *C07K 2319/55* (2013.01)

(58) Field of Classification Search
CPC .................................................. A61K 39/08
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 5,547,871 | A | 8/1996 | Black et al. |
| 5,730,969 | A | 3/1998 | Hora et al. |
| 5,736,139 | A | 4/1998 | Kink et al. |
| 5,919,463 | A | 7/1999 | Thomas et al. |
| 6,291,212 | B1 | 9/2001 | Sledziewski et al. |
| 6,365,573 | B1 | 4/2002 | Gluckman et al. |
| 6,733,760 | B1 | 5/2004 | Wilkins et al. |
| 8,257,709 | B2 | 9/2012 | Ambrosino et al. |
| 8,557,548 | B2 | 10/2013 | Anderson et al. |
| 8,921,529 | B2 | 12/2014 | Shone et al. |
| 8,986,697 | B2 | 3/2015 | Ma et al. |
| 9,181,632 | B1 | 11/2015 | Murgolo et al. |
| 9,315,555 | B2 | 4/2016 | Shone et al. |
| 9,598,472 | B2 | 3/2017 | Ellingsworth et al. |
| 10,357,557 | B2 | 7/2019 | Ellingsworth et al. |
| 10,821,166 | B2 | 11/2020 | Ellingsworth et al. |
| 11,478,540 | B2 | 10/2022 | Ellingsworth et al. |
| 2012/0020996 | A1 | 1/2012 | Telfer et al. |
| 2012/0282293 | A1 | 11/2012 | Galen |
| 2015/0313984 | A1 | 11/2015 | Boutriau et al. |
| 2017/0239340 | A1 | 8/2017 | Ellingsworth et al. |
| 2019/0290747 | A1 | 9/2019 | Ellingsworth et al. |
| 2021/0121554 | A1 | 4/2021 | Ellingsworth et al. |

FOREIGN PATENT DOCUMENTS

| | | |
|---|---|---|
| EP | 0399843 A2 | 11/1990 |
| WO | WO 1996/002555 A1 | 2/1996 |
| WO | WO 1997/002836 A1 | 1/1997 |

(Continued)

OTHER PUBLICATIONS

[No Author Listed] *Clostridium difficile*—VLA84. Valneva Product Page, dated Dec. 13, 2019. Submitted in Opposition of EP 2714911 on Dec. 20, 2019. 2 pages.

[No Author Listed] EPO Acknowledgement of Receipt of documents submitted in Opposition of EP 2714911, dated Dec. 20, 2020. 2 pages.

[No Author Listed] EPO Summary of Facts and Submissions in Opposition of EP 1965823, dated Oct. 4, 2018. Submitted in Opposition of EP2714911 on Dec. 20, 2019. 33 pages.

[No Author Listed] Sanofi Pasteur Announces Favorable Phase II Study Results for Investigational *Clostridium difficile* Vaccine at the American Society for Microbiology Meeting. Sanofi Pasteur Media Center. May 19, 2014. Retrieved from //sanofipasteurus.mediaroom. com/sanofi-pasteur-announces-favorable-phase-- ii-study-results-for-investigational-clostridium-difficile-vaccine-at-the--american-society-for-microbiology-meeting on May 15, 2015.

(Continued)

*Primary Examiner* — Albert M Navarro
(74) *Attorney, Agent, or Firm* — Wolf, Greenfield & Sacks, P.C.

(57) ABSTRACT

This present invention provides C-TAB.G5 and C-TAB.G5.1 isolated polypeptides comprising the receptor binding domains of *C. difficile* toxin A and toxin B as set

(56) References Cited

FOREIGN PATENT DOCUMENTS

| | | |
|---|---|---|
| WO | WO 1998/029134 A2 | 7/1998 |
| WO | WO 2000/061762 A1 | 10/2000 |
| WO | WO 2001/024822 A2 | 4/2001 |
| WO | WO 2001/054720 A1 | 8/2001 |
| WO | WO 2001/093903 A1 | 12/2001 |
| WO | WO 2001/093905 A1 | 12/2001 |
| WO | WO 2002/013857 A2 | 2/2002 |
| WO | WO 2002/032451 A1 | 4/2002 |
| WO | WO 2002/095027 A2 | 11/2002 |
| WO | WO 2003/047602 A1 | 6/2003 |
| WO | WO 2006/024024 A2 | 3/2006 |
| WO | WO 2008/058944 A1 | 5/2008 |
| WO | WO 2009/035707 A1 | 3/2009 |
| WO | WO 2010/017383 A1 | 2/2010 |
| WO | WO 2011/060431 A2 | 5/2011 |
| WO | WO 2012/028741 A1 | 3/2012 |
| WO | WO 2012/163810 A1 | 12/2012 |
| WO | WO 2012/163811 A1 | 12/2012 |
| WO | WO 2012/163817 A2 | 12/2012 |
| WO | WO 2014/086787 A1 | 6/2014 |
| WO | WO 2014/096393 A1 | 6/2014 |

OTHER PUBLICATIONS

[No Author Listed] Valneva Announces Positive Phase I Results for its *Clostridium difficile* Vaccine Candidate. Press Release, dated Aug. 26, 2013. Submitted in Opposition of EP 2714911 on Dec. 20, 2019. 4 pages.

[No Author Listed] Valneva announces positive phase I results for its *Clostridium difficile* vaccine candidate. Valneva SE. Aug. 26, 2013.

[No Author Listed] Valneva Announces Positive Phase II Results for its *Clostridium difficile* Vaccine Candidate. Press Release, dated Jul. 25, 2016. Submitted in Opposition of EP 2714911 on Dec. 20, 2019. 4 pages.

[No Author Listed] Valneva announces successful completion of phase II for *Clostridium difficile* vaccine candidate. Valneva SE. Jul. 25, 2016.

[No Author Listed] Valneva Auxiliary Requests 12-14 in Opposition of EP 2753352. Submitted Feb. 28, 2019. 6 pages.

[No Author Listed] Valneva Auxiliary Requests 15-16 in Opposition of EP 2753352. Submitted Dec. 20, 2019. 4 pages.

[No Author Listed] Valneva Auxiliary Requests 4-11 in Opposition of EP 2753352. Submitted Jan. 11, 2019. 16 pages.

[No Author Listed] Valneva Confirmatory Declaration for David Flyer, dated Oct. 11, 2019. Submitted in Opposition of EP 2714911 on Dec. 20, 2019. 2 pages.

[No Author Listed] Valneva Confirmatory Declaration for Gerald Strohmaier, dated Oct. 29, 2019. Submitted in Opposition of EP2714911 on Dec. 20, 2019. 2 pages.

[No Author Listed] Valneva Confirmatory Declaration for Gregory Glenn, dated Oct. 8, 2019. Submitted in Opposition of EP2714911 on Dec. 20, 2019. 2 pages.

[No Author Listed] Valneva Confirmatory Declaration for Jing-Hui Tian, dated Oct. 9, 2019. Submitted in Opposition of EP 2714911 on Dec. 20, 2019. 2 pages.

[No Author Listed] Valneva Confirmatory Declaration for Larry Ellingsworth, dated Oct. 12, 2019. Submitted in Opposition of EP 2714911 on Dec. 20, 2019. 2 pages.

[No Author Listed] Valneva Confirmatory Declaration for Stefanie Kluepfel-Stahl, dated Oct. 9, 2019. Submitted in Opposition of EP2714911 on Dec. 20, 2019. 2 pages.

[No Author Listed] Valneva Confirmatory Declaration for Steven R. Fuhrmann, dated Oct. 8, 2019. Submitted in Opposition of EP 2714911 on Dec. 20, 2019. 2 pages.

[No Author Listed] Valneva reports positive phase II results for its *Clostridium difficile* vaccine candidate. Valneva SE. Nov. 30, 2015.

[No Author Listed] Valneva Submission in Opposition Proceedings against EP 2714911, dated Dec. 20, 2019. 2 pages.

[No Author Listed] Valneva Submission in Opposition Proceedings against EP 2753352, dated Dec. 20, 2019. 2 pages.

[No Author Listed] Valneva's Response to Appeal by Glaxosmithkline Biologicals S.A. in EP 2714911. Submitted Dec. 20, 2019. 49 pages.

[No Author Listed] Valneva's Response to Opponent's Appeal in EP 2753352. Submitted Dec. 20, 2019. 46 pages.

Aboudola et al., *Clostridium difficile* vaccine and serum immunoglobulin G antibody response to toxin A. Infect Immun. Mar. 2003;71(3):1608-10.

Albesa-Jové et al., Four distinct structural domains in *Clostridium difficile* toxin B visualized using SAXS. J Mol Biol. Mar. 12, 2010;396(5):1260-70. doi: 10.1016/j.jmb.2010.01.012. Epub Jan. 11, 2010. Filed in EP Patent 2714911 opposition proceedings on Aug. 29, 2017 as "D6" by Valneva Austria GmbH.

Altschul et al., Basic local alignment search tool. J Mol Biol. Oct. 5, 1990;215(3):403-10.

Aota et al., Codon usage tabulated from the GenBank Genetic Sequence Data. Nucleic Acids Res. 1988;16 Suppl:r315-402.

Assignment document 1 (U.S. Appl. No. 61/490,707), filed Oct. 25, 2011.

Assignment document 2 (U.S. Appl. No. 61/490,734), filed Oct. 25, 2011.

Assignment document 3 (U.S. Appl. No. 61/490,716), filed Oct. 25, 2011.

Assignment in respect of PCT/EP2012/059805. Filed in EP Patent 2714911 opposition proceedings on Aug. 29, 2017 as "D2" by Valneva Austria GmbH.

Assignment relating to U.S. Appl. No. 61/490,707 signed Oct. 2011. Filed in EP Patent 2714911 opposition proceedings on Feb. 14, 2018 as "D12" by GlaxoSmithKline Biologicals S.A.

Assignment relating to U.S. Appl. No. 61/490,716 signed Oct. 2011. Filed in EP Patent 2714911 opposition proceedings on Feb. 14, 2018 as "D14" by GlaxoSmithKline Biologicals S.A.

Assignment relating to U.S. Appl. No. 61/490,734 signed Oct. 2011. Filed in EP Patent 2714911 opposition proceedings on Feb. 14, 2018 as "D13" by GlaxoSmithKline Biologicals S.A.

Auxiliary Requests 3-7 (new) and 12-16. Filed in EP Patent 2714911 opposition proceedings on Jan. 24, 2019 by GlaxoSmithKline Biologicals S.A.

Auxiliary Requests 5-12. 32 pages. Filed in EP Patent 2714911 opposition proceedings on Nov. 29, 2018 by GlaxoSmithKline Biologicals S.A.

Babcock et al., Human monoclonal antibodies directed against toxins A and B prevent *Clostridium difficile*-induced mortality in hamsters. Infect Immun. Nov. 2006;74(11):6339-47. Epub Sep. 11, 2006.

Barroso et al., Nucleotide sequence of *Clostridium difficile* toxin B gene. Nucleic Acids Res. Jul. 11, 1990;18(13):4004.

Belyi et al., Construction of a fusion protein carrying antigenic determinants of enteric clostridial toxins. FEMS Microbiol Lett. Aug. 29, 2003;225(2):325-9.

Bezay et al., Safety, immunogenicity and dose response of VLA84, a new vaccine candidate against *Clostridium difficile*, in healthy volunteers. Vaccine. May 17, 2016;34(23):2585-92. doi: 10.1016/j.vaccine.2016.03.098. Epub Apr. 11, 2016.

BLAST Alignment between SEQ ID No. 4 and WO 2010/017383 SEQ ID No. 21. Oct. 25, 2017.

BLAST Alignment between SEQ ID No. 4 and WO 2012/163817 SEQ ID No. 21. Oct. 25, 2017.

BLAST Alignment between SEQ ID No. 4 and WO 2012/163817 SEQ ID No. 23. Oct. 25, 2017.

BLAST Alignment between SEQ ID No. 4 and WO 2012/163817 SEQ ID No. 6. Oct. 25, 2017.

Board of Appeal decision T517/14. Filed in EP Patent 2714911 opposition proceedings on Jun. 26, 2018 as "D19" by GlaxoSmithKline Biologicals S.A. 54 pages.

Certificate of Amendment of IOMAI Corporation to Intercell USA, Inc. Filed in EP Patent 2714911 opposition proceedings on Nov. 28, 2018 as "D35" by Valneva Austria GmbH.

Correspondence and assignments filed with WIPO during prosecution of PCT/EP2011/065304. Filed in EP Patent 2714911 opposition proceedings on Feb. 14, 2018 as "D15" by GlaxoSmithKline Biologicals S.A.

(56) References Cited

OTHER PUBLICATIONS

Cryz et al., Human immunodeficiency virus-1 principal neutralizing domain peptide-toxin A conjugate vaccine. Vaccine. Jan. 1995;13(1):67-71.
Curran et al., Rates of aminoacyl-tRNA selection at 29 sense codons in vivo. J Mol Biol. Sep. 5, 1989;209(1):65-77.
Curriculum vitae and list of publications of Urban Lundberg. Filed in EP Patent 2753352 opposition proceedings on Jan. 11, 2019 as "D30" by Valneva Austria GmbH.
Curriculum vitae for Cindy Castado. Filed in EP Patent 2714911 opposition proceedings on Nov. 29, 2018 as "D24" by GlaxoSmithKline Biologicals S.A.
Curriculum vitae for Philippe Hermand. Filed in EP Patent 2714911 opposition proceedings on Nov. 29, 2018 as "D23" by GlaxoSmithKline Biologicals S.A.
Curriculum vitae of Dr Urban Lundberg. Filed in EP Patent 2714911 opposition proceedings on Nov. 28, 2018 as "D36" by Valneva Austria GmbH.
Curriculum vitae of John R. Van Amsterdam. Filed in EP Patent 2714911 opposition proceedings on Nov. 28, 2018 as "D28" by Valneva Austria GmbH.
CV of Michael K Jones. Filed in EP Patent 2714911 opposition proceedings on Jan. 24, 2019 as "D47" by GlaxoSmithKline Biologicals S.A.
Czerkinsky et al., Oral administration of a streptococcal antigen coupled to cholera toxin B subunit evokes strong antibody responses in salivary glands and extramucosal tissues. Infect Immun. Apr. 1989;57(4):1072-7.
De Bruyn et al., A Phase II Study of the Safety and Immunogenicity of Different Vaccination Schedules of a Candidate *Clostridium difficile* Toxoid Vaccine: Vaccination Schedule Selection for Phase III. E-215. Retrieved from http://www.asmonlineeducation.com/php/asm2014abstracts/data/papers/E-215.- htm on May 27, 2014.
Decision of Nov. 15, 2018 of the Opposition Division in EP2242512. Filed in EP Patent 2714911 opposition proceedings on Nov. 28, 2018 as "D38" by Valneva Austria GmbH.
Decision of Jan. 2, 2018 of the Opposition Division in respect of EP 2429574. Filed in EP Patent 2714911 opposition proceedings on Nov. 28, 2018 as "D21" by Valneva Austria GmbH.
Decision of the EPO Technical Board of Appeal for Publication No. EP 2753352 mailed Mar. 4, 2022. 34 pages.
Declaration by Cindy Castado. Filed in EP Patent 2714911 opposition proceedings on Nov. 29, 2018 as "D22" by GlaxoSmithKline Biologicals S.A.
Declaration by Michael K. Jones. Filed in EP Patent 2714911 opposition proceedings on Jan. 24, 2019 as "D46" by GlaxoSmithKline Biologicals S.A.
Declaration by Philippe Hermand. Filed in EP Patent 2714911 opposition proceedings on Nov. 29, 2018 as "D21" by GlaxoSmithKline Biologicals S.A.
Declaration of John R. Van Amsterdam. Filed in EP Patent 2714911 opposition proceedings on Nov. 28, 2018 as "D27" by Valneva Austria GmbH.
Declaration of Sylvain Hansen. Filed in EP Patent 2714911 opposition proceedings on Jan. 24, 2019 as "D51" by GlaxoSmithKline Biologicals S.A.
Demarest et al., Structural characterization of the cell wall binding domains of *Clostridium difficile* toxins A and B; evidence that Ca2+ plays a role in toxin A cell surface association. J Mol Biol. Mar. 11, 2005;346(5):1197-206.
Devereux et al., A comprehensive set of sequence analysis programs for the VAX. Nucleic Acids Res. Jan. 11, 1984;12(1 Pt 1):387-95.
Dickinson et al., Dissociation of *Escherichia coli* heat-labile enterotoxin adjuvanticity from ADP-ribosyltransferase activity. Infect Immun. May 1995;63(5):1617-23.
Dingle et al., Functional properties of the carboxy-terminal host cell-binding domains of the two toxins, TcdA and TcdB, expressed by *Clostridium difficile*. Glycobiology. Sep. 2008;18(9):698-706. doi: 10.1093/glycob/cwn048. Epub May 28, 2008.

Douce et al., Intranasal immunogenicity and adjuvanticity of site-directed mutant derivatives of cholera toxin. Infect Immun. Jul. 1997;65(7):2821-8.
Dove et al., Molecular characterization of the *Clostridium difficile* toxin A gene. Infect Immun. Feb. 1990;58(2):480-8.
Experimental report. Filed in EP Patent 2714911 opposition proceedings on Nov. 28, 2018 as "D37" by Valneva Austria GmbH.
Experimental Report. Filed in EP Patent 2714911 opposition proceedings on Aug. 29, 2017 as "D9" by Valneva Austria GmbH.
Experimental Report. Filed in EP Patent 2714911 opposition proceedings on Jan. 11, 2019 as "D39" by Valneva Austria GmbH.
Extract from Register of EP Patents for EP 2753352. Filed in EP Patent 2714911 opposition proceedings on Aug. 29, 2017 as "D1a" by Valneva Austria GmbH.
GAP Alignment of SEQ ID No. 4 of the Patent with sequences of D4 using Needleman and Wunsch global alignment ("Comparator 1 versus reference sequence"). Filed in EP Patent 2753352 opposition proceedings on Jan. 11, 2019 as "D30" by GlaxoSmithKline Biologicals S.A.
Garel, Functional adaptation of tRNA population. J Theor Biol. Jan. 1974;43(1):211-25.
Gerding et al., Treatment of *Clostridium difficile* infection. Clin Infect Dis. Jan. 15, 2008;46 Suppl 1:S32-42. doi: 10.1086/521860.
Ghose et al, Anaerobe (2016);37:85-95. Filed in EP Patent 2714911 opposition proceedings on Nov. 29, 2018 as "D25" by GlaxoSmithKline Biologicals S.A.
Ghose et al., Transcutaneous immunization with *Clostridium difficile* toxoid A induces systemic and mucosal immune responses and toxin A-neutralizing antibodies in mice. Infect Immun. Jun. 2007;75(6):2826-32. Epub Mar. 19, 2001.
Giannasca et al., Active and passive immunization against *Clostridium difficile* diarrhea and colitis. Vaccine. Feb. 17, 2004;22(7):848-56.
Glenn et al., Murine IgG subclass antibodies to antigens incorporated in liposomes containing lipid A. Immunol Lett. Jul.-Aug. 1995;47(1-2):73-8.
Grantham et al., Codon catalog usage and the genome hypothesis. Nucleic Acids Res. Jan. 11, 1980;8(1):r49-162.
Grantham et al., Codon catalog usage is a genome strategy modulated for gene expressivity. Nucleic Acids Res. Jan. 10, 1981;9(1):r43-74.
Greco et al., Carbohydrate recognition by *Clostridium difficile* toxin A. Nat Struct Mol Biol. May 2006;13(5):460-1. Epub Apr. 16, 2006. Filed in EP Patent 2714911 opposition proceedings on Aug. 29, 2017 as "D5" by Valneva Austria GmbH.
Ho et al., Crystal structure of receptor-binding C-terminal repeats from *Clostridium difficile* toxin A. Proc Natl Acad Sci U S A. Dec. 20, 2005;102(51):18373-8. Epub Dec. 12, 2005.
Ikemura, Correlation between the abundance of *Escherichia coli* transfer RNAs and the occurrence of the respective codons in its protein genes. J Mol Biol. Feb. 15, 1981;146(1):1-21.
Ikemura, Correlation between the abundance of *Escherichia coli* transfer RNAs and the occurrence of the respective codons in its protein genes: a proposal for a synonymous codon choice that is optimal for the *E. coli* translational system. J Mol Biol.Sep. 25, 1981;151(3):389-409.
Invention Agreement between IOMAI Corporation and Ellingsworth, Larry dated Feb. 12, 2001. Filed in EP Patent 2714911 opposition proceedings on Nov. 28, 2018 as "D29" by Valneva Austria GmbH.
Invention Agreement between IOMAI Corporation and Flyer, David dated Dec. 8, 2001. Filed in EP Patent 2714911 opposition proceedings on Nov. 28, 2018 as "D30" by Valneva Austria GmbH.
Invention Agreement between IOMAI Corporation and Fuhrmann, Steven dated Jan. 2, 2003. Filed in EP Patent 2714911 opposition proceedings on Nov. 28, 2018 as "D32" by Valneva Austria GmbH.
Invention Agreement between IOMAI Corporation and Glenn, Gregory dated Feb. 9, 1999. Filed in EP Patent 2714911 opposition proceedings on Nov. 28, 2018 as "D33" by Valneva Austria GmbH.
Invention Agreement between IOMAI Corporation and Kluepfel-Stahl, Stefanie dated Jul. 8, 2008. Filed in EP Patent 2714911 opposition proceedings on Nov. 28, 2018 as "D34" by Valneva Austria GmbH.

(56) References Cited

OTHER PUBLICATIONS

Invention Agreement between IOMAI Corporation and Tian, Jing-Hui dated Jan. 8, 2001. Filed in EP Patent 2714911 opposition proceedings on Nov. 28, 2018 as "D31" by Valneva Austria GmbH.
Johnson, Recurrent *Clostridium difficile* infection: a review of risk factors, treatments, and outcomes. J Infect. Jun. 2009;58(6):403-10. doi: 10.1016/j.jinf.2009.03.010. Epub Apr. 5, 2009.
Kaslow et al., *Clostridium difficile* and methicillin-resistant *Staphylococcus aureus*: emerging concepts in vaccine development. Annu Rev Med. 2011;62:201-15. doi: 10.1146/annurev-med-051109-101544.
Kelly et al., The host immune response to *Clostridium difficile*. J Med Microbiol. Aug. 2011;60(Pt 8):1070-9. doi: 10.1099/jmm.0.030015-0. Epub Mar. 17, 2011.
Kim et al., Immunization of adult hamsters against *Clostridium difficile*-associated ileocecitis and transfer of protection to infant hamsters. Infect Immun. Dec. 1987;55(12):2984-92.
Kink et al., Antibodies to recombinant *Clostridium difficile* toxins A and B are an effective treatment and prevent relapse of C. difficile-associated disease in a hamster model of infection. Infect Immun. May 1998;66(5):2018-25.
Kitchin et al., A Phase 2 Study Evaluating the Safety, Tolerability, and Immunogenicity of Two 3-Dose Regimens of a *Clostridium difficile* Vaccine in Healthy US Adults Aged 65 to 85 Years. Clin Infect Dis. May 24, 2019. pii: ciz153. doi: 10.1093/cid/ciz153.
Kotloff et al., Safety and immunogenicity of increasing doses of a *Clostridium difficile* toxoid vaccine administered to healthy adults. Infect Immun. Feb. 2001;69(2):988-95.
Kurland, Codon bias and gene expression. FEBS Lett. Jul. 22, 1991;285(2):165-9.
Kyne et al., Association between antibody response to toxin A and protection against recurrent *Clostridium difficile* diarrhoea. Lancet. Jan. 20, 2001;357(9251):189-93.
Lyerly et al., Vaccination against lethal enterocolitis with a nontoxic recombinant peptide of toxin A. Curr Microbiol. 1990;21:29-32.
Main Request and Auxiliary Requests 1-4. Filed in EP Patent 2714911 opposition proceedings on Feb. 14, 2018 by GlaxoSmithKline Biologicals S.A. 35 pages.
Makoff et al., Expression of tetanus toxin fragment C in *E. coli*: high level expression by removing rare codons. Nucleic Acids Res. Dec. 25, 1989;17(24):10191-202.
Medzhitov et al., Innate immunity: impact on the adaptive immune response. Curr Opin Immunol. Feb. 1997;9(1):4-9.
Needleman et al., A general method applicable to the search for similarities in the amino acid sequence of two proteins. J Mol Biol. Mar. 1970;48(3):443-53.
Notice of Appeal for EP2714911B dated May 31, 2019. Opposition by Valneva Austria GmbH.
Notice of Opposition against the granted patent of EP 2753352. Oct. 25, 2017.
Opposition against EP Patent 2714911 by Valneva Austria GmbH, dated Aug. 29, 2017. 34 pages.
Opposition Division decision on "CRISPR" case EP2771468. Filed in EP Patent 2714911 opposition proceedings on Jan. 24, 2019 as "D50" by GlaxoSmithKline Biologicals S.A.
PCT Request form on WO 2012/028741. Filed in EP Patent 2714911 opposition proceedings on Jun. 26, 2018 as "D18" by GlaxoSmithKline Biologicals S.A. 6 pages.
Pedersen, *Escherichia coli* ribosomes translate in vivo with variable rate. EMBO J. Dec. 1, 1984;3(12):2895-8.
Preliminary opinion of Dec. 13, 2017 of the Opposition Division in EP2215124. Filed in EP Patent 2714911 opposition proceedings on Nov. 28, 2018 as "D22" by Valneva Austria GmbH.
Preliminary opinion of Jul. 13, 2018 of the Opposition Division in EP2940044. Filed in EP Patent 2714911 opposition proceedings on Nov. 28, 2018 as "D24" by Valneva Austria GmbH.
Preliminary opinion of Nov. 20, 2017 of the Opposition Division in EP2242512. Filed in EP Patent 2714911 opposition proceedings on Nov. 28, 2018 as "D25" by Valneva Austria GmbH.
Preliminary opinion of Apr. 30, 2018 of the Opposition Division in EP1737491. Filed in EP Patent 2714911 opposition proceedings on Nov. 28, 2018 as "D23" by Valneva Austria GmbH.
Preliminary opinion of the Board issued on Jun. 14, 2017 in T 239/16. Filed in EP Patent 2714911 opposition proceedings on Nov. 28, 2018 as "D26" by Valneva Austria GmbH.
Press release from Intercell AG referred to as Exhibit 2 in D46 and available from US Securities and Exchange Commission website www.sec.gov/archives. Filed in EP Patent 2714911 opposition proceedings on Jan. 24, 2019 as "D48" by GlaxoSmithKline Biologicals S.A.
Pruitt et al., Structural organization of the functional domains of *Clostridium difficile* toxins A and B. Proc Natl Acad Sci U S A. Jul. 27, 2010;107(30):13467-72. doi: 10.1073/pnas.1002199107. Epub Jul. 12, 2010. Filed in EP Patent 2714911 opposition proceedings on Aug. 29, 2017 as "D7" by Valneva Austria GmbH.
Randall et al., Novel intermediates in the synthesis of maltose-binding protein in *Escherichia coli*. Eur J Biochem. Jun. 1980;107(2):375-9.
Reply to the observations made by the patent proprietor(s), filed in Opposition against EP Patent 2714911, dated Jan. 11, 2019. Valneva Austria GmbH.
Response to Opposition against EP Patent 2714911 dated Feb. 14, 2018. GlaxoSmithKline Biologicals S.A. 19 pages.
Response to submissions filed by Opponent in Opposition against EP Patent 2714911, dated Jun. 26, 2018. GlaxoSmithKline Biologicals S.A. 9 pages.
Result of oral proceedings in Opposition against EP Patent 2714911, dated Jan. 30, 2019.
Revill et al., Tiacumicin B: macrolide antibiotic treatment of C. difficile-associated diarrhea. Drugs of the Future. 2006;31(6):494-497.
Ryan et al., Protective immunity against *Clostridium difficile* toxin A induced by oral immunization with a live, attenuated Vibrio cholerae vector strain. Infect Immun. Jul. 1997;65(7):2941-9.
Scheiblhofer et al., Influence of protein fold stability on immunogenicity and its implications for vaccine design. Expert Rev Vaccines. May 2017;16(5):479-489. doi: 10.1080/14760584.2017.1306441. Epub Mar. 24, 2017. Filed in EP Patent 2714911 opposition proceedings on Nov. 29, 2018 as "D26" by GlaxoSmithKline Biologicals S.A.
Sorensen et al., Codon usage determines translation rate in *Escherichia coli*. J Mol Biol. May 20, 1989;207(2):365-77.
Submission following summons for Opposition against EP Patent 2714911 dated Nov. 28, 2018. Valneva Austria GmbH. 11 pages.
Submission following summons for Opposition against EP Patent 2714911 dated Nov. 29, 2018. GlaxoSmithKline Biologicals S.A.
Submission in Opposition proceedings against EP Patent 2714911 following summons to attend oral proceedings dated Jan. 24, 2019. GlaxoSmithKline Biologicals S.A. 14 pages.
Summons to attend oral proceedings pursuant to Rule 115(1) EPC dated Jul. 26, 2018. GlaxoSmithKline Biologicals S.A.
T1201/14. Filed in EP Patent 2714911 opposition proceedings on Jan. 24, 2019 as "D49" by GlaxoSmithKline Biologicals S.A.
Tillotson et al., *Clostridium difficile*—a moving target. F1000 Med Rep. 2011;3:6. doi: 10.3410/M3-6. Epub Mar. 1, 2011.
U.S. Appl. No. 61/379, 892. Filed in EP Patent 2714911 opposition proceedings on Aug. 29, 2017 as "D1b" by Valneva Austria GmbH.
Varenne et al., Translation is a non-uniform process. Effect of tRNA availability on the rate of elongation of nascent polypeptide chains. J Mol Biol. Dec. 15, 1984;180(3):549-76.
Varfolomeeva et al., Genetic engineering approach to producing fragments of toxins A and B for diagnosis and immunotherapy of *Clostridium difficile* infection. Mol Genetics Microb Virol. 2003;3:6-10.
Venn diagram evidencing added matter in Claim 2 ("Claim 2 as granted"). Filed in EP Patent 2753352 opposition proceedings on Jan. 11, 2019 as "D29" by GlaxoSmithKline Biologicals S.A.
Von Eichel-Streiber et al., *Clostridium difficile* toxin A carries a C-terminal repetitive structure homologous to the carbohydrate binding region of streptococcal glycosyltransferases. Gene. Nov. 30, 1990;96(1):107-13.

(56) References Cited

OTHER PUBLICATIONS

Voth et al., *Clostridium difficile* toxins: mechanism of action and role in disease. Clin Microbiol Rev. Apr. 2005;18(2):247-63.
Wada et al., Codon usage tabulated from the GenBank genetic sequence data. Nucleic Acids Res. Apr. 25, 1991;19 Suppl:1981-6.
Ward et al., Local and systemic neutralizing antibody responses induced by intranasal immunization with the nontoxic binding domain of toxin A from *Clostridium difficile*. Infect Immun. Oct. 1999;67(10):5124-32.

Figure 1A

C-TAB.G5 nucleic acid

```
ATGGTAACAGGAGTATTAAAGGACCTAATGGATTTGAGTATTTGCACCTGCTAATACTCACAATAATAACATAGAAGGTCAG
GCTATAGTTACCAGAGAACAAATTCTTAACTTTGAATGGCAAAAATATATTTGATAATGACTCAAAAGCAGTTACTGGATGG
CAAACCATTGATGGTAAAAAATATTACTTAATCTTAACACTGCTGAAGCAGCTACTGGATGGCAAACTATTGATGGTAAAAAA
TATTACTTAATCTTAACACTGCTGAAGCAGCTACTGGATGTAAAAATATTACTTAATACTACACTT
TCATAGCCTCAACTGGTTATACAGAGTATTAATGGTAAACATTTTATTTAATACTGATATACTGAGATAGGAGTGTTTAA
AGGACCCTAATGGATTGAATCTTGCACCTGCTAATACTTCATAATAACAACAGTAGAAGGTCAAGCTATACTTACCAAAATAA
ATCTTAACTTGAATGGTAAAAAATATTACTTGGTAGTGACTGGTAAAGTCGGACTATTGATGGTAAAAA
ATATTACTTAATAACACTGCTGTTGCAGTTACTAGCTCACCTGCTAATACAGATGGTAAACATTTTATTTAATACTGATATACAGT
TCTATAGCTTCAACTGGTTATACAGATGGTAAACATCTGCTAATACAGATGCTAAGCTACTGGTTGGTAACTATTGATGGTAATAG
AGGACCTGATGGATTTGAATACTTTGCACCTGCTAATATTTGGTAGTGGTAAATTCAAAGACTAGCTACTGGTTATCAAATGTAATAG
ATTCCTATATTTACATGACAATATACAGCTATGGGTGCAATATGATGGCTCTAATGGATCGATTTAAAGGACTGAAATGGTTAC
TATTACTTCGAGCTAATACAGCTAATACAGCTAGTGGGTCTAATGGATTGAATGATGGTAAAATATAACGGATGCTAACAATAGAAGGTCAA
GCTATACGTTATCAAAATAGATTCCTACATTATTACTTGGAAATACTGCTAATAATTGGTAACTTGTCGACTTGGATCAATTGGAGATTGGATGGAC
AACTATTAATGGTAAAGTAAAATAAGCCCCTCAATTAATGCCTGATATATGCCAGATCTATGCCAGATCTATCGCATAATCATAATTTGATACTGT
ATATTCTTGGTGTTGATGGATTATACTTAAATGGAGTAAATACTTAATCCAATTAACAGGTTACAACAGCAATTGATTTGATAATGCAAAATTATTA
TTTCAACCAAAGTGGATGAAATACTAGAATGGTTACACAGGGAAGCAATTGGATTGAAAGATGCACTATATTTAGCCCAGTGATTTAAAGGTCTAAATCA
TGAAAACCTAGAAATGGAAATGGAAGAATTGAAAATAACACTATATTCGTGAAAATGAAGAAGTGAAGAAATCTC
GGAGCTGTAGAGTAATAAATCTATTTCAATTCGATGTGTGTGAAATAGATGGATGTGAAATCTCCACTAGGCAGAGATTGCAAAAAGGAAGTGATTTAGGAAATGAAGAATTGAAGATTGAAG
AATAGGTGATTATAATAATAGTAGGTTACACATGGAATTATTTGCTCATCATAATTTGATGATTCATTTACAGCTGTAGTTGCATTACAGCTGTAGTTGCATTAAATGATGGTCAATTATATTTA
GATGATTCTGGTGTTATGAAGTAGTTACACTGGTTAAATATTTGCTCATCATAATTTGATGATTCATTTACAGCTGTAGTTGCATTAAATGATGGTCAATTATATTTA
AGGAGTATTAACAGAAGAATGGATTAAATTCAATAATAAATTACTATTTGATGATTCCTCTGACTCGTAGTTGATGGTGAAAGATTTAGAG
ATATTCTGGTATATTATTTGATGAAGATACAGCAAGACATATGAATGATAAGTCTCTACTTGTGCATTAAATGATGGTATTCAATTATTTA
GATGTTCAAGATGGTAATTGCAAGTGGATTGGATTTCACTATATAGATGATGATAAAGTGGATTTCACTATAGATAGTGATAAAGTATAGATTCGTA
AGTACAAAACATGAATGGACAATATTCTATAGATGATGATAATATATACGGGACAAGGATGGATAATTTACGGACAAGGATGGATATAACTTAGTGAAT
AAATATTTCACCTGCTAATACTTGTAAATACTGATATTTACGGACAAGGATGGATAATATATACGGACAAGGATGGATAATTTAGTGAAT
GATGTATATTTTGGAGTGAAATGGATATAGAGAAAACATGGCAAAAACTAAGACATTGAAAATAAAATTGGTATGATGAAATGAAATGGATATATTTC
AACTCCAGAAACTAAAAAGCATAAAGTGAAATACTATTTATCAAATAAAATCAATAACTAAATATTTGATGAAGAGGCATATATATGAAGAGA
ACGGGTCTTATATCATTGAAAGAATACTGTGAATACTGATATTTTAATGCAATTGGTTATATAAATATGAAGAATAGAAGAGATTCTATATGCACATCAAA
AGATGTTCTATTTGGTGAAGATGGTCATGTCAGGAGAATCAATAAACAATAAACTAACAACACACACAACGATAGATTAGATAGATGATAATAGATGATAATAGATGATAATAGATGATAATAGATGATAATAGAT
ATACTTTGGATGAGAGAATTGCAGCAACTGGTTCAGTTATTATGTGAGGAGTATATATTTTTGATCCTGATCCTGATACAGCTCAATTAGTGATTAG
TGAATAG
```

Figure 1B

C-TAB.G5 amino acid

MVTGVFKGPNGFEYFAPANTHNNNIEGQAIVYQNKFLTLNGKKYYFDNDSKAVTGWQTIDG
KKYYFNLNTAEAATGWQTIDGKKYYFNLNTAEAATGWQTIDGKKYYFNTNTFIASTGYTSING
KHFYFNTDGIMQIGVFKGPNGFEYFAPANTHNNNIEGQAILYQNKFLTLNGKKYYFGSDSKA
VTGLRTIDGKKYYFNTNTAVAVTGWQTIDGKKYYFNTNTSIASTGYTIISGKHFYFNTDGIMQI
GVFKGPDGFEYFAPANTDANNIEGQAIRYQNRFLYLHDNIYYFGNNSKAATGWVTIDGNRYY
FEPNTAMGANGYKTIDNKNFYFRNGLPQIGVFKGSNGFEYFAPANTDANNIEGQAIRYQNRF
LHLLGKIYYFGNNSKAVTGWQTINGKVYYFMPDTAMAAGGLFEIDGVIYFFGVDGVKAPGIY
GRSMHNLITGFVTVGDDKYYFNPINGGAASIGETIIDDKNYYFNQSGVLQTGVFSTEDGFKYF
APANTLDENLEGEAIDFTGKLIIDENIYFDDNYRGAVEWKELDGEMHYFSPETGKAFKGLN
QIGDYKYYFNSDGVMQKGFVSINDNKHYFDDSGVMKVGYTEIDGKHFYFAENGEMQIGVFN
TEDGFKYFAHHNEDLGNEEGEEISYSGILNFNNKIYYFDDSFTAVVGWKDLEDGSKYYFDED
TAEAYIGLSLINDGQYYFNDDGIMQVGFVTINDKVFYFSDSGIIESGVQNIDDNYFYIDDNGIVQ
IGVFDTSDGYKYFAPANTVNDNIYGQAVEYSGLVRVGEDVYYFGETYTIETGWVYDMENESD
KYYFNPETKKACKGINLIDDIKYYFDEKGIMRTGLISFENNNYYFNENGEMQFGYINIEDKMFY
FGEDGVMQIGVFNTPDGFKYFAHQNTLDENFEGESINYTGWLDLDEKRYYFTDEYIAATGSV
IIDGEEYYFDPDTAQLVISE*

Figure 2A

C-TAB.G5.1 nucleic acid

```
ATGGTTACAGGTGTGTTTCAAAGGTCCGAACGGCTTTGAATATTTTGCACCGGCAAATACCCACAATAATAATATTGAAGGCCAGGCC
ATCGTGTATCAGAATAAATTCTGACCCTGAACGGCAAAATACTATTCGATAACGATAGCAAAGCAGTTACCGGTTGGCAAAC
ATTGATGGCAAAAATATTACTTCAACCTGAATCACCGTACACGGAAGAACCAGCAACCTACCCGGTGGCAGACGATCGTAAAAGTACTATTT
AACCTGAACACAGCGGAAGCGCTACAGCTGGCAGAAGAATATATTTAATACCAATACCTTATTGCCAGC
ACCGGCTATACCAGCATTAATGCAAACACTTCTATTTAACCTCGATCAGCGAAGGTCGTATTATGCAGATCGGTGTGTTAAGGGCCCTAATGGT
TTTGAGTACTTCGCTCCGGCTAATACCGATCGCAAATAACATCGATCGAAGGTCAGCAATTCTGTACCAGAACAACCGGCAAGAATATTATTCAATCAAAC
GGTAAGAAATATTACTTGGTACCGGTTGCCCGTTGACAGGTTGGCAGAGATAAATGGTGCAGAAGTTACTACTTCAACCAGCATTGCAAGTACCGGTTA
ACCGCAGTGGCCGTGACAGGTTGCCCGTTGACAGGATAAATGGTAAGAAGAAGAATACTTCAACCAGCATTGCAAGTACCGGTTA
TACCATTATCAGCGGCAAATACAGATCAATACCTTACTTGACGTAAGAGACGGCATTATCCAGATTGCAGATTGCGGTTTTCAAAGGTCCCGATGGGTCCCGATGGGTCGAGTA
CTTTGCCCCTGCAAATACAGATCAATCAAAAGCAGCCACCGGTTGGGTTACAATTGATGGTAATCGTTATTACTTTGAGCCGAATACCGCAAT
CTATTACTTCGGCAATAATTCAAAAGCAGCCACCGGTTGGGTTACAATTGATGGTAATCGTTATTACTTTGAGCCGAATACCGCAAT
GGGTGCAAATGGTTATAAACCATCGATAACAACCGATGAACAACCATCGAACCAAGGCCAAGGATTTTATTTTGAGGATTGCAGCAGTTGGTGTTTTAAGGGTAGCAAT
GCTGGCAAATTTATTACTTGGCAACTATAATAGCAAGCGGTGACAAGCGGTGACAACCATTACGGTAAGTTAAGTTATTATTCATGCC
GGATACCGCTATGGCAGCAGCCGGTAAAGCCTATGCGTGTTGAATTGATGCGTGTTACCGGTTTTATTATTTTGGCGTGGATGGTGTTAAGCACCGG
GTATTATGGTCGTAGCATGCATAATCTGATACGACTATTATTTTGTAACACGAGGGGTGTTCCGACGTAAATACTACTTAATCCGATTAATGGTGG
TGCAGCAAGCATTGGTGAACACAATATTTGCTCTCTGCGAATACGACTGGATGATAATATTCGCGGGTTGAAGAACTGGTGAAGCAATGCTCACCGATCAGAGATCATAACTTGCGATCATCATAAGAATGAAGATCTG
TCCGGAAACCGTAAGCCTTAAAAGGTCTGAATCAGATCGGGATCTCGCGGCGATATTAACAAGATACCGGAGAGCCTATATTGGTCTGAGCCTGATTA
CTTGTGAGCATTAACGACAACAAACACTATTTGACGAGTAGCGGCATATAGCGCAGCCAATATAGCGGCCTATAAAGTGTCTATTTCAGCGATAG
ATGATGGCCAGTATTATTCAACGATGGTGTTCAGAACGATAAACGACATAACGATAACGGTATTGTGACATCGATAACGGTATTGTTCAGATTGGCGTGTTTGAT
CGGCATTATGAAAGCGGGTGGTTATAAATTTCGCACCAGAGTGTTCAGAACGATAAACGACATCGATACGTATTGTTCAGATTGGCGTGTTTGAT
ACCTCGGCGGAAGATGGTTTTATTGGGTAAAAAAAGCGGAAGTGCCAATGAAACGTTAATCTGATGCAGCGGTATTGATATTTGAATTGAAAGGTCTGTTC
GTGTTGGCGAAGATGTTCAATCATCCGGAAACCTGCAAGCAACAACTGCCAAAGCGATACTAGTTGGCGATATCCGGTGATGGCGCAGTTGGGTTATGATGAAGCGACAAGT
ACTATTCAATCCGGATCGATTAGCGTTTGGTAGCGAAAAGCGAAAACCCGATGAGACGAGATATGGCTATATCAAGAGCATTAT
GCCTACCGGTCGATTAGCGTTGGTGAGGACGGTGATATCAATCCAAAGCGATGATATAGCGTTGACGTAACTAATGGTAAGCATTATTGGA
CAAATGTTTATTTGGTGAAAACTTTCGAGGACGGTGATATCAATCCAAAGCGATAGTCGGTTTTTAATACCGGTAAGCATTATTCACACGAGGA
ACCCCTGATGAAACGTAGCGTAGCGGTTATTATTGATGGTAGCGAAAATATACCGGTGATGGCTGATCGGATACGGAATACCGAGACGACAAGA
TACATTGCAGCAACGGTAGCGTTATTATTGATGGTAGCGAAAATATACCGGTGATGGCTGATCGGATACGGAATACCGAGACGACAAGA
TACATTGCAGCAACGGTAGCGTTATTATTGATGGTGAGGAATAATACTTCGATCGGATACGGAATACCGAGACGACAGCTGGTTATTAGCGGAATAA
```

Figure 2B

C-TAB.G5.1 amino acid (M*)VTGVFKGPNGFEYFAPANTHNNIEGQAIVYQNKFLTLNGKKYYFDNDSKAVTGWQTID
GKKYYFNLNTAEAATGWQTIDGKKYYFNLNTAEAATGWQTIDGKKYYFNTNTFIASTGYTSIN
GKHFYFNTDGIMQIGVFKGPNGFEYFAPANTDANNIEGQAILYQNKFLTLNGKKYYFGSDSK
AVTGLRTIDGKKYYFNTNTAVAVTGWQTINGKKYYFNTNTSIASTGYTIISGKHFYFNTDGIMQ
IGVFKGPDGFEYFAPANTDANNIEGQAIRYQNRFLYLHDNIYYFGNNSKAATGWTIDGNRY
YFEPNTAMGANGYKTIDNKNFYFRNGLPQIGVFKGSNGFEYFAPANTDANNIEGQAIRYQNR
FLHLLGKIYYFGNNSKAVTGWQTINGKVYYFMPDTAMAAAGGLFEIDGVIYFFGVDGVKAPGI
YGRSMHNLITGFVTVGDDKYYFNPINGGAASIGETIIDDKNYFNQSGVLQTGVFSTEDGFKY
FAPANTLDENLEGEAIDFTGKLIIDENIYYFDDNYRGAVEWKELDGEMHYFSPETGKAFKGLN
QIGDYKYYFNSDGVMQKGFVSINDNKHYFDDSGVMKVGYTEIDGKHFYFAENGEMQIGVFN
TEDGFKYFAHHNEDLGNEEGEEISYSGILNFNNKIYYFDDSFTAVVGWKDLEDGSKYYFDED
TAEAYIGLSLINDGQYYFNDDGIMQVGFVTINDKVFYFSDSGIIESGVQNIDDNYFYIDDNGIV
QIGVFDTSDGYKYFAPANTVNDNIYGQAVEYSGLVRVGEDVYYFGETYTIETGWIDMENES
DKYYFNPETKKACKGINLIDDIKYYFDEKGIMRTGLISFENNNYYFNENGEMQFGYINIEDKMF
YFGEDGVMQIGVFNTPDGFKYFAHQNTLDENFEGESINYTGWLDLDEKRYYFTDEYIAATGS
VIIDGEEYYFDPDTAQLVISE

*the N-terminal Met is cleaved off during expression

Figure 3

Antibody titers on day 14 (1st immunization) and day 28 (2nd immunization) in mice

| C-TAB immunization | Anti-C-TAB | | | Anti-Toxin A | | | Anti-Toxin B | | |
|---|---|---|---|---|---|---|---|---|---|
| | Pre* | Day 14 | Day 28 | Pre | Day 14 | Day 28 | Pre | Day 14 | Day 28 |
| 0 | 2 | 1 | 1 | 1 | 2 | 1 | 1 | 1 | 1 |
| 100 (154) ng | 5 | 3 | 349 | 4 | 8 | 122 | 1 | 1 | 4 |
| 300 (462) ng | 4 | 2 | 1,172 | 3 | 4 | 530 | 1 | 1 | 5 |
| 1,000 (1,540) ng | 5 | 144 | 5,199 | 9 | 100 | 2,382 | 1 | 1 | 4 |
| 3,000 (4,620) ng | 3 | 1,105 | 24,047 | 2 | 655 | 11,563 | 1 | 1 | 284 |
| 10,000 (15,400) ng | 5 | 11,195 | 84,519 | 4 | 6,980 | 48,595 | 2 | 46 | 2,724 |
| PBS + 50 µg alum | 9 | 3 | 3 | 2 | 1 | 1 | 1 | 2 | 2 |
| 10 (15.4) ng + 50 µg alum | 6 | 45,375 | 123,373 | 4 | 21,157 | 87,492 | 1 | 1 | 436 |
| 30 (46.2) ng + 50 µg alum | 5 | 42,410 | 152,074 | 4 | 18,691 | 111,424 | 1 | 1 | 3,835 |
| 100 (154) ng + 50 µg alum | 2 | 44,777 | 250,705 | 2 | 34,660 | 150,931 | 1 | 4 | 13,558 |
| 300 (462) ng + 50 µg alum | 2 | 97,667 | 389,670 | 2 | 23,187 | 234,546 | 1 | 154 | 20,955 |
| 1,000 (1,540) ng + 50 µg alum | 8 | 110,184 | 268,865 | 8 | 26,864 | 188,545 | 1 | 1,558 | 31,088 |

* pre-bleed

Figure 5

Antibody titers on day 28 (post 2nd immunization) in mice

| GP | Vaccine | | Antibody titers | | |
|----|---------|---------|---------|---------|---------|
| | C-TAB.G5 | Adjuvant | Anti-C-TAB | Anti-toxin A | Anti-toxin B |
| 1 | PBS | --- | 0 | 0 | 0 |
| 2 | 3 µg | No adjuvant | 27,930 | 19,001 | 422 |
| 3 | 10 µg | No adjuvant | 51,518 | 34,058 | 1,464 |
| 4 | 30 µg | No adjuvant | 69,836 | 50,907 | 1,801 |
| 5 | 3 µg | 50 µg alum | 584,447 | 241,362 | 45,181 |
| 6 | 10 µg | 50 µg alum | 789,145 | 311,657 | 67,462 |
| 7 | 30 µg | 50 µg alum | 1,081,219 | 404,399 | 53,849 |

Figure 6

TNA and protection against challenge with toxin A or toxin B in mice

| Vaccine | Toxin A | | Toxin B | |
|---|---|---|---|---|
| | TNA | Protection*, % | TNA | Protection*, % |
| PBS | 0 | 16.6 | 0 | 0 |
| 3 µg C-TAB.G5 | 103 | 100 | 0 | 0 |
| 10 µg C-TAB.G5 | 171 | 100 | 0 | 12.5 |
| 30 µg C-TAB.G5 | 150 | 100 | 0 | 50 |
| 3 µg C-TAB.G5 + alum | 683 | 100 | 339 | 100 |
| 10 µg C-TAB.G5 + alum | 778 | 100 | 300 | 100 |
| 30 µg C-TAB.G5 + alum | 1010 | 100 | 669 | 87.5 |

*Challenge dose:
toxin A: 25 ng/mouse
toxin B: 50 ng/mouse

Figure 7

Comparison of C-TAB.G5 immunogenicity in young vs. old mice

| Age | C-TAB.5 immunization | IgG titers | | | TNA | | Protection*, % | |
|---|---|---|---|---|---|---|---|---|
| | | C-TAB | Toxin A | Toxin B | Toxin A | Toxin B | Toxin A | Toxin B |
| Y | PBS | 0 | 1 | 1 | 0 | 0 | 25 | 0 |
| O | PBS | 25 | 4 | 1 | 0 | 0 | 0 | 25 |
| Y | 10 µg | 48,911 | 34,519 | 2,338 | 184 | 0 | 0 | 0 |
| Y | 30 µg | 91,110 | 47,559 | 3,722 | 285 | 0 | 100 | 0 |
| O | 10 µg | 3,186 | 2,970 | 6 | 6 | 0 | 100 | 71 |
| O | 30 µg | 19,636 | 8,924 | 151 | 58 | 0 | 62.5 | 25 |
| Y | 10 µg + alum | 580,987 | 302,148 | 41,603 | 779 | 1,428 | 100 | 85 |
| Y | 30 µg + alum | 747,839 | 451,641 | 55,705 | 682 | 1,042 | 100 | 100 |
| O | 10 µg + alum | 99,981 | 61,105 | 2,455 | 283 | 0 | 100 | 75 |
| O | 30 µg + alum | 351,373 | 134,631 | 11,211 | 682 | 0 | 100 | 100 |

*Challenge dose:
toxin A: 25 ng/mouse
toxin B: 50 ng/mouse

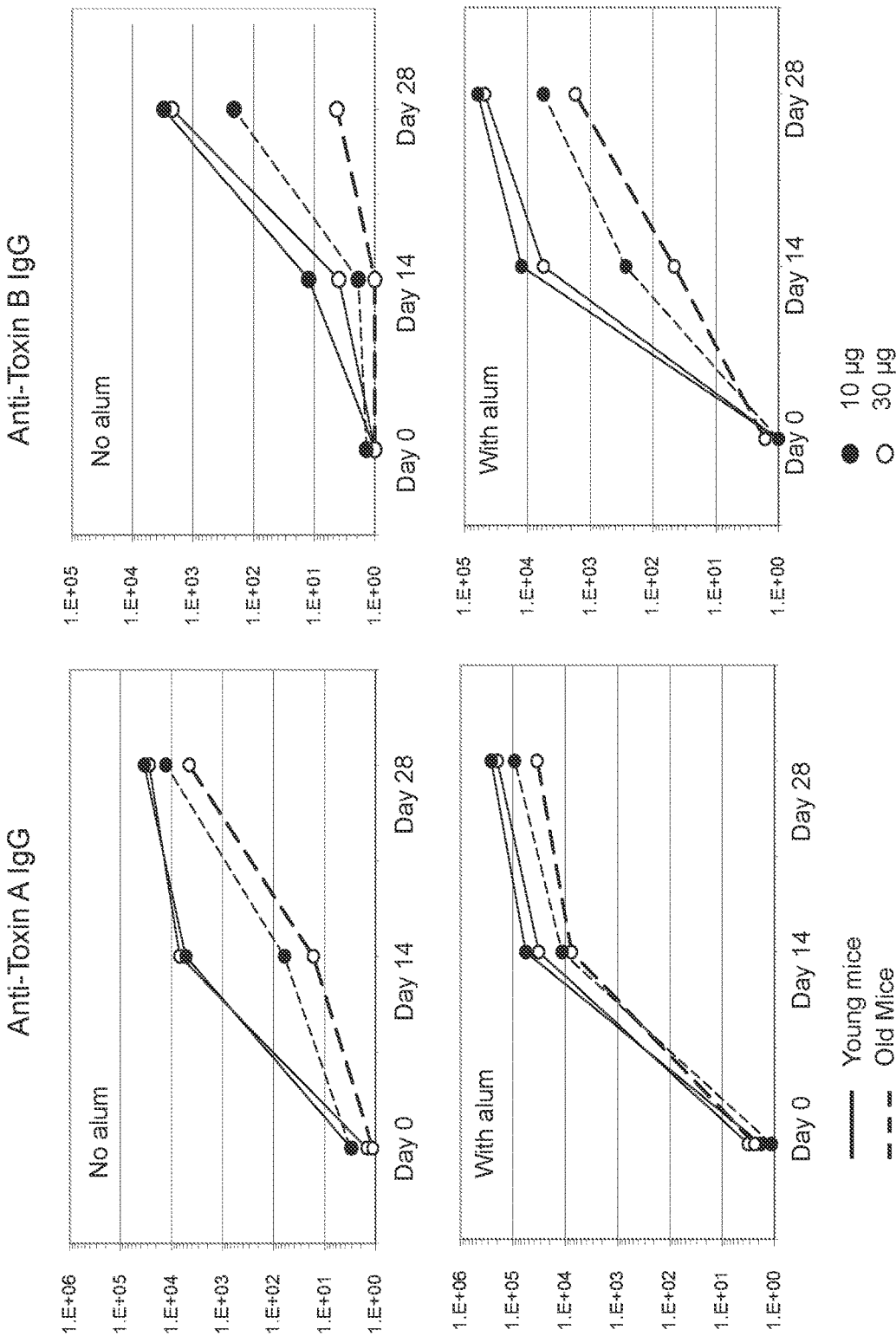

Figure 9

Comparison of the immunogenicity of C-TAB.G5.1 and C. difficile toxoid A and B

| Antigen | Dose, μg | Study Day | Anti-C-TAB No alum | Anti-C-TAB Alum | Anti-Toxin A* No alum | Anti-Toxin A* Alum | Anti-Toxin B* No alum | Anti-Toxin B* Alum |
|---|---|---|---|---|---|---|---|---|
| C-TAB | 10 | 14 | 4 | 30,271 | 1 | 21,238 | 1 | 10 |
|  |  | 28 | 987 | 574,975 | 1,249 | 1,134,277 | 2 | 15,081 |
|  | 30 | 14 | 1,274 | 64,228 | 1,391 | 31,391 | 2 | 3,836 |
|  |  | 28 | 23,301 | 898,654 | 44,069 | 1,055,061 | 379 | 53,063 |
| Toxoid | 10 | 14 | 6,802 | 48,496 | 9,275 | 49,081 | 19 | 2,659 |
|  |  | 28 | 20,140 | 978,277 | 72,954 | 1,128,721 | 380 | 40,295 |
|  | 30 | 14 | 17,810 | 86,595 | 22,319 | 64,214 | 70 | 5,833 |
|  |  | 28 | 65,536 | 731,416 | 348,019 | 1,292,560 | 4,967 | 43,098 |

\* Immunization with toxoid induces antibody to the N-terminal portion of the toxin molecule which is read out in the anti-toxin ELISA, while immunization with C-TAB induces antibody to the C-terminal portion of the toxin molecule.

Figure 10

TNA and protection data in comparative C-TAB.G5.1 and toxoid A/B study

| Antigen | Dose, µg | Alum | Toxin A challenge | | Toxin B challenge | |
|---|---|---|---|---|---|---|
| | | | TNA | Protection, % | TNA | Protection, % |
| PBS | - | - | 0 | 12.5 | 0 | 7.1 |
| C-TAB | 10 | - | 0 | 100 | 0 | 12.5 |
| | | + | 532 | 100 | 0 | 100 |
| | 30 | - | 98 | 100 | 0 | 25 |
| | | + | 735 | 100 | 487 | 100 |
| Toxoid | 10 | - | 362 | 100 | 0 | 0 |
| | | + | 769 | 100 | 261 | 100 |
| | 30 | - | 1291 | 100 | 0 | 37.5 |
| | | + | 1330 | 100 | 692 | 100 |

*Challenge dose:
toxin A: 28 ng/mouse
toxin B: 50 ng/mouse

Figure 11A

Anti-C-TAB IgG antibody response in hamsters

| Group | Vaccine | Pre* | Day 14 | Day 28 | Day 35 |
|---|---|---|---|---|---|
| 1 | PBS | 12 | 18 | 8 | 6 |
| 2 | 10 µg C-TAB.G5.1 | 44 | 320 | 16,105 | 15,100 |
| 3 | 10 µg C-TAB.G5.1 + alum | 30 | 25,958 | 227,632 | 257,474 |
| 4 | 30 µg G5.1 | 35 | 745 | 20,377 | 56,476 |
| 5 | 30 µg C-TAB.G5.1 + alum | 54 | 101,331 | 602,697 | 411,660 |
| 6 | 100 µg C-TAB.G5.1 | 19 | 2,508 | 31,978 | 42,131 |
| 7 | 100 µg C-TAB.G5.1 + alum | 9 | 156,909 | 1,021,300 | 789,069 |

* pre-bleed

Figure 11B

Anti-toxin A IgG antibody response in hamsters

| Group | Vaccine | Pre* | Day 14 | Day 28 | Day 35 |
|---|---|---|---|---|---|
| 1 | PBS | 5 | 15 | 6 | 3 |
| 2 | 10 µg C-TAB.G5.1 | 5 | 117 | 2,988 | 3,233 |
| 3 | 10 µg C-TAB.G5.1 + alum | 10 | 32,375 | 294,613 | 226,237 |
| 4 | 30 µg C-TAB.G5.1 | 6 | 486 | 6,872 | 16,336 |
| 5 | 30 µg C-TAB.G5.1 + alum | 4 | 89,773 | 517,244 | 276,755 |
| 6 | 100 µg C-TAB.G5.1 | 10 | 224 | 2,053 | 2,675 |
| 7 | 100 µg C-TAB.G5.1 + alum | 3 | 88,889 | 412,052 | 277,145 |

Figure 11C

Anti-toxin B IgG antibody response in hamsters

| Group | Vaccine | Pre* | Day 14 | Day 28 | Day 35 |
|---|---|---|---|---|---|
| 1 | PBS | 10 | 9 | 5 | 6 |
| 2 | 10 µg C-TAB.G5.1 | 25 | 271 | 9,627 | 16,104 |
| 3 | 10 µg C-TAB.G5.1 + alum | 6 | 5,046 | 69,084 | 75,377 |
| 4 | 30 µg C-TAB.G5.1 | 18 | 375 | 14,621 | 47,642 |
| 5 | 30 µg C-TAB.G5.1 + alum | 17 | 19,204 | 270,035 | 191,430 |
| 6 | 100 µg C-TAB.G5.1 | 8 | 263 | 5,029 | 32,928 |
| 7 | 100 µg C-TAB.G5.1 + alum | 22 | 48,726 | 1,912,238 | 757,756 |

* pre-bleed

Figure 13

TNA and protection against *in vivo* toxin challenge in hamster

| Vaccine | Toxin A challenge* | | Toxin B challenge* | |
|---|---|---|---|---|
| | TNA | Protection, % | TNA | Protection, % |
| PBS | 0 | 16.6 | 0 | 50 |
| 10 µg C-TAB.G5.1 | 267 | 100 | 0 | 83 |
| 30 µg C-TAB.G5.1 | 509 | 100 | 0 | 100 |
| 100 µg C-TAB.G5.1 | 179 | 83 | 0 | 50 |
| 10 µg C-TAB.G5.1 + alum | 5,025 | 100 | 2,061 | 100 |
| 30 µg C-TAB.G5.1 + alum | 2,824 | 100 | 4,598 | 100 |
| 100 µg C-TAB.G5.1 + alum | 3,262 | 100 | 16214 | 100 |

*Challenge dose:
toxin A: 75 ng/hamster
toxin B: 125 ng/hamster

Survival curves of *C. difficile* spore challenge study in hamsters

Figure 15

Anti-C-TAB antibody responses in monkeys

| Study Day | +Alum | | +Alum | | +Alum | |
|---|---|---|---|---|---|---|
| | Anti-C-TAB | | Anti-Toxin A | | Anti-Toxin B | |
| Pre-Bleed | 330 | 486 | 1,222 | 1,751 | 566 | 744 |
| Day 14 | 1,179 | 463,164 | 2,670 | 278,162 | 872 | 17,892 |
| Day 28 | 31,518 | 2,688,109 | 23,726 | 1,128,621 | 10,104 | 179,050 |
| Day 42 | 344,025 | 1,875,802 | 137,221 | 2,331,556 | 166,415 | 517,139 |

Figure 17

Immunogenicity of C-TAB.G5, C-TABNCTB and C-TADCTB in mice

Anti-C-TAB

| Dose | C-TAB.G5 | C-TANCTB | C-TADCTB |
|---|---|---|---|
| 0.3 µg | 2,397 | 2,196 | 2,062 |
| 1 µg | 5,030 | 15,933 | 2,396 |
| 3 µg | 37,542 | 20,699 | 27,717 |
| 10 µg | 58,132 | 87,783 | 92,496 |
| 30 µg | 95,179 | 278,713 | 278,534 |

Anti-Toxin A

| Dose | C-TAB.G5 | C-TANCTB | C-TADCTB |
|---|---|---|---|
| 0.3 µg | 2,127 | 1,235 | 1,464 |
| 1 µg | 3,960 | 10,644 | 1,257 |
| 3 µg | 28,701 | 13,178 | 13,590 |
| 10 µg | 40,992 | 55,013 | 32,597 |
| 30 µg | 64,063 | 152,425 | 163,932 |

Anti-Toxin B

| Dose | C-TAB.G5 | C-TANCTB | C-TADCTB |
|---|---|---|---|
| 0.3 µg | 31 | 23 | 266 |
| 1 µg | 122 | 175 | 269 |
| 3 µg | 2,170 | 1,284 | 4,241 |
| 10 µg | 1,409 | 5,004 | 17,926 |
| 30 µg | 4,616 | 8,327 | 138,098 |

Figure 18

Protection against challenge with toxin B* in mice

| Vaccine§ | C-TAB.G5 | | C-TABNCTB | | C-TADCTB | |
|---|---|---|---|---|---|---|
| | Survival/total | Protection, % | Survival/total | Protection, % | Survival/total | Protection, % |
| 0.33 µg | 2/6 | 33 | 1/6 | 17 | 4/6 | 67 |
| 1 µg | 4/6 | 67 | 2/6 | 33 | 2/6 | 33 |
| 3.3 µg | 2/6 | 33 | 3/6 | 50 | 4/6 | 67 |
| 10 µg | 3/6 | 50 | 2/6 | 33 | 5/6 | 83 |
| 33 µg | 2/5 | 33 | 2/6 | 33 | 6/6 | 100 |

*Challenge dose: 50 ng/mouse
§ Negative control - vaccination with PBS: 2/6, 33 % protection

Figure 19

Comparison of TNA and protective efficacy of C-TAB.G5.1 and C-TADCTB in hamsters

| Vaccine | Toxin A challenge* | | Toxin B challenge* | |
|---|---|---|---|---|
| | TNA | Protection, % | TNA | Protection, % |
| PBS | 0 | 16.6 | 0 | 50 |
| 10 μg C-TAB.G5.1 | 267 | 100 | 0 | 83 |
| 10 μg C-TAB.G5.1 + alum | 5,025 | 100 | 2,061 | 100 |
| 30 μg C-TAB.G5.1 | 509 | 100 | 0 | 100 |
| 30 μg C-TAB.G5.1 + alum | 2,824 | 100 | 4,598 | 100 |
| 100 μg C-TAB.G5.1 | 3,262 | 83 | 0 | 30 |
| 100 μg C-TAB.G5.1 + alum | 3,262 | 100 | 16,214 | 100 |
| 30 μg C-TADCTB | 159 | 100 | 2,886 | 100 |
| 30 μg C-TADCTB + alum | 1,101 | 100 | 5,614 | 100 |

*Challenge dose:
toxin A – 75 ng/hamster
toxin B – 125 ng/hamster

Figure 20A

TNA and protection against challenge with toxin A or B in mice immunized in different regimens

| C-TAB.5.1 immunization, days | Toxin A challenge§ | | Toxin B challenge§ | |
|---|---|---|---|---|
| | TNA* | Protection, % | TNA** | Protection, % |
| PBS | 0 | 0 | 0 | 0 |
| 0/3/14 | 51 | 25 | 0 | 12.5 |
| 0/3/14 + alum | 742 | 75 | 399 | 28.6 |
| 0/7/21 | 71 | 100 | 9 | 12.5 |
| 0/7/21 + alum | 1316 | 100 | 1318 | 37.5 |
| 0/14/28 | 107 | 100 | 24 | 37.5 |
| 0/14/28 + alum | 1798 | 100 | 1275 | 87.5 |

\* Geometric mean of one experiment, n=2
\*\* Geometric mean of three experiments, n=6

§ Challenge dose:
toxin A: 28 ng/mouse
toxin B: 50 ng/mouse

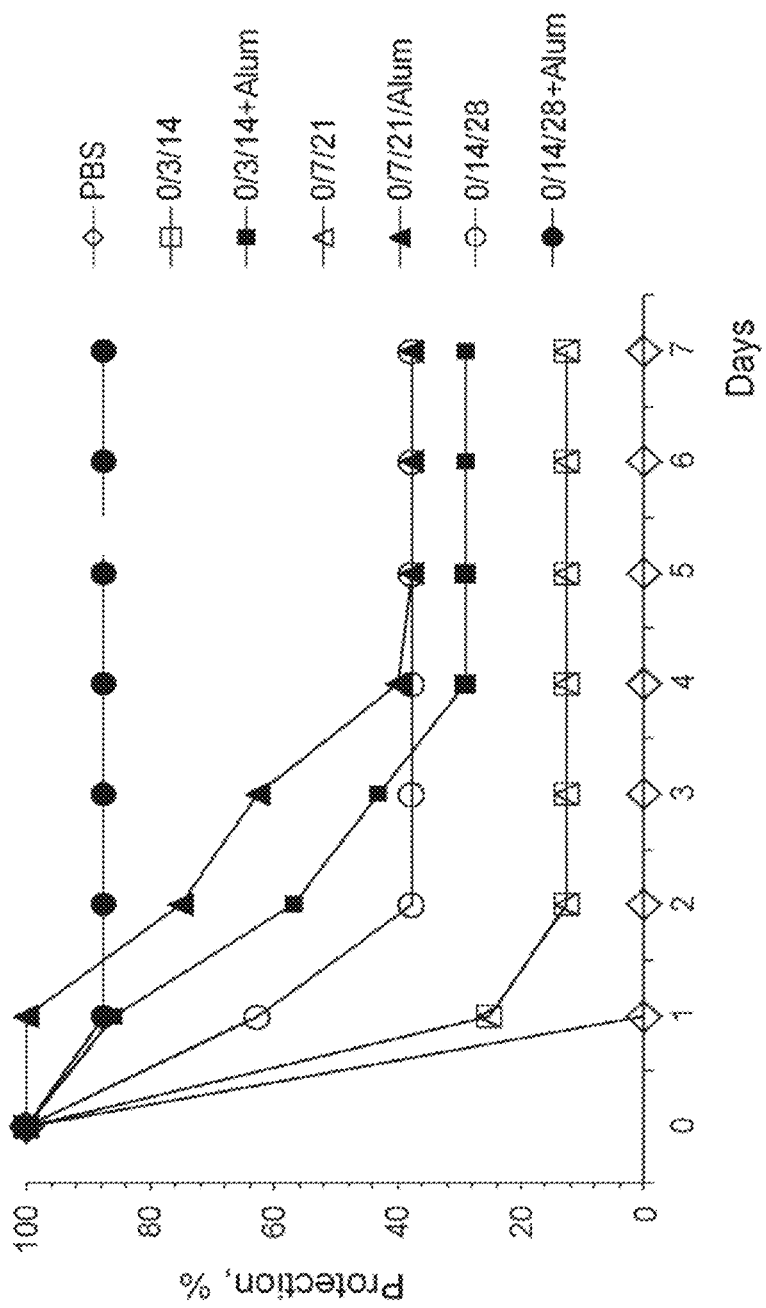

Figure 21

Protection against challenge with toxin A in mice received one dose of the vaccine

| Immunization group | Toxin A challenge | |
|---|---|---|
| | Survival/total | Protection, % |
| Naïve | 3/12 | 25 |
| Day 21 | 6/8 | 75 |
| Day 35 | 6/8 | 75 |
| Day 49 | 8/8 | 100 |

ISOLATED POLYPEPTIDE OF THE TOXIN A AND TOXIN B PROTEINS OF *C. DIFFICILE* AND USES THEREOF

RELATED APPLICATIONS

This application is a continuation of U.S. application Ser. No. 17/406,765, filed Aug. 19, 2021, which is continuation of U.S. application Ser. No. 17/061,891, filed Oct. 2, 2020, now issued as U.S. Pat. No. 11,357,844, which is a continuation of U.S. application Ser. No. 16/295,031, filed Mar. 7, 2019, now issued as U.S. Pat. No. 10,821,166, which is a continuation of U.S. application Ser. No. 15/421,808, filed Feb. 1, 2017 and now issued as U.S. Pat. No. 10,357,557, which is a division of U.S. application Ser. No. 14/342,565, filed Oct. 28, 2014 and now issued as U.S. Pat. No. 9,598,472, which is a national stage filing under 35 U.S.C. § 371 of international application PCT/EP2011/065304, filed Sep. 5, 2011, which was published under PCT Article 21(2) in English, the disclosure of each of which is incorporated by reference herein in its entirety.

REFERENCE TO AN ELECTRONIC SEQUENCE LISTING

The contents of the electronic sequence listing (I042270115US05-SEQ-JRV.xml; Size: 69,064 bytes; and Date of Creation: Sep. 8, 2022) is herein incorporated by reference in its entirety.

FIELD OF THE INVENTION

The present invention relates to an isolated polypeptide containing the receptor binding domains of the *Clostridium difficile* toxin A and toxin B and its use as a vaccine. This isolated polypeptide provides anti-toxin immunity to both toxins.

BACKGROUND OF THE INVENTION

*Clostridium difficile* is the leading cause of nosocomial antibiotic associated diarrhea and has become a major health problem in hospitals, nursing home and other care facilities. The cost to hospitals has been estimated to be 2 billion dollars in Europe and 3.2 billion dollars in the United States.

The causative agent is a gram positive, spore forming anaerobic bacterium, commonly found through out the environment but also present in the intestinal tract of 2-3% of the healthy adult population. *C. difficile* associated disease (CDAD) is induced by the disruption of the normal colonic flora, usually the result of the administration of antibiotics. Following exposure to *C. difficile* spores in the environment, the organism may colonize the intestinal mucosa where the production of disease causing toxins can result in CDAD. Disease may range from mild uncomplicated diarrhea to severe pseudomembranous colitis and toxic megacolon.

CDAD has become increasingly more problematic in health care settings. A recent study reported that 31% of hospital patients who receive antibiotics become colonized with *C. difficile* and 56% of those patients who become colonized go on to develop CDAD. Overall, *C. difficile* is responsible for 10-25% of all antibiotic associated diarrheas, 50-75% of antibiotic related colitis and 90-100% of antibiotic related pseudomembranous colitis. Treatment of CDAD involves discontinuation of the causal antibiotic followed by treatment with either metronidazole or vancomycin. Relapsing after antibiotic treatment is discontinued occurs in approximately 20% of patients, often the result of recolonization by *C. difficile.*

In 2003, a *C. difficile* outbreak in Quebec, Canada indicated the emergence of a more virulent strain of *C. difficile* known as North American Phenotype 1/027 (NAP1). NAP1 has been associated with greater virulence, poor outcomes and greater morbidity and mortality rates compared to previous strains. The emergence of this strain adds to the problems already encountered in trying to contain the incidence of CDAD.

Fidaxomicin (Dificid©) for prevention of recurrent disease is the first in a new class of narrow spectrum macrocyclic antibiotic drugs (Revill, P.; Serradell, N.; Bolos, J. (2006). "Tiacumicin B: macrolide antibiotic treatment of *C. difficile*-associated diarrhea". *Drugs of the Future* 31 (6): 494-497). It is a fermentation product obtained from the actinomycete *Dactylosporangium aurantiacum* subspecies *hamdenesis*. Fidaxomicin is non-systemic, meaning it is minimally absorbed into the bloodstream, it is bactericidal, and it has demonstrated selective eradication of pathogenic *Clostridium difficile* with minimal disruption to the multiple species of bacteria that make up the normal, healthy intestinal flora. The maintenance of normal physiological conditions in the colon can reduce the probability of *Clostridium difficile* infection recurrence (Johnson, Stuart (2009-06). "Recurrent *Clostridium difficile* infection: a review of risk factors, treatments, and outcomes". *Journal of Infection* 58 (6): 403-410). Although it is thought, that the introduction of this new class of antibiotic drug will improve the treatment of CDAD, there is still a medical need for a preventative drug, in particular for high risk patients such as the elderly and the immunocompromised patients.

CDAD is the result of the actions of two exotoxins produced by *C. difficile*, toxin A and toxin B (also referred to as CTA and CTB, respectively). Both toxins are high molecular weight (~300 kDa) secreted proteins that possess multiple functional domains (Voth D E and Ballard J D, Clinical Microbiology Reviews 18:247-263 (2005)). The N-terminal domain of both toxins contains ADP-glucosyltransferase activity that modifies Rho-like GTPases. This modification causes a loss of actin polymerization and cytoskeletal changes resulting in the disruption of the colonic epithelial tight junctions. This leads to excessive fluid exudation into the colon and a resulting diarrhea. The central domain contains a hydrophobic domain and is predicted to be involved in membrane transport. The C-terminal domain of both toxins contain multiple homologous regions called repeating units (RUs) that are involved in toxin binding to target cells (Ho et al, Howell 102:18373-18378 (2005)). The repeating units are classified as either short (21-30 amino acids) or long (~50 amino acids). Repeating units combine to form clusters, each usually containing one long and 3-5 short repeating units. The full length toxin A possesses 39 repeating units (ARUs) organized into 8 clusters (Dove et al. Infect. Immun. 58:480-488 (1990), while the full length toxin B contains 24 repeating units (BRUs) organized into 5 clusters (Barroso et al., Nucleic Acids Res. 18:4004 (1990); Eichel-Streiber et al., Gene 96:107-113 (1992)).

A number of studies, from both animal models and from the clinic, have indicated a role for anti-toxin antibody in the protection from *C. difficile* associated disease. Hamsters immunized with formalin inactivated toxin A and toxin B generated high levels of anti-toxin antibody and were protected from a lethal challenge of *C. difficile* bacteria (Giannasca P J and Warny M, Vaccine 22:848-856 (2004)). In addition, passive transfer of mouse anti-toxin antibody protected hamsters in a dose dependent manner. Kyne L et al. (The Lancet 357:189-193 (2001)) reported that the development of an anti-toxin A antibody response during an initial episode of CDAD correlated with protection against disease recurrence.

The determinants recognized by protective anti-toxin antibodies have been localized to the C-terminal domain containing the reating units which function as the receptor binding domain. Initially, Lyerly et al. (Current Microbiology 21:29-32 (1990)) revealed that the toxin A C-terminal domain containing 33 repeating units is capable of inducing the production of neutralizing anti-toxin antibody and may protect from *C. difficile* infection. In this study hamsters were injected subcutaneously with the purified recombinant polypeptide multiple times prior to challenge with the bacteria, however only partial protection was achieved. Another study (Ryan et al., Infect. Immun. 65:2941-49 (1997)) showed that the isolated polypeptide containing 720 amino acid residues from the C-terminus of CTA and the secretion signal of *E. coli* hemolysin A (expressed in *Vibrio cholerae*) induced protective systemic and mucosal immunity against a small dose of CTA in the rabbit CDAD model.

It was also reported that antibody response against the C-terminal domain of both toxin A and B was necessary to achieve full protection (Kink and Williams, Infect. Immun. 66:2018-25 (1998), U.S. Pat. No. 5,736,139 (1998)). This study revealed that the C-terminal domain of each toxin was most effective in generating toxin-neutralizing antibodies. It demonstrated the effectiveness of orally deliverd avian antibodies (antitoxin) raised against C-terminal domain of CTA and CTB in the hamster lethal model. The results also indicate that the antitoxin may be effective in the treatment and management of CDAD in humans. In another study, human anti-toxin A and B monoclonal antibodies were reported confer protection against *C. difficile* induced mortality in hamsters (Babcock et al., Infect. Immun. 74:6339-6347 (2006)). Protection was only observed by antibodies directed against the receptor binding domain of either toxin and enhanced protection was observed following treatment with both anti-toxin A and B antibodies.

On the other hand, Ward et al. (Infect. Immun. 67: 5124-32 (1999)) considered 14 repeating units from *C. difficile* toxin A (14 CTA) for the study of adjuvant activity. The repeating units were cloned and expressed either with the N-terminal polyhistidine tag (14 CTA-HIS) or fused to the nontoxic binding domain from tetanus toxin (14 CTA-TETC). Both fusion proteins administered intranasally generated anti-toxin A serum antibodies but no response at the mucosal surface in mice. Enhanced systemic and mucosal anti-toxin A responses were seen following co-administration with *E. coli* heat-labile toxin (LT) or its mutated form LTR72. Based on the data, Ward et al. suggested using non-toxic 14 CTA-TETC fusion as a mucosal adjuvant in human vaccine directed against clostridial pathogens.

Recent biochemical studies on the repeating unit domains of *C. difficile* toxins has looked at the minimal sequence requirements for forming stable tertiary structure (Demarest S J et al., J. Mol. Bio. 346:1197-1206 (2005)). An 11 repeating unit peptide derived from toxin A was found with a correct tertiary structure but 6 and 7 repeating units from toxins A and B did not. The correctly folded 11 repeating unit segment was found to maintain the receptor binding property. A second study examined the functional properties of toxin A fragments containing 6, 11 or 15 repeating units (Dingle T, Glycobiology 18:698-706 (2008)). Only the 11 and 15 repeat units were capable of competitively inhibiting the toxin neutralizing ability of anti-toxin A antibody. While all 3 fragments were found to have hemagglutinating activity, the longer fragments displayed higher hemagglutinating activity than the shorter ones. The data indicates that toxin receptor binding domain structure and immunogenicity are retained in domain fragments that contain greater than 11-14 repeats.

Thomas et al. (WO97/02836, U.S. Pat. No. 5,919,463 (1999)) also disclosed *C. difficile* toxin A, toxin B and certain fragments thereof (e.g., C-terminal domain containing some or all of the repeating units) as mucosal adjuvants. They showed that intranasal administration of CTA or CTB significantly enhanced mucosal immune response to a heterologous antigen such as *Helicobacter pylori* urease, ovalbumin, or keyhole limpet hemocyanin (KLH) in multiple mouse compartments and was associated with protection against the challenge with *Helicobacter*. Additionally, the adjuvant activity of a toxin A fusion protein was evaluated: 794 C-terminal amino acid residues of CTA comprising ARUs (toxin A repeating units) were fused to glutatione-S-transferase (GST) and resulted polypeptide GST-ARU was expressed in *E. coli*. This study demonstrated significant enhancement of immune response by GST-ARU to co-administered antigens in serum and mucosal secretions.

All of these studies suggest potential use of a non-toxic, recombinant protein comprising either *C. difficile* toxin A, or toxin B, or fragments thereof, or their combinations for producing an active vaccine against CDAD. Currently, no vaccine against *C. difficile* is commercially available, although a candidate vaccine consisting of formalin-detoxified entire toxins A and B has been evaluated in human phase I and IIa studies. It is reported that parenteral immunization with this vaccine induces anti-toxin IgG and toxin-neutralizing antibody responses (Kotloff K L et al., Infect. Immun. 69:988-995 (2001); Aboudola S et al., Infect. Immun. 71:1608-1610 (2003)).

The literature further indicates that the construction of a recombinant fusion protein containing both toxin A and B receptor binding domains of *C. difficile*, either in their entirety or fragments thereof, would be an efficient and commercially viable approach for vaccine development. Such an approach has been attempted as a two part fusion protein of a 700 base pair fragment of toxin A and a 1300 base pair fragment of toxin B by Varfolomeeva et al. (Mol. Genetics, Microb. and Virol. 3:6-10 (2003)). This approach has also been described by Belyi and Varfolomeeva (FEMS Letters 225:325-9 (2003)) demonstrating construction of the recombinant fusion protein consisting of three parts: two C-terminal domains composed of repeating units of *C. difficile* toxin A and toxin B followed by the fragment of *Clostridium perfringens* enterotoxin Cpe. The fusion protein was expressed in *E. coli* but the product was accumulated in inclusion bodies and was not stable. Moreover, the yield of pure product achieved in this study (50 μg per 100 ml culture) was considerably low.

Wilkins et al. (WO 00/61762, U.S. Pat. No. 6,733,760 (2004)) also described the use of recombinant *C. difficile* toxin A and B repeating units (recombinant ARU and recombinant BRU) and their polysaccharide conjugates for the preparation of a vaccine against CDAD. The resulting recombinant ARU protein comprised 867 amino acid residues while the recombinant BRU protein contains 622 amino acids in length. Unlike the previously mentioned studies, this work demonstrated high-level expression of recombinant ARU and BRU soluble proteins in *E. coli*. Mice vaccinated with recombinant ARU and with polysaccharide-conjugated recombinant ARU both mounted a high level of neutralizing anti-toxin A antibodies and were highly protected against lethal challenge with *C. difficile* toxin A. In addition, Wilkins et al. suggested using a recombinant fusion protein consisting of both ARU and BRU for the preparation of a vaccine.

There is an interest in developing a vaccine against CDAD. A recombinant fusion protein consisting of ARU and BRU may be potentially useful as a vaccine.

SUMMARY OF THE INVENTION

The present invention provides new tools and methods for the design, production and use of the toxin A and toxin B from *C. difficile*. The present invention provides an isolated polypeptide C-TAB comprising SEQ ID NO: 2 (C-TAB.G5) or a derivative thereof, SEQ ID NO: 4 (C-TAB.G5.1). The C-TAB.G5 or C-TAB.G5.1 comprises 19 repeating units of the C-terminal domain of toxin A fused to 23 repeating units of the C-terminal domain of toxin B. The present invention also includes compositions and formulations comprising the C-TAB.G5 or C-TAB.G5.1 isolated polypeptide. The compositions or formulations may contain the isolated polypeptide, an additional antigen, an adjuvant, and/or an excipient. Alternatively, the compositions or formulations may consist essentially of the isolated polypeptide without an adjuvant or other active ingredients (but optionally comprising an excipient such as a carrier, buffer and/or stabilizer). Moreover, the compositions or formulations of the invention may be administered concomitantly with other drugs such as an antibiotic in particular e.g. in subjects with recurrent CDAD or in subjects requiring frequent and/or prolonged antibiotic use.

The present invention also provides a vaccine comprising the isolated polypeptide of the present invention. The vaccine may further comprise an adjuvant, such as such as alum, an adjuvant derived from an ADP-ribosylating exotoxin or others. The vaccine may be administered in a one dose regimen, two dose regimen (administered e.g. within 3 to 20 days, e.g. after 10 to 15 days of the first dose), three dose regimen (administered e.g. after about 7 days and about 21 days of the first dose), or more than three dose regimen, preferably a two or three dose regimen, wherein the dose comprises a 20 µg to 200 µg amount of the polypeptide of the invention.

The present invention provides a method of preventing, treating, or alleviating one or more symptoms of a disease, such as CDAD by administering the isolated polypeptide of the invention to a subject in need thereof. The C-TAB.G5 or C-TAB.G5.1 isolated polypeptide may be administered to the subject intramuscularly or by other routes of delivery.

In one embodiment, the present invention provides a method of preventing a disease, such as CDAD by administering the isolated polypeptide of the inventions or a composition comprising said polypeptide to a subject at risk of CDAD, such as e.g. a subject with the following profile: i) a subject with a weaker immune system such as e.g. an elderly subject (e.g. a subject above 65 years of age) or a subject below 2 years of age; ii) an immunocompromised subject such as e.g. a subject with AIDS; iii) a subject taking or planning to take immunosuppressing drugs; iv) a subject with planned hospitalization or a subject that is in hospital; v) a subject in or expected to go to an intensive care unit (ICU); vi) a subject that is undergoing or is planning to undergo gastrointestinal surgery; vii) a subject that is in or planning to go to a long-term care such as a nursing home; viii) a subject with co-morbidities requiring frequent and/or prolonged antibiotic use; ix) a subject that is a subject with two or more of the above mentioned profiles, such as e.g. an elderly subject that is planning to undergo a gastrointestinal surgery; x) a subject with inflammatory bowel disease; and/or xi) a subject with recurrent CDAD such as e.g. a subject having experienced one or more episodes of CDAD.

In one embodiment, the invention provides methods of producing the C-TAB.G5 or C-TAB.G5.1 isolated polypeptide. The C-TAB.G5 or C-TAB.G5.1 isolated polypeptide may be produced from a nucleic acid encoding the C-TAB.G5 or C-TAB.G5.1 isolated polypeptide using a bacterial expression system, such as an *E. coli* expression system.

In one embodiment the present invention provides the C-TAB.G5 or C-TAB.G5.1 isolated polypeptide wherein the 19 repeating units of toxin A are connected to the 23 repeating units of toxin B via a linker consisting of at least 4, 5, 6, 7, 8, 9, or 10 amino acid residues. By way of example, the linker of the present invention may comprise the sequence RSMH (Arg-Ser-Met-His) (amino acids 439-442 of SEQ ID NO: 2 or SEQ ID NO: 4).

In another embodiment the invention provides a variant of the isolated polypeptide that comprises at least one mutation (e.g., insertion, substitution or deletion), for example in the ARU and/or BRU. The sequence of the variant may have 85%, 86%, 87%, 88%, 89%, 90%, 91%, 92%, 93%, 94%, 95%, 96%, 97%, 98%, or 99% identity to SEQ ID NO: 2.

This invention also provides methods for producing the C-TAB.G5 or C-TAB.G5.1 isolated polypeptide or variants thereof through recombinant DNA engineering, bacterial fermentation and protein purification. In one embodiment, the present invention provides methods for constructing the nucleic acid encoding the C-TAB.G5 or C-TAB.G5.1 isolated polypeptide. In another embodiment, the invention provides methods of producing the C-TAB.G5 or C-TAB.G5.1 isolated polypeptide using a bacterial expression system, such as an *E. coli* expression system.

The invention further provides methods for preventing and treating CDAD in subjects in need thereof, such as humans. In this method the C-TAB.G5 or C-TAB.G5.1 is administered to a subject either alone or co-administered with one or more adjuvants such as alum or others. Subjects may be healthy individuals who are at risk for exposure to *C. difficile*, human subjects who have been treated and recovered from *C. difficile* infection and who are at risk for re-infection by *C. difficile*, or human subjects who are currently infected with *C. difficile* and whose condition may be improved by induction of *C. difficile* toxin-neutralizing antibody.

The present invention provides an immunogenic composition comprising C-TAB.G5 or C-TAB.G5.1. The immunogenic composition may further include an adjuvant to enhance an antigen-specific immune response and/or a pharmaceutically acceptable carrier and/or other components in a formulation suitable for application to a subject in need thereof. The immunogenic composition may be delivered by intramuscular (IM) delivery, intradermal (ID) delivery, subcutaneous (SC) delivery, intraperitoneal (IP) delivery, oral delivery, nasal delivery, buccal delivery, or rectal delivery.

In another embodiment of the invention the immunogenic composition elicits antibodies that bind native *C. difficile* toxins and neutralize their cytotoxic activity thus providing long-term, active protection, and/or treatment against *C. difficile* associated disease (CDAD).

Accordingly, the invention provides immunogenic compositions useful for the prevention or treatment of *C. difficile* associated disease in subjects in need thereof.

In another embodiment, the invention provides nucleic acids and fragments or variants thereof that encode C-TAB.G5 or C-TAB.G5.1. The invention also provides expression vectors comprising the nucleic acid encoding C-TAB.G5 or C-TAB.G5.1.

Another embodiment of the present invention provides antibodies and fragments thereof, such as neutralizing, humanized, monoclonal, chimeric and polyclonal antibodies, specific for C-TAB.G5 or C-TAB.G5.1. The antibodies or fragments thereof may recognize toxin A and/or toxin B.

Another embodiment provides a vaccine comprising a polypeptide having the amino acid sequence of SEQ ID NO: 2 or SEQ ID NO: 4.

Another embodiment of this invention provides diagnostic kits comprising the nucleic acids, polypeptides and/or antibodies of the invention.

Other embodiments and advantages of the invention are set forth in part in the description, which follows, and in part, may be obvious from this description, or may be learned from the practice of the invention.

BRIEF DESCRIPTION OF THE DRAWINGS

FIG. 1A shows the nucleic acid encoding the C-TAB.G5 isolated polypeptide (SEQ ID NO: 1). FIG. 1B shows the amino acid sequence of the C-TAB.G5 isolated polypeptide (SEQ ID NO: 2). The amino acid linker between the toxin A domain and the toxin B domain is underlined.

FIG. 2A shows the nucleic acid encoding the C-TAB.G5.1 isolated polypeptide (SEQ ID NO: 3). FIG. 2B shows the amino acid sequence of the C-TAB.G5.1 isolated polypeptide (SEQ ID NO: 4). The amino acid linker between the toxin A domain and the toxin B domain is underlined.

FIG. 3 shows the enhancement of antibody production in C-TAB.G5 vaccinated mice by increasing doses of C-TAB.G5 and co-delivery with alum adjuvant. Mice received two vaccinations by IM injection. IgG titers for anti-C-TAB, anti-toxin A and anti-toxin B antibodies were evaluated by ELISA two weeks after the first and second injection.

FIG. 5 shows antibody titers over one log dose range in mice immunized with C-TAB.G5 in the presence or absence of alum. IgG titers were evaluated by ELISA two weeks after the second immunization. The data demonstrate that alum significantly augments antibody production in vaccinated mice.

FIG. 6 shows protective effect in mice vaccinated with C-TAB.G5 (with and without alum) and then exposed to a lethal dose of toxin A or toxin B. Mice receiving two vaccinations (IM) in two week interval were challenged (IP) three weeks later. Toxin A and toxin B neutralizing antibodies (TNA) were assessed two weeks after the second injection, and the percent of animals survived the lethal challenge was determined. Increased doses of C-TAB.G5 conferred greater TNA production, as well as increased protection to the lethal challenge. The presence of alum further increased TNA production, as well as conferring higher survival at lower doses.

FIG. 7 shows a comparison of antibody response and protection efficacy of C-TAB.G5 in vaccinated young (6-7 weeks) and old (18 months) mice. Mice receiving two vaccinations (IM) in two week interval were challenged (IP) three weeks later. ELISA IgG titers for anti-C-TAB, anti-toxin A and anti-toxin B antibodies, TNA production as well as overall survival were assessed. Young mice demonstrated higher antibody response even without alum, and both groups showed improved survival when vaccinated in the presence of alum.

FIG. 8 shows a comparison of the kinetics of anti-C-TAB IgG antibody development in vaccinated young and old mice. Young mice demonstrated greater rates and earlier IgG production, and both groups demonstrated improved responses when vaccinated in the presence of alum.

FIG. 9 shows a comparison in anti-C-TAB, anti-toxin A and anti-toxin B antibody production in mice immunized with either C-TAB.G5.1 or toxoid A and B mixture (1:1). Mice received two vaccinations IM injection. IgG titers for anti-C-TAB, anti-toxin A and anti-toxin B antibodies were evaluated by ELISA two weeks after the second injection. Immunization with toxoid induces antibody to the N-terminal portion of the toxin molecule while immunization with C-TAB induces antibody to the C-terminal portion of the toxin molecule.

FIG. 10 shows a comparison in TNA production and protection against challenge with toxin A or B in mice immunized with either C-TAB.G5.1 or toxoid A and B mixture. Mice receiving two vaccinations (IM) in two week interval were challenged (IP) three weeks later with a lethal dose of toxin A or toxin B.

FIGS. 11A-11C show anti-C-TAB (FIG. 11A), anti-toxin A (FIG. 11B), and anti-toxin B (FIG. 11C) IgG production in hamsters immunized with C-TAB.G5.1 with and without alum. Hamsters received three vaccinations by IM injection on day 0 and day 14. IgG titers for anti-C-TAB, anti-toxin A and anti-toxin B antibodies were evaluated by ELISA on days 14, 28 and 35.

FIG. 13 shows a comparison in TNA and protection in hamsters immunized with C-TAB.G5.1 with or without alum. Two weeks after the third vaccination hamsters received a lethal dose of toxin A or toxin B by IP injection.

FIG. 15 shows anti-C-TAB, anti-toxin A, and anti-toxin B antibody production in cyanomologous monkeys immunized with C-TAB.G5.1 in the presence or absence of alum. Two groups of monkeys (three per group, 4-6 years) received 200 μg of C-TAB.G5.1 with or without 250 μg alum. Blood samples were taken on study days 0, 14, 28 and 42. ELISA method was used to assess anti-C-TAB, anti-toxin A and anti-toxin B IgG titers.

FIG. 17 shows a comparison of immunogenicity of C-TAB.G5, C-TABNCTB and C-TADCTB in mice. Mice received two vaccinations of each recombinant protein in two week interval by IM injection. All immunizations were done in the absence of alum adjuvant. IgG titers for anti-C-TAB, anti-toxin A and anti-toxin B antibodies were evaluated by ELISA two weeks after the second injection. All three fusion proteins demonstrate high immunogenicity.

FIG. 18 shows protection against challenge with native toxin B in mice. Mice were immunized as indicated for FIG. 17 and three weeks later they were challenged by IP injection with a lethal dose of native toxin B.

FIG. 19 shows a comparison in TNA and protection in hamsters vaccinated with either C-TAB.G5.1 or C-TADCTB in the absence or presence of alum. Two weeks after the third vaccination hamsters received a lethal dose of toxin A or toxin B by IP injection.

FIGS. 20A and 20B show TNA production and protection against challenge with toxin A or toxin B in mice immunized with C-TAB.G5.1 in different regimens. Comparison in TNA production and protection between groups of mice vaccinated by IM injection three times on day 0, 3 and 14, or on day 0, 7 and 21, or on day 0, 14 and 28. Three weeks after the last injection mice were challenged with a lethal dose of toxin A or toxin B (FIG. 20A is in table form and FIG. 20B is in graph form).

FIG. 21 shows protection (survival) against challenge with *C. difficile* toxin A (55 ng/mouse) in mice immunized with a single shot of 10 µg C-TAB.G5.1 and 12.5 µg alum (in 100 µl). Said challenge was done 21 days, 35 days or 49 days after immunization.

DETAILED DESCRIPTION

General Description

Figure 4:
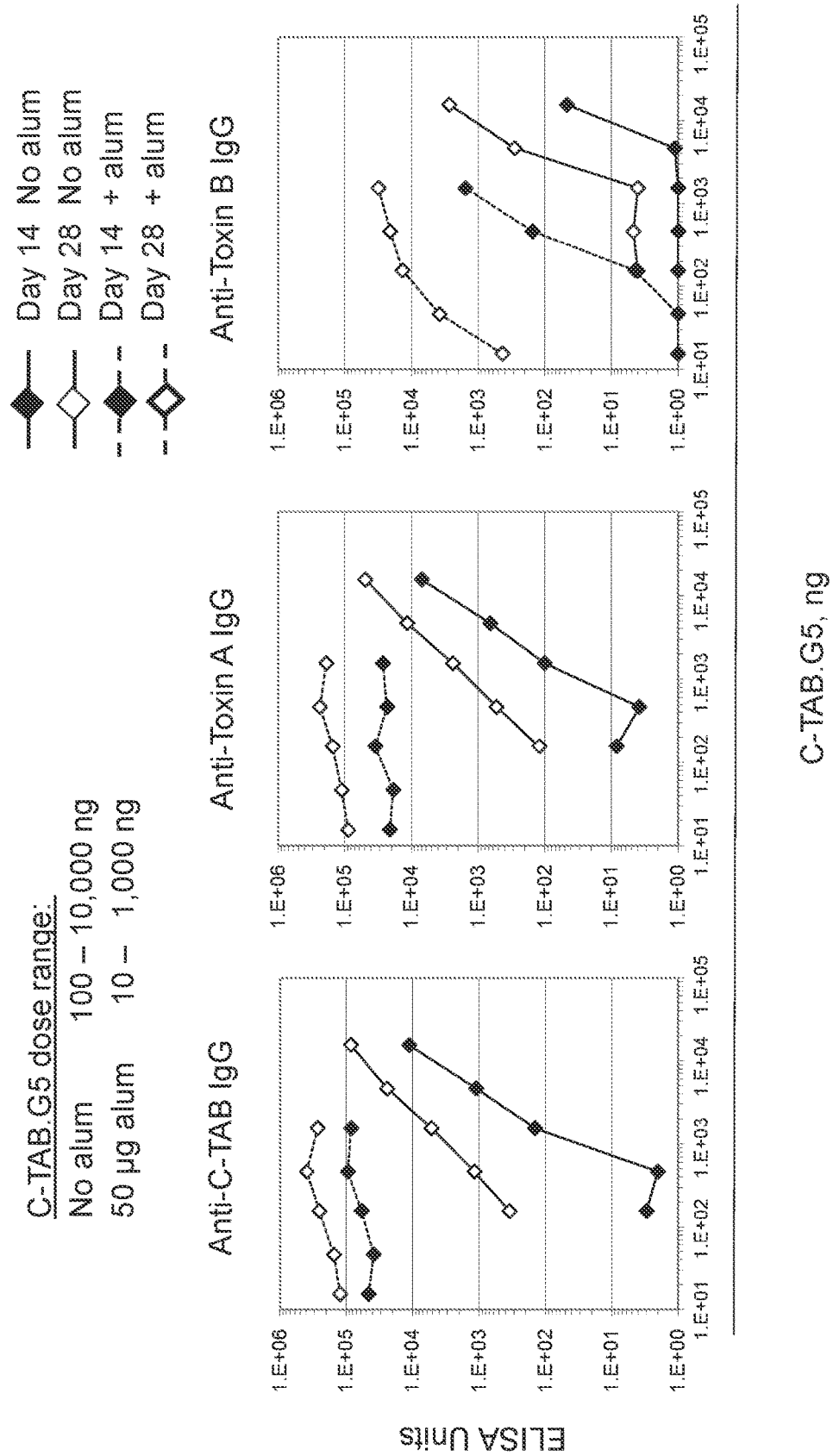
FIG. 4 shows a graphical representation of anti-C-TAB, anti-toxin A, and anti-toxin B IgG induction in mice receiving increasing doses of C-TAB.G5 with and without alum by two IM injection.

The present invention provides an immunogenic composition for inducing protective and/or therapeutic immune responses to *C. difficile* toxins A and B comprising use of a isolated polypeptide C-TAB.G5 (SEQ ID NO: 2) or a derivative thereof, C-TAB.G5.1 (SEQ ID NO: 4). that comprises 19 repeating units (RU) of toxin A and 23 repeating units (RU) of toxin B or peptide fragments, or variants thereof.

The present invention also provides methods of producing the C-TAB.G5 or C-TAB.G5.1 isolated polypeptide and the method of preparing the composition (e.g. a vaccine) useful for prevention and/or treatment of CDAD in mammals. The following description provides more details and examples for the construction, expression, and purification of the recombinant isolated polypeptides, their use as antigens for inducing a specific-immune response as well as evaluating protection in subjects. The subjects may be animals or humans.

The C-TAB.G5 or C-TAB.G5.1 isolated polypeptides for use in the methods and compositions of the present invention may be prepared using any of several standard methods. For example, the C-TAB.G5 or C-TAB.G5.1 may be produced using standard recombinant DNA techniques, wherein a suitable host cell is transformed with an appropriate expression vector containing a part of a toxin-encoding nucleic acid fragment (see e.g. Dove et al., Infect. Immun. 58:480-8 (1990), and Barroso et al., Nucleic Acids Research 18:4004 (1990). Any of a wide variety of expression systems may be used to produce the recombinant polypeptides. C-TAB.G5 or C-TAB.G5.1 may be produced in a prokaryotic host (e.g. a bacterium, such as *E. coli* or *Bacillus*) or in an eukaryotic host (e.g. yeast cells, mammalian cells (e.g. COS1, NIH3T3, or JEG3 cells), or insect cells (e.g. *Spodoptera frugiperda* (SF9) cells)). Such cells are available, for example, from the American Type Culture Collection (ATCC). The method of transformation and transfection and the choice of expression vector will depend on the host system selected. Transformation and transfection methods are described by, e.g., Ausubel et al., ISBN: 047132938X C-TAB.G5 or C-TAB.G5.1, particularly short fragments, may also be produced by chemical synthesis, e.g., by the methods described in Solid Phase Peptide Synthesis, 1984, 2nd ed., Stewart and Young, Eds., Pierce Chemical Co., Rockford, Ill., or by standard in vitro translation methods.

In addition to the C-TAB.G5 or C-TAB.G5.1 sequences, the present invention provides variants thereof that are functionally active and immunogenic. The variants may have the same level of immunogenicity as C-TAB.G5 or C-TAB.G5.1. The variant may have amino acid substitutions, deletions, or insertions as compared to SEQ ID NO: 2 or SEQ ID NO: 4. Genes encoding C-TAB.G5 or C-TAB.G5.1 or variants thereof may be made using standard methods (see below; also see, e.g. Ausubel et al., supra).

In addition to the C-TAB.G5 or C-TAB.G5.1 sequences, the present invention provides further derivatives of C-TAB.G5 that comprise additional repeats. By way of example, a fusion protein, C-TABNCTB (SEQ ID NO: 18, encoded by SEQ ID NO: 17), comprises, like C-TAB.G5, 19 repeating units of CTA (amino acids 2272-2710), 23 repeating units of CTB (amino acids 1850-2366), and a further additional 10 repeats of CTB (amino acids 1834-2057) fused to the C-terminus of CTB. A further variant, C-TADCTB fusion protein (SEQ ID NO: 20, encoded by SEQ ID NO:19) comprises C-TAB.G5 (19 repeats of CTA and 23 repeats of CTB) plus an additional 24 repeating units of CTB (amino acids 1834-2366) fused to the C-terminus of C-TAB.G5. A variant may also comprise additional copies of C-TAB.G5 or portions thereof. For example, C-TADCTB comprises a double portion of the repeating units of CTB present in C-TAB.G5.

The present invention provides methods for high level expression C-TAB.G5 or C-TAB.G5.1 in bacterial system such as *E. coli* comprising introducing a nucleic acid encoding C-TAB.G5 or C-TAB.G5.1 into a bacterial host cell and expressing C-TAB.G5 or C-TAB.G5.1.

In addition, the C-TAB.G5 or C-TAB.G5.1 isolated polypeptide of the present invention may be covalently coupled or cross-linked to adjuvants (see, e.g., Cryz et al., Vaccine 13:67-71(1994); Liang et al., J. Immunology 141:1495-501 (1988) and Czerkinsky et al., Infect. Immun. 57:1072-77 (1989)).

The present invention provides a vaccine comprising the C-TAB.G5 or C-TAB.G5.1 isolated polypeptide that can protect and provide therapy against CDAD. The vaccine of the present invention comprises a novel antigen which can be delivered intramuscularly (IM), intradermally (ID), subcutaneously (SC), orally, nasally, buccally, or rectally routes. The vaccine may provide immune protection or induce antibodies for passive immunization.

The C-TAB.G5 or C-TAB.G5.1 isolated polypeptide of the present invention provides a vaccine to immunize against CDAD. The C-TAB.G5 or C-TAB.G5.1 isolated polypeptide of the present invention or variants thereof, is a combined vaccine candidate targeted to broaden the protective coverage against *C. difficile* associated diseases, such as CDAD, to a level not known or published hitherto. This concept of a single vaccine offering protection or a diminished severity of *C. difficile* associated diseases represents a unique step forward in managing public health at a global level and especially reducing the severity of epidemics (e.g. nursing homes, cruise ships).

As used herein, "toxin A protein" or "toxin B protein" refers to toxic proteins of *C. difficile* that are primarily responsible for CDAD. Toxin A and toxin B comprise multiple repeating units responsible for immunogenicity in the C-terminal binding domains.

As used herein "wild-type" or "native" refers to a full length protein comprised of a nucleic acid or amino acid sequence as would be found endogenously in a host cell.

As used herein, the terms "*Clostridium difficile* associated disease", "*Clostridium difficile* related disease", "*Clostridium difficile*-associated disease", "*Clostridium difficile* toxin-mediated disease", "*Clostridium difficile* infection", and "CDAD" refer to diseases caused, directly or indirectly, by infection with *Clostridium difficile*.

"Antigen" refers to a substance that induces a specific immune response when presented to immune cells of an organism. For example, an antigen may be a nucleic acid, a protein, a polypeptide, a peptide, a glycoprotein, a carbohydrate, a lipid, a glycolipid, a lipoprotein, a fusion protein, a phospholipid, or a conjugate of a combination thereof. An antigen may comprise a single immunogenic epitope, or a multiplicity of immunogenic epitopes recognized by a B-cell receptor (i.e., antibody on the membrane of the B cell) or a T-cell receptor. Antigen may be provided as a virus-like-particle (VLP) or a whole microbe or microorganism such as, for example, a bacterium or virion. The antigen may be an inactivated or attenuated live virus. The antigen may be obtained from an extract or lysate, either from whole cells or membrane alone; or antigen may be chemically synthesized or produced by recombinant means. An antigen may be administered by itself or with an adjuvant. A single antigen molecule may have both antigen and adjuvant properties.

By "adjuvant" is meant any substance that is used to specifically or non-specifically potentiate an antigen-specific immune response, perhaps through activation of antigen presenting cells. Examples of adjuvants include an oil emulsion (e.g., complete or incomplete Freund's adjuvant), Montanide incomplete Seppic adjuvant such as ISA, oil in water emulsion adjuvants such as the Ribi adjuvant system, syntax adjuvant formulation containing muramyl dipeptide, aluminum salt adjuvant (ALUM), polycationic polymer, especially polycationic peptide, especially polyarginine or a peptide containing at least two LysLeuLys motifs, especially KLKLLLLLKLK (SEQ ID NO: 21), immunostimulatory oligodeoxynucleotide (ODN) containing non-methylated cytosine-guanine dinucleotides (CpG) in a defined base context (e.g., as described in WO 96/02555) or ODNs based on inosine and cytidine (e.g., as described in WO 01/93903), or deoxynucleic acid containing deoxy-inosine and/or deoxyuridine residues (as described in WO 01/93905 and WO 02/095027), especially Oligo(dIdC)$_{13}$ (as described in WO 01/93903 and WO 01/93905), neuroactive compound, especially human growth hormone (described in WO 01/24822), or combinations thereof, a chemokine (e.g., defensins 1 or 2, RANTES, MIP1-α, MIP-2, interleukin-8, or a cytokine (e.g., interleukin-1β, -2, -6, -10 or -12; interferon-γ; tumor necrosis factor-α; or granulocyte-monocyte-colony stimulating factor) (reviewed in Nohria and Rubin, 1994), a muramyl dipeptide variant (e.g., murabutide, threonyl-MDP or muramyl tripeptide), synthetic variants of MDP, a heat shock protein or a variant, a variant of *Leishmania major* LeIF (Skeiky et al., 1995, J. Exp. Med. 181: 1527-1537), non-toxic variants of bacterial ADP-ribosylating exotoxins (bAREs) including variants at the trypsin cleavage site (Dickenson and Clements, (1995) Infection and Immunity 63 (5): 1617-1623) and/or affecting ADP-ribosylation (Douce et al., 1997) or chemically detoxified bAREs (toxoids), QS21, Quill A, N-acetylmuramyl-L-alanyl-D-isoglutamyl-L-alanine-2-[1,2-dipalmitoyl-s-glycero-3-(hydroxyphosphoryloxy)]ethylamide (MTP-PE) and compositions containing a metabolizable oil and an emulsifying agent. An adjuvant may be administered with an antigen or may be administered by itself, either by the same route as that of the antigen or by a different route than that of the antigen. A single adjuvant molecule may have both adjuvant and antigen properties.

By "effective amount" is meant an amount of a therapeutic agent sufficient to induce or enhance an antigen-specific immune response, for an antigen, or treat or diagnose a condition, for a drug. Such induction of an immune response may provide a treatment such as, for example, immunoprotection, desensitization, immunosuppression, modulation of autoimmune disease, potentiation of cancer immunosurveillance, or therapeutic vaccination against an established infectious disease. Treatment includes curing, amelioration, or prevention.

By "nucleic acid" is meant either a single deoxyribonucleic acid base or a ribonucleic acid or a sequence thereof joined by phosphodiester bonds.

By "therapeutic agent" is meant any molecule capable of use in treating a disease, alleviating the symptoms of a disease, preventing a disease, or diagnosing a disease. For example, a therapeutic agent may be an antigen or a drug.

By "subject" is meant an animal. The subject may be any animal, including any vertebrate. The subject may be a domestic livestock, laboratory animal (including but not limited to, rodents such as a rat, hamster, gerbil, or mouse) or pet animal. In one embodiment, the animal may be a mammal. Examples of mammals include humans, primates, marsupials, canines, monkeys, rodents, felines, apes, whales, dolphins, cows, pigs, and horses. The subject may be in need of treatment of a disease or may be in need of a prophylactic treatment.

As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term "antibody" means not only full-length antibody molecules but also fragments of antibody molecules retaining antigen binding ability. Such fragments are also well known in the art and are regularly employed both in vitro and in vivo. In particular, as used herein, the term "antibody" means not only full-length immunoglobulin molecules but also antigen binding active fragments such as the well-known active fragments F(ab')2, Fab, Fv, and Fd.

As used herein, the term "variants" may include proteins and/or polypeptides and/or peptides that are different from a wild-type polypeptide, wherein one or more residues have been conservatively substituted with a functionally similar residue, and further which displays substantially identical functional properties of the wild-type polypeptide. Examples of conservative substitutions include substitution of one non-polar (hydrophobic) residue for another (e.g. isoleucine, valine, leucine or methionine) for another, substitution of one polar (hydrophilic) residue for another (e.g. between arginine and lysine, between glutamine and asparagine, between glycine and serine), substitution of one basic residue for another (e.g. lysine, arginine or histidine), or substitution of one acidic residue for another (e.g. aspartic acid or glutamic acid). A variant may include any polypeptide having a tertiary structure substantially identical to a polypeptide of the invention which also displays the functional properties of the polypeptides as described herein. A variant may be a mutant of a wild-type polypeptide.

As used herein "treatment" may include any type of intervention used in an attempt to alter the natural course of the individual or cell. Treatment may include, but is not limited to, administration of e.g., a pharmaceutical composition, alone or in combination with other treatment modalities generally known in the art. The "treatment" may be performed prophylactically, or subsequent to the initiation of a pathologic event.

As used herein, "pharmaceutically acceptable carrier" may include any material which, when combined with an active ingredient, allows the ingredient to retain biological activity and is non-reactive with the subject's immune system. The pharmaceutically acceptable carriers and/or excipients may include buffers, stabilizers, diluents, preservatives, and solubilizers. In general, the nature of the carrier or excipients will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e. g. powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, "fusion" may refer to nucleic acids and polypeptides that comprise sequences that are not found naturally associated with each other in the order or context in which they are placed according to the present invention. A fusion nucleic acid or polypeptide does not necessarily comprise the natural sequence of the nucleic acid or polypeptide in its entirety. Fusion proteins have the two or more segments joined together through normal peptide bonds. Fusion nucleic acids have the two or more segments joined together through normal phosphodiester bonds.

Isolated Polypeptides

The present invention provides the C-TAB.G5 or C-TAB.G5.1 isolated polypeptides as set forth in SEQ ID NO: 2 and SEQ ID NO: 4, respectively, that comprises 19 repeating units of *C. difficile* toxin A and 23 repeating units of *C. difficile* toxin B. A homolog of C-TAB.G5, such as C-TAB.G5.1, may differ from C-TAB.G5 by 1, 2, 3, 4, 5, 6, 7, 8, 9, or 10 amino acids. The C-TAB.G5.1 polypeptide is a fusion protein containing the same C-terminal domain of toxin B as C-TAB.G5, but the C-terminal domain of toxin A derived from *C. difficile* VPI-10463 strain which is a homolog of the according C-TAB.G5 polypeptide derived from *C. difficile* 630 strain and differs by two amino acids at positions 155-156. The C-TAB.G5.1 coding sequence, as set forth in SEQ ID NO: 3, was codon optimized for improved expression within an *E. coli* host cell. The C-TAB.G5 or C-TAB.G5.1 isolated polypeptides of the present invention may be effective in neutralizing the toxic effects of *C. difficile* toxin A and toxin B.

Toxin A and toxin B are encoded by the trdA (SEQ ID NO: 5) and trdB (SEQ ID NO: 7) genes, of the *C. difficile* strain 630, respectively. Structurally, the *C. difficile* toxins comprise an ADP-glucosyl transferase domain, a cysteine protease domain, a hydrophobic region, and a receptor binding region. The C-terminal domain contains highly repetitive units (RUs) (also known as combined repetitive oligopeptides (CROPS)). The RUs may be long or short oligopeptides and may comprise 20 to 50 amino acids with a consensus YYF motif that is repeated. The RUs are grouped in clusters. As an example, toxin A, strain 630 (SEQ ID NO: 6) encoded by the wild-type trdA gene (SEQ ID NO: 5) contains 39 RUs. The 39 RUs are grouped into 8 clusters. Toxin B, strain 630 (SEQ ID NO: 8) encoded by the wild-type trdB gene (SEQ ID NO: 7) contains 24 RUs which are grouped into 5 clusters. Tables 1 and 2 below show the amino acid positions of each of the RUs in *C. difficile* toxin A and toxin B encoded by the trdA gene and trdB gene.

TABLE 1

| Toxin A Repeating Units (ARU) | | | | |
|---|---|---|---|---|
| CLUSTER | REPEAT | AA START (SEQ ID NO: 6) | AA END (SEQ ID NO: 6) | SEQ |
| 1 | S1 | 1832 | 1852 | GLININNSLFYFDPIEFNLVT |
|   | S1 | 1853 | 1873 | GWQTINGKKYYFDINTGAALI |
|   | S3 | 1874 | 1893 | SYKIINGKHFYFNNDGVMQL |
|   | L | 1894 | 1924 | GVFKGPDGFEYFAPANTQNNNIEGQAIVYQS |
| 2 | S1 | 1925 | 1944 | KFLTLNGKKYYFDNNSKAVT |
|   | S2 | 1945 | 1965 | GWRIINNEKYYFNPNNAIAAV |
|   | S3 | 1966 | 1986 | GLQVIDNNKYYFNPDTAIISK |
|   | S4 | 1987 | 2007 | GWQTVNGSRYYFDTDTAIAFN |
|   | S5 | 2008 | 2027 | GYKTIDGKHFYFDSDCVVKI |
|   | L | 2028 | 2058 | GVFSTSNGFEYFAPANTYNNNIEGQAIVYQS |

TABLE 1-continued

Toxin A Repeating Units (ARU)

| CLUSTER | REPEAT | AA START (SEQ ID NO: 6) | AA END (SEQ ID NO: 6) | SEQ |
|---|---|---|---|---|
| 3 | S1 | 2059 | 2078 | KFLTLNGKKYYFDNNSKAVT |
|  | S2 | 2079 | 2099 | GWQTIDSKKYYFNTNTAEAAT |
|  | S3 | 2100 | 2120 | GWQTIDGKKYYFNTNTAEAAT |
|  | S4 | 2121 | 2141 | GWQTIDGKKYYFNTNTAIAST |
|  | S5 | 2142 | 2161 | GYTIINGKHFYFNTDGIMQI |
|  | L | 2162 | 2192 | GVFKGPNGFEYFAPANTDANNIEGQAILYQN |
| 4 | S1 | 2193 | 2212 | EFLTLNGKKYYFGSDSKAVT |
|  | S2 | 2213 | 2233 | GWRIINNKKYYFNPNNAIAAI |
|  | S3 | 2234 | 2253 | HLCTINNDKYYFSYDGILQN |
|  | S4 | 2254 | 2275 | GYITIERNNFYFDANNESKMVT |
|  | L | 2276 | 2306 | GVFKGPNGFEYFAPANTHNNNIEGQAIVYQN |
| 5 | S1 | 2307 | 2326 | KFLTLNGKKYYFDNDSKAVT |
|  | S2 | 2328 | 2347 | GWQTIDGKKYYFNLNTAEAAT |
|  | S3 | 2348 | 2368 | GWQTIDGKKYYFNLNTAEAAT |
|  | S4 | 2369 | 2389 | GWQTIDGKKYYFNTNTFIAST |
|  | S5 | 2390 | 2409 | GYTSINGKHFYFNTDGIMQI |
|  | L | 2410 | 2440 | GVFKGPNGFEYFAPANTDANNIEGQAILYQN |
| 6 | S1 | 2441 | 2460 | KFLTLNGKKYYFGSDSKAVT |
|  | S2 | 2461 | 2481 | GLRTIDGKKYYFNTNTAVAVT |
|  | S3 | 2482 | 2502 | GWQTINGKKYYFNTNTSIAST |
|  | S4 | 2503 | 2522 | GYTIISGKHFYFNTDGIMQI |
|  | L | 2523 | 2553 | GVFKGPDGFEYFAPANTDANNIEGQAIRYQN |
| 7 | S1 | 2554 | 2573 | RFLYLHDNIYYFGNNSKAAT |
|  | S1 | 2574 | 2594 | GWVTIDGNRYYFEPNTAMGAN |
|  | S3 | 2595 | 2613 | GYKTIDNKNFYFRNGLPQI |
|  | L | 2614 | 2644 | GVFKGSNGFEYFAPANTDANNIEGQAIRYQN |
| 8 | S1 | 2645 | 2664 | RFLHLLGKIYYFGNNSKAVT |
|  | S2 | 2665 | 2686 | GWQTINGKVYYFMPDTAMAAAG |
|  | S3 | 2687 | 2670 | GLFEIDGVIYFFGVDGVKAPGIYG |

S: indicates a Short repeating unit
L: indicates a Long repeating unit

TABLE 2

Toxin B Repeating Units (BRU)

| CLUSTER | REPEAT | AA START (SEQ ID NO: 8) | AA END (SEQ ID NO: 8) | SEQ |
|---|---|---|---|---|
| 1 | S1 | 1834 | 1854 | GLIYINDSLYYFKPPVNNLIT |
|  | S2 | 1855 | 1876 | GFVTVGDDKYYFNPINGGAASI |

TABLE 2-continued

Toxin B Repeating Units (BRU)

| CLUSTER | REPEAT | AA START (SEQ ID NO: 8) | AA END (SEQ ID NO: 8) | SEQ |
|---------|--------|-------------------------|------------------------|-----|
|         | S3     | 1877                    | 1896                   | GETIIDDKNYYFNQSGVLQT |
|         | L      | 1897                    | 1926                   | GVFSTEDGFKYFAPANTLDENLEGEAIDFT |
| 2       | S1     | 1927                    | 1946                   | GKLIIDENIYYFDDNYRGAV |
|         | S2     | 1947                    | 1967                   | EWKELDGEMHYFSPETGKAFK |
|         | S3     | 1968                    | 1987                   | GLNQIGDYKYYSNSDGVMQK |
|         | S4     | 1988                    | 2007                   | GFVNINDKTFYFDDSGVMKS |
|         | S5     | 2008                    | 2027                   | GYTEIDGKHFYFAENGEMQI |
|         | L      | 2028                    | 2057                   | GVFNTEDGFKYFAHHNEDLGNEEGEEISYS |
| 3       | S1     | 2058                    | 2078                   | GILNFNNKIYYFDDSFTAVVG |
|         | S2     | 2079                    | 2099                   | WKDLEDGSKYYFDEDTAEAYI |
|         | S3     | 2100                    | 2119                   | GLSLINDGQYYFNDDGIMQV |
|         | S4     | 2120                    | 2139                   | GFVTINDKVFYFSDSGIIES |
|         | S5     | 2140                    | 2159                   | GVQNIDDNYFYIDDNGIVQI |
|         | L      | 2160                    | 2189                   | GVFDTSDGYKYFAPANTVNDNIYGQAVEYS |
| 4       | S1     | 2190                    | 2212                   | GLVRVGEDVYYFGETYTIETGWI |
|         | S2     | 2213                    | 2233                   | YDMENESDKYYFNPETKKACK |
|         | S3     | 2234                    | 2253                   | GINLIDDIKYYFDEKGIMRT |
|         | S4     | 2254                    | 2273                   | GLISFENNNYYFNENGEMQF |
|         | S5     | 2274                    | 2293                   | GYINIEDKMFYFGEDGVMQI |
|         | L      | 2294                    | 2323                   | GVFNTPDGFKYFAHQNTLDENFEGESINYT |
| 5       | S1     | 2324                    | 2343                   | GWLDLDEKRYYFTDEYIAAT |
|         | S2     | 2344                    | 2366                   | GSVIIDGEEYYFDPDTAQLVISE |

S: indicates a Short repeating unit
L: indicates a Long repeating unit

Accordingly, the C-TAB.G5 and C-TAB.G5.1 isolated polypeptides comprises 19 RUs from the C-terminal domain of *C. difficile* toxin A and 23 RUs from the C-terminal domain of *C. difficile* toxin B, respectively. The C-TAB.G5 or C-TAB.G5.1 comprises toxin A amino acids 2272-2710 of SEQ ID NO: 6 fused to toxin B amino acids 1850-2366 of SEQ ID NO: 8. The C-TAB.G5 or C-TAB.G5.1 isolated polypeptide comprises the amino acid sequence as set forth in SEQ ID NO: 2 and SEQ ID NO: 4, respectively.

The respective RUs in the C-TAB.G5 or C-TAB.G5.1 isolated polypeptide may also be from variants of *C. difficile* toxin A or toxin B. These RUs in the C-TAB isolated polypeptide may also be a combination of naturally occurring or variants of *C. difficile* toxin A or toxin B.

The RUs in the C-TAB.G5 or C-TAB.G5.1 isolated polypeptides comprise long RUs and short RUs, and the long RUs and the short RUs are arranged into a cluster. The C-TAB.G5 or C-TAB.G5.1 isolated polypeptides of the present invention comprises 4 clusters of 3 to 5 short RUs followed by one long RU of *C. difficile* toxin A and 5 clusters of 3 to 5 short RUs followed by one long RU of *C. difficile* toxin B.

The short and long RUs contain conserved motifs. The short repeating unit may comprise 15, 16, 17, 18, 19, 20, 21, 22, 23, 24, 25, or 26 amino acids. Each short repeating unit may comprise conserved tyrosine motifs, such as YYF, FYF, YFF, FYI, or HYF. A short repeat unit may further comprise an aspartate/histidine residue prior to the tyrosine motif if the following repeating unit is a long repeating unit. The long repeating unit may comprise 27, 28, 29, 30, 31, 32, 33, 34, or 35 amino acids. Each long repeating unit may comprise a tyrosine repeat motif such as FEYF (SEQ ID NO: 22), FKYF (SEQ ID NO: 23), or YKYF (SEQ ID NO: 24).

In the present invention, the toxin A and toxin B portions of the C-TAB.G5 or C-TAB.G5.1 isolated polypeptides may be fused directly together. The toxin A and toxin B portions may be spaced apart by a linker region. A linker region may comprise 1, 2, 3, 4, 5, 6, 7, 8, 9, 10, 11 to 15, 20 to 30, 40, 45, or 50 amino acids. Those skilled in the art will recognize that the linker region may be adapted to alter the positioning of the toxin A and toxin B portions so that in their expressed and folded shape each toxin repeating unit in the C-TAB.G5 or C-TAB.G5.1 isolated polypeptides is positioned to optimally expose potential epitopes and to retain its immunogenicity. The RUs and the clusters in the C-TAB isolated polypeptides may also be separated by linkers. In one embodiment, the linker comprises the peptide RSMH (439-442 of SEQ ID NO: 2 or SEQ ID NO: 4).

The C-TAB isolated polypeptides of the present invention may have at least 85%, 86%, 87%, 88%, 89%, 90%, 91%, 92%, 93%, 94%, 95%, 96%, 97%, 98%, or 99% sequence identity or sequence similarity with SEQ ID NO: 2 or SEQ ID NO: 4. As known in the art "similarity" between two polypeptides or polynucleotides is determined by comparing the amino acid or nucleotide sequence and its conserved nucleotide or amino acid substitutes of one polynucleotide or polypeptide to the sequence of a second polynucleotide or polypeptide. Also known in the art is "identity" which means the degree of sequence relatedness between two polypeptide or two polynucleotide sequences as determined by the identity of the match between two strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity and similarity between two polynucleotide or polypeptide sequences, the terms "identity" and "similarity" are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., SIAM J. Applied Math., 48: 1073 (1988). Methods commonly employed to determine identity or similarity between two sequences include, but are not limited to those disclosed in Guide to Huge Computers, Martin J. Bishop, ed., Academic Press, San Diego, 1994, and Carillo, H., and Lipman, D., SIAM J. Applied Math. 48:1073 (1988).

The C-TAB.G5 or C-TAB.G5.1 isolated polypeptides of the present invention are immunogenic. For example, the C-TAB.G5 or C-TAB.G5.1 isolated polypeptides of the present invention may have at least 50%, 60%, 70%, 80%, or 90% of the immunological activity of the corresponding bacterial toxin A, and the C-TAB.G5 or C-TAB.G5.1 isolated polypeptides may have at least 50%, 60%, 70%, 80%, or 90% of the immunological activity of the corresponding bacterial toxin B. The C-TAB.G5 or C-TAB.G5.1 isolated polypeptides of the present invention may be used as vaccines for treating, preventing, or alleviating the symptoms of CDAD.

The C-TAB.G5 or C-TAB.G5.1 isolated polypeptides of the present invention also include variants of the C-TAB.G5 or C-TAB.G5.1 isolated polypeptide having SEQ ID NO: 2 or SEQ ID NO: 4, respectively. The variants may have amino acid insertions, substitutions and/or deletions that have minimal to no effect on the activity, function or shape of the isolated polypeptide. Examples of such substitutions include the substitution of one non-polar residue for another, the substitution of one polar residue for another, the substitution of one basic residue for another, or the substitution of one acidic residue for another. The C-TAB.G5 or C-TAB.G5.1 isolated polypeptide variants may further include insertions, substitutions and/or deletions of amino acids in a comparison to the amino acid sequence of the extracellular domain of native toxin A or toxin B that yield minimal effect on the activity, function and/or structure of the polypeptide. Those skilled in the art will recognize non-natural amino acids may also be used. Non-natural amino acids include, for example, beta-alanine (beta-Ala), or other omega-amino acids, such as 3-amino propionic, 2,3-diamino propionic (2,3-diaP), 4-amino butyric and so forth, alpha-aminisobutyric acid (Aib), sarcosine (Sat), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) 2-naphthylalanine (2-Nal); 1,2,3, 4-tetrahydroisoquinoline-3-carboxylic acid (Tic); beta-2-thienylalanine (Thi); and methionine sulfoxide (MSO).

The nucleotide sequences encoding C-TAB.G5 or C-TAB.G5.1 isolated polypeptides of the present invention may be codon optimized to enhance expression in varying host cells. Codon optimization refers to modifying the nucleotide sequence in order to enhance protein expression in a host cell of interest by replacing one or more codons of the native sequence with codons that are more frequently used in the genes of that host cell or in the genes of the host the cell was derived from. Various species exhibit particular bias for certain codons of a particular amino acid. The present invention provides codon-optimized nucleotide sequence encoding the C-TAB.G5.1 isolated polypeptide for enhanced expression in *E. coli*.

The C-TAB.G5 or C-TAB.G5.1 isolated polypeptides of the present invention may be prepared by any known techniques. For example, the isolated polypeptides may be expressed through genetic engineering. By way of example, the translation of recombinant DNA. The C-TAB.G5 or C-TAB.G5.1 isolated polypeptides may also be prepared synthetically. By way of example, the C-TAB.G5 or C-TAB.G5.1 isolated polypeptides may be synthesized using the solid-phase synthetic technique initially described by Merrifield (J. Am Chem. Soc. 85:2149-2154), which is incorporated herein by reference. Other polypeptide synthesis techniques may be found, for example, Kent et al. (1985) in Synthetic Peptides in Biology and Medicine, eds. Alitalo et al., Elsevier Science Publishers, 295-358.

The C-TAB.G5 or C-TAB.G5.1 isolated polypeptides of the present invention may be isolated or obtained in substantially pure form. Substantially pure means that the proteins and/or polypeptides and/or peptides are essentially free of other substances with which they may be found in nature or in vivo systems to an extent practical and appropriate for their intended use. In particular, the C-TAB.G5 or C-TAB.G5.1 isolated polypeptides are sufficiently pure and are sufficiently free from other biological constituents of their host cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified isolated polypeptide of the invention may be admixed with a pharmaceutically acceptable carrier in a pharmaceutical preparation, the isolated polypeptide may comprise only a certain percentage by weight of the preparation. The isolated polypeptide is nonetheless substantially pure in that it has been substantially separated from the substances with which it may be associated in living systems.

The present invention further provides isolated C-TAB.G5 or C-TAB.G5.1 isolated polypeptides comprising additional polypeptides. The additional polypeptides may be fragments of a larger polypeptide. In one embodiment, there are one, two, three, four, or more additional polypeptides fused to the C-TAB.G5 or C-TAB.G5.1 isolated polypeptides. In some embodiments, the additional polypeptides are fused toward the amino terminus of the C-TAB.G5 or C-TAB.G5.1 isolated polypeptides. In other embodiments, the additional polypeptides are fused toward the carboxyl terminus of the C-TAB.G5 or C-TAB.G5.1 isolated polypeptides. In further embodiments, the additional polypeptides flank the C-TAB.G5 or C-TAB.G5.1 isolated polypeptides. In yet further embodiments, the additional polypeptides are dispersed between the toxin A portion and the toxin B portion of the C-TAB.G5 or C-TAB.G5.1 isolated polypeptides.

In some embodiments, the additional polypeptides aid in directing the secretion or subcellular localization of the C-TAB.G5 or C-TAB.G5.1 isolated polypeptides. Such polypeptides are referred to as a "signal sequence." A secretory signal is described, for example U.S. Pat. Nos. 6,291,212 and 5,547,871, both of which are herein incorporated by reference in their entirety. Secretory signal sequence encodes secretory peptides. A secretory peptide is an amino acid sequence that acts to direct the secretion of C-TAB.G5 or C-TAB.G5.1 from a cell. Secretory peptides are generally characterized by a core of hydrophobic amino acids and are typically (but not exclusively) found at the amino termini of newly synthesized proteins. The secretory peptide may be cleaved from C-TAB.G5 or C-TAB.G5.1 isolated polypeptide during secretion. Secretory peptides may contain processing sites that allow cleavage of the signal peptide from the mature protein as it passes through the secretory pathway. Processing sites may be encoded within the signal peptide or may be added to the signal peptide by, for example, in vitro mutagenesis. Secretory signal sequences may be required for a complex series of post-translational processing steps to allow for secretion of C-TAB.G5 or C-TAB.G5.1. The signal sequence may immediately follow the initiation codon and encodes a signal peptide at the amino-terminal end of C-TAB.G5 or C-TAB.G5.1. The signal sequence may precede the stop codon and encodes a signal peptide at the carboxy-terminal end of C-TAB.G5 or C-TAB.G5.1. In most cases, the signal sequence is cleaved off by a specific protease, called a signal peptidase. Examples of a secretory signal sequences include, but are not limited to ompA, pelB, and ST pre-pro.

In some embodiments, the additional polypeptides aid the stabilization, structure and/or the purification of the C-TAB.G5 or C-TAB.G5.1 isolated polypeptides. In some embodiments the additional polypeptides may comprise an epitope. In other embodiments, the additional polypeptides may comprise an affinity tag. By way of example, fusion of a polypeptide comprising an epitope and/or an affinity tag to the C-TAB.G5 or C-TAB.G5.1 isolated polypeptide may aid purification and/or identification of the polypeptide. By way of example, the polypeptide segment may be a His-tag, a myc-tag, an S-peptide tag, a MBP tag (maltose binding protein), a GST tag (glutathione S-transferase), a FLAG tag, a thioredoxin tag, a GFP tag (green fluorescent protein), a BCCP (biotin carboxyl carrier protein), a calmodulin tag, a Strep tag, an HSV-epitope tag, a V5-epitope tag, and a CBP tag. The use of such epitopes and affinity tags is known to those skilled in the art.

In further embodiments, the additional polypeptides may provide a C-TAB.G5 or C-TAB.G5.1 isolated polypeptide comprising sites for cleavage of the polypeptide. As an example, a polypeptide may be cleaved by hydrolysis of the peptide bond. In some embodiments, the cleavage is performed by an enzyme. In some embodiments, cleavage occurs in the cell. In other embodiments, cleavage occurs through artificial manipulation and/or artificial introduction of a cleaving enzyme. By way of example, cleavage enzymes may include pepsin, trypsin, chymotrypsin, thrombin, and/or Factor Xa. Cleavage allows ease of isolating the C-TAB.G5 or C-TAB.G5.1 isolated polypeptides from the polypeptides. Cleavage may further allow for the separation of the toxin A portion from the toxin B portion. Cleavage may also allow isolation of the C-TAB.G5 or C-TAB.G5.1 isolated polypeptide fused to polypeptides from other polypeptides, such as through cleavage of an epitope utilized to purify the expressed protein.

The C-TAB.G5 or C-TAB.G5.1 isolated polypeptides may further possess additional structural modifications not shared with the same organically synthesized peptide, such as adenylation, carboxylation, glycosylation, hydroxylation, methylation, phosphorylation or myristylation. These added structural modifications may be further be selected or preferred by the appropriate choice of recombinant expression system. On the other hand, fusion polypeptides may have its sequence extended by the principles and practice of organic synthesis.

The present invention also provides nucleic acids encoding the C-TAB.G5 or C-TAB.G5.1 isolated polypeptides comprising a polypeptide portion obtained from C. difficile toxin A and a polypeptide portion obtained from C. difficile toxin B. Nucleic acids may include single or double stranded forms of deoxyribonucleotides or ribonucleotides or polymers thereof. The present invention provides ribonucleic acids encoding the C-TAB.G5 or C-TAB.G5.1 isolated polypeptides. The present invention also provides for nucleic acids that hybridize under stringent conditions to a nucleic acid encoding the C-TAB.G5 or C-TAB.G5.1 isolated polypeptide and the complement thereof. Stringent conditions refer to the degree of homology between a probe and a filter-bound nucleic acid; the higher the stringency, the higher percent homology between the probe and filter bound nucleic acid. The temperature for a stringent wash may be determined based on the Tm of the nucleic acid (based on G/C content). Stringent conditions may further be affected by the concentration of salt in a buffer, such as standard sodium citrate (SSC). The present invention provides for nucleic acids having about 85%, 86%, 87%, 88%, 89%, 90%, 91%, 92%, 93%, 94%, 95%, 96%, 97%, 98%, or 99% sequence similarity or sequence identity with SEQ ID NO: 1.

The C-TAB.G5 or C-TAB.G5.1 isolated polypeptide may further comprise a linker region, for instance a linker less than about 50, 40, 30, 20, 10, 9, 8, 7, 6, 5, 4, 3, 2, or 1 amino acid residues. The linker can be covalently linked to and between the polypeptide portion derived from toxin A or portion thereof and the polypeptide portion derived from toxin B.

The present invention provides nucleic acids encoding the C-TAB.G5 or C-TAB.G5.1 isolated polypeptides that are degenerate to SEQ ID NO: 1 or SEQ ID NO: 3, respectively. The degeneracy of the genetic code permits variations of the nucleotide sequence of a toxin A protein, a toxin B protein and/or isolated polypeptide of interest, while still producing a polypeptide having the identical amino acid sequence as the polypeptide encoded by the native DNA sequence. The procedure, known as "codon optimization" (described in U.S. Pat. No. 5,547,871 which is incorporated herein by reference in its entirety) provides one with a means of designing such an altered DNA sequence. The design of codon optimized genes should take into account a variety of factors, including the frequency of codon usage in an organism, nearest neighbor frequencies, RNA stability, the potential for secondary structure formation, the route of synthesis and the intended future DNA manipulations of that gene. In particular, available methods may be used to alter the codons encoding a given isolated polypeptide with those most readily recognized by yeast when yeast expression systems are used, or by insect cells when the insect cell expression system is used. The degeneracy of the genetic code also permits the same amino acid sequence to be encoded and translated in many different ways. For example, leucine, serine and arginine are each encoded by six different codons, while valine, proline, threonine, alanine and glycine are each encoded by four different codons. However, the frequency of use of such synonymous codons varies from genome to genome among eukaryotes and prokaryotes. For example, synonymous codon-choice patterns among mammals are very similar, while evolutionarily distant organisms such as yeast (such as S. cerevisiae), bacteria (such as E. coli) and insects (such as D. melanogaster) reveal a clearly different pattern of genomic codon use frequencies (Grantham, R., et al., Nucl. Acid Res., 8, 49-62 (1980); Grantham, R., et al., Nucl. Acid Res., 9, 43-74 (1981); Maroyama, T., et al., Nucl. Acid Res., 14, 151-197 (1986); Aota, S., et al., Nucl. Acid Res., 16, 315-402 (1988); Wada, K., et al., Nucl. Acid Res., 19 Supp., 1981-1985 (1991); Kurland, C. G., FEBS Lett., 285, 165-169 (1991)). These differences in codon-choice patterns appear to contribute to the overall expression levels of individual genes by modulating peptide elongation rates. (Kurland, C. G., FEBS Lett., 285, 165-169 (1991); Pedersen, S., EMBO J., 3, 2895-2898 (1984); Sorensen, M. A., J. Mol. Biol., 207, 365-377 (1989); Randall, L. L., et al., Eur. J. Biochem., 107, 375-379 (1980); Curran, J. F., and Yarus, M., J. Mol. Biol., 209, 65-77 (1989); Varenne, S., et al., J. Mol. Biol., 180, 549-576 (1984), Varenne, S., et al., J. Mol, Biol., 180, 549-576 (1984); Garel, J.-P., J. Theor. Biol., 43, 211-225 (1974); Ikemura, T., J. Mol. Biol., 146, 1-21 (1981); Ikemura, T., J. Mol. Biol., 151, 389-409 (1981)).

The preferred codon usage frequencies for a synthetic gene should reflect the codon usages of nuclear genes derived from the exact (or as closely related as possible) genome of the cell/organism that is intended to be used for recombinant protein expression.

Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, et al., Nucl. Acid Res. 12(1):387 (1984)), BLASTP, BLASTN, FASTA (Atschul, et al., J. Mol. Biol. 215:403 (1990)). The degree of similarity or identity referred to above is determined as the degree of identity between the two sequences, often indicating a derivation of the first sequence from the second. The degree of identity between two nucleic acids may be determined by means of computer programs known in the art such as GAP provided in the GCG program package (Needleman and Wunsch J. Mol. Biol. 48:443-453 (1970)). For purposes of determining the degree of identity between two nucleic acids for the present invention, GAP is used with the following settings: GAP creation penalty of 5.0 and GAP extension penalty of 0.3.

The present invention also provides a vector comprising a nucleic acid encoding for the C-TAB.G5 or C-TAB.G5.1 isolated polypeptide. A vector may be any of a number of nucleic acids into which a desired sequence may be inserted by restriction and ligation for transport between different genetic environments or for expression in a host cell. Vectors are typically composed of DNA, although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

Vectors may further contain a promoter sequence. A promoter may include an untranslated nucleic acid usually located upstream of the coding region that contains the site for initiating transcription of the nucleic acid. The promoter region may also include other elements that act as regulators of gene expression. In further embodiments of the invention, the expression vector contains an additional region to aid in selection of cells that have the expression vector incorporated. The promoter sequence is often bounded (inclusively) at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes.

Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., p-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

An expression vector is one into which a desired nucleic acid may be inserted by restriction and ligation such that it is operably joined to regulatory sequences and may be expressed as an RNA transcript. Expression refers to the transcription and/or translation of an endogenous gene, transgene or coding region in a cell.

A coding sequence and regulatory sequences are operably joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The C-TAB.G5 or C-TAB.G5.1 isolated polypeptides of the present invention may be produced by expressing the encoding nucleic acid in host cells. The nucleic acid may be transformed or transfected into host cells. Accordingly, some aspects of the present invention include the transformation and/or transfection of nucleic acid encoding the C-TAB.G5 or C-TAB.G5.1 isolated polypeptides. Transformation is the introduction of exogenous or heterologous nucleic acid to the interior of a prokaryotic cell. Transfection is the introduction of exogenous or heterologous nucleic acid to the interior of a eukaryotic cell. The transforming or transfecting nucleic acid may or may not be integrated (covalently linked) into chromosomal DNA making up the genome of the cell. In prokaryotes, for example, the transforming nucleic acid may be maintained on an episomal element such as a plasmid or viral vector. With respect to eukaryotic cells, a stably transfected cell is one in which the transfecting nucleic acid has become integrated into a chromosome so that it is inherited by daughter cells through chromosome replication. This stability is demonstrated by the ability of the eukaryotic cell to establish cell lines or clones comprised of a population of daughter cells containing the transfected nucleic acid.

Higher eukaryotic cell cultures may be used to express the proteins of the present invention, whether from vertebrate or invertebrate cells, including insects, and the procedures of propagation thereof are known (see, for example, Kruse et al. (1973) Tissue Culture, Academic Press).

Host cells and vectors for replicating the nucleic acids and for expressing the encoded C-TAB.G5 or C-TAB.G5.1 isolated polypeptides are also provided. Any vectors or host cells may be used, whether prokaryotic or eukaryotic. Many vectors and host cells are known in the art for such purposes. It is well within the skill of the art to select an appropriate set for the desired application.

DNA sequences encoding toxin A and toxin B, or portions thereof may be cloned from a variety of genomic or cDNA libraries derived from *C. difficile* and other known toxin A and toxin B expressing prokaryotes known in the art. The techniques for isolating such DNA sequences using probe-based methods are conventional techniques and are well known to those skilled in the art. Probes for isolating such DNA sequences may be based on published DNA or protein sequences. Alternatively, the polymerase chain reaction (PCR) method disclosed by Mullis et al. (U.S. Pat. No. 4,683,195) and Mullis (U.S. Pat. No. 4,683,202), incorporated herein by reference may be used. The choice of library and selection of probes for the isolation of such DNA sequences is within the level of ordinary skill in the art.

Suitable host cells maybe derived from prokaryotes or eukaryotes. Suitable prokaryote hosts include: *Pseudomonas* such as *P. aeruginosa, Escherichia coli, Staphylococcus* such as *S. aureus* and *S. epidermidis, Serratia marcescens, Bacillus* such as *B. subtillis* and *B. megaterium, Clostridium sporogenes, Enterococcus faecalis, Micrococcus* such as *M. luteus* and *M. roseus*, and *Proteus vulgaris*. Suitable host cells for expressing the polypeptides of the present invention in higher eukaryotes include: yeasts such as *Saccharomyces* (e.g. *S. cerevisiae*); 293 (human embryonic kidney) (ATCC CRL-1573); 293F (Invitrogen, Carlsbad CA); 293T and variant 293T/17 (293tsA1609neo and variant ATCC CRL-11268) (human embryonic kidney transformed by SV40 T antigen); COS-7 (monkey kidney CVI line transformed by SV40)(ATCC CRL1651); BHK (baby hamster kidney cells) (ATCC CRL10); CHO (Chinese hamster ovary cells); mouse Sertoli cells; CVI (monkey kidney cells) (ATCC CCL70); VERO76 (African green monkey kidney cells) (ATCC CRL1587); HeLa (human cervical carcinoma cells) (ATCC CCL2); MDCK (canine kidney cells) (ATCC CCL34); BRL3A (buffalo rat liver cells) (ATCC CRL1442); W138 (human lung cells) (ATCC CCL75); HepG2 (human liver cells) (HB8065); and MMT 060652 (mouse mammary tumor) (ATCC CCL51).

In other embodiments, the present invention provides nucleic acids encoding an isolated polypeptide comprising the C-TAB.G5 or C-TAB.G5.1 isolated polypeptides and additional polypeptides. Vectors useful for constructing eukaryotic expression systems for the production of fusion polypeptides comprise nucleic acid encoding the isolated polypeptide operatively linked to an appropriate transcriptional activation sequence, such as a promoter and/or operator. Other typical features may include appropriate ribosome binding sites, termination codons, enhancers, terminators, or replicon elements. These additional features can be inserted into the vector at the appropriate site or sites by conventional splicing techniques such as restriction endonuclease digestion and ligation.

In some embodiments, additional nucleic acids may be fused to the nucleic acid encoding the C-TAB.G5 or C-TAB.G5.1 isolated polypeptides. The fused nucleic acid may encode polypeptides that may aid in purification and/or immunogenicity and/or stability without shifting the codon reading frame of the C-TAB.G5 or C-TAB.G5.1 isolated polypeptide. The fused nucleic acids may encode a secretory sequence, that may or may not be cleaved from the C-TAB.G5 or C-TAB.G5.1 isolated polypeptides. The fused nucleic acids may not elongate the expressed polypeptide significantly. The fused nucleic acids may encode for less than sixty extra amino acids to the C-TAB.G5 or C-TAB.G5.1 isolated polypeptides. In some embodiments, the fused nucleic acids follow after the nucleic acid encoding the C-TAB.G5 or C-TAB.G5.1 isolated polypeptides. In other embodiments, the fused nucleic acids precede the nucleic acid encoding the C-TAB.G5 or C-TAB.G5.1 isolated polypeptides. In other embodiments, the fused nucleic acids flank the nucleic acid encoding the C-TAB.G5 or C-TAB.G5.1 isolated polypeptides.

In some embodiments, the fused nucleic acids may encode for a polypeptide to aid purification of the C-TAB.G5 or C-TAB.G5.1 isolated polypeptides. In some embodiments the fused nucleic acid will encode for an epitope and/or an affinity tag. Examples of polypeptides that aid purification include, but are not limited to, a His-tag, a myc-tag, an S-peptide tag, a MBP tag, a GST tag, a FLAG tag, a thioredoxin tag, a GFP tag, a BCCP, a calmodulin tag, a Strep tag, an HSV-epitope tag, a V5-epitope tag, and a CBP tag. In other embodiments, the fused nucleic acid may encode for a C-TAB.G5 or C-TAB.G5.1 isolated polypeptide that has a site directed for, or prone to, cleavage. In one embodiment, the fused nucleic acid may encode for polypeptides comprising sites of enzymatic cleavage. In further embodiments, the enzymatic cleavage may aid in isolating the C-TAB.G5 or C-TAB.G5.1 isolated polypeptides, as well as other fused polypeptide segments, from yet other polypeptides. By way of example, an intermediary nucleic acid that encodes for an enzymatic cleavage site placed between nucleic acids that encode for C-TAB.G5 or C-TAB.G5.1 isolated polypeptide and an epitope may allow for later separation of the expressed C-TAB.G5 or C-TAB.G5.1 isolated polypeptides and the epitope. Such sites may also be present between the toxin A portion and the toxin B portion.

The present invention also provides for expression systems designed to assist in expressing and providing the C-TAB.G5 or C-TAB.G5.1 isolated polypeptides. The expression system may comprise a host cell transformed or transfected with a nucleic acid encoding the C-TAB.G5 or C-TAB.G5.1 isolated polypeptide. The host cell may be a prokaryote. The prokaryote may be *E. coli*. The host cell may be an eukaryotic cell.

The expression system may further comprise agents to aid in selection of host cells successfully transformed or transfected with a nucleic acid encoding the C-TAB.G5 or C-TAB.G5.1 isolated polypeptides. For example, the nucleic acid encoding the C-TAB.G5 or C-TAB.G5.1 isolated polypeptide may further express a gene to assist the host cell in resistance to antibiotics, such as genes to resist kanamycin or gentamycin or ampicillin or penicillin. Such resistant genes will allow for selection of host cells that have properly incorporated the nucleic acid encoding the C-TAB.G5 or C-TAB.G5.1 isolated polypeptide, as is known to those skilled in the art.

Another aspect of the invention is directed to the generation of antibodies. Examples of antibodies encompassed by the present invention, include, but are not limited to, antibodies produced by immunizing a subject with the C-TAB.G5 or C-TAB.G5.1 isolated polypeptide. Antibodies generated by immunizing with the C-TAB.G5 or C-TAB.G5.1 isolated polypeptide may bind specifically to toxin A or toxin B, or they may cross react with the C-TAB.G5 or C-TAB.G5.1 isolated polypeptide. The antibodies produced by the C-TAB.G5 or C-TAB.G5.1 isolated polypeptide of the present invention may be characterized using methods well known in the art.

The antibodies produced by using the C-TAB.G5 or C-TAB.G5.1 isolated polypeptide of the present invention can encompass monoclonal antibodies, polyclonal antibodies, antibody fragments (e.g., Fab, Fab', F(ab')2, Fv, Fc, etc.), chimeric antibodies, bispecific antibodies, heavy chain only antibodies, heteroconjugate antibodies, single chain (ScFv), single domain antibodies, variants thereof, isolated polypeptides comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. Preferred antibodies are derived from murine, rat, human, rabbit, canine, porcine, dromedary, camel, llama, feline, primate, or any other origin (including chimeric, fragment and/or humanized antibodies).

In other embodiments, the antibodies produced by immunizing with the C-TAB.G5 or C-TAB.G5.1 isolated polypeptide are then humanized by methods known in the art. A humanized antibody is an immunoglobulin molecule that contains minimal sequence derived from non-human immunoglobulin. In yet other embodiments, fully human antibodies are obtained by using commercially available mice that have been engineered to express specific human immunoglobulin proteins. In other embodiments, the antibodies are chimeric. A chimeric antibody is an antibody that combines characteristics from two different antibodies. Methods of preparing chimeric antibodies are known in the art.

In other embodiments, the nucleotide sequence that encodes the antibodies is obtained and then cloned into a vector for expression or propagation. In another embodiment, antibodies are made recombinantly and expressed using methods known in the art. By way of example, the C-TAB.G5 or C-TAB.G5.1 isolated polypeptide may be used as an antigen for the purposes of isolating recombinant antibodies by these techniques. Antibodies can be made recombinantly by using the gene sequence to express the antibody recombinantly in host cells. Methods for making variants of antibodies and recombinant antibodies are known in the art.

In other embodiments, the antibodies are bound to a carrier by conventional methods in the art, for use in, for example, isolating or purifying native toxin A or toxin B or detecting native toxin A or toxin B or *C. difficile* in a biological sample or specimen.

Compositions and Formulations

The present invention also provides compositions comprising C-TAB.G5 or C-TAB.G5.1 isolated polypeptides. The compositions may be pharmaceutical compositions comprising the C-TAB.G5 or C-TAB.G5.1 isolated polypeptide and a pharmaceutically acceptable carrier. The compositions used in the methods of the invention generally comprise, by way of example and not limitation, and effective amount of the C-TAB.G5 or C-TAB.G5.1 isolated polypeptide (e.g., an amount sufficient to induce an immune response) of the invention or an antibody against the C-TAB.G5 or C-TAB.G5.1 isolated polypeptides (e.g., an amount of a neutralizing antibody sufficient to mitigate infection, alleviate a symptom of infection and/or prevent infection). The pharmaceutical composition may further comprise pharmaceutically acceptable carriers, excipients, or stabilizers known in the art (see generally Remington, (2005) The Science and Practice of Pharmacy, Lippincott, Williams and Wilkins).

The C-TAB.G5 or C-TAB.G5.1 isolated polypeptide of the invention may be used for methods for immunizing or treating humans and/or animals with the CDAD. Therefore, the C-TAB.G5 or C-TAB.G5.1 isolated polypeptides may be used within a pharmaceutical composition. The pharmaceutical composition of the present invention may further encompass pharmaceutically acceptable carriers and/or excipients. The pharmaceutically acceptable carriers and/or excipients useful in this invention are conventional and may include buffers, stabilizers, diluents, preservatives, and solubilizers. Remington's Pharmaceutical Sciences, by E. W. Martin, Mack Publishing Co., Easton, PA, 15th Edition (1975), describes compositions and formulations suitable for pharmaceutical delivery of the polypeptides herein disclosed. In general, the nature of the carrier or excipients will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e. g. powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In one embodiment the pharmaceutical composition may further comprise an immunostimulatory substance, such as an adjuvant. The adjuvant can be selected based on the method of administration and may include mineral oil-based adjuvants such as Freund's complete and incomplete adjuvant, Montanide incomplete Seppic adjuvant such as ISA, oil in water emulsion adjuvants such as the Ribi adjuvant system, syntax adjuvant formulation containing muramyl dipeptide, aluminum hydroxide or aluminum salt adjuvant (alum), polycationic polymer, especially polycationic peptide, especially polyarginine or a peptide containing at least two LysLeuLys motifs, especially KLKLLLLLKLK (SEQ ID NO: 21), immunostimulatory oligodeoxynucleotide (ODN) containing non-methylated cytosine-guanine dinucleotides (CpG) in a defined base context (e.g. as described in WO 96/02555) or ODNs based on inosine and cytidine (e.g. as described in WO 01/93903), or deoxynucleic acid containing deoxy-inosine and/or deoxyuridine residues (as described in WO 01/93905 and WO 02/095027), especially Oligo(dIdC)$_{13}$ (as described in WO 01/93903 and WO 01/93905), neuroactive compound, especially human growth hormone (described in WO 01/24822), or combinations thereof. Such combinations are according to the ones e.g. described in WO 01/93905, WO 02/32451, WO 01/54720, WO 01/93903, WO 02/13857, WO 02/095027 and WO 03/047602. Preferably, the adjuvant is aluminum hydroxide adjuvant.

Acceptable carriers, excipients, or stabilizers are nontoxic to recipients at the dosages and concentrations that are administered. Carriers, excipients or stabilizers may further comprise buffers. Examples of excipients include, but are not limited to, carbohydrates (such as monosaccharide and disaccharide), sugars (such as sucrose, mannitol, and sorbitol), phosphate, citrate, antioxidants (such as ascorbic acid and methionine), preservatives (such as phenol, butanol, benzanol; alkyl parabens, catechol, octadecyldimethylbenzyl ammonium chloride, hexamethoniuni chloride, resorcinol, cyclohexanol, 3-pentanol, benzalkonium chloride, benzethonium chloride, and m-cresol), low molecular weight polypeptides, proteins (such as serum albumin or immunoglobulins), hydrophilic polymers amino acids, chelating agents (such as EDTA), salt-forming counter-ions, metal complexes (such as Zn-protein complexes), and non-ionic surfactants (such as TWEEN™ and polyethylene glycol).

The pharmaceutical composition of the present invention may further comprise additional agents that serve to enhance and/or complement the desired effect. By way of example, to enhance the immunogenicity the C-TAB.G5 or C-TAB.G5.1 isolated polypeptide of the invention being administered as a subunit vaccine, the pharmaceutical composition may further comprise an adjuvant.

An example of a pharmaceutical composition may be an immunogenic composition. The present invention provides immunogenic compositions comprising the C-TAB.G5 or C-TAB.G5.1 isolated polypeptides. The immunogenic composition may further include a pharmaceutically acceptable carrier or other carriers and/or excipients in a formulation suitable for injection in a mammal. An immunogenic composition is any composition of material that elicits an immune response in a mammalian host when the immunogenic composition is injected or otherwise introduced. The immune response may be humoral, cellular, or both. A booster effect refers to an increased immune response to an immunogenic composition upon subsequent exposure of the mammalian host to the same immunogenic composition. A humoral response results in the production of antibodies by the mammalian host upon exposure to the immunogenic composition.

The immunogenic compositions of the present invention elicit an immune response in a mammalian host, including humans and other animals. The immune response may be either a cellular dependent response or an antibody dependent response or both; and further the response may provide immunological memory or a booster effect or both in the mammalian host. These immunogenic compositions are useful as vaccines and may provide a protective response by the mammalian subject or host to infection by strains of *C. difficile*.

The present invention further includes methods for producing an immunogenic composition by constructing the nucleic acid encoding the C-TAB.G5 or C-TAB.G5.1 isolated polypeptide and expressing C-TAB.G5 or C-TAB.G5.1 isolated polypeptide component in a microbial host; recovering the C-TAB.G5 or C-TAB.G5.1 isolated polypeptide from a culture of the host; conjugating the C-TAB.G5 or C-TAB.G5.1 isolated polypeptide to a second protein component, and recovering the conjugated protein and polysaccharide component. The nucleic acid encoding the C-TAB.G5 or C-TAB.G5.1 isolated polypeptide may be maintained throughout the growth of the host by constant and stable selective pressure. Maintenance of the expression vector may be conferred by incorporation in the expression vector of a genetic sequence that encodes a selective genotype, the expression of which in the microbial host cell results in a selective phenotype. A selective genotype sequence may also include a gene complementing a conditional lethal mutation. Other genetic sequences may be incorporated in the expression vector, such as other drug resistance genes or genes that complement lethal mutations. Microbial hosts may include: Gram positive bacteria; Gram negative bacteria, such as *E. coli*; yeasts; filamentous fungi; mammalian cells; insect cells; or plant cells.

The methods of the present invention also provide for a level of expression of the C-TAB.G5 or C-TAB.G5.1 isolated polypeptide in the host at a level greater than about 50 mg/liter of the culture, a level greater than about 100 mg/liter, a level greater than about 500 mg/liter, or a level greater than about 1 g/liter. This invention also provides that the protein may be recovered by any number of methods known to those in the art for the isolation and recovery of proteins, such as by ammonium sulfate precipitation followed by ion exchange chromatography.

The present invention further includes methods for preparing the immunogenic composition that provides that the protein component is conjugated to a second protein component by one of a number of means known to those in the art, such as an amidization reaction.

The present invention also provides formulations comprising the C-TAB.G5 or C-TAB.G5.1 isolated polypeptide for treating and preventing CDAD. In one embodiment, the formulation may include the C-TAB.G5 or C-TAB.G5.1 isolated polypeptide of the present invention, an adjuvant, and a pharmaceutically acceptable carrier. In another embodiment, the formulation includes the C-TAB.G5 or C-TAB.G5.1 isolated polypeptide of the present invention, or consists essentially of one or more C-TAB.G5 or C-TAB.G5.1 isolated polypeptides of the present invention. The formulation may comprise the C-TAB.G5 or C-TAB.G5.1 isolated polypeptide of the present invention and an adjuvant. The formulation may further include an additional antigen or a drug. Moreover, the formulation may include one or more drugs and may in addition to the isolated polypeptide and/or adjuvant include one or more drugs.

The formulation comprising the C-TAB.G5 or C-TAB.G5.1 isolated polypeptide may be in liquid or dry form. A dry formulation may be easily stored and transported. Dry formulations break the cold chain required from the vaccine's place of manufacture to the locale where vaccination occurs. Alternatively, the dry, active ingredient of the formulation per se may be an improvement by providing a solid particulate form that is taken up and processed by antigen presenting cells. These possible mechanisms are discussed not to limit the scope of the invention or its equivalents, but to provide insight into the operation of the invention and to guide the use of this formulation in immunization and vaccination.

Dry formulations of the C-TAB.G5 or C-TAB.G5.1 isolated polypeptide may be provided in various forms: for example, fine or granulated powders, lyophilized powder, uniform films, pellets, and tablets. It may be air dried, dried with elevated temperature, lyophilized, freeze or spray dried, coated or sprayed on a solid substrate and then dried, dusted on a solid substrate, quickly frozen and then slowly dried under vacuum, or combinations thereof. If different molecules are active ingredients of the formulation, they may be mixed in solution and then dried, or mixed in dry form only.

Formulations comprising the C-TAB.G5 or C-TAB.G5.1 isolated polypeptide in liquid or solid form, such as a dry form, may be applied with one or more adjuvants at the same or separate sites or simultaneously or in frequent, repeated applications. The formulation may include other antigens such that administration of the formulation induces an immune response to multiple antigens. In such a case, the other antigens may have different chemical structures so as to induce an immune response specific for different antigens. At least one antigen and/or adjuvant may be maintained in dry form prior to administration. Subsequent release of liquid from a reservoir or entry of liquid into a reservoir containing the dry ingredient of the formulation will at least partially dissolve that ingredient.

Solids (e.g., particles of nanometer or micrometer dimensions) may also be incorporated in the formulation. Solid forms (e.g., nanoparticles or microparticles) may aid in dispersion or solubilization of active ingredients; provide a point of attachment for adjuvant, C-TAB.G5 or C-TAB.G5.1 isolated polypeptide, or both to a substrate that can be opsonized by antigen presenting cells, or combinations thereof. Prolonged release of the formulation from a porous solid formed as a sheet, rod, or bead acts as a depot.

At least one ingredient or component of the formulation (i.e., C-TAB.G5 or C-TAB.G5.1 isolated polypeptide, adjuvant, or drug) may be provided in dry form prior to administration of the formulation. This formulation may also be used in conjunction with conventional enteral, mucosal, or parenteral immunization techniques.

The formulation comprising the C-TAB.G5 or C-TAB.G5.1 isolated polypeptide may be manufactured under aseptic conditions acceptable to appropriate regulatory agencies (e.g., Food and Drug Administration, EMEA for biologicals and vaccines. Optionally, components such as desiccants, excipients, stabilizers, humectants, preservatives, or combinations thereof may be included in the formulation even though they are immunologically inactive. They may, however, have other desirable properties or characteristics.

Processes for manufacturing a pharmaceutical formulation are well known. The components of the formulation may be combined with a pharmaceutically-acceptable carrier or vehicle, as well as any combination of optional additives (e.g., diluents, binders, excipients, stabilizers, desiccants, preservatives, colorings). The use of solid carriers, and the addition of excipients to assist in solubilization of dry components or stabilizers of immunogenic or adjuvant activity, are preferred embodiments. See, generally, Ullmann's Encyclopedia of Industrial Chemistry, $6^{th}$ Ed. (electronic edition, 2003); Remington's Pharmaceutical Sciences, $22^{nd}$ (Gennaro, 2005, Mack Publishing); Pharmaceutical Dosage Forms, $2^{nd}$ Ed. (various editors, 1989-1998, Marcel Dekker); and Pharmaceutical Dosage Forms and Drug Delivery Systems (Ansel et al., 2005, Williams & Wilkins).

Good manufacturing practices are known in the pharmaceutical industry and regulated by government agencies (e.g., Food and Drug Administration, EMEA. Sterile liquid formulations may be prepared by dissolving an intended component of the formulation in a sufficient amount of an appropriate solvent, followed by sterilization by filtration to remove contaminating microbes. Generally, dispersions are prepared by incorporating the various sterilized components of the formulation into a sterile vehicle which contains the basic dispersion medium. For production of solid forms that are required to be sterile, vacuum drying or freeze drying can be used.

In general, solid dosage forms (e.g., powders, granules, pellets, tablets) can be made from at least one active ingredient or component of the formulation.

Suitable tableting procedures are known. The formulation may also be produced by encapsulating solid forms of at least one active ingredient, or keeping them separate from liquids in compartments or chambers. The size of each dose and the interval of dosing to the subject may be used to determine a suitable size and shape of the tablet, capsule, compartment, or chamber.

Formulations will contain an effective amount of the active ingredients (e.g., drug, antigen and adjuvant) together with carrier or suitable amounts of vehicle in order to provide pharmaceutically-acceptable compositions suitable for administration to a human or animal.

The relative amounts of active ingredients, such as amounts of the C-TAB.G5 or C-TAB.G5.1 isolated polypeptide, within a dose and the dosing schedule may be adjusted appropriately for efficacious administration to a subject (e.g., animal or human). This adjustment may also depend on the subject's particular disease or condition, and whether treatment or prophylaxis is intended. To simplify administration of the formulation to the subject, each unit dose contains the active ingredients in predetermined amounts for a single round of immunization.

There are numerous causes of polypeptide instability or degradation, including hydrolysis and denaturation. In the case of denaturation, the conformation or three-dimensional structure of the protein is disturbed and the protein unfolds from its usual globular structure. Rather than refolding to its natural conformation, hydrophobic interaction may cause clumping of molecules together (i.e., aggregation) or refolding to an unnatural conformation. Either of these results may entail diminution or loss of immunogenic or adjuvant activity. Stabilizers may be added to lessen or prevent such problems.

The formulation, or any intermediate in its production, may be pretreated with protective agents (i.e., cryoprotectants and dry stabilizers) and then subjected to cooling rates and final temperatures that minimize ice crystal formation. By proper selection of cryoprotective agents and use of pre-selected drying parameters, almost any formulation might be cryoprepared for a suitable desired end use.

It should be understood in the following discussion of optional additives like excipients, stabilizers, desiccants, and preservatives are described by their function. Thus, a particular chemical may act as some combination of recipient, stabilizer, desiccant, and/or preservative. Such chemical would be immunologically-inactive because it does not directly induce an immune response, but it increases the response by enhancing immunological activity of the antigen or adjuvant: for example, by reducing modification of the antigen or adjuvant, or denaturation during drying and dissolving cycles.

Stabilizers include cyclodextrin and variants thereof (see U.S. Pat. No. 5,730,969). Suitable preservatives such as sucrose, mannitol, sorbitol, trehalose, dextran, and glycerin can also be added to stabilize the final formulation (Howell and Miller, 1983). A stabilizer selected from nonionic surfactants, D-glucose, D-galactose, D-xylose, D-glucuronic acid, salts of D-glucuronic acid, trehalose, dextrans, hydroxyethyl starches, and mixtures thereof may be added to the formulation. Addition of an alkali metal salt or magnesium chloride may stabilize the C-TAB.G5 or C-TAB.G5.1 isolated polypeptide, optionally including serum albumin and freeze-drying to further enhance stability. The C-TAB.G5 or C-TAB.G5.1 isolated polypeptide may also be stabilized by contacting it with a saccharide selected from the group consisting of dextran, chondroitin sulfuric acid, starch, glycogen, insulin, dextrin, and alginic acid salt. Other sugars that can be added include monosaccharides, disaccharides, sugar alcohols, and mixtures thereof (e.g., glucose, mannose, galactose, fructose, sucrose, maltose, lactose, mannitol, xylitol). Polyols may stabilize a polypeptide, and are water-miscible or water-soluble. Suitable polyols may be polyhydroxy alcohols, monosaccharides and disaccharides including mannitol, glycerol, ethylene glycol, propylene glycol, trimethyl glycol, vinyl pyrrolidone, glucose, fructose, arabinose, mannose, maltose, sucrose, and polymers thereof. Various excipients may also stabilize polypeptides, including serum albumin, amino acids, heparin, fatty acids and phospholipids, surfactants, metals, polyols, reducing agents, metal chelating agents, polyvinyl pyrrolidone, hydrolyzed gelatin, and ammonium sulfate.

As an example, the C-TAB.G5 or C-TAB.G5.1 isolated polypeptide formulation can be stabilized in sucrose, trehalose, poly(lactic acid) (PLA) and poly(lactide-co-glycolide) (PLGA) microspheres by suitable choice of excipient or stabilizer (Sanchez et al., 1999). Sucrose, or trehalose may be advantageously used as an additive because it is a non-reducing saccharide, and therefore does not cause aminocarbonyl reactions with substances bearing amino groups such as proteins. Sucrose or trehalose may be combined with other stabilizers such as saccharides.

Additionally, the formulation comprising the C-TAB.G5 or C-TAB.G5.1 isolated polypeptide may include therapeutic agents, such as e.g. anesthetics, analgesics, anti-inflammatories, steroids, antibiotics, antiarthritics, anorectics, antihistamines, and antineoplastics. Examples of such therapeutic agents include lidocaine and nonsteroidal anti-inflammatory drugs (NSAID). In another embodiment, the therapeutic agents are antigens and adjuvants. In still another embodiment, the formulation comprising antigen and/or adjuvant may be applied separately but along with other therapeutic agents, such e.g anesthetics, analgesics, anti-inflammatories, steroids, antibiotics, antiarthritics, anorectics, antihistamines, and antineoplastics. In a preferred embodiment, the antibiotics are fidaxomicin, metronidazole or vancomycin.

The formulation comprising the C-TAB.G5 or C-TAB.G5.1 isolated polypeptide may be delivered via various routes of administration such as e.g. intramuscularly.

Polymers may be added to the formulation and may act as an excipient, stabilizer, and/or preservative of an active ingredient as well as reducing the concentration of the active ingredient that saturates a solution used to dissolve the dry form of the active ingredient. Such reduction occurs because the polymer reduces the effective volume of the solution by filling the "empty" space. Thus, quantities of antigen/adjuvant can be conserved without reducing the amount of saturated solution. An important thermodynamic consideration is that an active ingredient in the saturated solution will be "driven" into regions of lower concentration. In solution, polymers can also stabilize and/or preserve the antigen/adjuvant-activity of solubilized ingredients of the formulation. Such polymers include ethylene or propylene glycol, vinyl pyrrolidone, and 0-cyclodextrin polymers and copolymers.

A single or unit dose of the formulation comprising the C-TAB.G5 or C-TAB.G5.1 isolated polypeptide suitable for administration is provided. The amount of adjuvant and/or C-TAB.G5 or C-TAB.G5.1 isolated polypeptide in the unit dose may be anywhere in a broad range from about 0.001 μg to about 10 mg. This range may be from about 0.1 ug to about 1 mg; a narrower range is from about 5 μg to about 500 μg. Other suitable ranges are between about 20 μg to about 200 μg, such as e.g. about 20 μg, about 75 μg or about 200 μg. A preferred dose for a C-TAB.G5 or C-TAB.G5.1 isolated polypeptide is from about 20 μg or 200 μg or less. The ratio between C-TAB.G5 or C-TAB.G5.1 isolated polypeptide and adjuvant may be about 1:1 or about 1:1.25, but higher ratios may also be used (e.g., about 1:10 or less), or lower ratios of C-TAB isolated polypeptide to adjuvant may also be used (e.g., about 10:1 or more).

The C-TAB.G5 or C-TAB.G5.1 isolated polypeptide may be used as an antigen and may be presented to immune cells, and an antigen-specific immune response is induced. This may occur before, during, or after infection by a pathogen, such as *C. difficile*. Only C-TAB.G5 or C-TAB.G5.1 isolated polypeptide may be required, but no additional adjuvant, if the immunogenicity of the formulation is sufficient to not require adjuvant activity. The formulation may include an additional antigen such that application of the formulation induces an immune response against multiple antigens (i.e., multivalent). Antigen-specific lymphocytes may participate in the immune response and, in the case of participation by B lymphocytes, antigen-specific antibodies may be part of the immune response. The formulations described above may include desiccants, excipients, humectants, stabilizers, and preservatives known in the art.

The formulation comprising the C-TAB.G5 or C-TAB.G5.1 isolated polypeptide of the present invention may be used to treat a subject (e.g., a human or animal in need of treatment such as prevention of disease, protection from effects of infection, reducing or alleviating the symptoms of a disease, such as CDAD, or combinations thereof). E.g. the formulation comprising the C-TAB.G5 or C-TAB.G5.1 isolated polypeptide of the present invention may be used to treat a subject at risk of CDAD, such as e.g. a subject with the following profile: i) a subject with a weaker immune system such as e.g. an elderly subject (e.g. a subject above 65 years of age) or a subject below 2 years of age; ii) an immunocompromised subject such as e.g. a subject with AIDS; iii) a subject taking or planning to take immunosuppressing drugs; iv) a subject with planned hospitalization or a subject that is in hospital; v) a subject in or expected to go to an intensive care unit (ICU); vi) a subject that is undergoing or is planning to undergo gastrointestinal surgery; vii) a subject that is in or planning to go to a long-term care such as a nursing home; viii) a subject with co-morbidities requiring frequent and/or prolonged antibiotic use; ix) a subject that is a subject with two or more of the above mentioned profiles, such as e.g. an elderly subject that is planning to undergo a gastrointestinal surgery; x) a subject with inflammatory bowel disease; and/or xi) a subject with recurrent CDAD such as e.g. a subject having experienced one or more episodes of CDAD.

The treatment may vaccinate the subject against infection by the pathogen or against its pathogenic effects such as those caused by toxin secretion. The formulation may be used therapeutically to treat existing disease, protectively to prevent disease, to reduce the severity and/or duration of disease, to ameliorate symptoms of disease, or combinations thereof.

The formulations comprising C-TAB.G5 or C-TAB.G5.1 isolated polypeptides may be delivered by various routes of administration including but not limited to oral, subcutaneous, intradermal, intravenous, intra-arterial, intramuscular, intracardial, intraspinal, intrathoracical, intraperitoneal, intraventricular, and/or sublingual routes.

The formulation may also comprise one or more adjuvants or combinations of adjuvants. Usually, the adjuvant and the formulation are mixed prior to presentation of the antigen but, alternatively, they may be separately presented within a short interval of time.

Adjuvants include, for example, an oil emulsion (e.g., complete or incomplete Freund's adjuvant), Montanide incomplete Seppic adjuvant such as ISA, oil in water emulsion adjuvants such as the Ribi adjuvant system, syntax adjuvant formulation containing muramyl dipeptide, aluminum hydroxide or salt adjuvant (ALUM), polycationic polymer, especially polycationic peptide, especially polyarginine or a peptide containing at least two LysLeuLys motifs, especially KLKLLLLLKLK (SEQ ID NO: 21), immunostimulatory oligodeoxynucleotide (ODN) containing nonmethylated cytosine-guanine dinucleotides (CpG) in a defined base context (e.g. as described in WO 96/02555) or ODNs based on inosine and cytidine (e.g. as described in WO 01/93903), or deoxynucleic acid containing deoxyinosine and/or deoxyuridine residues (as described in WO 01/93905 and WO 02/095027), especially Oligo(dIdC)$_{13}$ (as described in WO 01/93903 and WO 01/93905), neuroactive compound, especially human growth hormone (described in WO 01/24822), or combinations thereof, a chemokine (e.g., defensins 1 or 2, RANTES, MIP1-α, MIP-2, interleukin-8, or a cytokine (e.g., interleukin-1β, -2, -6, -10 or -12; interferon-γ; tumor necrosis factor-α; or granulocyte-monocyte-colony stimulating factor) (reviewed in Nohria and Rubin, 1994), a muramyl dipeptide variant (e.g., murabutide, threonyl-MDP or muramyl tripeptide), synthetic variants of MDP, a heat shock protein or a variant, a variant of *Leishmania major* LeIF (Skeiky et al., 1995), non-toxic variants of bacterial ADP-ribosylating exotoxins (bAREs) including variants at the trypsin cleavage site (Dickenson and Clements, 1995) and/or affecting ADP-ribosylation (Douce et al., 1997), or chemically detoxified bAREs (toxoids), QS21, Quill A, N-acetylmuramyl-L-alanyl-D-isoglutamyl-L-alanine-2-[1,2-dipalmitoyl-s-glycero-3-(hydroxyphosphoryloxy)]ethylamide (MTP-PE) and compositions containing a metabolizable oil and an emulsifying agent, wherein the oil and emulsifying agent are present in the form of an oil-in-water emulsion having oil droplets substantially all of which are less than one micron in diameter (see, for example, EP 0399843). Also, see Richards et al. (1995) for other adjuvants useful in immunization.

An adjuvant may be chosen to preferentially induce antibody or cellular effectors, specific antibody isotypes (e.g., IgM, IgD, IgA1, IgA2, secretory IgA, IgE, IgG1, IgG2, IgG3, and/or IgG4), or specific T-cell subsets (e.g., CTL, Th1, Th2 and/or $T_{DTH}$) (see, for example, Munoz et al., 1990; Glenn et al., 1995).

Unmethylated CpG dinucleotides or motifs are known to activate B cells and macrophages (Stacey et al., 1996). Other forms of DNA can be used as adjuvants. Bacterial DNAs are among a class of structures which have patterns allowing the immune system to recognize their pathogenic origins to stimulate the innate immune response leading to adaptive immune responses (Medzhitov and Janeway, 1997, Curr. Opin. Immunol. 9(1): 4-9). These structures are called pathogen-associated molecular patterns (PAMPs) and include lipopolysaccharides, teichoic acids, unmethylated CpG motifs, double-stranded RNA, and mannins. PAMPs induce endogenous signals that can mediate the inflammatory response, act as co-stimulators of T-cell function and control the effector function. The ability of PAMPs to induce these responses play a role in their potential as adjuvants and their targets are APCs such as macrophages and dendritic cells. PAMPs could also be used in conjunction with other adjuvants to induce different co-stimulatory molecules and control different effector functions to guide the immune response, for example from a Th2 to a Th1 response.

Other aspects of the invention is directed toward use of the C-TAB.G5 or C-TAB.G5.1 isolated polypeptide as vaccinating agent. The vaccines or immunogenic compositions of the present invention may employ an effective amount of the antigen. There will be included an amount of antigen which will cause the subject to produce a specific and sufficient immunological response so as to impart protection to the subject from subsequent exposure to *C. difficile*. The antigen may be the C-TAB.G5 or C-TAB.G5.1 isolated polypeptide. In one embodiment, the C-TAB.G5 or C-TAB.G5.1 isolated polypeptide is administered by itself or in combination with an adjuvant.

Another aspect of the invention includes use of the C-TAB.G5 or C-TAB.G5.1 isolated polypeptide as a subunit vaccine. A subunit vaccine refers to the use of a fragment of a pathogen as an inoculating agent. Those skilled in the art will know subunit vaccines offer a means to generate antibodies to a particular part or region of a pathogen.

Dosage schedule of administration and efficacy of the vaccine can be determined by methods known in the art. The amount of the vaccine and the immunization regimen may depend on the particular antigen and the adjuvant employed, the mode and frequency of administration, and the desired effect (e.g., protection and/or treatment). In general, the vaccine of the invention may be administered in amounts ranging between 1 µg and 100 mg, such as e.g. between 60 µg and 600 µg. A single dose of the vaccine comprising the C-TAB.G5 or C-TAB.G5.1 isolated polypeptide may be in a range from about 1 µg to about 1 mg, preferably from about 5 µg to about 500 µg, more preferably from about 20 µg to about 200 µg. The ratio between C-TAB.G5 or C-TAB.G5.1 isolated polypeptide and adjuvant such as alum may be about 1:1 such as e.g. 1:1.25, but higher ratios may also be used (e.g., about 1:10 or less), or lower ratios may also be used (e.g., about 10:1 or more). In an embodiment, in the vaccine comprising the C-TAB.G5 or C-TAB.G5.1 isolated polypeptide the adjuvant aluminum hydroxide will be used in a range from about 50 µg/mL to about 200 µg/mL, preferably in the amount about 125 µg/mL of the final formulation.

The vaccine comprising the C-TAB.G5 or C-TAB.G5.1 isolated polypeptide can be administered orally, intravenously, subcutaneously, intra-arterially, intramuscularly, intracardially, intraspinally, intrathoracically, intraperitoneally, intraventricularly, and/or sublingually.

The immunization regimen can be determined by methods known in the art. Administration of the vaccine can be repeated as is determined to be necessary by one skilled in the art. For example, a priming dose may be followed by 1, 2, 3 or more booster doses at weekly, bi-weekly or monthly intervals. In an embodiment of the present invention, the priming dose is followed by one or two booster administration in intervals from about 7 to about 14 days such as e.g. after 7 days and 21 days after first prime. In a preferred embodiment, the therapeutically effective amount of the vaccine is administered two or three times in intervals of 14 days+/−1, 2 or 3 days (bi-weekly) to a subject. In an embodiment of the present invention, the therapeutically effective amount of the vaccine is administered once.

Still another aspect is directed to the population which can be treated according to the present invention. In one embodiment, the population includes healthy individuals who are at risk of exposure to *C. difficile*, especially, the individuals impending hospitalization or residence in a care facility, as well as personals in hospitals, nursing homes and other care facilities. In another embodiment, the population includes previously infected patients who relapsed after discontinuation of antibiotic treatment, or patients for whom antibiotic treatment is not efficient.

In one more embodiment of the invention, the population includes individuals who are at least 18 years or more of age. In one preferred embodiment, the human subject is from 18 to 65 years old. In another preferred embodiment, the human subject is elderly individuals over 65 years of age. The latter age group being the most vulnerable population suffering from *C. difficile* infections. In some more embodiment, the human subject is younger than 18 years of age.

Methods of Using the C-TAB.G5 or C-TAB.G5.1 Isolated Polypeptide

The present invention also provides methods of using the isolated polypeptide. For example, the C-TAB.G5 or C-TAB.G5.1 isolated polypeptide may be used to prevent or treat diseases associated with *C. difficile*. By way of example, introducing the isolated polypeptides of the present invention into the immune system of a subject may induce an immune response that includes the subject producing antibodies directed against the isolated polypeptide. Such antibodies are useful for recognizing *C. difficile*.

The present invention provides methods of delivering isolated polypeptides to a subject comprising administering the isolated polypeptide to a subject. The isolated polypeptide may be administered as a liquid or as a solid. The isolated polypeptide may further include a pharmaceutically acceptable carrier.

The present invention also provides methods for identifying and isolating variable domains of an antibody that recognize and bind to toxin A and or toxin B comprising use of the C-TAB.G5 or C-TAB.G5.1 isolated polypeptide to produce an immune response, purifying and then characterizing the antibodies produced in response to the C-TAB.G5 or C-TAB.G5.1 isolated polypeptide. Identified epitopes may be of use for cloning further antibodies or fragments thereof.

One aspect of the present invention is directed in part to the treatment, the prevention, and the detection of *C. difficile*. In some embodiments, a subject, such as an animal, receives treatment and/or prevention and/or detection of *C. difficile*. In other embodiments, the animal is a human. For example, the polypeptides of the present invention may be used to raise antibodies to *C. difficile* in vivo. By way of further example, the polypeptides of the present invention may be used to determine if a subject produces antibodies to *C. difficile*. In some embodiments, the polypeptide is used to isolate antibodies. By way of example, polypeptides may be bound to an affinity matrix.

By way of further example, the nucleic acid of the present invention can be used to transform and/transfect cells to recombinantly produce the polypeptides and/or antibodies of the present invention. The nucleic acids of the present invention may also be used, for example, to determine if a subject is infected with *C. difficile*. By way of example, this can be achieved using methods of radiolabeled hybridization.

By way of further example, the antibodies of the present invention can be used to recognize an infection by *C. difficile*. By way of example, the antibodies can recognize native toxin A and/or toxin B as an antigen. The antibodies of the present invention can also be used to fight an infection by *C. difficile*. By way of example, humanized antibodies or antibody fragments or monoclonal antibodies can employ a subject's own immune response to a *C. difficile* infection. By way of further example, the antibodies of the present invention may be coupled to a cytokine or a toxin or an enzyme or a marker to assist in treating and detecting an infection.

Further aspects of the present invention relate to diagnostic assays. The present invention is of use with many assays known in the art. Those skilled in the art will recognize the wide array of research based uses for the polypeptides, nucleic acids and antibodies of the present invention. The polypeptides, antibodies and nucleic acids of the present invention may, for example, be labeled, such as with a radioactive, chemilu minescent, fluorescent and/or dye molecules. The antibodies, nucleic acids and polypeptides of the present invention lend themselves to use assays for example DNA assays (such as southern blotting), RNA assays (such as northern blotting), protein assays (such as western blotting), chromatographic assays (such as gas, liquid, HPLC, size-exclusion), immunoassays (such as ELISA) and structural assays (such as crystallography and NMR spectroscopy). The antibodies, polypeptides and nucleic acids of the present invention may further be used as probes. Assays which amplify the signals from a probe are also known to those skilled in the art.

Kits

The present invention provides kits comprising by way of example, and not limitation, nucleic acids encoding the C-TAB.G5 or C-TAB.G5.1 isolated polypeptide, the C-TAB.G5 or C-TAB.G5.1 isolated polypeptide, and/or antibodies against the C-TAB.G5 or C-TAB.G5.1 isolated polypeptide. The kits may include one or more containers and instructions for use in accordance with any of the methods of the invention described herein. The C-TAB.G5 or C-TAB.G5.1 isolated polypeptide and/or antibodies of the invention may be used in a variety of assays including immunoassays for detecting *C. difficile*. In one embodiment, the C-TAB.G5 or C-TAB.G5.1 isolated polypeptide serves to function as an antigen for the purposes of detecting antibody in biological samples. The containers may be unit doses, bulk packages (e.g., multi-dose packages) or sub-unit doses. The kits of this invention are in suitable packaging. Also contemplated are packages for use in combination with a specific device, such as an inhaler, nasal administration device or an infusion device. A kit may have a sterile access port. The container may also have a sterile access port. Kits may optionally provide additional components such as buffers and interpretive information.

The kits may be used to detect the presence of *C. difficile* or to detect a disease associated with *C. difficile*, such as CDAD. The kits may be used to prevent or treat diseases associated with *C. difficile*. The kits of the present invention may also be used to alleviate the symptoms of a disease associated with *C. difficile*.

Without further description, it is believed that one of ordinary skill in the art can, using the preceding description and the following illustrative examples, make and utilize the claimed invention. The following working examples therefore, specifically point out preferred embodiments of the present invention, and are not to be construed as limiting in any way the remainder of the disclosure. All articles, publications, patents and documents referred to throughout this application are hereby incorporated by reference in their entirety.

EXAMPLES

Example 1: Preparation of the C-TAB.G5 and C-TAB.G5.1 Isolated Polypeptides

This Example describes the preparation of isolated polypeptides comprising portions of the *C. difficile* toxins A (CTA) and B (CTB) for expression in *E. coli* cells. The method described below can be used for making various isolated polypeptides comprising CTA and CTB. As an example, an isolated polypeptide comprising a portion of the C-terminal domain of CTA and a portion of the C-terminal domain of CTB is described.

Example 1.1: Cloning of the C-TAB.G5 and C-TAB.G5.1 Gene Constructs

The portion of CTA gene (Accession No. YP-001087137) encoding amino acids 2026 to 2710 of the C-terminal domain was amplified by PCR from genomic DNA of *C. difficile* strain 630 (ATCC BAA-1382) using the following primers:

```
forward:
                                        (SEQ ID NO: 9)
5'-caccACTAGTatgaacttagtaactggatggc-3'
and reverse:
                                       (SEQ ID NO: 10)
5'- CTCGAGttagccatatatcccaggggc -3'.
```

Amplification with the forward primer created a SpeI site, and amplification with the reverse primer created of a XhoI site.

The portion of CTB gene (Accession No: YP-00108735) encoding amino acids 1850 to 2366 of the C-terminal domain was amplified by PCR using the following primers:

```
forward:
                                       (SEQ ID NO: 11)
5'-caccATGCATatgagtttagttaatagaaaacag-3' and reverse:
                                       (SEQ ID NO: 12)
5'-ggcCTCGAGctattcactaatcactaattgagc-3'.
```

Amplification with the forward primer created a NsiI site, and amplification with the reverse primer created a XhoI site.

PCR reactions were performed using PCR Super-Mix (Invitrogen). The cycle conditions was 95° C. for 2 minutes, 95° C. for 45 seconds, 55° C. for 50 seconds, 68° C. for 8 minutes (30 cycles), and 72° C. for 10 minutes. The PCR products were purified with Quick gene extraction kit (Invitrogen) and ligated into the PCR 2.1 TOPO vector (Invitrogen). The ligation mixtures were used to transform *E. coli* Mech-1 cells by heat shock. The transformants were plated on plates of ImMedia Amp Blue (Invitrogen). White colonies were picked and cultured in 15 ml tubes with 4 ml of LB medium containing 100 µg/ml ampicillin. Cultures were incubated overnight at 37° C. and plasmids were extracted with Quick plasmid miniprep kit (Invitrogen).

The CTA gene fragment in the PCR 2.1-TOPO/TA vector was digested with SpeI and XhoI, and the fragment was cloned into an intermediate vector, also digested with SpeI and XhoI, using T4 DNA Ligase. A linker containing three restriction sites (BgLII-NsiI-SacI) was then inserted at the 3' end of the CTA gene fragment by PCR using the following set of synthetic primers:

```
forward:
                                       (SEQ ID NO: 13)
5'-AGATCTATGCATGAGCTCctcgagcccaaa acgaaaggctcagc-3' reverse:
                                       (SEQ ID NO: 14)
5'-cggtccggggccatatatcccaggggcttttactcc-3'.
```

The CTB gene fragment in PCR 2.1-TOPO/TB was digested with NsiI and XhoI, and the digested CTB gene fragment was ligated to the intermediate vector containing the CTA gene and linker, which was also digested with NsiI and XhoI. The CTB gene was inserted 3' to the linker giving the construct sequence 5'-CTA-linker-CTB-3'. This fusion construct is referred to as C-TAB.V1 intermediate vector.

The C-TAB.G5 gene was amplified by PCR from C-TAB.V1 intermediate vector using the primers:

```
forward:
                                       (SEQ ID NO: 15)
5'- caccCCATTGatggtaacaggagtatttaaagga reverse:
                                       (SEQ ID NO: 16)
5'-CTCGAGctattcactaatcactaattgagctg.
```

PCR reactions were performed using PCR Super mix (Invitrogen). The cycle condition was 95° C. for 2 minutes, 95° C. for 45 seconds, 55° C. for 50 seconds, 68° C. for 4 minutes (30 cycles) and 72° C. for 10 minutes. The PCR products were purified with Quick gene extraction kit (Invitrogen) and ligated into the PCR2.1-TOPO vector (Invitrogen). The ligation mixtures were used to transform *E. coli* Mech-1 cells by heat shock. The transformants were plated on plates of ImMedia Amp Blue (Invitrogen). White colonies were picked and cultured in 15 ml tubes with 4 ml of LB medium containing 100 µg/ml ampicillin. Cultures were incubated overnight at 37° C. and plasmids were extracted with Quick plasmid mini-prep kit (Invitrogen). The C-TAB.G5 fusion gene in the PCR 2.1-TOPOTA vector was digested with NcoI and XhoI restriction enzyme. These C-TAB fragments were ligated into the pET28 expression vector digested with the same restriction enzymes. This resulting construct encodes the toxin A C-terminal domain from amino acids 2272 to 2710 fused to toxin B C-terminal domain from amino acids 1851 to 2366. The pET28/C-TAB.G5 construct was transformed into *E. coli* BL21 (DE3) for expression. Five colonies containing the C-TAB.G5 fusion gene were selected for analysis.

The C-TAB.G5.1 coding sequence was obtained by codon optimization for improved expression within an *E. coli* host cells. The codon usage was adapted to the codon bias of *E. coli* genes. In addition, GC content was adjusted to prolong mRNA half life; a region of very high (>80%) or very low (<30%) GC content have been avoided. Therefore, the optimized gene allows high and stable expression rates in *E. coli*. The codon optimized C-TAB.G5.1 gene was synthesized in situ and subcloned into the expression vector pET-28b(+).

DNA Sequencing: Plasmid DNA sequences were confirmed using dye terminator cycle sequencing chemistry with d-Rhodamine dyes. Sequencing data were analyzed using Jellyfish software.

Example 1.2: Expression of the Recombinant C-TAB.G5 or C-TAB.G5.1 Fusion Proteins in *E. coli*

Expression of C-TAB.G5 and C-TAB.G5.1 gene constructs may be done using standard procedure for expression in *E. coli*.

Screening colonies for expression of the recombinant C-TAB fusion protein: For the purpose of screening, colonies were picked and grown in 15 ml Falcon tubes with 4 ml of LB media with 50 µg/ml kanamycin. The tubes were cultured overnight at 37° C. with mixing at 250 rpm. Following initial growth phase, 1 ml of culture from each tube was transferred to a 24-well tissue culture plate and expression was induced with 1 mM isopropyl-β-D-1-thio-galacto-puranoside (IPTG) for 3 h at 30° C. The cell pellets were collected by centrifugation at 12,000 g for 1 min in microcentrifuge. Cell pellet lysates were prepared, and the soluble fraction was assayed by SDS-PAGE and Western Blot analysis for expression of C-TAB fusion protein. Positive clones were selected for further evaluation.

Batch fermentation for C-TAB.G5 expression: Seed cultures were grown in five 500 ml shake flasks each containing 150 ml Super Broth medium supplemented with 30 µg/ml kanamycin. Cultures were grown for 12 h at 28° C. with continuous agitation at 275 rpm until $OD_{600}$ reached 2-2.5. The shake flasks were used to inoculate a fermenter containing 10 L Super Broth. The culture was grown approximately 4.5 h at 37° C. to $OD_{600}$=3.5-4. For induction of the product expression 0.1 mM IPTG was added and growth continued for additional 4 h at 25° C. Then the cells were harvested by centrifugation and the cell paste stored frozen at −70° C. A typical product specific expression rate achieved by this fermentation process was about 200 mg/ml.

Fed-batch fermentation for C-TAB.G5.1 preparation: An aliquot of 500 µl of the glycerol stock of a seed bank (stored at −75° C.) was used to inoculate 100 ml pre-culture medium supplemented with 30 µg/ml kanamycin in a 1 L shake flask. The pre-culture was incubated at 37° C. under constant agitation at ~150 rpm for approximately 7 h until it reached $OD_{600}$=1.0-2.0. 25 mL of pre-culture was used to inoculate 7 L batch fermentation medium in a standard industry 15 L fermenter equipped with process control system, able to perform fed-batch fermentations. 7 L batch culture phase was carried for 12 h at 37° C. ($OD_{600}$=12-15) until glucose was exhausted. Glucose feed phase (biomass production) was then initiated by an exponential feed mode at a specific growth rate constant µ=0.25/h at 37° C. for 6 h ($OD_{600}$=40-50). One hour before switching to a constant feed phase and induction with a final concentration of 1 mM IPTG (product production), temperature was reduced to 30° C. to lower the risk of inclusion body formation. Product expression phase was continued for another 5 h with constant feed at 30° C. ($OD_{600}$=~100), resulting in a total fermentation process time of 23 h and a final culture volume of ~8.2 L. A wet cell biomass of about 1.2 kg was harvested by centrifugation and stored at ≤−70° C. A typical product specific expression rate reached by such fed-batch fermentation was up to 1.3 g/L.

Example 1.3: Purification of the Recombinant C-TAB.G5 or C-TAB.G5.1 Fusion Proteins Purification of C-TAB.G5 analytical sample: Frozen cell paste was thawed and resuspended in 10 mM citric acid/NaOH buffer at pH 5.6, and the cell slurry was passed two times through a homogenizer (GEA Niro Soavi homogenizer) at 550 bar. The suspension was centrifuged two times: once at 13500 rpm for 30 minutes and the second time at 18000 rpm in an ultracentrifuge for one hour. The supernatants were pooled, and the pH adjusted to 5.6 with 50 mM citric acid buffer pH 3. Clarified cell lysates were passed over a SP fast flow column with 10 mM citric acid/NaOH buffer at pH 5.6. Proteins were eluted with a liner gradient of sodium chloride increasing from 0 to 500 mM in 20 mM NaPi. Fractions containing the C-TAB.G5 were pooled. The conductivity was adjusted down to 5 mS/cm with distilled $H_2O$. Tris was added to a 25 mM final concentration. The pooled fractions were passed over a DEAE fast flow column. Protein was eluted with a linear gradient of sodium chloride increasing from 50 to 500 mM in 25 mM Tris. Again, fractions containing C-TAB.G5 were pooled and 1.5 M Na-Citrate, pH 7.5 was added to a final concentration of 0.4 M. The C-TAB.V1 pool was loaded onto a phenol Sepharose HP column equilibrated with 25 mM Tris, 0.4 M Na-Citrate pH 7.5. C-TAB.G5 fusion protein was eluted with a reducing salt concentration in a liner gradient using 5 mM Tris, pH 7.5. All columns were monitored by an AKTA Prime chromatography system. Purified C-TAB fusion protein was buffer exchanged to PBS using a 50 K membrane.

Purification of C-TAB.G5.1 bulk preparation: Biomass was stored at −80° C. until processing. 450 g frozen cell paste (equivalent to 2.90 L fermenter) is diluted with 4 volumes of lysis buffer (20 mM Hepes, pH 7.5, ~0.6 mS/cm) (e.g. 450 g paste+1800 mL buffer) and thawed by this way for ~1 h±0.5 h under mechanical agitation. Optional, remaining clumps can be resuspended using an Ultraturrax (e.g. 5 min at 8000 rpm). Cell lysis is done on a Niro Soavi Panda high homogenizer (640±25 bar, 3 cycles). The lysate is cooled down to <10° C. using a heat exchanger and kept at this temperature until centrifugation. The crude cell lysate is submitted to a batch centrifugation step (Beckmann Avanti JLA 60.25) operated at 14000 rpm (30000 g) at 4° C. for 30 min. The supernatants are collected and pooled. The semi-liquid part of the pellet is discarded too, to decrease the risk of clogging the filtration step. The pooled supernatants are then filtered through a Supercap PDH4 100/5 inch depth filter capsule (Pall) (250 $cm^2$ effective filtration area). The remaining lysate in the filter housing is flushed out with lysis buffer. After clarification, an aliquot of 1M Tris stock solution, pH 7.5 is added to the lysate to a final concentration of 25 mM. The buffer composition of final lysate is 20 mM Hepes, 25 mM Tris, pH 7.5, conductivity ~6 mS/cm). The lysate might be still slightly turbid after filtration, but this does not affect the following capture step. Capture step is performed at room temperature with DEAE Sepharose FF (GE Healthcare) in a XK50/30 column (GE Healthcare) of following dimensions: diameter 50 mm, packed bed height 20 cm, packed bed volume ~400 mL. The loading density is approx. 0.8 to 1.2 g biomass/mL gel. The process is run by an Äkta Explorer system (GE Healthcare) and monitored at 280 nm. Equilibration is performed at 100 cm/h with approx. 5 CV of 25 mM Tris, 20 mM Hepes, 25 mM NaCl, pH 7.5, conductivity ~5 mS/cm until pH, conductivity and 280 nm absorbance are stable. The lysate is loaded onto the column at 75 cm/h and the flow through is discarded. When all filtrated lysate is loaded, flow is resumed with approx. 5 CV of equilibration buffer until the 280 nm absorbance is stabilized. Impurities are removed from the column during wash step 2 with 5 CV of 25 mM Tris, 175 mM NaCl, pH 7.5, conductivity 19 mS/cm. The C-TAB protein is eluted from the column by step elution with 3 CV of 25 mM Tris, 375 mM NaCl, pH 7.5, conductivity 36 mS/cm. The collection of the C-TAB containing fractions begins when 280 nm absorbance starts to increase (usually after 1 CV) and lasts for about 0.5 to 1.0 CV. The pooled fractions containing C-TAB can be stored at 2-8° C. over night. Intermediate purification step is done with SP-Sepharose FF (GE Healthcare) in a XK50/30 column (GE Healthcare) at room temperature with the following dimensions: diameter 50 mm, packed bed height 20 cm, packed bed volume ~400 mL. The maximum loading density is approx. 4-5 mg C-TAB/mL gel. The process is run by an Äkta Explorer system (GE Healthcare) and monitored at 280 nm. Equilibration, washing and linear gradient elution steps are performed at a maximum flow rate of 200 cm/h (65 mL/min) unless exceeding back pressure (>4 bar) prevents it. Equilibration is performed with approx. 5-10 CV of buffer G at 200 cm/h until pH, conductivity and 280 nm absorbance are stable. Before loading, the DEAE pool has to be adjusted to allow binding of C-TAB on SP-FF resin. DEAE pool is diluted 25 fold with SP-FF equilibration buffer (10 mM citric acid, 2 mM EDTA, pH 5.5±0.1, conductivity ~2 mS/cm) to a final conductivity of not more than 3.5 mS/cm, pH 5.5±0.1. If necessary additional MilliQ water is added to achieve the desired conductivity. Note that low conductivity is very critical to allow binding of C-TAB onto SP-FF. The sample is loaded onto the column at 150 cm/h and the flow through is discarded. After loading the sample, flow is resumed with approx. 5 CV of equilibration buffer at 200 cm/h until the 280 nm absorbance is stabilized. Elution is done by linear gradient at 100 cm/h from 0% equilibration buffer to 30% 20 mM sodium phosphate, 500 mM NaCl, pH 7.0 over 10 CV. Fractions are collected and pooling is performed by UV 280 nm absorbance. Pooling starts at 15% of peak maximum and ends at 15% of peak maximum. The pool is immediately adjusted to 400 mM citrate (final pH 7, approx. 49 mS/cm) using a 1.5 M citrate stock solution, pH 8.0. The adjusted SPFF pool should have pH 7 and approx. 49 mS/cm and is stored at 2-8° C. over night.

Polishing chromatography step is performed with Phenyl-Sepharose HP (GE Healthcare) in a XK50/30 column (GE Healthcare) at room temperature with the following dimensions: diameter 50 mm, packed bed height 15 cm, packed bed volume ~300 mL. The loading density is approx. 4-5 mg C-TAB/mL gel. The process is run by an Äkta Explorer system (GE Healthcare) and monitored at 280 nm. Equilibration, loading, washing and elution steps are performed at a maximum flow rate of 100 cm/h (33 mL/min) unless exceeding back pressure (>4 bar) prevents it. In such a case the flow rate has to be reduced. Equilibration is performed with approx. 5-10 CV of 25 mM Tris, 400 mM sodium citrate, pH 7.5, 46 mS/cm at 100 cm/h until pH, conductivity and 280 nm absorbance are stable. The sample is loaded onto the column at 100 cm/h and the flow through is discarded. After loading the sample, flow is resumed with approx. 5 CV of equilibration buffer at 100 cm/h until the 280 nm absorbance is stabilized. Elution is done by linear gradient at 100 cm/h from 100% equilibration buffer/0% 5 mM Tris, pH 7.5, 0.5 mS/cm to 100% 5 mM Tris, pH 7.5, 0.5 mS/cm over 20 CV. Fractions are collected and pooling is performed by UV280 nm absorbance. Pooling starts at approx. 10-15% of peak maximum and ends at approx. 20% of peak maximum. The adjusted pool is stored at 2-8° C. over night. Preparation of final C-TAB drug substance protein solution is achieved by 30 kDa cut-off tangential flow filtration (TFF, Pellicon 2 membrane, Millipore) operated at room temperature. The protein solution is diafiltered against formulation buffer (20 mM Histidine, 75 mM NaCl, 5% Sucrose, 0.025% Tween®80, pH 6.5) until the permeate pH equals 6.5±0.2).

Final protein concentration is adjusted to 2 mg/mL according to UV measurement at 280 nm using 1.566 as the specific extinction coefficient at 280 nm for C-TAB (protein conc. 1 mg/mL, 1 cm cuvette).

SDS-PAGE and Western Blot Analysis: Whole cell lysates and purified C-TAB.G5 or C-TAB.G5.1 fusion protein were resuspended in Nu-Page sample buffer containing beta-mercaptoethanol and boiled for 10 min. Samples (25 µl) were loaded onto 3-8% Tris-Acetate gel. Following electrophoresis (150 V for 1 h), proteins were visualized by staining the gels with simply blue stain or used for Western blot analysis.

C-TAB.G5 or C-TAB.G5.1 specific expression was determined by Western blot analysis using toxin-specific antibodies. Proteins were transferred at 23 V for 60 min onto a PVDF membrane using 1× Transfer buffer in 10% methanol. Membranes were blocked for 1 h at room temperature with 0.5% casein in phosphate buffered saline (PBS). Transfer membranes were incubated for 2 hrs at room temperature with either a monoclonal antibody against Toxin B (GenWay; clone B426M) or an in-house derived Guinea Pig polyclonal antibody against Toxin A (List Biological Labs). Washed membranes were incubated with horseradish peroxidase conjugated anti-guinea pig IgG or anti-mouse IgG. The blots were washed and AEC substrates were added. The blots were incubated with gentle mixing for 5-10 minutes. The blots were rinsed with water to stop color development.

RBC hemagglutination: The cell binding domain of toxin A but not toxin B has been shown to be capable of agglutinating rabbit red blood cells (RBCs). The agglutination process is the result of the binding of toxin A to a glycan sequence found on blood antigens on rabbit RBCs. Samples (C-TAB.G5 and native toxin A) are diluted to 100 µg/ml in PBS. In a V-bottom microtiter plate, two-fold serial dilutions are prepared in duplicate across the plate, starting at 100 µg/ml and leaving 50 µl of the dilution in each well. Fifty microliters of a 0.75% rabbit RBC/PBS suspension is added to each well of the microtiter plate and the plate is incubated for 1 h at room temperature. Hemagglutination is indicated by the failure to form a pellet of RBCs on the bottom of the plate. The hemagglutination titer of a sample is represented by the concentration of protein present in the well with the highest sample dilution in which no RBC pellet is observed.

Example 2: Dose Titration of the Recombinant C-TAB.G5 Fusion Protein in the Presence and Absence of Alum in Mice This study was to determine the feasibility of an in vivo dose titration of C-TAB.G5 with and without alum adjuvant as a C-TAB potency assay. The alum utilized was Alydragel, (alum hydroxide, Brenntag). C57BL/6 female mice (Charles River Labs.), aged between 8 and 9 weeks, were utilized for immunization. All animals received a first immunization by intramuscular (IM) injection (50 µl) into the right thigh muscle on day 0. The second immunization was done by IM injection into the left thigh muscle on day 14. A total of 72 mice were divided into 12 groups vaccinated as follows:

Group 1: PBS only
Group 2: 100 (154) ng C-TAB.G5
Group 3: 300 (462) ng C-TAB.G5
Group 4: 1,000 (1,540) ng C-TAB.G5
Group 5: 3,000 (4,620) ng C-TAB.G5
Group 6: 10,000 (15,400) ng C-TAB.G5
Group 7: PBS with 50 µg alum
Group 8: 10.0 (15.4) ng C-TAB.G5 with 50 µg alum OH
Group 9: 30.0 (46.2) ng C-TAB.G5 with 50 µg alum OH
Group 10: 100 (154) ng C-TAB.G5 with 50 µg alum OH
Group 11: 300 (462) ng C-TAB.G5 with 50 µg alum OH
Group 12: 1,000 (1,540) ng C-TAB.G5 with 50 µg alum OH In this study the protein concentration was firstly determined according to the standard protocol Quick Start™ Bradford Protein Assay (Bio-Rad). Lately, the protein concentration (shown in parentheses) was re-determined by UV measurement at 280 nm according to the procedure described in Example 1.3. In all follow-up studies the protein concentration was measured by UV method.

Blood samples were collected from all animals two weeks after the first immunization (study day 14) and two weeks after the second immunization (study day 28). The serum was stored at −20° C. until analyzed.

Serum IgG ELISA: Serum antibodies elicited to C-TAB.G5 or C-TAB.G5.1 (referred as C-TAB), toxin A and toxin B or toxoids thereof were evaluated in an enzyme linked immunosorbent assay (ELISA). Briefly, stock solutions of 1.0 µg/ml of toxin A, toxin B or the C-TAB.G5 isolated polypeptide were prepared in PBS and 100 µl were added to each well of a 96-well plates. After overnight incubation at 4° C., the plates were washed and blocked with 0.5% casein blocking buffer. Plates were washed again and serial, two-fold dilutions of test sera added to the plates. After a second overnight incubation at 4° C., plates were washed and incubated with peroxidase-conjugated anti-mouse IgG (H+L). After a 2 hours incubation at room temperature, the plates were again washed, peroxidase substrate (2,2'-azinobis(3-ethylbenzthiazoline-6-sulfonate) added and color allowed to develop for 2 h at room temperature. The reaction was stopped by adding 50 µl of 2% SDS to the wells. Plates are read with an ELISA plate reader at an absorbance of 405 nm. Serum antibody titers are reported as the geometric mean of ELISA Units, which are the serum dilutions that results in an OD 405 nm reading of 1.0. As a negative control a pool sample of pre-immune serum obtained from animals pre-bled before the first immunization was used to evaluate an antibody response.

Animals receiving C-TAB.G5 demonstrated a dose dependent increase in antibody titers, with the alum adjuvant allowing for significantly improved antibody titers at a lower dose of C-TAB.G5. FIG. 3 shows the titers for anti C-TAB, anti-toxin A and anti-toxin B IgG. FIG. 4 shows a graphical comparison of antibody titers in the presence or absence of alum.

Example 3: Immunogenicity and Protective Efficacy of C-TAB.G5 in Mice

This study was to evaluate the immunogenicity and protective efficacy of C-TAB.G5 in vaccinated mice receiving a lethal challenge of *C. difficile* toxin A or toxin B. Female C57BL/6 mice (Charles River Labs.), aged 6-7 weeks, were utilized for this study. All animals received the first vaccination by intramuscular (IM) injection (50 µl) into the right thigh muscle on day 0. The second vaccination was done by IM injection into the left thigh muscle on day 14. 116 mice were divided into groups vaccinated as follows:

Group 1: PBS only
Group 2: 3 µg C-TAB.G5
Group 3: 10 µg C-TAB.G5
Group 4: 30 µg C-TAB.G5
Group 5: 3 µg C-TAB.G5+50 µg alum OH
Group 6: 10 µg C-TAB.G5+50 µg alum OH
Group 7: 30 µg C-TAB.G5+50 µg alum OH
Group 8: PBS only
Group 9: 3 µg C-TAB.G5
Group 10: 10 µg C-TAB.G5
Group 11: 30 µg C-TAB.G5
Group 12: 3 µg C-TAB.G5+50 µg alum OH
Group 13: 10 µg C-TAB.G5+50 µg alum OH
Group 14: 30 µg C-TAB.G5+50 µg alum OH Blood samples were collected from all animals two weeks after the second immunization (study day 28). The serum was stored at −20° C. until analyzed. Serum antibody titers to C-TAB, toxin A and toxin B were then determined by ELISA and reported as ELISA Units (EU).

FIG. 5 shows serum antibody titers to C-TAB, toxin A and toxin B in mice evaluated two weeks after the second immunization (study day 28). This study demonstrated that the C-TAB.G5 fusion protein is highly immunogenic in mice and is able to induce strong antibody response against both toxin A and toxin B even without adding an adjuvant. The C-TAB.G5 immunogenicity can be significantly augmented (more than a one log) by co-delivery with alum hydroxide. The animals receiving C-TAB.G5 with or without alum demonstrated 2-fold increased antibody response over a one log dose range.

Besides evaluating antibody titers, the antibodies generated by immunization with C-TAB.G5 were assessed for their ability to neutralize native toxin A and B in in vitro toxin neutralization assay (TNA).

Toxin Neutralizing Antibody Assay (TNA). For in vitro analysis, 125 µl of either toxin A (5 ng/ml) or toxin B (1 ng/ml) was incubated with 125 µl of serial dilutions of anti-sera obtained from immunized mice. After one hr of incubation at 37° C., the toxin:serum mixture was added to microtiter wells containing Vero cells (monkey kidney cells), and the microtiter plates incubated for 18 hr. Incubation of either toxin A or B with Vero cells resulted in a change in cell morphology and a loss of cell adherence which was measured by neutral red staining of toxin treated cells after removal of non-adherent cells. The toxin neutralization titer of a serum is reported as the serum dilution which gives a 50% reduction in toxin activity.

The results of the TNA assay are shown in FIG. 6. The data indicate that antibodies generated following immunization with the C-TAB.G5 alone are capable of neutralizing the toxic activity of native toxin A but not toxin B. When the C-TAB.G5 was co-delivered with alum, TNA titers were augmented with approximately 6-fold increase in anti-toxin A TNA and only 2-fold lower titers in anti-toxin B TNA. This data indicates that the C-TAB.G5 isolated polypeptide not only retains the antibody recognition antigenic epitopes present in the native toxins, but comprises critical antigenic epitopes required for the generation of functional toxin neutralizing antibody. Thus, C-TAB.G5 is effective in neutralizing toxic effects of *C. difficile* toxin A and toxin B and, therefore, is useful in vaccination.

In addition to assessing antibody response, the ability of C-TAB.G5 immunization to protect mice from a lethal challenge of native toxins was determined. Three weeks after the second vaccination (study day 35) animals in vaccinated and non-vaccinated groups (N=8) received intraperitoneally (IP) a lethal dose of either 25 ng of toxin A or 50 ng of toxin B. Survival of the mice was monitored over the following 9 days and the results are shown in FIG. 6. This experiment demonstrated that immunization of mice with C-TAB.G5 in the absence of the alum adjuvant was capable of conferring 100% protection against a lethal challenge with native toxin A and 50% protection against toxin B challenge. Co-delivery of C-TAB.G5 with Alum enhanced the protective immunity to toxin B up to 100% protection. This data indicates that C-TAB.G5 vaccination induces an immune response sufficient to protect mice from the toxic effects of both toxin A and B in the lethal challenge model.

Example 4: Evaluation of the Immunogenicity and Protective Efficacy of C-TAB.G5 in Young and Aged Mice This study was to compare the immune response mounted against C-TAB.G5 in young and aged mice. Female C57BL/6 mice (Charles River Labs.), aged 6-7 weeks and 18 months, respectively, were utilized for this study. All animals received the first vaccination by intramuscular (IM) injection (50 µl) into the right thigh muscle on day 0. The second vaccination was done by IM injection into the left thigh muscle on day 14. 192 mice were divided into groups vaccinated as follows:
  Group 1: PBS to young mice
  Group 2: PBS to aged mice
  Group 3: 10 µg C-TAB.G5 to young mice
  Group 4: 30 µg C-TAB.G5 to young mice
  Group 5: 10 µg C-TAB.G5 to aged mice
  Group 6: 30 µg C-TAB.G5 to aged mice
  Group 7: 10 µg C-TAB.G5+50 µg alum OH to young mice
  Group 8: 30 µg C-TAB.G5+50 µg alum OH to young mice
  Group 9: 10 µg C-TAB.G5+50 µg alum OH to aged mice
  Group 10: 30 µg C-TAB.G5+50 µg alum OH to aged mice
  Group 11: PBS to young mice
  Group 12: PBS to aged mice
  Group 13: 10 µg C-TAB.G5 to young mice
  Group 14: 30 µg C-TAB.G5 to young mice
  Group 15: 10 µg C-TAB.G5 to aged mice
  Group 16: 30 µg C-TAB $5^{th}$ to aged mice
  Group 17: 10 µg C-TAB.G5+50 µg alum OH to young mice
  Group 18: 30 µg C-TAB.G5+50 µg alum OH to young mice
  Group 19: 10 µg C-TAB.G5+50 µg alum OH to aged mice
  Group 20: 30 µg C-TAB.G5+50 µg alum OH to aged mice Three weeks after the second vaccination (study day 35) animals in vaccinated and non-vaccinated groups (N=6) received a lethal challenge by intraperitoneal (IP) injection with 25 ng toxin A or 50 ng toxin B. Survival of the mice was monitored over the following 9 days.

Blood samples were collected from all animals two weeks after the first immunization (study day 14) and two weeks after the second immunization (study day 28). The serum was stored at −20° C. until analyzed. Serum antibody titers to C-TAB, toxin A and toxin B were then determined by and reported as ELISA Units (EU). Toxin A and toxin B neutralizing antibodies (TNA) were determined using Vero cells treated with a cytotoxic amount of recombinant toxin A and toxin B.

Young animals receiving the C-TAB.G5 vaccine demonstrated significantly higher levels of all antibodies tested, as compare to old animals. Especially high antibody titers were obtained in young mice vaccinated with C-TAB.G5 in the presence of alum hydroxide (FIG. 7). Particularly significant improvement was achieved in toxin B TNA titer. At the same time, there was no big difference between young and aged mice in ability to withstand the toxin A and toxin B challenges. However, both groups demonstrated improved protection rate when vaccinated in the presence of alum. FIG. 7 shows a comparison of C-TAB.G5 immunogenicity and protective efficacy in young vs. old mice. FIG. 8 shows the kinetics of anti-C-TAB antibody development in young and old mice.

Example 5: Comparison of the Immunogenicity and Protective Efficacy of C-TAB.G5.1 and Toxoid A and B This study was to compare the immunogenicity and protective efficacy of C-TAB.G5.1, vs. toxoid A/B. The toxoid A/B used was the mixture of equal parts (1:1) of toxoid A (lot #1009132) and toxoid B (lot #1009133). Toxoid was prepared by formalin fixation and provided by TechLab. Female C57BL/6 mice (Charles River Labs.), aged 6-7 weeks, were utilized for this study. All animals received the first vaccination by intramuscular (IM) injection (50 µl) into the right thigh muscle on day 0. The second vaccination was done by IM injection into the left thigh muscle on day 14. 180 mice were divided into groups vaccinated as follows:
  Group 1: PBS only
  Group 2: 10 µg C-TAB.G5.1
  Group 3: 30 µg C-TAB.G5.1
  Group 4: 10 µg C-TAB.G5.1+50 µg alum OH
  Group 5: 10 µg C-TAB.G5.1+50 µg alum OH
  Group 6: 30 µg toxoid A/B
  Group 7: 10 µg toxoid A/B
  Group 8: 30 µg toxoid A/B+50 µg alum OH
  Group 9: 30 µg toxoid A/B+50 µg alum OH
  Group 10: PBS
  Group 11: 10 µg C-TAB.G5.1
  Group 12: 30 µg C-TAB.G5.1
  Group 13: 10 µg C-TAB.G5.1+50 µg alum OH
  Group 14: 30 µg C-TAB.G5.1+50 µg alum OH
  Group 15: 10 µg toxoid A/B
  Group 16: 30 µg toxoid A/B
  Group 17: 10 µg toxoid A/B+50 µg alum OH
  Group 18: 30 µg toxoid A/B+50 µg alum OH Three weeks after the second vaccination (study day 35) animals in vaccinated and non-vaccinated groups (N=6) received a lethal challenge by intraperitoneal (IP) injection with 28 ng toxin A or 50 ng of toxin B. Survival of the mice was monitored over the following 9 days.

Blood samples were collected from all animals two weeks after the first immunization (study day 14) and two weeks after the second immunization (study day 28). The serum was stored at −20° C. until analyzed. Serum antibody titers to C-TAB, toxin A and toxin B were then determined by ELISA and reported as ELISA Units (EU). Toxin A and toxin B neutralizing antibodies (TNA) were determined using Vero cells treated with a cytotoxic amount of recombinant toxin A and toxin B.

This study demonstrates immunogenicity and protective efficacy of C-TAB.G5.1 and toxoid A/B in mice after two vaccinations. Animals receiving C-TAB.G5.1 showed lower but significant anti-C-TAB antibody titers, as compare to animals receiving toxoid A/B. Also, co-delivery of alum greatly augmented all tested antibody responses. As a result, the level of anti-C-TAB and anti-toxin A antibodies achieved in animals immunized either with C-TAB.G5.1 or with toxoid A/B in the presence of alum are similar. The only lower antibody titer was observed for anti-toxin B antibody when mice were immunized with C-TAB.G5.1, as compare to mice immunized with toxoid A/B. Noteworthy, unlike the antibodies generated against C-TAB.G5.1 recognizing epitopes in the C-terminal portion of the toxin molecules, antibodies induced with toxoid immunization were specific to the N-terminal portion of the toxin molecules, which was read out in the anti-toxin ELISA. Thus, anti-toxin A and anti-toxin B antibodies generated in mice immunized with C-TAB.G5.1 and toxoid A/B were antibodies of different specificity and, therefore, can not be compared directly. However, the data indicates that antibody response to C-TAB.G5.1 immunization is significantly high, like in case of immunization with toxoids. In addition, the toxin challenge study demonstrated that ability of C-TAB.G5.1 immunization to protect mice against from a lethal challenge is comparable to protection efficacy of toxoid A and B. FIG. 9 shows a comparison of the immunogenicity of C-TAB.G5.1 and toxoid A/B. FIG. 10 shows the toxin neutralization and protection data for mice immunized with C-TAB.G5.1 as compared to those immunized with toxoid A/B.

Example 5.1: Comparison of Antibody Titers and Protective Efficacy of C-TAB.G5.1 in Different Immunization Regimens This study was to compare the immunogenicity and protective efficacy of C-TAB.G5.1 in mice receiving three doses of the vaccine in different immunization regimens. Female C57BL/6 mice (Charles River Labs.), aged 6-7 weeks, were utilized for this study. 135 mice were divided into 14 groups. All animals in groups no. 2-13 received three vaccinations by intramuscular (IM) injection (50 μl) into the right thigh muscle or left thigh muscle in days indicated below. Mice in groups 1 and 8 did not received vaccination; they served as a negative control. The immunization was performed as follows:

| Group | Vaccine | Immunization day (route) |
|---|---|---|
| 1 | — | — |
| 2 | 10 μg G5.1 | 0 (R), 3 (L), 14 (R) |
| 3 | 10 μg G5.1 + 50 μg Alum | 0 (R), 3 (L), 14 (R) |
| 4 | 10 μg G5.1 | 0 (R), 7 (L), 21 (R) |
| 5 | 10 μg G5.1 + 50 μg Alum | 0 (R), 7 (L), 21 (R) |
| 6 | 10 μg G5.1 | 0 (R), 14 (L), 28 (R) |
| 7 | 10 μg G5.1 + 50 ug Alum | 0 (R) ,14 (L), 28 (R) |
| 8 | — | — |
| 9 | 10 μg G5.1 | 0 (R), 3 (L), 14 (R) |
| 10 | 10 μg G5.1 + 50 μg Alum | 0 (R), 3 (L), 14 (R) |
| 11 | 10 μg G5.1 | 0 (R), 7 (L), 21 (R) |
| 12 | 10 μg G5.1 + 50 μg Alum | 0 (R), 7 (L), 21 (R) |
| 13 | 10 μg G5.1 | 0 (R), 14 (L), 28 (R) |
| 14 | 10 μg G5.1 + 50 μg Alum | 0 (R), 14 (L), 28 (R) |

(R) = right thigh muscle (L)—left thigh muscle

Blood samples were collected from all animals on study day 0, 3, 7, 14, 21, 28, 35 and 42. The serum was stored at −20° C. until analyzed. Serum antibody titers to C-TAB, toxin A and toxin B were determined by ELISA and reported as ELISA Units (EU). Toxin A and toxin B neutralizing antibodies (TNA) were determined on study day 42 using Vero cells treated with a cytotoxic amount of recombinant toxin A and toxin B.

Three weeks after the last vaccination (study day 49) animals in vaccinated and non-vaccinated groups (N=8) received a lethal challenge by intraperitoneal (IP) injection with 28 ng toxin A or 50 ng toxin B. Survival of the mice was monitored over the following 9 days.

This study demonstrates that all antibody titers measured two weeks after the third vaccination or on study day 35 and 42 are comparable in all immunization regimens, although the immunization regimen of 0/14/28 shows the best antibody responses. If compare antibody titers measured two weeks after the second vaccination, then the immunization regimen of 0/14/28 is better than the immunization regimen of 0/7/21, and much better than the immunization regimen of 0/3/14. This study confirmed that anti-toxin A/B antibody titers are significantly enhanced when the antigen is co-injected with aluminum hydroxide (data not shown). The study also shows that even two doses of the vaccine with alum administered in two-week interval can elicit high antibody level, comparable to the level obtained after three dose vaccinations.

The level of toxin A/B neutralizing antibodies is much higher in the immunization regimen of 0/7/21 and 0/14/28 than in the immunization regimen of 0/3/14.

Complete protection against challenge with toxin A does not require alum in the immunization regimen of 0/7/21 and 0/14/28 but not in 0/3/14. The immunization regimen of 0/14/28/ with alum induced a highest level of protection (87.5%) against toxin B challenge, while the immunization regimen of 0/7/21 provides 37.5% of protection and 0/3/14 shows 28.6% of protection. Results of this study are shown in FIGS. 20A and 20B.

Example 6: Evaluation of the Immunogenicity and Protective Efficacy of the Recombinant C-TAB.G5.1 Fusion Protein in Hamsters This study was to further evaluate the immunogenicity of the recombinant fusion protein C-TAB.G5.1 administered with or without adjuvant in a different animal model.

Female hamsters (Harlan), aged over 7 weeks and weighing between 80 and 90 g were utilized for this study. All animals received the first vaccination by bolus (50 μl) intramuscular (IM) injection into the right thigh muscle on day 0. The second vaccination was by IM injection into the left thigh muscle on day 14 and the third vaccination was by IM injection on day 28. Hamsters were divided into groups (N=6) and vaccinated as follows:

Group 1: Formulation buffer only
Group 2: 10 μg C-TAB.G5.1
Group 3: 10 μg C-TAB.G5.1+100 μg alum OH
Group 4: 30 μg C-TAB.G5.1
Group 5: 30 μg C-TAB.G5.1+100 μg alum OH
Group 6: 100 μg C-TAB.G5.1
Group 7: 100 μg C-TAB.G5.1+100 μg alum OH
Group 10: Formulation buffer only
Group 11. 10 μg C-TAB.G5.1
Group 12. 10 μg C-TAB.G5.1+100 μg alum OH
Group 13. 30 μg C-TAB.G5.1
Group 14. 30 μg C-TAB.G5.1+100 μg alum OH
Group 15 100 μg C-TAB.G5.1
Group 16. 100 μg C-TAB.G5.1+100 μg alum OH Two weeks after the third vaccination (study day 42) animals in vaccinated and non-vaccinated groups (N=6)

received a lethal challenge by intraperitoneal (IP) injection with 75 ng toxin A or 125 ng toxin B. An extra 12 hamsters were used for a dose titration of toxin A or toxin B challenge on the day 44. Survival of the hamsters was monitored over the following 8 days.

Blood samples were collected from all animals two weeks after the first immunization (study day 14), after the second immunization (study day 28) and the third immunization (study day 35). The serum was stored at −20° C. until analyzed. Serum antibody titers to C-TAB, toxin A and toxin B were then determined by ELISA and reported as ELISA Units (EU). Toxin A and toxin B neutralizing antibodies (TNA) were determined using Vero cells treated with a cytotoxic amount of recombinant toxin A and toxin B.

Figure 12:
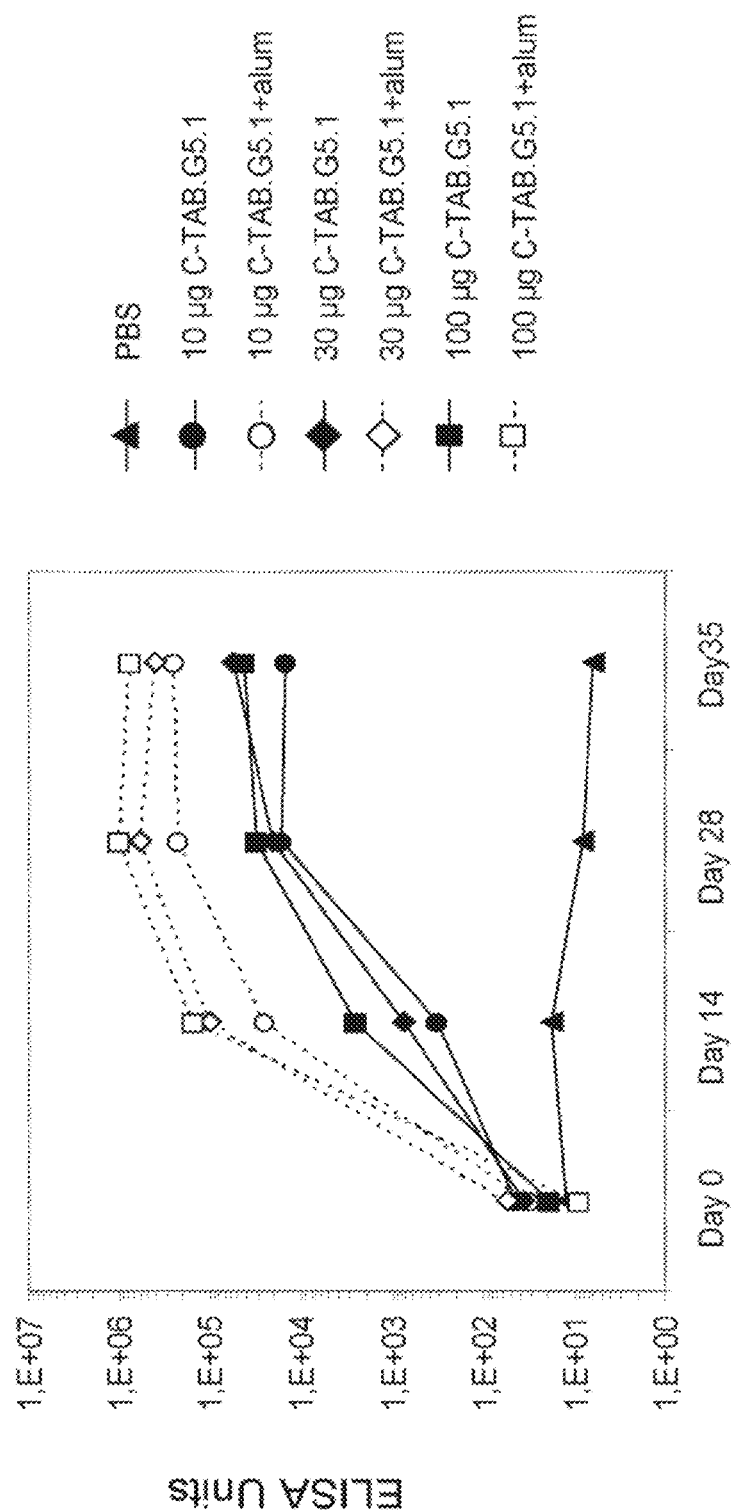
FIG. 12 shows a graphical representation of anti-C-TAB IgG antibody development in hamsters immunized with C-TAB.G5.1 with or without alum.

This study demonstrated that hamsters, similarly to mice, were able positively respond to the C-TAB.G5.1 vaccination. Animals receiving C-TAB.G5.1 demonstrated a dose dependent increase in all tested antibody titers, while the alum adjuvant significantly improved antibody titers at all doses of C-TAB.G5. The highest antibody titers were observed two weeks after the second shots (study day 28). FIGS. 11A-11C show antibody titers for each group of immunized hamsters. FIG. 12 shows the kinetics of anti-C-TAB antibody development in hamsters immunized with C-TAB.G5 in the presence or absence of alum hydroxide.

The results of the TNA assay are shown in FIG. 13. These results are similar to those obtained for mice and indicate that antibody generated against the C-TAB.G5.1 fusion protein in hamsters are effective in neutralizing toxic effects of *C. difficile* toxin A and toxin B.

FIG. 13 also shows protection data for hamsters immunized with C-TAB.G5.1 following a lethal toxin challenge. High protection was achieved even by vaccination with C-TAB.G5.1 in the absence of the adjuvant. The protection level was improved to 100% by adding alum to the vaccine.

Example 7: The Protective Efficacy of the C-TAB.G5.1 Fusion Protein Against a *C. difficile* Spore Challenge in Clindamycin-Treated Hamsters Following antibiotic treatment *C. difficile* can colonize the gut and, if toxigenic, may cause an antibiotic associated diarrhea. *C. difficile* associated disease (CDAD) of humans is modeled in hamsters using clindamycin to make the animals susceptible to colonization, diarrhea and death, usually within a few days after seeding with a toxigenic strain. To assess the efficacy of the C-TAB.G5.1 vaccine, vaccinated and non-vaccinated hamsters were challenged with clindamycin and *C. difficile* strain 630. 100 µg of C-TAB.G5.1 was mixed with 125 µg alum-hydroxide adjuvant. Female adult hamsters weighing ~100 g received 3 vaccinations by intramuscular (IM) injection on days 0, 14 and 28. The placebo was PBS. 48 hamsters were divided into groups of 8 as vaccinated as follows:

Group 1: PBS only+$10^2$ spore challenge
Group 2: C-TAB.G5.1+$10^2$ spore challenge
Group 3: PBS only+$10^3$ spore challenge
Group 4: C-TAB.G5.1+$10^2$ spore challenge
Group 5: PBS only+$10^4$ spore challenge
Group 6: C-TAB.G5.1+$10^4$ spore challenge On day 42 all animals in all groups received an oral dose of 10 mg clindamycin phosphate/kg body weight. On day 43 all animals in all groups were dosed by oral gavage with washed spores of *C. difficile* strain 630. Three levels of spore challenge were used (~$10^2$, $10^3$ and $10^4$). Observation, but no treatment, continued until day 54. At study termination, all surviving animals were disease free for ≥5 days.

Blood samples were drawn to obtain serum for serological studies on day 0, 14, 28, 42 and day 54 (end of study). Feces were collected on days 1 and 42, directly from the anus of the hamsters, or if needed, from among the bedding.

Figure 14:
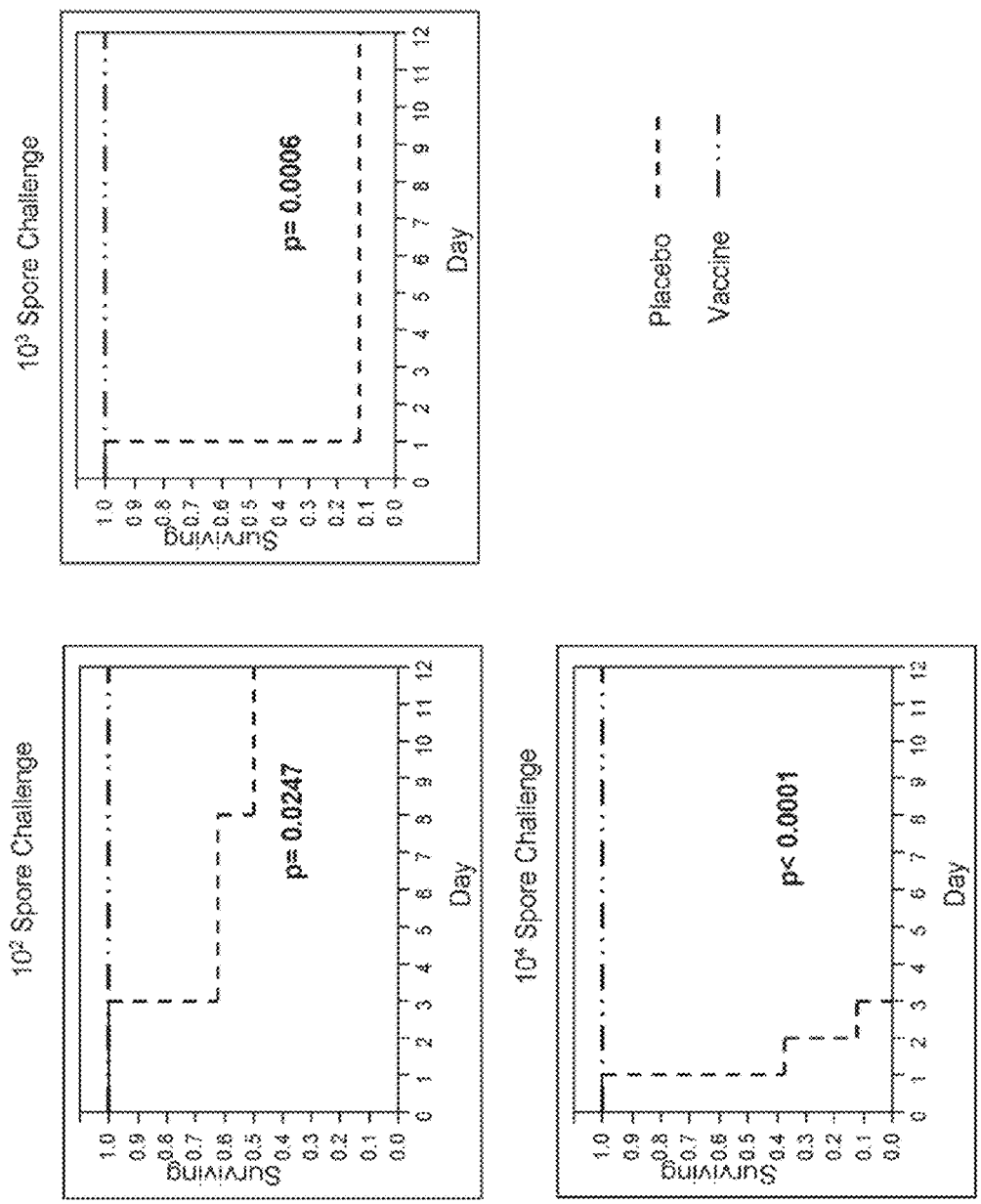
FIG. 14 shows survival of hamsters vaccinated with C-TAB.G5.1 following the intragastric administration of a lethal dose of *C. difficile* spores. Survival data was plotted as Kaplan-Meier survival fit curves and statistical analysis was done using a log rank analysis. At all spore doses ($10^2$, $10^3$ and $10^4$), 100% survival of hamsters in the vaccinated group was observed and survival was significantly enhanced when compared to the placebo group.

Results are shown on FIG. 14 demonstrating survival curves after spore challenge in hamsters. Survival data was plotted as Kaplan-Meier survival fit curves and statistical analysis was done using a log rank analysis. At all spore doses, 100% survival of hamsters in the vaccinated group was observed and survival was significantly enhanced when compared to the placebo group: $p=0.0245$ at $10^2$ spores, $p=0.0006$ at $10^3$ spores, $p<0.0001$ at $10^4$ spores.

Example 8: Immunogenicity and Protection Efficacy of C-TAB.G5.1 in Monkeys

This study was to evaluate the immunogenicity and protection of C-TAB.G5.1 in cynomolgus monkeys. Six female cynonomolgus monkeys, aged between 4 and 6 years and weighing between 2 and 4 kg, were used for this study. Two groups of three monkeys were arranged, the first group (Group 1) receiving 200 µg of C-TAB.G5.1 and the second (Group 2) receiving 200 µg of C-TAB.G5.1 and 250 µg alum. As alum adjuvant Rehydragel (Reheis, lot #534401, dilute in PBS to 2 mg/ml) was used. Before blood collection or immunization, animals were shaved (if necessary).

The $1^{st}$ (study day 0) and $3^{rd}$ (study day 28) immunizations were injected on the left arm (deltoid), the $2^{nd}$ immunization (study day 14) was injected to the right arm (deltoid). Group 1 received 200 µg C-TAB.G5.1 alone in 0.5 ml 1×PBS by IM injection and Group 2 received 200 µg C-TAB.G5.1 with 250 µg alum in 0.5 ml 1×PBS by IM injection.

At the established time points (study days 0, 14, 28 and 42), 2-3 mL of whole blood was obtained by standard methods into serum separator tubes. Serum samples were frozen at approximately −20° C. ELISA method was then used to assess anti-C-TAB, anti-toxin A and anti-toxin B IgG titers. Antibody titers were presented in ELISA Units (EU).

FIG. 15 shows that increased doses of C-TAB.G5.1 lead to increased antibody production recognizing all three proteins, while the presence of alum significantly improved antibody levels. The highest antibody titers were observed with two vaccinations on day 42. These data clearly indicate feasibility of using the recombinant C-TAB.G5 or C-TAB.G5.1 fusion proteins for vaccination subjects in need thereof.

Example 9: Comparison of the Immunogenicity of C-TAB.G5 and C-TAB.G5.1

This study was to compare the immunogenicity of C-TAB.G5 and C-TAB.G5.1 as well as the effect of two different buffers in which the C-TAB was delivered in. C57BL/6 female mice (Charles River Labs.), aged between 8 and 9 weeks, were utilized for immunization. All animals received the first immunization by intramuscular (IM) injection (50 µl) into the right thigh muscle on day 0. The second immunization was done by IM injection into the left thigh muscle on day 14. A total of 72 mice were divided into 12 groups vaccinated as follows:

Group 1: 1 µg C-TAB.G5 in PBS
Group 2: 3 µg C-TAB.G5 in PBS
Group 3: 10 µg C-TAB.G5 in PBS
Group 4: 30 µg C-TAB.G5 in PBS
Group 5: 1 µg C-TAB.G5 in histidine buffer
Group 6: 3 µg C-TAB.G5 in histidine buffer Group 7: 10 µg C-TAB.G5 in histidine buffer
Group 8: 30 µg C-TAB.G5 in histidine buffer
Group 9: 1 µg C-TAB.G5.1 in histidine buffer
Group 10: 3 µg C-TAB.G5.1 in histidine buffer
Group 11: 10 µg C-TAB.G5.1 in histidine buffer
Group 12: 30 µg C-TAB.G5.1 in histidine buffer Blood samples were collected from all animals two weeks after the second immunization (study day 28). The serum was stored at −20° C. until analyzed. Serum antibody titers to C-TAB, toxin A and toxin B were determined by ELISA and reported as ELISA Units.

Figure 16:
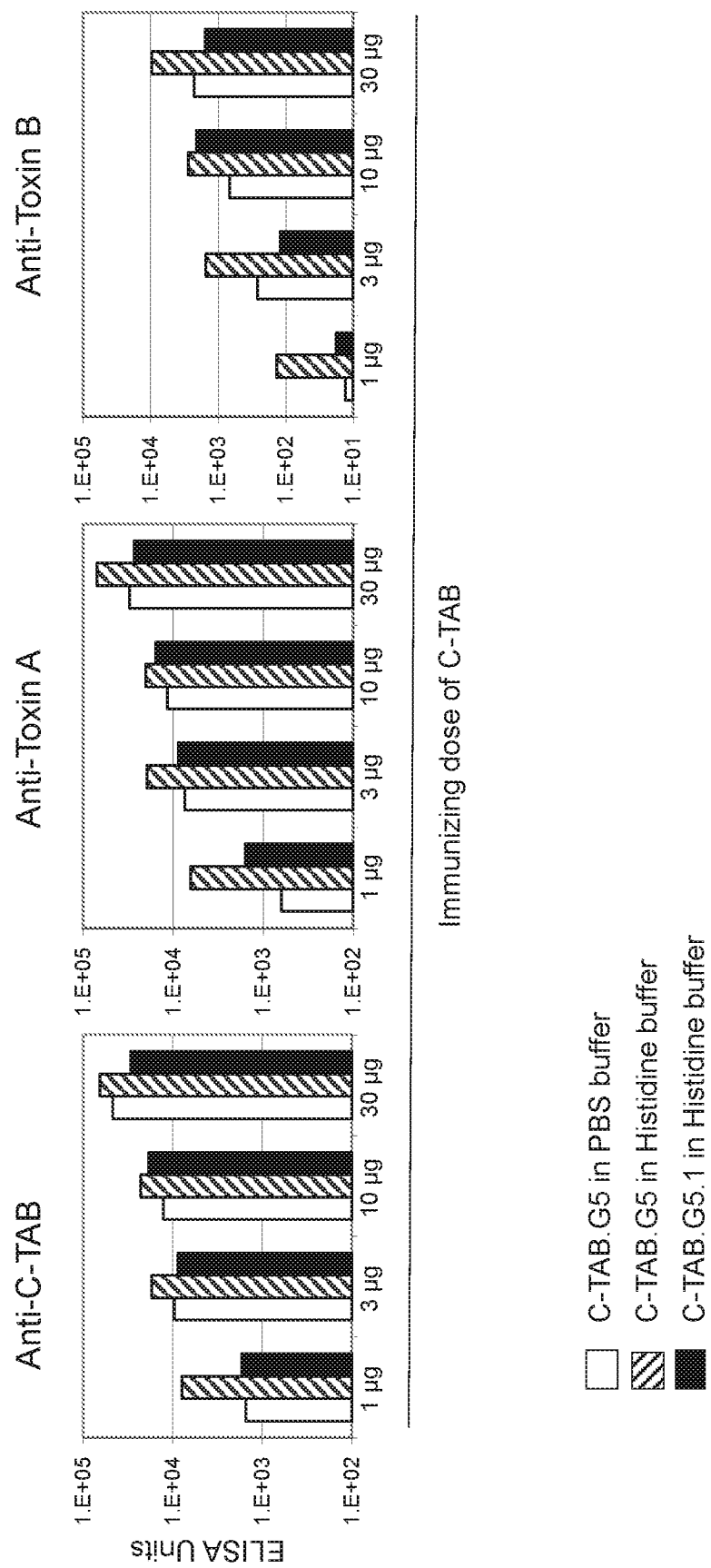
FIG. 16 shows a comparison of immunogenicity of C-TAB.G5 and C-TAB.G5.1 delivered over a 1 μg-30 μg dose range either in PBS or histidine buffer. Mice received two vaccinations (IM) in two week interval. IgG titers for anti-C-TAB, anti-toxin A and anti-toxin B antibodies were evaluated by ELISA two weeks after the second injection. All three antibody titers were not significantly different (T-test analysis) between C-TAB.G5 delivered in PBS or histidine buffer and C-TAB.G5.1 delivered in histidine buffer.

FIG. 16 shows that all antibody titers (anti-C-TAB, anti-toxin A and anti-toxin B) were not significantly different (as revealed by T-test analysis) over 1-30 µg dose range for three vaccine formulations. Slightly higher antibody production was achieved with C-TAB.G5 formulation in histidine buffer, as compare to PBS. No significant difference was observed between immunization with C-TAB.G5 and C-TAB.G5.1 histidine formulations. Thus, this study demonstrates the equal immunogenicity of C-TAB.G5 and C-TAB.G5.1 constructs.

Example 10: Preparation and Evaluation of the Alternative C-TABNCTB and C-TADCTB Fusion Proteins This Example describes the preparation of two other fusion proteins comprising one portion of the C-terminal domain of CTA and two portions of the C-terminal domain of CTB derived from *C. difficile* VPI-10463 strain. The C-TABNCTB fusion protein (SEQ ID NO: 18) comprises, like C-TAB.G5, 19 repeating units of CTA (amino acids 2272-2710), 23 repeating units of CTB (amino acids 1850-2366), plus additional 10 repeats of CTB (amino acids 1834-2057) fused to the C-terminus of CTB. The C-TADCTB fusion protein (SEQ ID NO: 20) comprises C-TAB.G5 sequence (19 repeats of CTA and 23 repeats of CTB) plus additional 24 repeating units of CTB (amino acids 1834-2366) fused to the C-terminus of C-TAB.G5. Thus, C-TADCTB comprises a double portion of repeating units of CTB. Cloning of the C-TABNCTB and C-TADCTB gene constructs was done in a way similar to that described in Example 1. 1 The recombinant fusion proteins were expressed in *E. coli* cells and purified using standard procedure as described in Example 1.2. The isolated polypeptides were evaluated in the immunogenicity and protection studies in animals.

Example 10.1: Comparison of the Immunogenicity and Protective Efficacy of C-TAB.G5, C-TABNCTB and C-TADCTB in Mice This study was to compare the immunogenicity and protective efficacy of C-TAB.G5, C-TABNCTB and C-TADCTB in mice vaccinated with five antigen doses over a two log range. Female C57BL/6 mice (Charles River Labs.), aged 6-7 weeks, were utilized for this study. All animals received two vaccinations: the first one by intramuscular (IM) injection (50 µl) into the right thigh muscle on day 0. The second vaccination was done by IM injection into the left thigh muscle on day 14. All immunizations were done in the absence of alum. Blood samples were collected two weeks after the second immunization (study day 28). The serum was stored at −20° C. until analyzed. Serum antibody titers to C-TAB, toxin A and toxin B were determined by ELISA and reported as ELISA Units (EU) shown in FIG. 17.

This study demonstrated that the alternative fusion proteins C-TADCTB and C-TABNCTB, as well as C-TAB.G5, are highly immunogenic and able to induce strong antibody response against both toxin A and toxin B even without adding an adjuvant.

In addition to assessing antibody response, the ability of C-TADCTB and C-TABNCTB immunization to protect mice from a lethal challenge of native toxin B was determined. Three weeks after the second vaccination (study day 35) animals in vaccinated and non-vaccinated groups (N=6) received intraperitoneally (IP) a lethal dose of 50 ng of toxin B. Survival of the mice was monitored over the following 9 days and the results are shown in FIG. 18. This experiment demonstrated that immunization of mice with 33 µg of C-TADCTB in the absence of alum was capable of conferring 100% protection against a lethal challenge with native toxin B, while the same dose of C-TAB.G5 and C-TABNCTB induces only partial protection. This data indicates that, similarly to C-TAB.G5, two other fusion proteins C-TADCTB and C-TABNCTB may be protective against the lethal challenge with the native toxin.

Example 10.2: Comparison of the Immunogenicity and Protective Efficacy of C-TAB.G5.1 and C-TADCTB in Hamsters This study was to further evaluate the immunogenicity of the alternative fusion protein C-TADCTB administered with or without alum adjuvant in a different animal model.

The study was designed as described in Example 6: female hamsters were vaccinated three times by IM injection (study day 0, 14 and 28) in the presence or absence of 100 µg alum hydroxide. Two weeks after the third vaccination (study day 42) all animals received a lethal challenge by intraperitoneal (IP) injection with 75 ng toxin A or 125 ng toxin B. Blood samples were collected on study day 14, 28 and 35 and serum antibody titers to C-TAB, toxin A and toxin B were determined by ELISA. Toxin A and toxin B neutralizing antibodies (TNA) were measured in day 35 sera. Survival of the hamsters was monitored and reported as % of protection.

This study demonstrated that the fusion protein C-TADCTB can induce anti-toxin antibody response in hamsters, similarly to mice. The alum adjuvant significantly improved all tested antibody titers. The results of the TNA assay shown in FIG. 19 indicate that antibody generated against C-TADCTB are effective in neutralizing toxic effects of *C. difficile* toxin A and toxin B. FIG. 19 also demonstrates comparison of protection data for hamsters immunized either with C-TAB.G5.1 or with C-TADCTB. High protection was achieved by vaccination with both recombinant fusion proteins.

Example 11: An Open-Label Phase 1 Study Assessing the Safety, Immunogenicity and Dose Response of a Pharmaceutical Composition Comprising C-TAB.G5.1

The pharmaceutical composition comprising C-TAB.G5.1, a recombinant fusion protein consisting of truncated *Clostridium difficile* (*C. difficile*) Toxin A and Toxin B, which will be administered at three different doses: 20 µg with $Al(OH)_3$ (alum), 75 and 200 µg without or with $Al(OH)_3$, respectively, intramuscular (IM) injection, three vaccinations on Day 0, 7 and 21.

Study Objectives
Primary:
   To investigate the safety and tolerability of a pharmaceutical composition comprising C-TAB.G5.1 up to 6 months after the third vaccination.
Secondary:
   To investigate the immune response measured against the vaccine antigen C-TAB.G5.1 and the native Toxins A and B of *C. difficile* to three different doses and two formulations on Days 0, 7, 14, 21, 28, 113, 201 after the first vaccination to obtain a first indication of the optimal dose and formulation.
   To investigate the capacity of C-TAB.G5.1 vaccine-induced IgG antibodies to neutralize *C. difficile* Toxins A and B in vitro.

Study Design

This is an open-label, partially randomized, dose escalation Phase 1 study which will consist of a part A in healthy adults aged between ≥18 and <65 years and a part B in healthy elderly ≥65 years, the latter age group being the most vulnerable population to suffer from *C. difficile* infections. Part A will be conducted with vaccination schedule Day 0, 7 and 21 in five treatment groups of 12 healthy adult subjects to study safety and dose response to 20 µg C-TAB.G5.1 vaccine with adjuvant, and to 75 µg and 200 µg of C-TAB.G5.1 vaccine with or without adjuvant, respectively. Safety and immunogenicity will be analyzed after all adult subjects of part A have received the third vaccination, all safety data will be reviewed by a Data Safety Monitoring Board (DSMB) prior to enrollment of subjects from part B. In case non-safe or futile treatment groups (i.e., doses that do not induce considerable IgG responses) are identified during the interim analysis, these treatment groups will be dropped and not carried forward to part B.

Part B of the study will seek dose confirmation in the elderly population. Accordingly, Part B will be conducted in 5 treatment groups of 20 elderly healthy subjects per group. Vaccination schedule Day 0, 7 and 21 will be applied. This study design will allow to compare dose responses in both adults and elderly. The latter age group will be the major target population for a *C. difficile* vaccine, representing the most vulnerable population for the two target indications in the development pathway of a *C. difficile* vaccine, i.e. prevention of recurrent *C. difficile* diarrhea and prevention of primary *C. difficile* infection in an age-based or age-risk based preventive vaccination approach. However, elderly subjects might be less responsive to vaccination than young adults; thus, dose confirmation in the elderly target population from an early development stage on is required. An interim analysis after all adults have been vaccinated will allow to drop non-safe or doses/formulations which do not induce considerable IgG responses in adults in order to mitigate the risk of exposing subjects in the elderly group to potentially unsafe or futile doses (e.g. lowest dose) and/or formulations (e.g. non-adjuvanted formulation) of the vaccine.

The C-TAB.G5.1 vaccine is an aqueous solution of C-TAB.G5.1 in 20 mM L-Histidine, 75 mM NaCl, 5% Sucrose, 0.025% Tween® 80; pH6.5 produced by standard methods.

SEQUENCES:

| Name | SEQ ID NOs: | Sequences |
|---|---|---|
| C-TAB.G5 (nucleic acid sequence) | 1 | ATGGTAACAGGAGTATTTAA AGGACCTAATGGATTTGAGT ATTTTGCACCTGCTAATACT CACAATAATAACATAGAAGG TCAGGCTATAGTTTACCAGA ACAAATTCTTAACTTTGAAT GGCAAAAAATATTATTTTGA TAATGACTCAAAAGCAGTTA CTGGATGGCAAACCATTGAT GGTAAAAAATATTACTTTAA TCTTAACACTGCTGAAGCAG CTACTGGATGGCAAACTATT GATGGTAAAAAATATTACTT TAATCTTAACACTGCTGAAG CAGCTACTGGATGGCAAACT ATTGATGGTAAAAAATATTA CTTTAATACTAACACTTTCA TAGCCTCAACTGGTTATACA AGTATTAATGGTAAACATTT TTATTTTAATACTGATGGTA TTATGCAGATAGGAGTGTTT AAAGGACCTAATGGATTTGA ATACTTTGCACCTGCTAATA CTCATAATAACAACATAGAA GGTCAAGCTATACTTTACCA AAATAAATTCTTAACTTTGA ATGGTAAAAAATATTACTTT GGTAGTGACTCAAAAGCAGT TACCGGATTGCGAACTATTG ATGGTAAAAAATATTACTTT AATACTAACACTGCTGTTGC AGTTACTGGATGGCAAACTA TTAATGGTAAAAAATACTAC TTTAATACTAACACTTCTAT AGCTTCAACTGGTTATACAA TTATTAGTGGTAAACATTTT TATTTTAATACTGATGGTAT TATGCAGATAGGAGTGTTTA AAGGACCTGATGGATTTGAA TACTTTGCACCTGCTAATAC AGATGCTAACAATATAGAAG GTCAAGCTATACGTTATCAA AATAGATTCCTATATTTACA TGACAATATATATTATTTTG GTAATAATTCAAAAGCAGCT ACTGGTTGGGTAACTATTGA TGGTAATAGATATTACTTCG AGCCTAATACAGCTATGGGT GCGAATGGTTATAAAACTAT TGATAATAAAAATTTTTACT TTAGAAATGGTTTACCTCAG ATAGGAGTGTTTAAAGGGTC TAATGGATTTGAATACTTTG CACCTGCTAATACGGATGCT AACAATATAGAAGGTCAAGC TATACGTTATCAAAATAGAT TCCTACATTTACTTGGAAAA ATATATTACTTTGGTAATAA TTCAAAAGCAGTTACTGGAT GGCAAACTATTAATGGTAAA GTATATTACTTTATGCCTGA TACTGCTATGGCTGCAGCTG GTGGACTTTTCGAGATTGAT GGTGTTATATATTTCTTTGG TGTTGATGGAGTAAAAGCCC CTGGGATATATGGCAGATCT ATGCATAATTTGATAACTGG ATTTGTGACTGTAGGCGATG ATAAATACTACTTTAATCCA ATTAATGGTGGAGCTGCTTC AATTGGAGAGACAATAATTG ATGACAAAAATTATTATTTC AACCAAAGTGGAGTGTTACA AACAGGTGTATTTAGTACAG AAGATGGATTTAAATATTTT GCCCCAGCTAATACACTTGA TGAAAACCTAGAAGGAGAAG |

SEQUENCES:

| Name | SEQ ID NOs: | Sequences |
|---|---|---|
| | | CAATTGATTTTACTGGAAAA |
| | | TTAATTATTGACGAAAATAT |
| | | TTATTATTTTGATGATAATT |
| | | ATAGAGGAGCTGTAGAATGG |
| | | AAAGAATTAGATGGTGAAAT |
| | | GCACTATTTTAGCCCAGAAA |
| | | CAGGTAAAGCTTTTAAAGGT |
| | | CTAAATCAAATAGGTGATTA |
| | | TAAATACTATTTCAATTCTG |
| | | ATGGAGTTATGCAAAAGGA |
| | | TTTGTTAGTATAAATGATAA |
| | | TAAACACTATTTTGATGATT |
| | | CTGGTGTTATGAAAGTAGGT |
| | | TACACTGAAATAGATGGCAA |
| | | GCATTTCTACTTTGCTGAAA |
| | | ACGGAGAAATGCAAATAGGA |
| | | GTATTTAATACAGAAGATGG |
| | | ATTTAAATATTTTGCTCATC |
| | | ATAATGAAGATTTAGGAAAT |
| | | GAAGAAGGTGAAGAAATCTC |
| | | ATATTCTGGTATATTAAATT |
| | | TCAATAATAAAATTTACTAT |
| | | TTTGATGATTCATTTACAGC |
| | | TGTAGTTGGATGGAAAGATT |
| | | TAGAGGATGGTTCAAAGTAT |
| | | TATTTTGATGAAGATACAGC |
| | | AGAAGCATATATAGGTTTGT |
| | | CATTAATAAATGATGGTCAA |
| | | TATTATTTTAATGATGATGG |
| | | AATTATGCAAGTTGGATTTG |
| | | TCACTATAAATGATAAAGTC |
| | | TTCTACTTCTCTGACTCTGG |
| | | AATTATAGAATCTGGAGTAC |
| | | AAAACATAGATGACAATTAT |
| | | TTCTATATAGATGATAATGG |
| | | TATAGTTCAAATTGGTGTAT |
| | | TTGATACTTCAGATGGATAT |
| | | AAATATTTTGCACCTGCTAA |
| | | TACTGTAAATGATAATATTT |
| | | ACGGACAAGCAGTTGAATAT |
| | | AGTGGTTTAGTTAGAGTTGG |
| | | GGAAGATGTATATTATTTTG |
| | | GAGAAACATATACAATTGAG |
| | | ACTGGATGGATATATGATAT |
| | | GGAAAATGAAAGTGATAAAT |
| | | ATTATTTCAATCCAGAAACT |
| | | AAAAAAGCATGCAAAGGTAT |
| | | TAATTTAATTGATGATATAA |
| | | AATATTATTTTGATGAGAAG |
| | | GGCATAATGAGAACGGGTCT |
| | | TATATCATTTGAAAATAATA |
| | | ATTATTACTTTAATGAGAAT |
| | | GGTGAAATGCAATTTGGTTA |
| | | TATAAATATAGAAGATAAGA |
| | | TGTTCTATTTTGGTGAAGAT |
| | | GGTGTCATGCAGATTGGAGT |
| | | ATTTAATACACCAGATGGAT |
| | | TTAAATACTTTGCACATCAA |
| | | AATACTTTGGATGAGAATTT |
| | | TGAGGGAGAATCAATAAACT |
| | | ATACTGGTTGGTTAGATTTA |
| | | GATGAAAGAGATATTATTT |
| | | TACAGATGAATATATTGCAG |
| | | CAACTGGTTCAGTTATTATT |
| | | GATGGTGAGGAGTATTATTT |
| | | TGATCCTGATACAGCTCAAT |
| | | TAGTGATTAGTGAATAG |
| C-TAB.G5 (amino acid sequence) | 2 | MVTGVFKGPNGFEYFAPANT HNNNIEGQAIVYQNKFLTLN GKKYYFDNDSKAVTGWQTID GKKYYFNLNTAEAATGWQTI DGKKYYFNTNTFIASTGYT |

| Name | SEQ ID NOs: | Sequences |
|---|---|---|
| | | SINGKHFYFNTDGIMQIGVF KGPNGFEYFAPANTHNNNIE GQAILYQNKFLTLNGKKYYF GSDSKAVTGLRTIDGKKYYF NTNTAVAVTGWQTINGKKYY FNTNTSIASTGYTIISGKHF YFNTDGIMQIGVFKGPDGFE YFAPANTDANNIEGQAIRYQ NRFLYLHDNIYYFGNNSKAA TGWVTIDGNRYYFEPNTAMG ANGYKTIDNKNFYFRNGLPQ IGVFKGSNGFEYFAPANTDA NNIEGQAIRYQNRFLHLLGK IYYFGNNSKAVTGWQTINGK VYYFMPDTAMAAAGGLFEID GVIYFFGVDGVKAPGIYGRS MHNLITGFVTVGDDKYYFNP INGGAASIGETIIDDKNYYF NQSGVLQTGVFSTEDGFKYF APANTLDENLEGEAIDFTGK LIIDENIYYFDDNYRGAVEW KELDGEMHYFSPETGKAFKG LNQIGDYKYYFNSDGVMQKG FVSINDNKHYFDDSGVMKVG YTEIDGKHFYFAENGEMQIG VFNTEDGFKYFAHHNEDLGN EEGEEISYSGILNFNNKIYY FDDSFTAVVGWKDLEDGSKY YFDEDTAEAYIGLSLINDGQ YYFNDDGIMQVGFVTINDKV FYFSDSGIIESGVQNIDDNY FYIDDNGIVQIGVFDTSDGY KYFAPANTVNDNIYGQAVEY SGLVRVGEDVYYFGETYTIE TGWIYDMENESDKYYFNPET KKACKGINLIDDIKYYFDEK GIMRTGLISFENNNYYFNEN GEMQFGYINIEDKMFYFGED GVMQIGVFNTPDGFKYFAHQ NTLDENFEGESINYTGWLDL DEKRYYFTDEYIAATGSVII DGEEYYFDPDTAQLVISE |
| C-TAB.G5.1 (nucleic acid sequence) | 3 | CCATGGTTACAGGTGTTTTC AAAGGTCCGAACGGCTTTGA ATATTTTGCACCGGCAAATA CCCACAATAATAATATTGAA GGCCAGGCCATCGTGTATCA GAATAAATTTCTGACCCTGA ACGGCAAAAAATACTATTTC GATAACGATAGCAAAGCAGT TACCGGTTGGCAAACCATTG ATGGCAAAAAATATTACTTC AACCTGAATACCGCAGAAGC AGCAACCGGCTGGCAGACGA TCGACGGTAAAAAGTACTAT TTTAACCTGAACACAGCCGA AGCCGCTACAGGCTGGCAGA CAATAGATGGGAAGAAGTAT TATTTTAATACCAATACCTT TATTGCCAGCACCGGCTATA CCAGCATTAATGGCAAACAC TTCTATTTTAACACCGATGG TATTATGCAGATCGGTGTGT TTAAGGGCCCTAATGGTTTT GAGTACTTCGCTCCGGCTAA TACCGATGCAAATAACATCG AAGGTCAGGCAATTCTGTAC CAGAACAAATTTTTAACGCT GAACGGTAAGAAATATTACT TTGGTAGCGATTCAAAAGCC GTTACCGGTCTGCGTACGAT CGACGGCAAGAAATATTATT TCAATACAAACACCGCAGTT |

| Name | SEQ ID NOs: | Sequences |
|---|---|---|
| | | GCCGTGACAGGTTGGCAGAC GATAAATGGTAAGAAGTACT ACTTCAACACCAATACCAGC ATTGCAAGTACCGGTTATAC CATTATCAGCGGCAAACACT TTTACTTCAATACAGACGGC ATTATGCAGATTGGCGTTTT CAAAGGTCCGGATGGTTTCG AGTACTTTGCCCCTGCAAAT ACAGATGCAAACAATATTGA GGGACAGGCAATTCGCTATC AGAATCGTTTTCTGTATCTG CACGATAACATCTATTACTT CGGCAATAATTCAAAAGCAG CCACCGGTTGGGTTACAATT GATGGTAATCGTTATTACTT TGAGCCGAATACCGCAATGG GTGCAAATGGTTATAAAACC ATCGATAACAAAAATTTTTA TTTCCGCAACGGTCTGCCGC AGATTGGTGTTTTTAAGGGT AGCAATGGCTTCGAGTATTT TGCGCCAGCCAACACCGATG CCAACAACATTGAAGGCCAA GCGATTCGTTATCAAAACCG CTTTCTGCATCTGCTGGGCA AAATTTATTACTTTGGCAAC AATAGCAAAGCGGTGACGGG CTGGCAAACCATTAACGGTA AAGTTTATTATTTCATGCCG GATACCGCTATGGCAGCAGC CGGTGGTCTGTTTGAAATTG ATGGCGTGATTTATTTTTTT GGCGTGGATGGTGTTAAAGC ACCGGGTATTTATGGTCGTA GCATGCATAATCTGATTACC GGTTTTGTTACCGTGGGCGA CGATAAATACTTTAATC CGATTAATGGTGGTCAGCA AGCATTGGTGAAACCATTAT CGATGACAAAAACTATTATT TTAACCAGAGCGGTGTTCTG CAGACAGGTGTTTTTAGCAC CGAAGATGGCTTCAAATATT TTGCTCCTGCGAATACACTG GATGAAAATCTGGAAGGTGA AGCAATTGATTTTACCGGCA AACTGATCATCGACGAGAAC ATCTACTATTTTGATGATAA TTATCGCGGTGCCGTGGAAT GGAAAGAACTGGATGGTGAA ATGCACTATTTTAGTCCGGA AACCGGTAAAGCCTTTAAAG GTCTGAATCAGATCGGCGAT TACAAGTATTACTTTAATTC AGATGGCGTGATGCAGAAAG GCTTTGTGAGCATTAACGAC AACAAACACTATTTTGACGA CAGCGGTGTGATGAAAGTGG GTTATACCGAAATCGACGGG AAACATTTTATTTTGCCGA AAACGGCGAAATGCAGATTG GAGTATTTAATACCGAGGAC GGCTTTAAATACTTTGCCCA TCATAATGAAGATCTGGGTA ATGAAGAAGGCGAAGAAATT AGCTATAGCGGCATTCTGAA TTTTAATAACAAGATCTATT ATTTCGATGATAGCTTCACC GCAGTTGTTGGTTGGAAAGA TCTGGAAGATGGCAGCAAAT ATTATTTTGATGAAGATACC GCAGAGGCCTATATTGGTCT GAGCCTGATTAATGATGGCC |
| | | AGTATTATTTCAACGATGAT GGTATCATGCAGGTTGGTTT TGTGACCATCAACGATAAAG TGTTCTATTTCAGCGATAGC GGCATTATTGAAAGCGGTGT TCAGAACATCGACGATAACT ATTTCTACATCGATGATAAC GGTATTGTTCAGATTGGCGT GTTTGATACCTCCGATGGTT ATAAATATTTCGCACCAGCC AATACCGTGAACGATAATAT TTATGGTCAGGCAGTTGAAT ATTCAGGTCTGGTTCGTGTT GGCGAAGATGTTTATTATTT TGGCGAAACCTATACCATTG AAACCGGCTGGATCTATGAT ATGGAAAACGAGAGCGACAA GTACTATTTCAATCCGGAAA CGAAAAAGCCTGCAAAGGC ATTAATCTGATCGACGATAT TAAGTACTACTTTGACGAAA AAGGCATTATGCGTACCGGT CTGATTAGCTTTGAGAACAA CAACTATTACTTCAATGAGA ACGGTGAGATGCAGTTTGGC TATATCAACATCGAGGACAA AATGTTTATTTTGGTGAGG ACGGTGTGATGCAGATAGGG GTTTTTAATACACCGGATGG GTTTAAGTATTTTGCACATC AGAACACCCTGGATGAAAAC TTTGAAGGCGAAAGCATTAA TTATACCGGTTGGCTGGATC TGGATGAGAAACGTTATTAT TTCACCGACGAATACATTGC AGCAACCGGTAGCGTTATTA TTGATGGTGAGGAATATTAC TTCGATCCGGATACAGCACA GCTGGTTATTAGCGAATAAC TCGAG |
| C-TAB.G5.1 (amino acid sequence) | 4 | VTGVFKGPNGFEYFAPANTH NNNIEGQAIVYQNKFLTLNG KKYYFDNDSKAVTGWQTIDG KKYYFNLNTAEAATGWQTID GKKYYFNLNTAEAATGWQTI DGKKYYFNTNTFIASTGYTS INGKHFYFNTDGIMQIGVFK GPNGFEYFAPANTDANNIEG QAILYQNKFLTLNGKKYYFG SDSKAVTGLRTIDGKKYYFN TNTAVAVTGWQTINGKKYYF NTNTSIASTGYTIISGKHFY FNTDGIMQIGVFKGPDGFEY FAPANTDANNIEGQAIRYQN RFLYLHDNIYYFGNNSKAAT GWVTIDGNRYYFEPNTAMGA NGYKTIDNKNFYFRNGLPQI GVFKSNGFEYFAPANTDAN NIEGQAIRYQNRFLHLLGKI YYFGNNSKAVTGWQTINGKV YYFMPDTAMAAAGGLFEIDG VIYFFGVDGVKAPGIYGRSM HNLITGFVTVGDDKYYFNPI NGGAASIGETIIDDKNYYFN QSGVLQTGVFSTEDGFKYFA PANTLDENLEGEAIDFTGKL IIDENIYYFDDNYRGAVEWK ELDGEMHYFSPETGKAFKGL NQIGDYKYYFNSDGVMQKGF VSINDNKHYFDDSGVMKVGY TEIDGKHFYFAENGEMQIGV FNTEDGFKYFAHHNEDLGNE EGEEISYSGILNFNNKIYYF |

| Name | SEQ ID NOs: | Sequences |
|---|---|---|
| | | DDSFTAVVGWKDLEDGSKYY FDEDTAEAYIGLSLINDGQY YFNDDGIMQVGFVTINDKVF YFSDSGIIESGVQNIDDNYF YIDDNGIVQIGVFDTSDGYK YFAPANTVNDNIYGQAVEYS GLVRVGEDVYYFGETYTIET GWIYDMENESDKYYFNPETK KACKGINLIDDIKYYFDEKG IMRTGLISFENNNYYFNENG EMQFGYINIEDKMFYFGEDG VMQIGVFNTPDGFKYFAHQN TLDENFEGESINYTGWLDLD EKRYYFTDEYIAATGSVIID GEEYYFDPDTAQLVISE |
| Nucleic acid sequence of trdA (strain 630) | 5 | atgtcttaatatctaaaga agagttaataaaactcgcat atagcattagaccaagagaa aatgagtataaaactatact aactaatttagacgaatata ataagttaactacaaacaat aatgaaaataaatatttaca attaaaaaactaaatgaat caattgatgttttttatgaat aaatataaaacttcaagcag aaatagagcactctctaatc taaaaaaagatatattaaaa gaagtaattcttattaaaaa ttccaatacaagccctgtag aaaaaaatttacattttgta tggataggtggagaagtcag tgatattgctcttgaataca taaaacaatgggctgatatt aatgcagaatataatattaa actgtggtatgatagtgaag cattcttagtaaatacacta aaaaaggctatagttgaatc ttctaccactgaagcattac agctactagaggaagagatt caaaatcctcaatttgataa tatgaaattttacaaaaaaa ggatggaatttatatatgat agacaaaaaaggtttataaa ttattataaatctcaaatca ataaacctacagtacctaca atagatgatattataaagtc tcatctagtatctgaatata atagagatgaaactgtatta gaatcatatagaacaaattc tttgagaaaaataaaatagta atcatgggatagatatcagg gctaatagtttgtttacaga acaagagttattaaatattt atagtcaggagttgttaaat cgtggaaatttagctgcagc atctgacatagtaagattat tagccctaaaaaattttggc ggagtatatttagatgttga tatgcttccaggtattcact ctgatttatttaaaacaata tctagacctagctctattgg actagaccgttgggaaatga taaaattagaggctattatg aagtataaaaaatatataaa taattatacatcagaaaact ttgataaacttgatcaacaa ttaaaagataattttaaact cattatagaaagtaaaagtg aaaaatctgagatattttct aaattagaaaatttaaatgt atctgatcttgaaattaaaa tagcttttcgctttaggcagt gttataaatcaagccttgat atcaaaacaaggttcatatc ttactaacctagtaatagaa caagtaaaaaatagatatca attttttaaaccaacaccttta acccagccatagagtctgat aataacttcacagatactac taaaattttttcatgattcat tatttaattcagctaccgca gaaaactctatgtttttttaac aaaaatagcaccatacttac aagtaggtttatgccagaa gctcgctccacaataagttt aagtggtccaggagcttatg cgtcagcttactatgatttc ataaatttacaagaaaatac tatagaaaaaactttaaaag catcagatttaatagaattt aaattcccagaaaataatct atctcaattgacagaacaag aaataaatagtctatggagc tttgatcaagcaagtgcaaa atatcaatttgagaaatatg taagagattatactggtgga tctctttctgaagacaatgg ggtagactttaataaaaata ctgccctcgacaaaaactat ttattaaataataaaattcc atcaaacaatgtagaagaag ctggaagtaaaaattatgtt cattatatcatacagttaca aggagatgatataagttatg aagcaacatgcaatttattt tctaaaaatcctaaaaatag tattattatacaacgaaata tgaatgaaagtgcaaaaagc tacttttaagtgatgatgg agaatctattttagaattaa ataaataggatacctgaa agattaaaaaataaggaaaa agtaaaagtaaccttttattg gacatggtaaagatgaattc aacacaagcgaatttgctag attaagtgtagattcacttt ccaatgagataagttcattt ttagataccataaaattaga tatatcacctaaaaatgtag aagtaaacttacttggatgt aatatgtttagttatgattt taatgttgaagaaacttatc ctgggaagttgctattaagt attatggacaaaattacttc cactttacctgatgtaaata aaaattctattactataggga gcaaatcaatatgaagtaag aattaatagtgagggaagaa aagaacttctggctcactca ggtaaatggataaataaaga agaagctattatgagcgatt tatctagtaaagaatacatt tttttttgattctatagataa taagctaaaagcaaagtcca agaatattccaggattagca tcaatatcagaagatataaa aacattattacttgatgcaa gtgttagtcctgatacaaaa tttatttaaataatcttaa gcttaatattgaatcttcta ttggtgattacatttatat gaaaaatagagcctgttaa aaatataattcacaattcta tagtgatttaatagatgag ttcaatctacttgaaaatgt atctgatgaattatatgaat taaaaaaattaaataatcta |

-continued

SEQUENCES:

| Name | SEQ ID NOs: | Sequences |
|---|---|---|
| | | gatgagaagtatttaatatc |
| | | ttttgaagatatctcaaaaa |
| | | ataattcaacttactctgta |
| | | agatttattaacaaaagtaa |
| | | tggtgagtcagtttatgtag |
| | | aaacagaaaagaaattttt |
| | | tcaaaatatagcgaacatat |
| | | tacaaaagaaataagtacta |
| | | taaagaatagtataattaca |
| | | gatgttaatggtaatttatt |
| | | ggataatatacagttagatc |
| | | atacttctcaagttaataca |
| | | ttaaacgcagcattctttat |
| | | tcaatcattaatagattata |
| | | gtagcaataaagatgtactg |
| | | aatgatttaagtacctcagt |
| | | taaggttcaacttttatgctc |
| | | aactatttagtacaggttta |
| | | aatactatatgactctat |
| | | ccaattagtaaatttaatat |
| | | caaatgcagtaaatgatact |
| | | ataaatgtactacctacaat |
| | | aacagaggggatacctattg |
| | | tatctactatattagacgga |
| | | ataaacttaggtgcagcaat |
| | | taaggaattactagacgaac |
| | | atgacccattactaaaaaaa |
| | | gaattagaagctaaggtggg |
| | | tgtttttagcaataaaatgt |
| | | cattatctatagctgcaact |
| | | gtagcttcaattgttggaat |
| | | aggtgctgaagttactattt |
| | | tcttattacctatagctggt |
| | | atatctgcaggaataaccttc |
| | | attagttaataatgaattaa |
| | | tattgcatgataaggcaact |
| | | tcagtggtaaactatttttaa |
| | | tcatttgtctgaatctaaaa |
| | | aatatggccctcttaaaaca |
| | | gaagatgataaaatttagt |
| | | tcctattgatgatttagtaa |
| | | tatcagaaatagattttaat |
| | | aataattcgataaaactagg |
| | | aacatgtaatatattagcaa |
| | | tggaggggggatcaggacac |
| | | acagtgactggtaatatga |
| | | tcactttttctcatctccat |
| | | ctataagttctcatattcct |
| | | tcattatcaatttattctgc |
| | | aataggtatagaaacagaaa |
| | | atctagatttttcaaaaaa |
| | | ataatgatgttacctaatgc |
| | | tccttcaagagtgttttggt |
| | | gggaaactggagcagttcca |
| | | ggtttaagatcattggaaaa |
| | | tgacggaactagattacttg |
| | | attcaataagagatttatac |
| | | ccaggtaaattttactggag |
| | | attctatgctttttttcgatt |
| | | atgcaataactacattaaaa |
| | | ccagtttatgaagacactaa |
| | | tattaaaattaaactagata |
| | | aagatactagaaacttcata |
| | | atgccaactataactactaa |
| | | cgaaattagaaacaaattat |
| | | cttattcatttgatggagca |
| | | ggaggaacttactctttatt |
| | | attatcttcatatccaatat |
| | | caacgaatataaatttatct |
| | | aaagatgatttatggatatt |
| | | taatattgataatgaagtaa |
| | | gagaaatatctatagaaaat |
| | | ggtactattaaaaaaggaaa |
| | | gttaataaaagatgttttaa |

-continued

SEQUENCES:

| Name | SEQ ID NOs: | Sequences |
|---|---|---|
| | | gtaaaattgatataaataaa |
| | | aataaacttattataggcaa |
| | | tcaaacaatagattttcag |
| | | gcgatatagataataaagat |
| | | agatatatattcttgacttg |
| | | tgagttagatgataaaatta |
| | | gtttaataatagaaataaat |
| | | cttgttgcaaaatcttatag |
| | | tttgttattgtctggggata |
| | | aaaattatttgatatccaat |
| | | ttatctaatattattgagaa |
| | | aatcaatactttaggcctag |
| | | atagtaaaaatatagcgtac |
| | | aattcacctgatgaatctaa |
| | | taataaatattttggagcta |
| | | tatctaaaacaagtcaaaaa |
| | | agcataatacattataaaaa |
| | | agacagtaaaaatatattag |
| | | aattttataatgacagtaca |
| | | ttagaatttaacagtaaaga |
| | | ttttattgctgaagatataa |
| | | atgtatttatgaaagatgat |
| | | attaatactataacaggaaa |
| | | atactatgttgataataata |
| | | ctgataaaagtatagatttc |
| | | tctatttctttagttagtaa |
| | | aaatcaagtaaaagtaaatg |
| | | gattatatttaaatgaatcc |
| | | gtatactcatcttacccttga |
| | | ttttgtgaaaaattcagatg |
| | | gacaccataatacttctaat |
| | | tttatgaatttatttttgga |
| | | caatataagtttctggaaat |
| | | tgtttgggtttgaaaatata |
| | | aattttgtaatcgataaata |
| | | cttttacccttgttggtaaaa |
| | | ctaatcttggatatgtagaa |
| | | tttattttgtgacaataataa |
| | | aaaatatagatatatatttg |
| | | gtgaatggaaaacatcgtca |
| | | tctaaaagcactatatttag |
| | | cggaaatggtagaaatgttg |
| | | tagtagagcctatatataat |
| | | cctgatacgggtgaagatat |
| | | atctacttcactagatttt |
| | | cctatgaacctctctatgga |
| | | atagatagatatatcaataa |
| | | agtattgatagcacctgatt |
| | | tatatacaagtttaataaat |
| | | attaataccaattattattc |
| | | aaatgagtactaccctgaga |
| | | ttatagttcttaacccaaat |
| | | acattccacaaaaaagtaaa |
| | | tataaatttagatagttctt |
| | | cttttgagtataaatggtct |
| | | acagaaggaagtgactttat |
| | | tttagttagatacttagaag |
| | | aaagtaataaaaaaatatta |
| | | caaaaaataagaatcaaagg |
| | | tatcttatctaatactcaat |
| | | catttaataaaatgagtata |
| | | gattttaaagatattaaaaa |
| | | actattcattaggatatataa |
| | | tgagtaattttaaatcattt |
| | | aattctgaaaatgaattaga |
| | | tagagatcatttaggattta |
| | | aaataatagataataaaact |
| | | tattactatgatgaagatag |
| | | taaattagttaaaggattaa |
| | | tcaatataaataattcatta |
| | | ttctattttgatcctataga |
| | | atttaacttagtaactggat |
| | | ggcaaactatcaatggtaaa |
| | | aaatattattttgatataaa |

| Name | SEQ ID NOs: | Sequences |
|---|---|---|
| | | tactggagcagctttaatta |
| | | gttataaaattattaatggt |
| | | aaacacttttatttaataa |
| | | tgatggtgtgatgcagttgg |
| | | gagtatttaaaggacctgat |
| | | ggatttgaatattttgcacc |
| | | tgccaatactcaaaataata |
| | | acatagaaggtcaggctata |
| | | gtttatcaaagtaaattctt |
| | | aactttgaatggcaaaaaat |
| | | attattttgataatgactca |
| | | aaagcagtcactggatggag |
| | | aattattaacaatgagaaat |
| | | attactttaatcctaataat |
| | | gctattgctgcagtcggatt |
| | | gcaagtaattgacaataata |
| | | agtattatttcaatcctgac |
| | | actgctatcatctcaaaagg |
| | | ttggcagactgttaatggta |
| | | gtagatactactttgatact |
| | | gataccgctattgccttaa |
| | | tggttataaaactattgatg |
| | | gtaaacacttttattttgat |
| | | agtgattgtgtagtgaaaat |
| | | aggtgtgtttagtacctcta |
| | | atggatttgaatattttgca |
| | | cctgctaatacttataataa |
| | | taacatagaaggtcaggcta |
| | | tagtttatcaaagtaaattc |
| | | ttaactttgaatggtaaaaa |
| | | atattactttgataataact |
| | | caaaagcagttaccggatgg |
| | | caaactattgatagtaaaaa |
| | | atattacttaatactaaca |
| | | ctgctgaagcagctactgga |
| | | tggcaaactattgatggtaa |
| | | aaaatattactttaatacta |
| | | acactgctgaagcagctact |
| | | ggatggcaaactattgatgg |
| | | taaaaaatattactttaata |
| | | ctaacactgctatagcttca |
| | | actggttatacaattattaa |
| | | tggtaaacattttatttta |
| | | atactgatggtattatgcag |
| | | ataggagtgtttaaaggacc |
| | | taatggatttgaatattttg |
| | | cacctgctaatacggatgct |
| | | aacaacatagaaggtcaagc |
| | | tatactttaccaaaatgaat |
| | | tcttaactttgaatggtaaa |
| | | aaatattactttggtagtga |
| | | ctcaaaagcagttactggat |
| | | ggagaattattaacaataag |
| | | aaatattactttaatcctaa |
| | | taatgctattgctgcaattc |
| | | atctatgcactataaataat |
| | | gacaagtattactttagtta |
| | | tgatggaattcttcaaaatg |
| | | gatatattactattgaaaga |
| | | aataatttctattttgatgc |
| | | taataatgaatctaaaatgg |
| | | taacaggagtatttaaagga |
| | | cctaatggatttgagtattt |
| | | tgcacctgctaatactcaca |
| | | ataataacatagaaggtcag |
| | | gctatagtttaccagaacaa |
| | | attcttaactttgaatggca |
| | | aaaatattattttgataat |
| | | gactcaaaagcagttactgg |
| | | atggcaaccattgatggta |
| | | aaaaatattactttaatctt |
| | | aacactgctgaagcagctac |
| | | tggatggcaaactattgatg |
| | | gtaaaaaatattactttaat |

| Name | SEQ ID NOs: | Sequences |
|---|---|---|
| | | cttaacactgctgaagcagc |
| | | tactggatggcaaactattg |
| | | atggtaaaaaatattacttt |
| | | aatactaacactttcatagc |
| | | ctcaactggttatacaagta |
| | | ttaatggtaaacatttttat |
| | | tttaatactgatggtattat |
| | | gcagataggagtgtttaaag |
| | | gacctaatggatttgaatac |
| | | tttgcacctgctaatactca |
| | | taataatacatagaaggtc |
| | | aagctatactttaccaaaat |
| | | aaattcttaactttgaatgg |
| | | taaaaaatattactttggta |
| | | gtgactcaaaagcagttacc |
| | | ggattgcgaactattgatgg |
| | | taaaaaatattacttttaata |
| | | ctaacactgctgttgcagtt |
| | | actggatggcaaactattaa |
| | | tggtaaaaaatactacttta |
| | | atactaacacttctatagct |
| | | tcaactggttatacaattat |
| | | tagtggtaaacatttttatt |
| | | ttaatactgatggtattatg |
| | | cagataggagtgtttaaagg |
| | | acctgatggatttgaatact |
| | | ttgcacctgctaatacagat |
| | | gctaacaatagaaggtca |
| | | agctatacgttatcaaaata |
| | | gattcctatatttacatgac |
| | | aatatattattttggtaa |
| | | taattcaaaagcagctactg |
| | | gttgggtaactattgatggt |
| | | aatagatattacttcgagcc |
| | | taatacagctatgggtgcga |
| | | atggttataaaactattgat |
| | | aataaaattttttactttag |
| | | aaatggtttacctcagatag |
| | | gagtgtttaaagggtctaat |
| | | ggatttgaatactttgcacc |
| | | tgctaatacggatgctaaca |
| | | atatagaaggtcaagctata |
| | | cgttatcaaaatagattcct |
| | | acatttacttggaaaaatat |
| | | attactttggtaataattca |
| | | aaagcagttactggatggca |
| | | aactattaatggtaaagtat |
| | | attactttatgcctgatact |
| | | gctatggctgcagctggtgg |
| | | acttttcgagattgatggtg |
| | | ttatatatttctttggtgtt |
| | | gatggagtaaaagccctgg |
| | | gatatatggctaa |
| Amino acid sequence of trdA (strain 630) | 6 | MSLISKEELIKLAYSIRPRE NEYKTILTNLDEYNKLTTNN NENKYLQLKKLNESIDVFMN KYKTSSRNRALSNLKKDILK EVILIKNSNTSPVEKNLHFV WIGGEVSDIALEYIKQWADI NAEYNIKLWYDSEAFLVNTL KKAIVESSTTEALQLLEEEI QNPQFDNMKFYKKRMEFIYD RQKRFINYYKSQINKPTVPT IDDIIKSHLVSEYNRDETVL ESYRTNSLRKINSNHGIDIR ANSLFTEQELLNIYSQELLN RGNLAAASDIVRLLALKNFG GVYLDVDMLPGIHSDLFKTI SRPSSIGLDRWEMIKLEAIM KYKKYINNYTSENFDKLDQQ LKDNFKLIIESKSEKSEIFS KLENLNVSDLEIKIAFALGS VINQALISKQGSYLTNLVIE |

| Name | SEQ ID NOs: | Sequences |
|---|---|---|
| | | QVKNRYQFLNQHLNPAIESD NNFTDTTKIFHDSLFNSATA ENSMFLTKIAPYLQVGFMPE ARSTISLSGPGAYASAYYDF INLQENTIEKTLKASDLIEF KFPENNLSQLTEQEINSLWS FDQASAKYQFEKYVRDYTGG SLSEDNGVDFNKNTALDKNY LLNNKIPSNNVEEAGSKNYV HYIIQLQGDDISYEATCNLF SKNPKNSIIIQRNMNESAKS YFLSDDGESILELNKYRIPE RLKNKEKVKVTFIGHGKDEF NTSEFARLSVDSLSNEISSF LDTIKLDISPKNVEVNLLGC NMFSYDFNVEETYPGKLLLS IMDKITSTLPDVNKNSITIG ANQYEVRINSEGRKELLAHS GKWINKEEAIMSDLSSKEYI FFDSIDNKLKAKSKNIPGLA SISEDIKTLLLDASVSPDTK FILNNLKLNIESSIGDYIYY EKLEPVKNIIHNSIDDLIDE FNLLENVSDELYELKKLNNL DEKYLISFEDISKNNSTYSV RFINKSNGESVYVETEKEIF SKYSEHITKEISTIKNSIIT DVNGNLLDNIQLDHTSQVNT LNAAFFIQSLIDYSSNKDVL NDLSTSVKVQLYAQLFSTGL NTIYDSIQLVNLISNAVNDT INVLPTITEGIPIVSTILDG INLGAAIKELLDEHDPLLKK ELEAKVGVLAINMSLSIAAT VASIVGIGAEVTIFLLPIAG ISAGIPSLVNNELILHDKAT SVVNYFNHLSESKKYGPLKT EDDKILVPIDDLVISEIDFN NNSIKLGTCNILAMEGGSGH TVTGNIDHFFSSPSISSHIP SLSIYSAIGIETENLDFSKK IMMLPNAPSRVFWWETGAVP GLRSLENDGTRLLDSIRDLY PGKFYWRFYAFFDYAITTLK PVYEDTNIKIKLDKDTRNFI MPTITTNEIRNKLSYSFDGA GGTYSLLLSSYPISTNINLS KDDLWIFNIDNEVREISIEN GTIKKGKLIKDVLSKIDINK NKLIIGNQTIDFSGDIDNKD RYIFLTCELDDKISLIIEIN LVAKSYSLLLSGDKNYLISN LSNIIEKINTLGLDSKNIAY NYTDESNNKYFGAISKTSQK SIIHYKKDSKNILEFYNDST LEFNSKDFIAEDINVFMKDD INTITGKYYVDNNTDKSIDF SISLVSKNQVKVNGLYLNES VYSSYLDFVKNSDGHHNTSN FMNLFLDNISFWKLFGFENI NFVIDKYFTLVGKTNLGYVE FICDNNKNIDIYFGEWKTSS SKSTIFSGNGRNVVVEPIYN PDTGEDISTSLDFSYEPLYG IDRYINKVLIAPDLYTSLIN INTNYYSNEYYPEIIVLNPN TFHKKVNINLDSSSFEYKWS TEGSDFILVRYLEESNKKIL QKIRIKGILSNTQSFNKMSI DFKDIKKLSLGYIMSNFKSF NSENELDRDHLGFKIIDNKT YYYDEDSKLVKGLININNSL FYFDPIEFNLVTGWQTINGK KYYFDINTGAALISYKIING |

| Name | SEQ ID NOs: | Sequences |
|---|---|---|
| | | KHFYFNNDGVMQLGVFKGPD GFEYFAPANTQNNNIEGQAI VYQSKFLTLNGKKYYFDNDS KAVTGWRIINNEKYYFNPNN AIAAVGLQVIDNNKYYFNPD TAIISKGWQTVNGSRYYFDT DTAIAFNGYKTIDGKHFYFD SDCVVKIGVFSTSNGFEYFA PANTYNNNIEGQAIVYQSKF LTLNGKKYYFDNNSKAVTGW QTIDSKKYYFNTNTAEAATG WQTIDGKKYYFNTNTAEAAT GWQTIDGKKYYFNTNTAIAS TGYTIINGKHFYFNTDGIMQ IGVFKGPNGFEYFAPANTDA NNIEGQAILYQNEFLTLNGK KYYFGSDSKAVTGWRIINNK KYYFNPNNAIAAIHLCTINN DKYYFSYDGILQNGYITIER NNFYFDANNESKMVTGVFKG PNGFEYFAPANTHNNNIEGQ AIVYQNKFLTLNGKKYYFDN DSKAVTGWQTIDGKKYYFNL NTAEAATGWQTIDGKKYYFN LNTAEAATGWQTIDGKKYYF NTNTFIASTGYTSINGKHFY FNTDGIMQIGVFKGPNGFEY FAPANTHNNNIEGQAILYQN KFLTLNGKKYYFGSDSKAVT GLRTIDGKKYYFNTNTAVAV TGWQTINGKKYYFNTNTSIA STGYTIISGKHFYFNTDGIM QIGVFKGPDGFEYFAPANTD ANNIEGQAIRYQNRFLYLHD NIYYFGNNSKAATGWVTIDG NRYYFEPNTAMGANGYKTID NKNFYFRNGLPQIGVFKGSN GFEYFAPANTDANNIEGQAI RYQNRFLHLLGKIYYFGNNS KAVTGWQTINGKVYYFMPDT AMAAAGGLFEIDGVIYFFGV DGVKAPGIYG |
| Nucleic acid sequence of trdB (strain 630) | 7 | atgagtttagttaatagaaa acagttagaaaaaatggcaa atgtaagatttcgtactcaa gaagatgaatatgttgcaat attggatgctttagaagaat atcataatatgtcagagaat actgtagtcgaaaaatattt aaaattaaaagatataaata gtttaacagatatttatata gatacatataaaaaatctgg tagaaataaagccttaaaaa aatttaaggaatatctagtt acagaagtattagagctaaa gaataataatttaactccag ttgagaaaaatttacatttt gtttggattggaggtcaaat aaatgacactgctattaatt atataaaatcaatggaaaga tgtaaatagtgattataatgt taatgttttttatgatagta atgcatttttgataaacaca ttgaaaaaaactgtagtaga atcagcaataaatgatacac ttgaatcatttagagaaaac ttaaatgaccctagatttga ctataataaattcttcgaa aacgtatggaaataatttat gataaacagaaaaatttcat aaactactataaagctcaaa gagaagaaaatcctgaactt ataattgatgatattgtaaa |

```
gacatatctttcaaatgagt
attcaaaggagatagatgaa
cttaatacctatattgaaga
atccttaaataaaattacac
agaatagtggaaatgatgtt
agaaactttgaagaatttaa
aaatggagagtcattcaact
tatatgaacaagagttggta
gaaaggtggaatttagctgc
tgcttctgacatattaagaa
tatctgcattaaaagaaatt
ggtggtatgtatttagatgt
tgatatgttaccaggaatac
aaccagacttatttgagtct
atagagaaacctagttcagt
aacagtggatttttgggaaa
tgacaaagttagaagctata
atgaaatacaaagaatatat
accagaatatacctcagaac
attttgacatgttagacgaa
gaagttcaaagtagttttga
atctgttctagcttctaagt
cagataaatcagaaatattc
tcatcacttggtgatatgga
ggcatcaccactagaagtta
aaattgcatttaatagtaag
ggtattataaatcaagggct
aatttctgtgaaagactcat
attgtagcaatttaatagta
aaacaaatcgagaatagata
taaaatattgaataatagtt
taaatccagctattagcgag
gataatgattttaatactac
aacgaatacctttattgata
gtataatggctgaagctaat
gcagataatggtagatttat
gatggaactaggaaagtatt
taagagttggtttcttccca
gatgttaaaactactattaa
cttaagtggccctgaagcat
atgcggcagcttatcaagat
ttattaatgtttaaagaagg
cagtatgaatatccatttga
tagaagctgatttaagaaac
tttgaaatctctaaaactaa
tatttctcaatcaactgaac
aagaaatggctagcttatgg
tcatttgacgatgcaagagc
taaagctcaatttgaagaat
ataaaaggaattattttgaa
ggttctcttggtgaagatga
taatcttgattttctcaaa
atatagtagttgacaaggag
tatctttagaaaaaatatc
ttcattagcaagaagttcag
agagaggatatatacactat
attgttcagttacaaggaga
taaaattagttatgaagcag
catgtaacttatttgcaaag
actccttatgatagtgtact
gtttcagaaaaatatagaag
attcagaaattgcatattat
tataatcctggagatggtga
aatacaagaaatagacaagt
ataaaattccaagtataatt
tctgatagacctaagattaa
attaacatttattggtcatg
gtaaagatgaatttaatact
gatatatttgcaggttttga
tgtagattcattatccacag
aaatagaagcagcaatagat
ttagctaaagaggatatttc
tcctaagtcaatagaaataa
atttattaggatgtaatatg
tttagctactctatcaacgt
agaggagacttatcctggaa
aattattacttaaagttaaa
gataaaatatcagaattaat
gccatctataagtcaagact
ctattatagtaagtgcaaat
caatatgaagttagaataaa
tagtgaaggaagaagagaat
tattggatcattctggtgaa
tggataaataaagaagaaag
tattataaaggatatttcat
caaaagaatatatatcattt
aatcctaaagaaaataaaat
tacagtaaaatctaaaaatt
tacctgagctatctacatta
ttacaagaaattagaaataa
ttctaattcaagtgatattg
aactagaagaaaagtaatg
ttaacagaatgtgagataaa
tgttatttcaaatatagata
cgcaaattgttgaggaaagg
attgaagaagctaagaattt
aacttctgactctattaatt
atataaaagatgaatttaaa
ctaatagaatctatttctga
tgcactatgtgacttaaaac
aacagaatgaattagaagat
tctcattttatatctttga
ggacatatcagagactgatg
agggatttagtataagagtt
attaataaagaaactggaga
atctatatttgtagaaactg
aaaaaacaatattctctgaa
tatgctaatcatataactga
agagatttctaagataaaag
gtactatatttgatactgta
aatggtaagttagtaaaaaa
agtaaatttagatactacac
acgaagtaaatactttaaat
gctgcattttttatacaatc
attaatagaatataatagtt
ctaaagaatctcttagtaat
ttaagtgtagcaatgaaagt
ccaagtttacgctcaattat
ttagtactggtttaaatact
attacagatgcagccaaagt
tgttgaattagtatcaactg
cattagatgaaactatagac
ttacttcctacattatctga
aggattacctataattgcaa
ctattatagatggtgtaagt
ttaggtgcagcaatcaaaga
gctaagtgaaacgagtgacc
cattattaagacaagaaata
gaagctaagataggtataat
ggcagtaaatttaacaacag
ctacaactgcaatcattact
tcatctttggggatagctag
tggatttagtatactttag
ttcctttagcaggaatttca
gcaggtataccaagcttagt
aaacaatgaacttgtacttc
gagataaggcaacaaaggtt
gtagattattttaaacatgt
ttcattagttgaaactgaag
gagtatttactttattagat
gataaaataatgatgccaca
agatgatttagtgatatcag
aaatagattttaataataat
tcaatagtttaggtaaatg
tgaaatctggagaatggaag
gtggttcaggtcatactgta
actgatgatatagatcactt
cttttcagcaccatcaataa
```

| Name | SEQ ID NOs: | Sequences |
|---|---|---|
| | | catatagagagccacactta |
| | | tctatatatgacgtattgga |
| | | agtacaaaaagaagaacttg |
| | | attgtcaaaagatttaatg |
| | | gtattacctaatgctccaaa |
| | | tagagtatttgcttgggaaa |
| | | caggatggacaccaggttta |
| | | agaagcttagaaaatgatgg |
| | | cacaaaactgttagaccgta |
| | | taagagataactatgaaggt |
| | | gagttttattggagatattt |
| | | tgcttttatagctgatgctt |
| | | taataacaacattaaaacca |
| | | agatatgaagatactaatat |
| | | aagaataaatttagatagta |
| | | atactagaagttttatagtt |
| | | ccaataataactacagaata |
| | | tataagagaaaaattatcat |
| | | attctttctatggttcagga |
| | | ggaacttatgcattgtctct |
| | | ttctcaatataatatgggta |
| | | taaatatagaattaagtgaa |
| | | agtgatgtttggattataga |
| | | tgttgataatgttgtgagag |
| | | atgtaactatagaatctgat |
| | | aaaattaaaaaggtgattt |
| | | aatagaaggtattttatcta |
| | | cactaagtattgaagagaat |
| | | aaaattatcttaaatagcca |
| | | tgagttaatttttctggtg |
| | | aggtaaatggaagtaatgga |
| | | tttgtttctttaacattttc |
| | | aatttagaaggaataaatg |
| | | caattatagaagttgattta |
| | | ttatctaaatcatataaatt |
| | | acttatttctggcgaattaa |
| | | aaatattgatgttaaattca |
| | | aatcatattcaacagaaaat |
| | | agattatataggattcaata |
| | | gcgaattacagaaaaatata |
| | | ccatatagctttgtagatag |
| | | tgaaggaaaagagaatggtt |
| | | ttattaatggttcaacaaaa |
| | | gaaggtttatttgtatctga |
| | | attacctgatgtagttctta |
| | | taagtaaggtttatatggat |
| | | gatagtaagccttcatttgg |
| | | atattatagtaataatttga |
| | | aagatgtcaaagttataact |
| | | aaagataatgttaatatatt |
| | | aacaggttattatcttaagg |
| | | atgatataaaaatctctctt |
| | | tctttgactctacaagatga |
| | | aaaaactataaagttaaata |
| | | gtgtgcatttagatgaaagt |
| | | ggagtagctgagattttgaa |
| | | gttcatgaatagaaaggta |
| | | atacaaatacttcagattct |
| | | ttaatgagctttttagaaag |
| | | tatgaatataaaaagtattt |
| | | tcgttaattctcttacaatct |
| | | aatattaagtttatattaga |
| | | tgctaatttttataataagtg |
| | | gtactacttctattggccaa |
| | | tttgagtttatttgtgatga |
| | | aaatgataatatacaaccat |
| | | atttcattaagtttaataca |
| | | ctagaaactaattatactttt |
| | | atatgtaggaaatagacaaa |
| | | atatgatagtggaaccaaat |
| | | tatgatttagatgattctgg |
| | | agatatatcttcaactgtta |
| | | tcaatttctctcaaaagtat |
| | | ctttatggaatagacagttg |

| Name | SEQ ID NOs: | Sequences |
|---|---|---|
| | | tgttaataaagttgtaattt |
| | | caccaaatatttatacagat |
| | | gaaataaatataacgcctgt |
| | | atatgaaacaaataatactt |
| | | atccagaagttattgtatta |
| | | gatgcaaattatataaatga |
| | | aaaaataaatgttaatatca |
| | | atgatctatctatacgatat |
| | | gtatggagtaatgatggtaa |
| | | tgattttattcttatgtcaa |
| | | ctagtgaagaaaataaggtg |
| | | tcacaagttaaaataagatt |
| | | cgttaatgttttttaaagata |
| | | agactttggcaaataagcta |
| | | tcttttaactttagtgataa |
| | | acaagatgtacctgtaagtg |
| | | aaataatcttatcatttaca |
| | | ccttcatattatgaggatgg |
| | | attgattggctatgatttgg |
| | | gtctagtttctttatataat |
| | | gagaaatttttatattaataa |
| | | ctttggaatgatggtatctg |
| | | gattaatatatattaatgat |
| | | tcattatattatttttaaacc |
| | | accagtaaataatttgataa |
| | | ctggatttgtgactgtaggc |
| | | gatgataaatactactttaa |
| | | tccaattaatggtggagctg |
| | | cttcaattggagagacaata |
| | | attgatgacaaaaattatta |
| | | tttcaaccaaagtggagtgt |
| | | tacaaacaggtgtatttagt |
| | | acagaagatggatttaaata |
| | | ttttgccccagctaatacac |
| | | ttgatgaaaacctagaagga |
| | | gaagcaattgattttactgg |
| | | aaaattaattattgacgaaa |
| | | atatttattattttgatgat |
| | | aattatagaggagctgtaga |
| | | atggaaagaattagatggtg |
| | | aaatgcactattttagccca |
| | | gaaacaggtaaagcttttaa |
| | | aggtctaaatcaaataggtg |
| | | attataaatactattttcaat |
| | | tctgatggagttatgcaaaa |
| | | aggatttgttagtataaatg |
| | | ataataaacactattttgat |
| | | gattctggtgttatgaaagt |
| | | aggttacactgaaatagatg |
| | | gcaagcatttctactttgct |
| | | gaaaacggagaaatgcaaat |
| | | aggagtatttaatacagaag |
| | | atggatttaaatattttgct |
| | | catcataatgaagatttagg |
| | | aaatgaagaaggtgaagaaa |
| | | tctcatattctggtatatta |
| | | aatttcaataataaaattta |
| | | ctattttgatgattcattta |
| | | cagctgtagttggatggaaa |
| | | gatttagaggatggttcaaa |
| | | gtattattttgatgaagata |
| | | cagcagaagcatatataggt |
| | | ttgtcattaataaatgatgg |
| | | tcaatattattttaatgatg |
| | | atggaattatgcaagttgga |
| | | tttgtcactataaatgataa |
| | | agtcttctacttctctgact |
| | | ctggaattatagaatctgga |
| | | gtacaaaacatagatgacaa |
| | | ttatttctatatagatgata |
| | | atggtatagttcaaattggt |
| | | gtatttgatacttcagatggg |
| | | atataaatattttgcacctg |
| | | ctaatactgtaaatgataat |

| Name | SEQ ID NOs: | Sequences |
|---|---|---|
| | | atttacggacaagcagttga |
| | | atatagtggtttagttagag |
| | | ttggtgaagatgtatattat |
| | | tttggagaaacatatacaat |
| | | tgagactggatggatatatg |
| | | atatggaaaatgaaagtgat |
| | | aaatattatttcaatccaga |
| | | aactaaaaaagcatgcaaag |
| | | gtattaatttaattgatgat |
| | | ataaaatattattttgatga |
| | | gaagggcataatgagaacgg |
| | | gtcttatatcatttgaaaat |
| | | aataattattactttaatga |
| | | gaatggtgaaatgcaatttg |
| | | gttatataaatatagaagat |
| | | aagatgttctattttggtga |
| | | agatggtgtcatgcagattg |
| | | gagtatttaatacaccagat |
| | | ggatttaaatactttgcaca |
| | | tcaaaatactttggatgaga |
| | | attttgagggagaatcaata |
| | | aactatactggttggttaga |
| | | tttagatgaaagagatatt |
| | | attttacagatgaatatatt |
| | | gcagcaactggttcagttat |
| | | tattgatggtgaggagtatt |
| | | attttgatcctgatacagct |
| | | caattagtgattagtgaata |
| | | g |
| Amino acid sequence of trdB (strain 630) | 8 | MSLVNRKQLEKMANVRFRTQ EDEYVAILDALEEYHNMSEN TVVEKYLKLKDINSLTDIYI DTYKKSGRNKALKKFKEYLV TEVLELKNNNLTPVEKNLHF VWIGGQINDTAINYINQWKD VNSDYNVNVFYDSNAFLINT LKKTVVESAINDTLESFREN LNDPRFDYNKFFRKRMEIIY DKQKNFINYYKAQREENPEL IIDDIVKTYLSNEYSKEIDE LNTYIEESLNKITQNSGNDV RNFEEFKNGESFNLYEQELV ERWNLAAASDILRISALKEI GGMYLDVDMLPGIQPDLFES IEKPSSVTVDFWEMTKLEAI MKYKEYIPEYTSEHFDMLDE EVQSSFESVLASKSDKSEIF SSLGDMEASPLEVKIAFNSK GIINQGLISVKDSYCSNLIV KQIENRYKILNNSLNPAISE DNDPFNTTTNTFIDSIMAEAN ADNGRFMMELGKYLRVGFFP DVKTTINLSGPEAYAAAYQD LLMFKEGSMNIHLIEADLRN FEISKTNISQSTEQEMASLW SFDDARAKAQFEEYKRNYFE GSLGEDDNLDFSQNIVVDKE YLLEKISSLARSSERGYIHY IVQLQGDKISYEAACNLFAK TPYDSVLFQKNIEDSEIAYY YNPGDGEIQEIDKYKIPSII SDRPKIKLTPIGHGKDEFNT DIFAGFDVDSLSTEIEAAID LAKEDISPKSIEINLLGCNM FSYSINVEETYPGKLLLKVK DKISELMPSISQDSIIVSAN QYEVRINSEGRRELLDHSGE WINKEESIIKDISSKEYISF NPKENKITVKSKNLPELSTL LQEIRNNSNSSDIELEEKVM LTECEINVISNIDTQIVEER IEEAKNLTSDSINYIKDEFK LIESISDALCDLKQQNELED SHFISFEDISETDEGFSIRF INKETGESIFVETEKTIFSE YANHITEEISKIKGTIFDTV NGKLVKKVNLDTTHEVNTLN AAFFIQSLIEYNSSKESLSN LSVAMKVQVYAQLFSTGLNT ITDAAKVVELVSTALDETID LLPTLSEGLPIIATIIDGVS LGAAIKELSETSDPLLRQEI EAKIGIMAVNLTTATTAIIT SSLGIASGFSILLVPLAGIS AGIPSLVNNELVLRDKATKV VDYFKHVSLVETEGVFTLLD DKIMMPQDDLVISEIDFNNN SIVLGKCEIWRMEGGSGHTV TDDIDHFFSAPSITYREPHL SIYDVLEVQKEELDLSKDLM VLPNAPNRVFAWETGWTPGL RSLENDGTKLLDRIRDNYEG EFYWRYFAFIADALITTLKP RYEDTNIRINLDSNTRSFIV PIITTEYIREKLSYSFYGSG GTYALSLSQYNMGINIELSE SDVWIIDVDNVVRDVTIESD KIKKGDLIEGILSTLSIEEN KIILNSHEINFSGEVNGSNG FVSLTFSILEGINAIIEVDL LSKSYKLLISGELKILMLNS NHIQQKIDYIGFNSELQKNI PYSFVDSEGKENGFINGSTK EGLFVSELPDVVLISKVYMD DSKPSFGYYSNNLKDVKVIT KDNVNILTGYYLKDDIKISL SLTLQDEKTIKLNSVHLDES GVAEILKFMNRKGNTNTSDS LMSFLESMNIKSIFVNFLQS NIKFILDANFIISGTTSIGQ FEFICDENDNIQPYFIKFNT LETNYTLYVGNRQNMIVEPN YDLDDSGDISSTVINFSQKY LYGIDSCVNKVVISPNIYTD EINITPVYETNNTYPEVIVL DANYINEKINVNINDLSIRY VWSNDGNDFILMSTSEENKV SQVKIRFVNVFKDKTLANKL SFNFSDKQDVPVSEIILSFT PSYYEDGLIGYDLGLVSLYN EKFYINNFGMMVSGLIYIND SLYYFKPPVNNLITGFVTVG DDKYYFNPINGGAASIGETI IDDKNYYFNQSGVLQTGVFS TEDGFKYFAPANTLDENLEG EAIDFTGKLIIDENIYYFDD NYRGAVEWKELDGEMHYFSP ETGKAFKGLNQIGDYKYYFN SDGVMQKGFVSINDNKHYFD DSGVMKVGYTEIDGKHFYFA ENGEMQIGVFNTEDGFKYFA HHNEDLGNEEGEEISYSGIL NFNNKIYYFDDSFTAVVGWK DLEDGSKYYFDEDTAEAYIG LSLINDGQYYFNDDGIMQVG FVTINDKVFYFSDSGIIESG VQNIDDNYFYIDDNGIVQIG VFDTSDGYKYFAPANTVNDN IYGQAVEYSGLVRVGEDVYY FGETYTIETGWIYDMENESD KYYFNPETKKACKGINLIDD IKYYFDEKGIMRTGLISFEN NNYYFNENGEMQPGYINIED KMFYFGEDVMQIGVFNTPD GFKYFAHQNTLDENFEGESI NYTGWLDLDEKRYYFTDEYI |

-continued

SEQUENCES:

| Name | SEQ ID NOs: | Sequences |
|---|---|---|
| | | AATGSVIIDGEEYYFDPDTAQLVISE |
| Forward primer | 9 | caccACTAGTatgaacttagtaactggatggc |
| Reverse primer | 10 | CTCGAGttagccatatatcccagggggc |
| Forward primer | 11 | caccATGCATatgagtttagttaatagaaaacag |
| Reverse primer | 12 | ggcCTCGAGctattcactaatcactaattgagc |
| Forward primer | 13 | AGATCTATGCATGAGCTCctcgagcccaaaacgaaaggctcagc |
| Reverse primer | 14 | cggtccggggccatatatecaggggcttttactcc |
| Forward primer | 15 | caccCCATTGatggtaacaggagtatttaaagga |
| Reverse primer | 16 | CTCGAGctattcactaatcactaattgagctg |
| C-TADCTB (nucleic acid sequence) | 17 | atggtaacaggagtatttaaaggacctaatggatttgagtattttgcacctgctaatactcacaataataacatagaaggtcaggctatagtttaccagaacaaattcttaactttgaatggcaaaaaatattattttgataatgactcaaaagcagttactggatggcaaaccattgatggtaaaaaatattactttaatcttaacactgctgaagcagctactggatggcaaactattgatggtaaaaaatattacttcttaacactgctgaagcagctactggatggcaaactattgatggtaaaaaatattactttaatactaacactttcatagcctcaactggttatacaagtattaatggtaaacattttttatttaatactgatggtattatgcagataggagtgtttaaaggacctaatggatttgaatactttgcacctgctaatacggatgctaacaacatagaaggtcaagctatacgttatcaaaatagattcctatatttacatgacaatatatattattttgtaataattcaaaagcggctactggttgggtaactattga |

-continued

SEQUENCES:

| Name | SEQ ID NOs: | Sequences |
|---|---|---|
| | | tggtaatagatattacttcgagcctaatacagctatgggtgcgaatggttataaaactattgataataaaaattttttactttagaaatggtttacctcagataggagtgtttaaagggtctaatggatttgaatactttgcacctgctaatacggatgctaacaatatagaaggtcaagctatacgttatcaaaatagattcctacatttacttggaaaaatatattactttggtaataattcaaaagcagttactggatggcaaactattaatggtaaagtatattactttatgcctgatactgctatggctgcagctgtggacttttcgagattgatggtgttatatatttctttggtgttgatggagtaaaagcccctgggatatatggcAGATCTATGCATaatttgataactgaatttgtgactgtaggcgatgataaatactactttaatccaattaatggtggagctgcttcaattggagagacaataattgatgacaaaaattattatttcaaccaaagtggagtgttacaaacaggtgtatttagtacagaagatggatttaaatatttgccccagctaatacacttgatgaaacctagaaggagaagcaattgatttactggaaaattaattattgacgaaaatatttattattttgatgataattatagaggagctgtagaatggaaagaattagatggtgaaatgcactattttagcccagaaacaggtaaagcttttaaaggtctaaatcaaataggtgattataaatactatttcaattctgatggagttatgcaaaaggatttgttagtataaatgataaataaacactattttgatgattctggtgtatgaaagtaggttacactgaaatagatggcaagcatttctactttgctgaaaacggagaaatgcaaataggagtatttaatacagaagatggatttaaatattttgctcatcataatgaagatttaggaaatgaagaggtgaagaaatctcatattctggtatattaatttcaataataaaatttactattttgatgattcatttacagctgtagttggatgaaagattagaggatggttcaaagtattatttgatgaagatacagcagaagcatatataggtttgtcattaataaaatgatggtcaatattattttaatgatgatggaattatgcaagttggatttgtcactataaatgataaagtcttctacttctctgactctggaattatagaatctggagtacaaaacatagatgacaattatttctatatagatgataatggtatagttcaaattggtgtatttgatacttcagatggatatattaatattttgcacctgctaatactgtaaatgataatatttacggacaagcagttgaatatagtggtttagttagagttggggaagatgtatattatttggagaaacatatacaattgag |

SEQUENCES:

| Name | SEQ ID NOs: | Sequences |
|---|---|---|
| | | actggatggatatatgatat |
| | | ggaaaatgaaagtgataaat |
| | | attatttcaatccagaaact |
| | | aaaaaagcatgcaaaggtat |
| | | taatttaattgatgatataa |
| | | aatattattttgatgagaag |
| | | ggcataatgagaacgggtct |
| | | tatatcatttgaaaataata |
| | | attattacttttaatgagaat |
| | | ggtgaaatgcaatttggtta |
| | | tataaatatagaagataaga |
| | | tgttctattttggtgaagat |
| | | ggtgtcatgcagattggagt |
| | | atttaatacaccagatggat |
| | | ttaaatactttgcacatcaa |
| | | aatactttggatgagaattt |
| | | tgagggagaatcaataaact |
| | | atactggttggttagattta |
| | | gatgaaagagatattattt |
| | | tacagatgaatatattgcag |
| | | caactggttcagttattatt |
| | | gatggtgaggagtattattt |
| | | tgatcctgatacagctcaat |
| | | tagtgattagtgaaCTCGAG |
| | | ggattaatatattaatga |
| | | ttcattatattattttaaac |
| | | caccagtaaataatttgata |
| | | actggatttgtgactgtagg |
| | | cgatgataaatactacttta |
| | | atccaattaatggtgggagct |
| | | gcttcaattggagagacaat |
| | | aattgatgacaaaaattatt |
| | | atttcaaccaaagtggagtg |
| | | ttacaaacaggtgtattag |
| | | tacagaagatggattttaaat |
| | | attttgccccagctaataca |
| | | cttgatgaaacctagaagg |
| | | agaagcaattgattttactg |
| | | gaaaattaattattgacgaa |
| | | aatatttattattttgatga |
| | | taattatagaggagctgtag |
| | | aatggaaagaattagatggt |
| | | gaaatgcactattttagccc |
| | | agaaacaggtaaagctttta |
| | | aaggtctaaatcaaataggt |
| | | gattataaatactatttcaa |
| | | ttctgatggagttatgcaaa |
| | | aaggatttgttagtataaat |
| | | gataataaacactattttga |
| | | tgattctggtgttatgaaag |
| | | taggttacactgaaatagat |
| | | ggcaagcatttctactttgc |
| | | tgaaaacggagaaatgcaaa |
| | | taggagtatttaatacagaa |
| | | gatggatttaaatattttgc |
| | | tcatcataatgaagattttag |
| | | gaaatgaagaaggtgaagaa |
| | | atctcatattctggtatatt |
| | | aaatttcaataataaatt |
| | | actattttgatgattcattt |
| | | acagctgtagttggatggaa |
| | | agatttagaggatggttcaa |
| | | agtattattttgatgaagat |
| | | acagcagaagcatatatagg |
| | | tttgtcattaataaatgatg |
| | | gtcaatattattttaatgat |
| | | gatggaattatgcaagttgg |
| | | atttgtcactataaatgata |
| | | aagtcttctacttctctgac |
| | | tctggaattatagaatctgg |
| | | agtacaaacatagatgaca |
| | | attatttctatatagatgat |
| | | aatggtatagttcaaattgg |
| | | tgtatttgatacttcagatg |
| | | gatataaatattttgcacct |
| | | gctaatactgtaaatgataa |
| | | tatttacggacaagcagttg |
| | | aatatagtggtttagttaga |
| | | gttggggaagatgtatatta |
| | | ttttggagaaacatatacaa |
| | | ttgagactggatggatatat |
| | | gatatggaaaatgaaagtga |
| | | taaatattatttcaatccag |
| | | aaactaaaaagcatgcaaa |
| | | ggtattaatttaattgatga |
| | | tataaaatattattttgatg |
| | | agaagggcataatgagaacg |
| | | ggtcttatatcatttgaaaa |
| | | taataattattactttaatg |
| | | agaatggtgaaatgcaattt |
| | | ggttatataaaatatagaaga |
| | | taagatgttctattttggtg |
| | | aagatggtgtcatgcagatt |
| | | ggagtatttaatacaccaga |
| | | tggatttaaatactttgcac |
| | | atcaaaatactttggatgag |
| | | aattttgagggagaatcaat |
| | | aaactatactggttggttag |
| | | atttagatgaaaagagatat |
| | | tattttacagatgaatatat |
| | | tgcagcaactggttcagtta |
| | | ttattgatggtgaggagtat |
| | | tattttgatcctgatacagc |
| | | tcaattagtgattagtgaat |
| | | ag |
| C-TADCTB (amino acid sequence) | 18 | MVTGVFKGPNGFEYFAPANT HNNNIEGQAIVYQNKFLTLN GKKYYFDNDSKAVTGWQTID GKKYYFNLNTAEAATGWQTI DGKKYYFNLNTAEAATGWQT IDGKKYYFNTNTFIASTGYT SINGKHFYFNTDGIMQIGVF KGPNGFEYFAPANTDANNIE GQAILYQNKFLTLNGKKYYF GSDSKAVTGLRTIDGKKYYF NTNTAVAVTGWQTINGKKYY FNTNTSIASTGYTIISGKHF YFNTDGIMQIGVFKGPDGFE YFAPANTDANNIEGQAIRYQ NRFLYLHDNIYYFGNNSKAA TGWVTIDGNRYYFEPNTAMG ANGYKTIDNKNFYFRNGLPQ IGVFKGSNGFEYFAPANTDA NNIEGQAIRYQNRFLHLLGK IYYFGNNSKAVTGWQTINGK VYYFMPDTAMAAAGGLFEID GVIYFFGVDGVKAPGIYGRS MHNLITGFVTVGDDKYYFNP INGGAASIGETIIDDKNYYF NQSGVLQTGVFSTEDGFKYF APANTLDENLEGEAIDFTGK LIIDENIYYFDDNYRGAVEW KELDGEMHYFSPETGKAFKG LNQIGDYKYYFNSDGVMQKG FVSINDNKHYFDDSGVMKVG YTEIDGKHFYFAENGEMQIG VFNTEDGFKYFAHHNEDLGN EEGEEISYSGILNFNNKIYY FDDSFTAVVGWKDLEDGSKY YFDEDTAEAYIGLSLINDGQ YYFNDDGIMQVGFVTINDKV YYFSDSGIIESGVQNIDDNY FYIDDNGIVQIGVFDTSDGY KYFAPANTVNDNIYGQAVEY SGLVRVGEDVYYFGETYTIE TGWIYDMENESDKYYFNPET KKACKGINLIDDIKYYFDEK |

| Name | SEQ ID NOs: | Sequences |
|---|---|---|
| | | GIMRTGLISFENNNYYFNEN GEMQFGYINIEDKMFYFGED GVMQIGVFNTPDGFKYFAHQ NTLDENFEGESINYTGWLDL DEKRYYFTDEYIAATGSVII DGEEYYFDPDTAQLVISELE GLIYINDSLYYFKPPVNNLI TGFVTVGDDKYYFNPINGGA ASIGETIIDDKNYYFNQSGV LQTGVFSTEDGFKYFAPANT LDENLEGEAIDFTGKLIIDE NIYYFDDNYRGAVEWKELDG EMHYFSPETGKAFKGLNQIG DYKYYFNSDGVMQKGFVSIN DNKHYFDDSGVMKVGYTEID GKHFYFAENGEMQIGVFNTE DGFKYFAHHNEDLGNEEGEE ISYSGILNFNNKIYYFDDSF TAVVGWKDLEDGSKYYFDED TAEAYIGLSLINDGQYYFND DGIMQVGFVTINDKVFYFSD SGIIESGVQNIDDNYFYIDD NGIVQIGVFDTSDGYKYFAP ANTVNDNIYGQAVEYSGLVR VGEDVYYFGETYTIETGWIY DMENESDKYYFNPETKKACK GINLIDDIKYYFDEKGIMRT GLISFENNNYYFNENGEMQF GYINIEDKMFYFGEDGVMQI GVFNTPDGFKYFAHQNTLDE NFEGESINYTGWLDLDEKRY YFTDEYIAATGSVIIDGEEY YFDPDTAQLVISE |
| C-TANCTB (nucleic acid sequence) | 19 | atggtaacaggagtatttaa aggacctaatggatttgagt attttgcacctgctaatact cacaataataacatagaagg tcaggctatagtttaccaga acaaattcttaactttgaat ggcaaaaatattattttga taatgactcaaaagcagtta ctggatggcaaaccattgat ggtaaaaaatattactttaa tcttaacactgctgaagcag ctactggatggcaaaact attgatggtaaaaaatatta ctttaatactaacactttca tagcctcaactggttataca agtattaatggtaaacattt ttattttaatactgatggta ttatgcagataggagtgttt aaaggacctaatggatttga atactttgcacctgctaata cggatgctaacaacatagaa ggtcaagctatactttacca aaataaattcttaactttga atggtaaaaaatattacttt ggtagtgactcaaaagcagt taccggactgcgaactattg atggtaaaaaatattacttt aatactaacactgctgttgc agttactgatggcaaacta ttaatggtaaaaaatactac tttaatactaacacttctat agcttcaactggttatacaa ttattagtggtaaacatttt tatttaatactgatggtat tatgcagataggagtgttta aaggacctgatggatttgaa tactttgcacctgctaatac | agatgctaacaatatagaag gtcaagctatacgttatcaa aatagattcctatatttaca tgacaatatatattattttg gtaataattcaaaagcggct actggttgggtaactattga tggtaatagatattacttcg agcctaatacagctatgggt gcgaatggttataaaactat tgataataaaaattttttact ttagaaatggtttacctcag ataggagtgtttaaagggtc taatggatttgaatactttg cacctgctaatacggatgct aacaatatagaaggtcaagc tatacgttatcaaaatagat tcctacatttacttggaataa atatattactttggtaataa ttcaaaagcagttactggat ggcaaactattaatggtaaa gtatattactttatgcctga tactgctatggctgcagctg gtggacttttcgagattgat ggtgttatatatttctttgg tgttgatggagtaaaagccc ctgggatatatggcAGATCT ATGCAtaatttgataactgg atttgtgactgtaggcgatg ataaatactactttaatcca attaatggtggagctgcttc aattggagagacaataattg atgacaaaaattattatttc aaccaaagtggagtgttaca aacaggtgtatttagtacag aagatggatttaaatatttt gccccagctaatacacttga tgaaaacctagaaggagaag caattgattttactggaaaa ttaattattgacgaaaatat ttattattttgatgataatt atagaggagctgtagaatgg aaagaattagatggtgaaat gcactattttagcccagaaa caggtaaagcttttaaaggt ctaaatcaaataggtgatta taaatactattttcaattctg atggagttatgcaaaagga tttgttagtataaatgataa taaacactattttgatgatt ctggtgttatgaaagtaggt tacactgaaatagatggcaa gcatttctactttgctgaaa acggagaaatgcaaatagga gtatttaatacagaagatgg atttaaatattttgctcatc ataatgaagatttaggaaat gaagaaggtgaagaaatctc atattctggtatattaaatt tcaataataaaatttactat tttgatgattcatttacagc tgtagttggatggaaagatt tagaggatggttcaaagtat tattttgatgaagatacagc agaagcatatataggtttgt cattaataaatgatggtcaa tattatttttaatgatgatgg aattatgcaagttggatttg tcactataaatgataaagtc ttctacttctctgactggaa aattatagaatctggagtac aaaaacatagatgacaattat ttctatatagatgataatgg tatagttcaaattggtgtat ttgatacttcagatggatat |

SEQUENCES:

| Name | SEQ ID NOs: | Sequences |
|---|---|---|
| | | aaatattttgcacctgctaa |
| | | tactgtaaatgataatattt |
| | | acggacaagcagttgaatat |
| | | agtggtttagttagagttgg |
| | | ggaagatgtatattattttg |
| | | gagaaacatatacaattgag |
| | | actggatggatatatgatat |
| | | ggaaaatgaaagtgataaat |
| | | attatttcaatccagaaact |
| | | aaaaaagcatgcaaaggtat |
| | | taatttaattgatgatataa |
| | | aatattattttgatgagaag |
| | | ggcataatgagaacgggtct |
| | | tatatcatttgaaaataata |
| | | attattactttaatgagaat |
| | | ggtgaaatgcaatttggtta |
| | | tataaatatagaagataaga |
| | | tgttctattttggtgaagat |
| | | ggtgtcatgcagattggagt |
| | | atttaatacaccagatggat |
| | | ttaaatactttgcacatcaa |
| | | aatactttggatgagaattt |
| | | tgagggagaatcaataaact |
| | | atactggttggttagattta |
| | | gatgaaaagagatattattt |
| | | tacagatgaatatattgcag |
| | | caactggttcagttattatt |
| | | gatggtgaggagtattattt |
| | | tgatcctgatacagctcaat |
| | | tagtgattagtgaaCTCGAG |
| | | ggattaatatatattaatga |
| | | ttcattatattattttaaac |
| | | caccagtaaataatttgata |
| | | actggatttgtgactgtagg |
| | | cgatgataaatactacttta |
| | | atccaattaatggtggagct |
| | | gcttcaattggagagacaat |
| | | aattgatgacaaaaattatt |
| | | atttcaaccaaagtggagtg |
| | | ttacaaacaggtgtatttag |
| | | tacagaagatggatttaaat |
| | | attttgccccagctaataca |
| | | cttgatgaaaacctagaagg |
| | | agaagcaattgattttactg |
| | | gaaaattaattattgacgaa |
| | | aatatttattattttgatga |
| | | taattatagaggagctgtag |
| | | aatggaaagaattagatggt |
| | | gaaatgcactattttagccc |
| | | agaaacaggtaaagctttta |
| | | aaggtctaaatcaaataggt |
| | | gattataaatactatttcaa |
| | | ttctgatggagttatgcaaa |
| | | aaggatttgttagtataaat |
| | | gataataaacactattttga |
| | | tgattctggtgttatgaaag |
| | | taggttacactgaaatagat |
| | | ggcaagcatttctactttgc |
| | | tgaaaacggagaaatgcaaa |
| | | taggagtatttaatacagaa |
| | | gatggatttaaatattttgc |
| | | tcatcataatgaagatttag |
| | | gaaatgaagaaggtgaagaa |
| | | atctcatattct |
| C-TANCTB (amino acid sequence) | 20 | MVTGVFKGPNGFEYFAPANTHNNNIEGQAIVYQNKFLTLNGKKYYFDNDSKAVTGWQTIDGKKYYFNLNTAEAATGWQTIDGKKYYFNLNTAEAATGWQTIDGKKYYFNTNTFIASTGYTSINGKHFYFNTDGIMQIGVFKGPNGFEYFAPANTDANNIEGQAILYQNKFLTLNGKKYYFGSDSKAVTGLRTIDGKKYYFNTNTAVAVTGWQTINGKKYYFNTNTSIASTGYTIISGKHFYFNTDGIMQIGVFKGPDGFEYFAPANTDANNIEGQAIRYQNRFLYLHDNIYYFGNNSKAATGWVTIDGNRYYFEPNTAMGANGYKTIDNKNFYFRNGLPQIGVFKGSNGFEYFAPANTDANNIEGQAIRYQNRFLHLLGKIYYFGNNSKAVTGWQTINGKVYYFMPDTAMAAAGGLFEIDGVIYFFGVDGVKAPGIYGRSMHNLITGFVTVGDDKYYFNPINGGAASIGETIIDDKNYYFNQSGVLQTGVFSTEDGFKYFAPANTLDENLEGEAIDFTGKLIIDENIYYFDDNYRGAVEWKELDGEMHYFSPETGKAFKGLNQIGDYKYYFNSDGVMQKGFVSINDNKHYFDDSGVMKVGYTEIDGKHFYFAENGEMQIGVFNTEDGFKYFAHHNEDLGNEEGEEISYSGILNFNNKIYYFDDSFTAVVGWKDLEDGSKYYFDEDTAEAYIGLSLINDGQYYFNDDGIMQVGFVTINDKVFYFSDSGIIESGVQNIDDNYFYIDDNGIVQIGVFDTSDGYKYFAPANTVNDNIYGQAVEYSGLVRVGEDVYYFGETYTIETGWIYDMENESDKYYFNPETKKACKGINLIDDIKYYFDEKGIMRTGLISFENNNYYFNENGEMQFGYINIEDKMFYFGEDGVMQIGVFNTPDGFKYFAHQNTLDENFEGESINYTGWLDLDEKRYYFTDEYIAATGSVIIDGEEYYFDPDTAQLVISELEGLIYINDSLYYFKPPVNNLITGFVTVGDDKYYFNPINGGAASIGETIIDDKNYYFNQSGVLQTGVFSTEDGFKYFAPANTLDENLEGEAIDFTGKLIIDENIYYFDDNYRGAVEWKELDGEMHYFSPETGKAFKGLNQIGDYKYYFNSDGVMQKGFVSINDNKHYFDDSGVMKVGYTEIDGKHFYFAENGEMQIGVFNTEDGFKYFAHHNEDLGNEEGEEISYS |

Preferred Aspects:

Preferred Polypeptides and Uses Thereof:

1. An isolated polypeptide comprising an amino acid sequence having at least 85%, more preferably at least 90%, even more preferably at least 95%, most preferred 99% sequence identity to the amino acid sequence as set forth in SEQ ID NO: 2.

2. An isolated polypeptide comprising an amino acid sequence having at least 85%, more preferably at least 90%, even more preferably at least 95%, most preferred 99% sequence identity to the amino acid sequence as set forth in SEQ ID NO: 4.

3. The isolated polypeptide of aspect 1 or 2, wherein the polypeptide comprises 19 repeating units derived from the C-terminal domain of toxin A of *Clostridium difficile* and 23 repeating units derived from the C-terminal domain of toxin B of *Clostridium difficile*.

4. The isolated polypeptide of aspect 1, wherein the polypeptide has the amino acid sequence as set forth in SEQ ID NO: 2.

5. The isolated polypeptide of aspect 1, wherein the polypeptide has the amino acid sequence as set forth in SEQ ID NO: 4.

6. A polypeptides comprising an amino acid sequence having at least 85%, more preferably at least 90%, even more preferably at least 95%, most preferred 99% sequence identity to the amino acid sequence as set forth in SEQ ID NO: 4.

7. The polypeptide of aspect 6, wherein a hamster vaccinated with said isolated polypeptide survives intragastric administration of a lethal dose of *C. difficile* spores at all spore doses ($10^2$, $10^3$ and $10^4$).

8. The polypeptide of aspect 6 or 7, wherein the polypeptide comprises 19 repeating units derived from the C-terminal domain of toxin A of *Clostridium difficile*.

9. The polypeptide of any one of aspects 6 to 8, wherein the polypeptide comprises 23, 33 or 47 repeating units derived from the C-terminal domain of toxin B of *Clostridium difficile*.

10. The polypeptide of any one of aspects 6 to 9, wherein the polypeptide is selected from the group consisting of SEQ ID: 2, SEQ ID NO: 4, SEQ ID NO. 18, SEQ ID NO: 20 and a polypeptide that is 95%, 96%, 97%, 98%, 99% identical to any of SEQ ID: 2, SEQ ID NO: 4, SEQ ID NO. 18, or SEQ ID NO: 20.

11. The polypeptide of any one of aspects 6 to 10, wherein the polypeptide is isolated.

12. The polypeptide of any one of aspects 6 to 11 for use in medicine.

13. The polypeptide of any one of aspects 6 to 11 for the prevention and treatment of CDAD.

14. The polypeptide of any one of aspects 6 to 11 for the prevention of CDAD in a subject at risk of a CDAD.

15. The polypeptide of any one of aspects 6 to 11 for the prevention of CDAD in a subject at risk of a CDAD, wherein said subject at risk of CDAD is: i) a subject above 65 years of age or a subject below 2 years of age; ii) a subject with AIDS; iii) a subject taking or planning to take immunosuppressing drugs; iv) a subject with planned hospitalization or a subject that is in hospital; v) a subject in or expected to go to an intensive care unit; vi) a subject that is undergoing or is planning to undergo gastrointestinal surgery; vii) a subject that is in or planning to go to a long-term care such as a nursing home; viii) a subject with co-morbidities requiring frequent and/or prolonged antibiotic use; or ix) a subject with recurrent CDAD.

16. The use of the polypeptide any one of aspects 6 to 11 for the manufacture of a medicament for use in medicine.

17. The use of the polypeptide of any one of aspects 6 to 11 for the manufacture of a medicament for the prevention and treatment of CDAD.

18. The use of the polypeptide of any one of aspects 6 to 11 for the manufacture of a medicament for the prevention of CDAD in a subject at risk of a CDAD.

19. The use of the polypeptide of any one of aspects 6 to 11 for the manufacture of a medicament for the prevention of CDAD in a subject at risk of a CDAD, wherein said subject at risk of CDAD is: i) a subject above 65 years of age or a subject below 2 years of age; ii) a subject with AIDS; iii) a subject taking or planning to take immunosuppressing drugs; iv) a subject with planned hospitalization or a subject that is in hospital; v) a subject in or expected to go to an intensive care unit; vi) a subject that is undergoing or is planning to undergo gastrointestinal surgery; vii) a subject that is in or planning to go to a long-term care such as a nursing home; viii) a subject with co-morbidities requiring frequent and/or prolonged antibiotic use; or ix) a subject with recurrent CDAD.

20. A diagnostic kit for detecting a *C. difficile* infection in a subject comprising the polypeptide of any one of aspects 1 to 11.

Preferred Nucleic Acids:

1a. A nucleic acid comprising a nucleotide sequence encoding any of the polypeptides of any one of aspects 1 to 11.

2a. The nucleic acid of aspect 1a essentially consisting of a nucleotide sequence encoding the polypeptide of any one of aspect 1 to 11.

3a. The nucleic acid of aspect 1a or 2a comprising a nucleotide sequence selected from the group of SEQ ID NO: 1, SEQ ID NO: 3, SEQ ID NO: 17 and SEQ ID NO: 19.

4a. The nucleic acid of aspect 1a or 2a essentially consisting of a nucleotide sequence selected from the group of SEQ ID NO: 1, SEQ ID NO: 3, SEQ ID NO: 17 and SEQ ID NO: 19.

Preferred Pharmaceutical Compositions:

1c. A pharmaceutical composition comprising the polypeptide of any one of aspects 1 to 11 or a nucleic acid of any one of aspects 1a to 4a and a pharmaceutically acceptable carrier or excipient.

2c. The pharmaceutical composition of aspect 1c, wherein said composition elicits antibodies neutralizing both *C. difficile* toxin A and B.

3c. The pharmaceutical composition of aspect 1c or aspect 2c, wherein said composition elicits protective immune response in a subject against *C. difficile* toxin A and B.

4c. The pharmaceutical composition of any one of aspects 1c to 3c, further comprising an adjuvant.

5c. The pharmaceutical composition of aspect 4c, wherein the adjuvant comprises alum.

6c. The pharmaceutical composition of any one of aspects 1c to 5c, further comprising an additional antigen or a drug.

Preferred antibodies: ld. An antibody directed against a polypeptide of any of aspects 1 to 11, but not recognizing any of or both *C. difficile* toxin A (SEQ ID NO: 6) and B (SEQ ID NO: 8).

Preferred Methods

1e. A method for producing the polypeptide of any one of aspects 1 to 10 comprising introducing into a host cell a nucleic acid encoding the polypeptide, culturing the host cell under conditions that allow expression of the polypeptide, and isolating the polypeptide.

2e. The method of aspect 1e, wherein the host cell is *E. coli*.

3e. A method of treating and/or preventing *C. difficile* associated disease (CDAD) in a subject comprising administering to a subject in need thereof the isolated polypeptide of any one of aspects 1 to 11

4e. A method of inducing a specific immune response against both the toxin A and B of *C. difficile* in a subject comprising administering the polypeptide of any one of aspects 1 to 11 to a subject or the pharmaceutical composition of any one of aspects 1c to 6c 5e. A method of preventing a primary disease caused by *C. difficile* infection in a subject comprising administering the polypeptide of any one of aspects 1 to 11 to a subject or the pharmaceutical composition of any one of aspects 1c to 6c.

6e. A method of preventing a primary disease caused by *C. difficile* infection in a subject at risk of *C. difficile* associated disease (CDAD), wherein said subject at risk of CDAD is: i) a subject above 65 years of age or a subject below 2 years of age; ii) a subject with AIDS; iii) a subject taking or planning to take immunosuppressing drugs; iv) a subject with planned hospitalization or a subject that is in hospital; v) a subject in or expected to go to an intensive care unit; vi) a subject that is undergoing or is planning to undergo gastrointestinal surgery; vii) a subject that is in or planning to go to a long-term care such as a nursing home; viii) a subject with co-morbidities requiring frequent and/or prolonged antibiotic use; or ix) a subject with recurrent CDAD; comprising administering the polypeptide of any one of aspects 1 to 11 to said subject or the pharmaceutical composition of any one of aspects 1c to 6c. 7e. The method of any one of aspects 1e to 6e, wherein the polypeptide or the pharmaceutical composition is administered to the subject intramuscularly, intradermally, subcutaneously, orally, nasally, or rectally, preferably intramuscularly.

8e. The method of any one of aspects 1e to 7e, wherein the polypeptide or the pharmaceutical composition is administered to the subject within at least two doses in a short time interval (weekly or bi-weekly).

9e. A method of detecting *C. difficile* in a biological sample comprising contacting the biological sample with the polypeptide of any one of aspects 1 to 11 and detecting binding of the polypeptide to the biological sample, wherein binding of the polypeptide is indicative of the presence of *C. difficile* in the biological sample.

SEQUENCE LISTING

```
Sequence total quantity: 24
SEQ ID NO: 1             moltype = DNA  length = 2877
FEATURE                  Location/Qualifiers
misc_feature             1..2877
                         note = C-TAB.G5 fusion DNA
source                   1..2877
                         mol_type = other DNA
                         organism = synthetic construct
SEQUENCE: 1
atggtaacag gagtatttaa aggacctaat ggatttgagt attttgcacc tgctaatact   60
cacaataata acatagaagg tcaggctata gtttaccaga acaaattctt aactttgaat  120
ggcaaaaaat attattttga taatgactca aaagcagtta ctggatggca aaccattgat  180
ggtaaaaaat attactttaa tcttaacact gctgaagcag ctactggatg gcaaactatt  240
gatggtaaaa aatattactt taatcttaac actgctgaag cagctactgg atggcaaact  300
attgatggta aaaaatatta ctttaatact aacactttca tagcctcaac tggttataca  360
agtattaatg gtaaacattt ttattttaat actgatggta ttatgcagat aggagtgttt  420
aaaggaccta atggatttga atactttgca cctgctaata ctcataataa caacatagaa  480
ggtcaagcta tactttacca aaataaattc ttaactttga atggtaaaaa atattacttt  540
ggtagtgact caaaagcagt taccggattg cgaactattg atggtaaaaa atattacttt  600
aatactaaca ctgctgttgc agttactgga tggcaaacta ttaatggtaa aaaatactac  660
tttaatacta acacttctat agcttcaact ggttatacaa ttattagtgg taaacatttt  720
tattttaata ctgatggtat tatgcagata ggagtgttta aaggacctga tggatttgaa  780
tactttgcac ctgctaatac agatgctaac aatatagaag tcaagctat acgttatcaa  840
aatagattcc tatatttaca tgacaatata tattattttg gtaataattc aaaagcagct  900
actggttggg taacttattga tggtaataga tattacttcg agcctaatac agctatgggt  960
gcgaatggtt ataaaactat tgataataaa aattttttact ttagaaatgg tttacctcag 1020
ataggagtgt ttaaagggtc taatggatttt gaatactttg cacctgctaa tacgatgct 1080
aacaatatag aaggtcaagc tatacgttat caaaatagat tcctacattt acttggaaaa 1140
atatattact ttggtaataa ttcaaaagca gttactggat ggcaaactat taatggtaaa 1200
gtatattact ttatgcctga tactgctatg gctgcagctg gtggactttt cgagattgat 1260
ggtgttatat atttctttgg tgttgatgga gtaaaagccc ctgggatata tggcagatct 1320
atgcataatt tgataactgg atttgtgact gtaggcgatg ataaatacta ctttaatcca 1380
attaatggtg gagctgcttc aattggagag acaataattg atgacaaaaa ttattatttc 1440
aaccaaagtg gagtgttaca aacaggtgta tttagtacag aagatggatt taaatattt  1500
gccccagcta atacacttga tgaaaaccta gaaggagaag caattgattt tactggaaaa 1560
ttaattattg acgaaaatat ttattatttt gatgataatt atagaggagc tgtagaatgg 1620
aaagaattag atggtgaaat gcactatttt agcccagaaa caggtaaagc tttttaaaggt 1680
ctaaatcaaa taggtgatta taaatactat ttcaattctg atggagttat gcaaaaagga 1740
tttgttagta taaatgataa taaacactat tttgatgatt ctggtgttat gaaagtaggt 1800
tacactgaaa tagatggcaa gcatttctac tttgctgaaa acggagaaat gcaaatagga 1860
gtatttaata cagaagatgg atttaaatat tttgctcatc ataatgaaga tttaggaaat 1920
gaagaaggtg aagaaatctc atattctggt atattaaatt tcaataataa aatttactat 1980
tttgatgatt catttacagc tgtagttgga tggaaagatt tagaggatgg ttcaaagtat 2040
tattttgatg aagatacagc agaagcatat ataggtttgt cattaataaa tgatggtcaa 2100
tattatttta atgatgatgg aattatgcaa gttggatttg tcactataaa tgataaagtc 2160
ttctacttct ctgactctgg aattataaga tctgagtac aaaacataga tgacaattat 2220
ttctatatag atgataatgg tatagttcaa attggtgtat ttgatacttc agatggatat 2280
aaatattttg cacctgctaa tactgtaaat gataatattt acggacaagc agttgaatat 2340
agtggtttag ttgagttgg ggaagatgta tattattttg gagaaacata tacaattgag 2400
actggatgga tatatgatat ggaaaatgaa agtgataaat attattttcaa tccagaaact 2460
aaaaaagcat gcaaaggtat taattaatt gatgatataa aatatattt tgatgagaag 2520
ggcataatga gaacgggtct tatatcattt gaaaataata attattactt taatgagaat 2580
ggtgaaatgc aatttggtta tataaatata gaagataaga tgttctattt tggtgaagat 2640
ggtgtcatgc agattggagt atttaataca ccagatggat ttaaatactt tgcacatcaa 2700
aatactttgg atgagaattt tgagggagaa tcaataaact atactggttg gttagattta 2760
gatgaaaaga gatattattt tacagatgaa tatattgcag caactggttc agttattatt 2820
gatggtgagg agtattatttt tgatcctgat acagctcaat tagtgattag tgaatag    2877

SEQ ID NO: 2             moltype = AA  length = 958
FEATURE                  Location/Qualifiers
```

| | | |
|---|---|---|
| REGION | 1..958 | |
| | note = C-TAB.G5 fusion protein | |
| source | 1..958 | |
| | mol_type = protein | |
| | organism = synthetic construct | |

SEQUENCE: 2

```
MVTGVFKGPN GFEYFAPANT HNNNIEGQAI VYQNKFLTLN GKKYYFDNDS KAVTGWQTID   60
GKKYYFNLNT AEAATGWQTI DGKKYYFNLN TAEAATGWQT IDGKKYYFNT NTFIASTGYT  120
SINGKHFYFN TDGIMQIGVF KGPNGFEYFA PANTHNNNIE GQAILYQNKF LTLNGKKYYF  180
GSDSKAVTGL RTIDGKKYYF NTNTAVAVTG WQTINGKKYY FNTNTSIAST GYTIISGKHF  240
YFNTDGIMQI GVFKGPDGFE YFAPANTDAN NIEGQAIRYQ NRFLYLHDNI YYFGNNSKAA  300
TGWVTIDGNR YYFEPNTAMG ANGYKTIDNK NFYFRNGLPQ IGVFKGSNGF EYFAPANTDA  360
NNIEGQAIRY QNRFLHLLGK IYYFGNNSKA VTGWQTINGK VYYFMPDTAM AAAGGLFEID  420
GVIYFFGVDG VKAPGIYGRS MHNLITGFVT VGDDKYYFNP INGGAASIGE TIIDDKNYYF  480
NQSGVLQTGV FSTEDGFKYF APANTLDENL EGEAIDFTGK LIIDENIYYF DDNYRGAVEW  540
KELDGEMHYF SPETGKAFKG LNQIGDYKYY FNSDGVMQKG FVSINDNKHY FDDSGVMKVG  600
YTEIDGKHFY FAENGEMQIG VFNTEDGFKY FAHHNEDLGN EEGEEISYSG ILNFNNKIYY  660
FDDSFTAVVG WKDLEDGSKY YFDEDTAEAY IGLSLINDGQ YYFNDDGIMQ VGFVTINDKV  720
FYFSDSGIIE SGVQNIDDNY FYIDDNGIVQ IGVFDTSDGY KYFAPANTVN DNIYGQAVEY  780
SGLVRVGEDV YYFGETYTIE TGWIYDMENE SDKYYFNPET KKACKGINLI DDIKYYFDEK  840
GIMRTGLISF ENNNYYFNEN GEMQFGYINI EDKMFYFGED GVMQIGVFNT PDGFKYFAHQ  900
NTLDENFEGE SINYTGWLDL DEKRYYFTDE YIAATGSVII DGEEYYFDPD TAQLVISE    958
```

| | | |
|---|---|---|
| SEQ ID NO: 3 | moltype = DNA   length = 2885 | |
| FEATURE | Location/Qualifiers | |
| misc_feature | 1..2885 | |
| | note = C-TAB.G5.1 fusion DNA | |
| source | 1..2885 | |
| | mol_type = other DNA | |
| | organism = synthetic construct | |

SEQUENCE: 3

```
ccatggttac aggtgttttc aaaggtccga acggctttga atattttgca ccggcaaata   60
cccacaataa taatattgaa ggccaggcca tcgtgtatca gaataaattt ctgaccctga  120
acggcaaaaa atactatttc gataacgata gcaaagcagt taccggttgg caaaccattg  180
atggcaaaaa atattacttc aacctgaata ccgcagaagc agcaaccggc tggcagacga  240
tcgacggtaa aaagtactat tttaacctga acacagccga agccgctaca ggctggcaga  300
caatagatgg gaagaagtat tattttaata ccaataccct tattgccagc accggctata  360
ccagcattaa tggcaaacac ttctatttta acaccgatgg tattatgcag atcggtgtgt  420
ttaagggccc taatggtttt gagtacttcg ctccggctaa taccgatgca aataacatcg  480
aaggtcaggc aattctgtac cagaacaaat ttttaacgct gaacggtaag aaatattact  540
ttggtagcga ttcaaaagcc gttaccggtc tgcgtacgat cgacggcaaa aaatattatt  600
tcaatacaaa caccgcagtt gccgtgacga gttggcagac gataaatggt aagaagtact  660
acttcaacac caataccagc attgcaagta ccggttatac cattatcagc ggcaaacact  720
tttacttcaa tacagacggc attatgcaga ttggcgtttt caaaggtccg gatggtttcg  780
agtactttgc ccctgcaaat acagatgcaa acaatattga gggacaggca attcgctatc  840
agaatcgttt tctgtatctg cacgataaca tctattactt cggcaataat tcaaaagcag  900
ccaccggttg ggttacaatt gatggtaatc gttattactt tgagccgaat accgcaatgg  960
gtgcaaatgg ttataaaacc atcgataaca aaaattttta tttccgcaac ggtctgccgc 1020
agattggtgt ttttaagggt agcaatggct tcgagtattt tgcgccagcc aacaccgatg 1080
ccaacaacat tgaaggccaa gcgattcgtt atcaaaaccg ctttctgcat ctgctgggca 1140
aaatttatta ctttggcaac aatagcaaag cggtgacggc ctggcaaacc attaacggta 1200
aagtttatta tttcatgccg gataccgcta tggcagcagc cggtggtctg tttgaaattg 1260
atggcgtgat ttatttttt ggcgtggatg gtgttaaagc accgggtatt tatggtcgta 1320
gcatgcataa tctgattacc ggttttgtta ccgtgggcga cgataaatac tactttaatc 1380
cgattaatgg tggtgcagca agcattggtg aaaccattat cgatgacaaa aactattatt 1440
ttaaccagag cggtgttctg cagacaggtg ttttagcac cgaagatggc ttcaaatatt 1500
ttgctcctgc gaatacactg atgaaaatc tggaaggtga agcaattgat ttaccggca 1560
aactgatcat cgacgagaac atctactatt tgatgataa ttatcgcggt gccgtgaatg 1620
ggaaagaact ggatggtgaa atgcactatt ttagtccgga aaccggtaaa gcctttaaag 1680
gtctgaatca gatcggcgat tacaagtatt actttaattc agatgcgtg atgcagaaag 1740
gctttgtgag cattaacgac aacaaacact attttgcca cagcggtgt atgaaagtgg 1800
gttataccga aatcgacggg aaacattttt attttgccga aaacggtgaa atgcagattg 1860
gagtatttaa taccgaggac ggctttaaat actttgccca tcataatgaa gatctgggta 1920
atgaagaagc gaagaaatt agctatagcg gcattctgaa ttttaataac aagatctatt 1980
atttcgatga tagcttcacc gcagttgttg gttggaaaga tctggaagat ggcagcaaat 2040
attattttga tgaagatacc gcagaggcct atattggtct gagcctgatt aatgatggcc 2100
agtattattt caacgatgat ggtatcatgc aggttggtt tgtgaccatc aacgataaag 2160
tgttctattt cagcgatagc ggcattattg aaagcggtgt tcagaacatc gacgataact 2220
atttctacat cgatgataac ggtattgttc agattggcgt gtttgatacc tccgatggtt 2280
ataaatattt cgcaccagcc aataccgtga acgataataa ttatggtcag gcagttgaat 2340
attcaggtct ggttcgtgtt ggcgaagatg tttattttt tggcgaaacc tataccttgg 2400
aaaccgtatt gatctatgat atggaaaacg agagcgacaa gtactatttc aatccgaaa 2460
cgaaaaaagc ctgcaaaggc attaatctga tcgacgatat taagtactac tttgacgaaa 2520
aaggcattat tgctaccggt ctgattagct tgagaacaa caactattac ttcaatgaga 2580
acggtgagat gcagtttggc tatatcaaca tcgaggacaa aatgttttat tttggtgagg 2640
acggtgtgat gcagataggg gttttaata caccggatgg gtttaagtat tttgcacatc 2700
agaacaccct ggatgaaaac tttgaaggcg aaagcattaa ttataccggt tggctggatc 2760
```

```
tggatgagaa acgttattat ttcaccgacg aatacattgc agcaaccggt agcgttatta    2820
ttgatggtga ggaatattac ttcgatccgg atacagcaca gctggttatt agcgaataac    2880
tcgag                                                                2885

SEQ ID NO: 4              moltype = AA  length = 957
FEATURE                   Location/Qualifiers
REGION                    1..957
                          note = C-TAB.G5.1 fusion protein
source                    1..957
                          mol_type = protein
                          organism = synthetic construct
SEQUENCE: 4
VTGVFKGPNG FEYFAPANTH NNNIEGQAIV YQNKFLTLNG KKYYFDNDSK AVTGWQTIDG     60
KKYYFNLNTA EAATGWQTID GKKYYFNLNT AEAATGWQTI DGKKYYFNTN TFIASTGYTS    120
INGKHFYFNT DGIMQIGVFK GPNGFEYFAP ANTDANNIEG QAILYQNKFL TLNGKKYYFG    180
SDSKAVTGLR TIDGKKYYFN TNTAVAVTGW QTINGKKYYF NTNTSIASTG YTIISGKHFY    240
FNTDGIMQIG VFKGPDGFEY FAPANTDANN IEGQAIRYQN RFLYLHDNIY YFGNNSKAAT    300
GWVTIDGNRY YFEPNTAMGA NGYKTIDNKN FYFRNGLPQI GVFKGSNGFE YFAPANTDAN    360
NIEGQAIRYQ NRFLHLLGKI YYFGNNSKAV TGWQTINGKV YYFMPDTAMA AAGGLFEIDG    420
VIYFFGVDGV KAPGIYGRSM HNLITGFVTV GDDKYYFNPI NGGAASIGET IIDDKNYYFN    480
QSGVLQTGVF STEDGFKYFA PANTLDENLE GEAIDFTGKL IIDENIYYFD DNYRGAVEWK    540
ELDGEMHYFS PETGKAFKGL NQIGDYKYYF NSDGVMQKGF VSINDNKHYF DDSGVMKVGY    600
TEIDGKHFYF AENGEMQIGV FNTEDGKYYF AHHNEDLGNE EGEEISYSGI LNFNNKIYYF    660
DDSFTAVVGW KDLEDGSKYY FDEDTAEAYI GLSLINDGQY YFNDDGIMQV GFVTINDKVF    720
YFSDSGIIES GVQNIDDNYF YIDDNGIVQI GVFDTSDGYK YFAPANTVND NIYGQAVEYS    780
GLVRVGEDVY YFGETYTIET GWIYDMENES DKYYFNPETK KACKGINLID DIKYYFDEKG    840
IMRTGLISFE NNNYYFNENG EMQFGYINIE DKMFYFGEDG VMQIGVFNTP DGFKYFAHQN    900
TLDENFEGES INYTGWLDLD EKRYYFTDEY IAATGSVIID GEEYYFDPDT AQLVISE       957

SEQ ID NO: 5              moltype = DNA  length = 8133
FEATURE                   Location/Qualifiers
source                    1..8133
                          mol_type = genomic DNA
                          note = Clostridium difficile strain 630
                          organism = unidentified
SEQUENCE: 5
atgtctttaa tatctaaaga agagttaata aaactcgcat atagcattag accaagagaa     60
aatgagtata aaactatact aactaattta gacgaatata ataagttaac tacaaacaat    120
aatgaaaata aatatttaca attaaaaaaa ctaaatgaat caattgatgt tttatgaat    180
aaatataaaa cttcaagcag aaatagagca ctctctaatc taaaaaaaga tatattaaaa    240
gaagtaattc ttattaaaaa ttccaataca agccctgtag aaaaaaattt acattttgta    300
tggataggtg gagaagtcag tgatattgct cttgaataca taaaacaatg ggctgatatt    360
aatgcagaat ataattaa actgtggtat gatagtaaga cattcttagt aaatacacta    420
aaaaaggcta tagttgaatc ttctaccact gaagcattac agctactaga ggaagagatt    480
caaaatcctc aatttgataa tatgaaattt acaaaaaaaa ggatggaatt tatatatgat    540
agacaaaaaa ggtttataaa ttattataaa tctcaaatca ataaacctac agtacctaca    600
atagatgata ttataaagtc tcatctagta tctgaataga atagagatga aactgtatta    660
gaatcatata gaacaaattc tttgagaaaa ataaatagta atcatgggat agatatcagg    720
gctaatagtt tgtttacaga acaagagtta ttaaatattt atagtcagga gttgttaaat    780
cgtgaaaatt tagctgcagc atctgacata gtaagattat tagccctaaa aaatttggc    840
ggagtatatt tagatgttga tatgcttcca ggtattcact ctgatttatt taaaacaata    900
tctagaccta gctctattgg actagaccgt tgggaaatga taaaattaga ggctatatg    960
aagtatataaa aatatataaa taattataca tcagaaaact ttgataaact tgatcaacaa   1020
ttaaagatta ttttaaact cattatagaa agtaaaagtg aaaaatctga gatttttct    1080
aaattagaaa attaaaagt atctgatctt gaaattaaa tagcttcgc tttaggcagt    1140
gttataaatc aagccttgat atcaaaacaa ggttcatatc ttactaacct agtaatagaa   1200
caagtaaaaa atagatatca attttttaaac aacaccttta acccagccat agagtctgat   1260
aataacttca cagatactac taaaattttt catgattcat tatttaattc agctaccgca   1320
gaaaactcta tgtttttaac aaaaaatagca ccatacttac aagtaggttt atgccagaa    1380
gctcgctcca caataagttt aagtggtcca ggagcttatg cgtcagctta ctatgatttc   1440
ataaatttac aagaaatac tatagaaaaa acttttaaaag catcagattt aatagaattt   1500
aaattcccag aaaataatct atctcaattg acagaacaag aaataaatag tctatggagc   1560
tttgatcaag caagtgcaaa atatcaattt gagaaatatg taagagatta tactggtgga   1620
tctctttctg aagacaatgg ggtagacttt aataaaaata ctgccctcga caaaaactat   1680
ttattaaata taaaaattcc atcaaacaat gtagaagaag ctggaagtaa aaattatgtt   1740
cattatatca tacagttaca aggagatgat aaagttatg aagcaacatg caatttattt   1800
tctaaaaatc ctaaaatag tattattata caacgaaata tgaatgaaag tgcaaaaagc   1860
tacttttaa gtgatgatgg agaatctatt ttagaattaa ataaatatag gatacctgaa   1920
agattaaaaa ataaggaaaa agtaaaagta acctttattg gacatggtaa agattgaattc   1980
aacacaagcg aatttgctag attaagtgta gattcacttt ccaatgagat aagttcattt   2040
ttagatacca taaaattaga tatataccct aaaaaatgtag aagtaaactt acttggatgt   2100
aatatgttta gttatgattt taatgttgaa gaacttatc ctgggaagtt gctattaagt   2160
attatgggaca aaattacttc cactttacct gatgtaaata aaattctat tactataggaa   2220
gcaaatcaat atgaagtaga aattaatagt gaggggaaga aagaacttct ggctcactca   2280
ggtaaatgca taaataaaga agaagctatt atgagcgatt tatctagtaa agaatacatt   2340
tttttgatt ctatagataa taagctaaaa gcaaagtcca agaatattcc aggattagca   2400
tcaatatcag aagatataaa aacattatta cttgatgcaa gtgttagtcc tgatacaaaa   2460
ttttatttaa ataatcttaa gcttaatatt gaatcttcta ttggtgatta catttattat   2520
gaaaaattag agcctgttaa aaatataatt cacaattcta tagatgattt aatagatgag   2580
```

```
ttcaatctac ttgaaaatgt atctgatgaa ttatatgaat taaaaaaatt aaataatcta   2640
gatgagaagt atttaatatc ttttgaagat atctcaaaaa ataattcaac ttactctgta   2700
agatttatta acaaaagtaa tggtgagtca gtttatgtag aaacagaaaa agaaattttt   2760
tcaaaatata gcgaacatat tacaaaagaa ataagtacta taaagaatag tataattaca   2820
gatgttaatg gtaatttatt ggataatata cagttagatc atacttctca agttaataca   2880
ttaaacgcag cattctttat tcaatcatta atagattata gtagcaataa agatgtactg   2940
aatgatttaa gtacctcagt taaggttcaa ctttatgctc aactatttag tacaggttta   3000
aatactatat atgactctat ccaattagta aatttaatat caaatgcagt aaatgatact   3060
ataaatgtac tacctacaat aacagagggg ataccttattg tatctactat attagacgga   3120
ataaacttag gtgcagcaat taaggaatta ctagacgaac atgacccatt actaaaaaaa   3180
gaattagaag ctaaggtggg tgttttagca ataaatatgt cattatctat agctgcaact   3240
gtagcttcaa ttgttggaat aggtgctgaa gttactattt tcttattacc tatagctggt   3300
atatctgcag gaataccttc attagttaat aatgaattaa tattgcatga taaggcaact   3360
tcagtggtaa actattttaa tcatttgtct gaatctaaaga aatatggccc tcttaaaaca   3420
gaagatgata aaattttagt tcctattgat gatttagtaa tatcagaaat agattttaat   3480
aataattcga taaaactagg aacatgtaat atattagcaa tggagggggg atcaggacac   3540
acagtgactg gtaatataga tcactttttc tcatctccat ctataagttc tcatattcct   3600
tcattatcaa tttattctgc aataggtata gaaacagaaa atctagattt ttcaaaaaaa   3660
ataatgatgt tacctaatgc tccttcaaga gtgttttggt gggaaactgg agcagttcca   3720
ggtttaagat cattggaaaa tgacggaact agattacttg attcaataag agatttatac   3780
ccaggtaaat tttactggag attctatgct tttttcgatt atgcaataac tacattaaaa   3840
ccagtttatg aagacactaa tattaaaatt aaactagata aaacttcata               3900
atgccaacta taactactaa cgaaattaga aacaaattat cttattcatt tgatggagca   3960
ggaggaactt actctttatt attatcttca tatccaatat caacgaatat aaatttatct   4020
aaaagatgatt tatggatatt taatattgat aatgaagtaa gagaaatatc tatagaaaat   4080
ggtactatta aaaaaggaaa gttaataaaa gatgttttaa gtaaaattga tataaataaa   4140
aataaactta ttataggcaa tcaaacaata gattttcag gcgatataga taataaagat   4200
agatatatat tcttgacttg tgagttagat gataaaatta gttaataat agaaataaat   4260
cttgttgcaa aatcttatag tttgttattg tctggggata aaaattattt gatatccaat   4320
ttatctaata ttattgagaa aatcaatact ttaggcctag atagtaaaaa tatagcgtac   4380
aattacactg atgaatcaaa taataaatat tttggagcta tatctaaaac aagtcaaaaa   4440
agcataatac attataaaaa agacagtaaa aatatattag aatttataa tgacagtaca   4500
ttagaattta acagtaaaga ttttattgct gaagatataa atgtatttat gaaagatgat   4560
attaatacta taacaggaaa atactatgtt gataatacta ctgataaaag tatagatttc   4620
tctatttctt tagttagtaa aaatcaagta aaagtaaatg gattatattt aaatgaatcc   4680
gtatactcat cttaccttga ttttgtgaaaa aattcagatg acaccataa tacttctaat   4740
tttatgaatt tatttttgga caatataagt ttctggaaat tgtttgggtt tgaaaatata   4800
aattttgtaa tcgataaaata cttttaccctt gttggtaaaa ctaatcttgg atatgtagaa   4860
tttatttgtg acaataataa aaatatagat atatattttg gtgaatggaa aacatcgtca   4920
tctaaaagca ctatatttag cggaaatggt agaaatgttg tagtagagcc tatatataat   4980
cctgatacgg gtgaagatat atctacttca ctagattttt cctatgaacc tctctatgga   5040
atagatagat atatcaataa agtattgata gcacctgatt tatatacaag tttaataaat   5100
attaatacca attattattc aaatgagtac taccctgaga ttatagttct taacccaaat   5160
acattccaca aaaagtaaa tataaattta gatagttctt cttttgagta taatggtct    5220
acagaaggaa gtgactttat tttagttaga tacttagaag aaagtaataa aaaaatatta   5280
caaaaaataa gaatcaaagg tatcttatct aatactcaat catttaataa aatgagtata   5340
gattttaaag tatattaaaaa actatcatta ggatatataa tggtaattt taaatcattt   5400
aattctgaaa atgaattaga tagagatcat ttaggatttta aaataataga taataaaact   5460
tattactatg atgaagatag taaattagtt aaaggattaa tcaatataaa taattcatta   5520
ttctattttg atcctataga atttaactta gtaactggat ggcaaactat caatggtaaa   5580
aaatattatt ttgatataaa tactggagca gctttaatta gttataaaat tattaatggt   5640
aaacactttt attttaataa tgatggtgtg atgcagttgg gagtatttaa aggacctgat   5700
ggatttgaat attttgcacc tgccaatact caaaataata acatagaagg tcaggctata   5760
gtttatcaaa gtaaattctt aactttgaat ggcaaaaaat attattttga taatgactca   5820
aaagcagtca ctggatggag aattattaac aatgagaaat attactttaa tcctaataat   5880
gctattgctg cagtcggatt gcaagtaatt gacaataata agtattttt caatcctgac   5940
actgctatca tctcaaaagg ttggcagact gttaatggta gtagatacta ctttgatact   6000
gataccgcta ttgcctttaa tggttataaa actattgatg gtaaacactt ttattttgat   6060
agtgattgtg tagtgaaaat aggtgtgttt agtacctcta atggatttga atattttgca   6120
cctgctacta cttataataa ggtcaggcta tgttttatca aagtaaaattc               6180
ttaactttga atggtaaaaa atattacttt gataataact caaaagcagt taccggatgg   6240
caaactattg atagtaaaaa atattacttt aatactaaca ctgctgaagc agctactgga   6300
tggcaaacta ttgatggtaa aaatattac tttaatacta acactgctga agcagctact   6360
ggatggcaaa ctattgatgg taaaaatat tactttaaca ctgctgaagc agctactgga   6420
actggttata caattattaa tggtaaacat ttttattttta atactgatgg tattatgcag   6480
ataggagtgt ttaaaggacc taatggattt gaatattttg cacctgctaa tacggatgct   6540
aacaacatag aaggtcaagc tatactttac caaaatgaat tcttaacttt gaatggtaaa   6600
aaatattact ttggtagtga ctcaaaagca gttactggat ggagaattat taacaataag   6660
aaatattact ttaatcctaa taatgctatt gctgcaattc atctatgcac tataaaataat   6720
gacaagtatt actttagtta tgatggaatt cttcaaaatg gatatattac tattgaaaga   6780
aataatttct attttgatgc taataatgaa tctaaaatgg taacaggagt atttaaagga   6840
cctaatggat tgagtatttt tgcacctgct aatactcaca ataatacaat agaaggtcag   6900
gctatagttt accagaacaa attcttaact tgaatggca aaaatatta ttttgataat   6960
gactcaaaag cagttactgg atggcaaacc attgatgta aaaaatatta cttttaatctt    7020
aacactgctg aagcagctac tggatggcaa actattgatg gtaaaaaata ttactttaat   7080
cttaacactg ctgaagcagc tactggatgg caaactattg atggtaaaaa atattactttt  7140
aatactaaca ctttcatagc ctcaactggt tatacaagta ttaatggtaa acatttttat   7200
tttaatactg atggtattat gcagataggag gtgtttaaaag gacctaatgg atttgaatac   7260
tttgcacctg ctaatactca taataataac atagaaggtc aagctatact ttaccaaaat   7320
```

-continued

```
aaattcttaa ctttgaatgg taaaaaatat tactttggta gtgactcaaa agcagttacc    7380
ggattgcgaa ctattgatgg taaaaaatat tactttaata ctaacactgc tgttgcagtt    7440
actggatggc aaactattaa tggtaaaaaa tactactta atactaacac ttctatagct    7500
tcaactggtt atacaattat tagtggtaaa cattttatt ttaatactga tggtattatg    7560
cagataggag tgtttaaagg acctgatgga tttgaatact ttgcacctgc taatacagat    7620
gctaacaata tagaaggtca agctatacgt tatcaaaata gattcctata tttacatgac    7680
aatatatatt attttggtaa taattcaaaa gcagctactg gttgggtaac tattgatggt    7740
aatagatatt acttcgagcc taatacagct atgggtgcga atggttataa aactattgat    7800
aataaaaatt tttactttag aaatggttta cctcagatag gagtgtttaa agggtctaat    7860
ggatttgaat actttgcacc tgctaatacg gatgctaaca atataggagg tcaagctata    7920
cgttatcaaa atagattcct acatttactt ggaaaaatat attactttgg taataattca    7980
aaagcagtta ctgatggcaa actattaat ggtaaagtat attactttat gcctgatact    8040
gctatggctg cagctggtgg actttcgag attgatggtg ttatatattt ctttggtgtt    8100
gatggagtaa aagcccctgg gatatatggc taa                                 8133

SEQ ID NO: 6            moltype = AA   length = 2710
FEATURE                 Location/Qualifiers
source                  1..2710
                        mol_type = protein
                        note = Clostridium difficile strain 630
                        organism = unidentified
SEQUENCE: 6
MSLISKEELI KLAYSIRPRE NEYKTILTNL DEYNKLTTNN NENKYLQLKK LNESIDVFMN     60
KYKTSSRNRA LSNLKKDILK EVILIKNSNT SPVEKNLHFV WIGGEVSDIA LEYIKQWADI    120
NAEYNIKLWY DSEAFLVNTL KKAIVESSTT EALQLLEEEI QNPQFDNMKF YKKRMEFIYD    180
RQKRFINYYK SQINKPTVPT IDDIIKSHLV SEYNRDETVL ESYRTNSLRK INSNHGIDIR    240
ANSLFTEQEL LNIYSQELLN RGNLAAASDI VRLLALKNFG GVYLDVDMLP GIHSDLFKTI    300
SRPSSIGLDR WEMIKLEAIM KYKKYINNYT SENFDKLDQQ LKDNFKLIIE SKSEKSEIFS    360
KLENLNVSDL EIKIAFALGS VINQALISKQ GSYLTNLVIE QVKNRYQFLN QHLNPAIESD    420
NNFTDTTKIF HDSLFNSATA ENSMFLTKIA PYLQVGFMPE ARSTISLSGP GAYASAYYDF    480
INLQENTIEK TLKASDLIEF KFPENNLSQL TEQEINSLWS FDQASAKYQF EKYVRDYTGG    540
SLSEDNGVDF NKNTALDKNY LLNNKIPSNN VEEAGSKNYV HYIIQLQGDD ISYEATCNLF    600
SKNPKNSIII QRNMNESAKS YFLSDDGESI LELNKYRIPE RLKNKEKVKV TFIGHGKDEF    660
NTSEFARLSV DSLSNEISSF LDTIKLDISP KNVEVNLLGC NMFSYDFNVE ETYPGKLLLS    720
IMDKITSTLP DVNKNSITIG ANQYEVRINS EGRKELLAHS GKWINKEEAI MSDLSSKEYI    780
FFDSIDNKLK AKSKNIPGLA SISEDIKTLL LDASVSPDTK FILNNLKLNI ESSIGDYIYY    840
EKLEPVKNII HNSIDDLIDE FNLLENVSDE LYELKKLNNL DEKYLISFED ISKNNSTYSV    900
RFINKSNGES VYVETEKEIF SKYSEHITKE ISTIKNSIIT DVNGNLLDNI QLDHTSQVNT    960
LNAAFFIQSL IDYSSNKDVL NDLSTSVKVQ LYAQLFSTGL NTIYDSIQLV NLISNAVNDT   1020
INVLPTITEG IPIVSTILDG INLGAAIKEL LDEHDPLLKK ELEAKVGVLA INMSLSIAAT   1080
VASIVGIGAE VTIFLLPIAG ISAGIPSLVN NELILHDKAT SVVNYFNHLS ESKKYGPLKT   1140
EDDKILVPID DLVISEIDFN NNSIKLGTCN ILAMEGGSGH TVTGNIDHFF SSPSISSHIP   1200
SLSIYSAIGI ETENLDFSKK IMMLPNAPSR VFWWETGAVP GLRSLENDGT RLLDSIRDLY   1260
PGKFYWRFYA FFDYAITTLK PVYEDTNIKI KLDKDTRNFI MPTITTNEIR NKLSYSFDGA   1320
GGTYSLLLSS YPISTNINLS KDDLWIFNID NEVREISIEN GTIKKGKLIK DVLSKIDINK   1380
NKLIIGNQTI DFSGDIDNKD RYIFLTCELD DKISLIIEIN LVAKSYSLLL SGDKNYLISN   1440
LSNIIEKINT LGLDSKNIAY NYTDESNNKY FGAISKTSQK SIIHYKKDSK NILEFYNDST   1500
LEFNSKDFIA EDINVFMKDD INTITGKYYV DNNTDKSIDF SISLVSKNQV KVNGLYLNES   1560
VYSSYLDFVK NSDGHHNTSN FMNLFLDNIS FWKLFGFENI NFVIDKYFTL VGKTNLGYVE   1620
FICDNNKNID IYFGEWKTSS SKSTIFSGNG RNVVVEPIYN PDTGEDISTS LDFSYEPLYG   1680
IDRYINKVLI APDLYTSLIN INTNYYSNEY YPEIIVLNPN TPHKKVNINL DSSSFEYKWS   1740
TEGSDFILVR YLEESNKKIL QKIRIKGILS NTQSFNKMSI DFKDIKKLSL GYIMSNFKSF   1800
NSENELDRDH LGFKIIDNKT YYYDEDSKLV KGLININNSL FYFDPIEFNL VTGWQTINGK   1860
KYYFDINTGA ALISYKIING KHFYNNDGV MQLGVFKGPD GFEYFAPANT QNNNIEGQAI   1920
VYQSKFLTLN GKKYYFDNDS KAVTGWRIIN NEKYYFNPNN AIAAVGLQVI DNNKYYFNPD   1980
TAIISKGWQT VNGSRYYFDT DTAIAFNGYK TIDGKHFYFD SDCVVKIGVF STSNGFEYFA   2040
PANTYNNNIE GQAIVYQSKF LTLNGKKYYF DNNSKAVTGW QTIDSKKYYF NTNTAEAATG   2100
WQTIDGKKYY FNTNTAEAAT GWQTIDGKKY YFNTNTAIAS TGYTIINGKH FYFNTDGIMQ   2160
IGVFKGPNGF EYFAPANTDA NNIEGQAILY QNEFLTLNGK KYYFGSDSKA VTGWRIINNK   2220
KYYFNPNNAI AAIHLCTINN DKYYFSYDGI LQNGYITIER NNFYFDANNE SKMVTGVFKG   2280
PNGFEYFAPA NTHNNNIEGQ AIVYQNKFLT LNGKKYYFDN DSKAVTGWQT IDGKKYYFNL   2340
NTAEAATGWQ TIDGKKYYFN LNTAEAATGW QTIDGKKYYF NTNTFIASTG YTSINGKHFY   2400
FNTDGIMQIG VFKGPNGFEY FAPANTHNNN IEGQAILYQN KPFLTNGKKY YFGSDSKAVT   2460
GLRTIDGKKY YFNTNTAVAV TGWQTINGKK YYFNTNTSIA STGYTIISGK HFYFNTDGIM   2520
QIGVFKGPDG FEYFAPANTD ANNIEGQAIR YQNRFLYLHD NIYYFGNNSK AATGWVTIDG   2580
NRYYFEPNTA MGANGYKTID NKNFYFRNGL PQIGVFKGSN GFEYFAPANT DANNIEGQAI   2640
RYQNRFLHLL GKIYYFGNNS KAVTGWQTIN GKVYYFMPDT AMAAAGGLFE IDGVIYFFGV   2700
DGVKAPGIYG                                                          2710

SEQ ID NO: 7            moltype = DNA   length = 7101
FEATURE                 Location/Qualifiers
source                  1..7101
                        mol_type = genomic DNA
                        note = Clostridium difficile strain 630
                        organism = unidentified
SEQUENCE: 7
atgagtttag ttaatagaaa acagttagaa aaaatggcaa atgtaagatt tcgtactcaa      60
gaagatgaat atgttgcaat attggatgct ttagaagaat catcaatat gtcagagaat     120
actgtagtcg aaaaatattt aaaattaaaa gatataaata gttaacagat atttatata      180
```

```
gatacatata aaaaatctgg tagaaataaa gccttaaaaa aatttaagga atatctagtt     240
acagaagtat tagagctaaa gaataataat ttaactccag ttgagaaaaa tttacatttt     300
gtttggattg gaggtcaaat aaatgacact gctattaatt atataaatca atggaaagat     360
gtaaatagtg attataatgt taatgttttt tatgatagta atgcattttt gataaacaca     420
ttgaaaaaaa ctgtagtaga atcagcaata aatgatacac ttgaatcatt tagagaaaac     480
ttaaatgacc ctagatttga ctataataaa ttcttcagaa aacgtatgga aataatttat     540
gataaacaga aaaatttcat aaactactat aaagctcaaa gagaagaaaa tcctgaactt     600
ataattgatg atattgtaaa gacatatctt tcaaatgagt attcaaagga gatagatgaa     660
cttaataccct atattgaaga atccttaaat aaaattacac agaatagtgg aaatgatgtt     720
agaaactttg aagaatttaa aaatggagag tcattcaact tatatgaaca agagttggta     780
gaaaggtgga atttagctgc tgcttctgac atattaagaa tatctgcatt aaaagaaatt     840
ggtggtatgt atttagatgt tgatatgtta ccaggaatac aaccagactt atttgagtct     900
atagagaaac ctagttcagt aacagtggat ttttgggaaa tgacaaagtt agaagctata     960
atgaaataca aagaatatat accagaatat acctcagaac attttgacat gttagacgaa    1020
gaagttcaaa gtagttttga atctgttcta gcttctaagt cagataaatc agaaatattc    1080
tcatcacttg gtgatatgga ggcatcacca ctagaagtta aaattgcatt taatagtaag    1140
ggtattataa atcaagggct aatttctgtg aaagactcat attgtagcaa tttaatagta    1200
aaacaaatcg agaatagata taaaatattg aataatagtt taaatccagc tattagcgag    1260
gataatgatt ttaatactac aacgaatacc tttattgata gtaatggc tgaagctaat      1320
gcagataatg gtagatttat gatggaacta ggaaagtatt taagagttgg tttcttccca    1380
gatgttaaaa ctactattaa cttaagtggc cctgaagcat atgcggcagc ttatcaagat    1440
ttattaatgt ttaaagaagg cagtatgaat atccatttga tgaagctga tttaagaaac     1500
tttgaaatct ctaaaactaa tatttctcaa tcaactgaac aagaaatggc tagcttatgg    1560
tcatttgacg atgcaagagc taaagctcaa tttgaagaat ataaaaggaa ttattttgaa    1620
ggttctcttg gtgaagatga taatcttgat ttttctcaaa atatagtagt tgacaaggag    1680
tatcttttag aaaaaaatac ttcattagca agaagttcag agagaggata tatacactat    1740
attgttcagt tacaaggaga taaaattagt tatgaagcaa catgtaactt atttgcaaag    1800
actccttatg atagtgtact gtttcagaaa aatatagaag attcagaaat tgcatattat    1860
tataatcctg gagatggtga aatacaagaa atagacaagt ataaaattcc aagtataatt    1920
tctgatagac ctaagattaa attaacattt attggtcatg gtaaagatga atttaatact    1980
gatatatttg caggttttga tgtagattca ttatccacag aaatagaagc agcaatagat    2040
ttagctaaag aggatatttc tcctaagtca atagaaataa atttattagg atgtaatatg    2100
tttagctact ctatcaacgt agaggagact tatcctggaa aattattact taaagttaaa    2160
gataaaatat cagaattaat gccatctata agtcaagact ctattatagt aagtgcaaat    2220
caatatgaag ttagaataaa tagtgaagga agaagagaat tattggatca ttctggtgaa    2280
tggataaaata aagaagaaag tattataaag gatatttcat caaagaata tatatcattt     2340
aatcctaaag aaaataaaat tacagtaaaa tctaaaaatt tacctgagct atctacatta    2400
ttacaagaaa ttagaaataa ttctaattca agtgatattg aactagaaga aaaagtaatg    2460
ttaacagaat gtgagataaa tgttatttca aatatagata cgcaaattgt tgaggaaagg    2520
attgaagaag ctaagaattt aacttctgac tctattaatt atataaaaga tgaatttaaa    2580
ctaatagaat ctatttctga tgcactatgt gacttaaaac aacagaatga attagaagat    2640
tctcatttta tatcttttga ggacatatca gagactgatg agggatttag tataagattt    2700
attaataaag aaactggaga atctatattt gtagaaactg aaaaaacaat attctctgaa    2760
tatgctaatc atataactga agagattict aagataaaag gtactatatt tgatactgta    2820
aatggtaagt tagtaaaaaa agtaaattta gatactacac acgaagtaaa tactttaaat    2880
gctgcatttt ttatacaatc attaatagaa tataatagtt ctaaagaatc tcttagtaat    2940
ttaagtgtag caatgaaagt ccaagttac gctcaattat ttagtactgg tttaaaatact    3000
attacagatg cagccaaagt tgttgaatta gtatcaactg cattagatga aactatagac    3060
ttacttccta cattatctga aggattacct ataattgcaa ctattataga tggtgtaagt    3120
ttaggtgcag caatcaaaga gctaagtgaa acgagtgacc cattattaag acaagaaata    3180
gaagctaaga taggtataat ggcagtaaat ttaacaacag ctacaactgc aatcattact    3240
tcatctttgg ggatagctag tggatttagt atactttag ttcctttagc aggaatttca      3300
gcaggtatac caagcttagt aaacaatgaa cttgtacttc gagataaggc aacaaaggtt    3360
gtagattatt ttaaacatgt ttcattagtt gaaactgaag gagtatttac tttattagat    3420
gataaaataa tgatgccaca agatgattta gtgatatcaa aaatagattt taataataat    3480
tcaatagttt taggtaaatg tgaaatctgg agaatggaag gtggttcagg tcatactgta    3540
actgatgata tagatcactt ctttcagca ccatcaataa catatagaga gccacactta     3600
tctatatatg acgtattgga agtacaaaaa gaagaacttg atttgtcaaa agatttaatg    3660
gtattaccta atgctccaaa tagagtattt gcttgggaaa caggatggaa accaggttta    3720
agaagcttag aaaatgatgg cacaaaactg ttagaccgta taagagataa ctatgaaggt    3780
gagttttatt ggagatatttt tgcttttata gctgatgctt taataacaac attaaaacca    3840
agatatgaag atactaatat aagaataaat ttagatagta atactagaag ttttatagtt    3900
ccaataataa ctacagaata tataagagaa aaattatcat attctttcta tggttcagga    3960
ggaacttatg cattgtctct ttctcaatat aatatgtata taaatataga attagtgaaa    4020
agtgatgttt ggattataga tgttgataat gttgtgagag atgtaactat agaatctgat    4080
aaaattaaaa aaggtgattt aatagaaggt atttatctta cactcaagtat tgaagagaat    4140
aaaattatct aaatagccca tgagattaat ttttctggtg aggtaaatgg aagtaatgga    4200
tttgtttctt taacattttc aattttagaa ggaataaatg caattataga agttaattta    4260
ttatctaaat catataaatt acttatttct ggcgaattaa aaatattgat gttaattca     4320
aatcatattc aacagaaaat agattatata ggattcaata gcgaattaca gaaaaatata    4380
ccatatagct ttgtagatag tgaaggaaaa gagaatggtt ttattaatgg ttcaacaaaa    4440
gaaggttat ttgtatctga attacctgat gtagttctta taagtaaggt ttatatggat     4500
gatagtaagc cttcatttgg atattatagt aataatttga aagatgtcaa agttataact    4560
aaagataatg ttaatatatt aacaggttat atgttaatga atctctctt                4620
tctttgactc tacaagatga aaaaactata aagttaaata gtgtgcattt agatgaaagt    4680
gggagtagctg agattttgaa gttcatgaat agaaaaggta atacaaatac ttcagattct    4740
ttaatgagct tttagaaag tatgaatata aaagtatttc tgttaatttt cttacaatct    4800
aatattaagt ttatattaga tgctaatttt ataataagtg gtactactc tattggccaa     4860
tttgagttta tttgtgatga aaatgataat atacaaccat atttcattaa gtttaataca    4920
```

-continued

```
ctagaaacta attatacttt atatgtagga aatagacaaa atatgatagt ggaaccaaat    4980
tatgatttag atgattctgg agatatatct tcaactgtta tcaatttctc tcaaaagtat    5040
ctttatggaa tagacagttg tgttaataaa gttgtaattt caccaaatat ttatacagat    5100
gaaataaata taacgcctgt atatgaaaca aataatactt atccagaagt tattgtatta    5160
gatgcaaatt atataaatga aaaaataaat gttaatatca atgatctatc tatacgatat    5220
gtatggagta atgatggtaa tgattttatt cttatgtcaa ctagtgaaga aaataaggtg    5280
tcacaagtta aaataagatt cgttaatgtt tttaaagata agactttggc aaataagcta    5340
tcttttaact ttagtgataa acaagatgta cctgtaagtg aaataatctt atcatttaca    5400
ccttcatatt atgaggatgg attgattggc tatgatttgg gtctagtttc tttatataat    5460
gagaaatttt atattaataa cttggaatg atggtatctg gattaatata tattaatgat    5520
tcattatatt atttaaacc accagtaaat aatttgataa ctggatttgt gactgtaggc    5580
gatgataaat actactttaa tccaattaat ggtggagctg cttcaattgg agagacaata    5640
attgatgaca aaaattatta tttcaaccaa agtggagtgt tacaaacagg tgtatttagt    5700
acagaagatg gatttaaata ttttgcccca gctaatacac ttgatgaaaa cctagaagga    5760
gaagcaattg atttctactg gaaattaatt attgacgaaa atatttatta ttttgatgat    5820
aattatagag gagctgtaga atggaaagaa ttagatggtg aaatgcacta ttttagccca    5880
gaaacaggta agcttttaa aggtctaaat caaataggtg attataaata ctatttcaat    5940
tctgatggag ttatgcaaaa aggatttgtt agtataaatg ataaaacata ttttgatgat    6000
gattctggtg ttatgaaagt aggttacact gaaatagatg gcaagcattt ctactttgct    6060
gaaaacggag aaatgcaaat aggagtattt aatacagaag atggatttaa atattttgct    6120
catcataatg aagatttagg aaatgaagaa ggtgaagaaa tctcatattc tggtatatta    6180
aatttcaata ataaaattta ctattttgat gattcattta cagctgtagt tggatggaaa    6240
gatttagagg atggttcaaa gtattatttt gatgaagata cagcagaagc atatataggt    6300
ttgtcattaa taaatgatgg tcaatattat tttaatgatg atggaattat gcaagttgga    6360
tttgtcacta taaatgataa agtcttctac ttctctgact ctggaattat agaatctgga    6420
gtacaaaaca tagatgacaa ttatttctat atagatgata atgatgtagt tcaaattggt    6480
gtatttgata cttcagatgg atataaatat tttgcacctg ctaatactgt aaatgataat    6540
atttacggac aagcagttga atatagtggt ttagttagag ttggtgaaga tgtatattat    6600
tttgagaaa catatacaat tgagactgga tggatatatg atatgaaaa tgaaagtgat    6660
aaatattatt tcaatccaga aactaaaaaa gcatgcaaat ttaattt aatgatgat    6720
ataaaatatt attttgatga gaagggcata atgagaacgg tcttatatc atttgaaaat    6780
aataattatt actttaatga gaatggtgaa atgcaatttg gttatataaa tatagaagat    6840
aagatgttct attttggtga agatggtgtc atgcagattg gagtatttaa tacaccagat    6900
ggatttaaat actttgcaca tcaaaatact ttggatgaga attttgaggg agaatcaata    6960
aactatactg gttggttaga tttagatgaa aagagatatt attttacaga tgaatatatt    7020
gcagcaactg gttcagttat tattgatggt gaggagtatt attttgatcc tgatacagct    7080
caattagtga ttagtgaata g                                              7101
```

```
SEQ ID NO: 8            moltype = AA   length = 2366
FEATURE                 Location/Qualifiers
source                  1..2366
                        mol_type = protein
                        note = Clostridium difficile strain 630
                        organism = unidentified
SEQUENCE: 8
MSLVNRKQLE KMANVRFRTQ EDEYVAILDA LEEYHNMSEN TVVEKYLKLK DINSLTDIYI    60
DTYKKSGRNK ALKKFKEYLV TEVLELKNNN LTPVEKNLPF VWIGGQINDT AINYINQWKD   120
VNSDYNVNVF YDSNAFLINT LKKTVVESAI NDTLESFREN LNDPRFDYNK FFRKRMEIIY   180
DKQKNFINYY KAQREENPEL IIDDIVKTYL SNEYSKEIDE LNTYIEESLN KITQNSGNDV   240
RNFEEFKNGE SFNLYEQELV ERWNLAAASD ILRISALKEI GGMYLDVDML PGIQPDLFES   300
IEKPSSVTVD FWEMTKLEAI MKYKEYIPEY TSEHFDMLDE EVQSSFESVL ASKSDKSEIF   360
SSLGDMEASP LEVKIAFNSK GIIINQGLISV KDSYCSNLIV KQIENRYKIL NNSLNPAISE   420
DNDFNTTTNT FIDSIMAEAN ADNGRFMMEL GKYLRVGFFP DVKTTINLSG PEAYAAAYQD   480
LLMFKEGSMN IHLIEADLRN FEISKTNISQ STEQEMASLW SFDDARAKAQ FEEYKRNYFE   540
GSLGEDDNLD FSQNIVVDKE YLLEKISSLA RSSERGYIHY IVQLQGDKIS YEAACNLFAK   600
TPYDSVLFQK NIEDSEIAYY YNPGDGEIQE IDKYKIPSII SDRPKIKLTF IGHGKDEFNT   660
DIFAGPDVDS LSTEIEAAID LAKEDISPKS IEINLLGCNM FSYSINVEET YPGKLLLKVK   720
DKISELMPSI SQDSIIVSAN QYEVRINSEG RRELLDHSGE WINKEESIIK DISSKEYISF   780
NPKENKITVK SKNLPELSTL LQEIRNNSNS SDIELEEKVM LTECEINVIS NIDTQIVEER   840
IEEAKNLTSD SINYIKDEFK LIESISDALC DLKQQNELED SHFISFEDIS ETDEGFSIRF   900
INKETGESIF VETEKTIFSE YANHITEEIS KIKGTIFDTV NGKLVKKVNL DTTHEVNTLN   960
AAFFIQSLIE YNSSKESLSN LSVAMKVQVY AQLFSTGLNT ITDAAKVVEL VSTALDETID  1020
LLPTLSEGLP IIATIIDGVS LGAAIKELSE TSDPLLRQEI EAKIGIMAVN LTTATTAIIT  1080
SSLGIASGFS ILLVPLAGIS AGIPSLVNNE LVLRDKATKV VDYFKHVSLV ETEGVFTLLD  1140
DKIMMPQDDL VISEIDFNNN SIVLGKCEIW RMEGGSGHTV TDDIDHFFSA PSITYREPHL  1200
SIYDVLEVQK EELDLSKDLM VLPNAPNRVF AWETGWTPGL RSLENDGTKL LDRIRDNYEG  1260
EFYWRYFAFI ADALITTLKP RYEDTNIRIN LDSNTRSFIV PIITTEYIRE KLSYSFYGSG  1320
GTYALSLSQY NMGINIELSE SDVWIIDVDN VVRDVTIESD KIKKGDLIEG ILSTLSIEEN  1380
KIILNSHEIN FSGEVNGSNG FVSLTFSILE GINAIIEVDL LSKSYKLLIS GELKILMLNS  1440
NHIQQKIDYI GFNSELQKNI PYSFVDSEGK ENGFINGSTK EGLFVSELPD VVLISKVYMD  1500
DSKPSFGYYS NNLKDVKVIT KDNVNILTGY YLKDDIKISL SLTLQDEKTI KLNSVHLDES  1560
GVAEILKFMN RKGNTNTSDS LMSFLESMNI KSIFVNFLQS NIKFILDANF IISGTTSIGQ  1620
FEFICDENDN IQPYFIKFNT LETNYTLYVG NRQNMIVEPN YDLDDSGDIS STVINFSQKY  1680
LYGIDSCVNK VVISPNIYTD EINITPVYET NNTYPEVIVL DANYINEKIN VNINDLSIRY  1740
VWSNDGNDFI LMSTSEENKV SQVKIRFVNV FKDKTLANKL SFNFSDKQDV PVSEIILSFT  1800
PSYYEDGLIG YDLGLVSLYN EKFYINNFGM MVSGLIYIND SLYYFKPPVN NLITGFVTVG  1860
DDKYYFNPIN GGAASIGETI IDDKNYYFNQ SGVLQTGVFS TEDGFKYFAP ANTLDENLEG  1920
EAIDFTGKLI IDENIYYFDD NYRGAVEWKE LDGEMHYFSP ETGKAFKGLN QIGDYKYYFN  1980
SDGVMQKGFV SINDNKHYFD DSGVMKVGYT EIDGKHYFFA ENGEMQIGVF NTEDGFKYFA  2040
```

```
HHNEDLGNEE GEEISYSGIL NFNNKIYYFD DSFTAVVGWK DLEDGSKYYF DEDTAEAYIG     2100
LSLINDGQYY FNDDGIMQVG FVTINDKVFY FSDSGIIESG VQNIDDNYFY IDDNGIVQIG     2160
VFDTSDGYKY FAPANTVNDN IYGQAVEYSG LVRVGEDVYY FGETYTIETG WIYDMENESD     2220
KYYFNPETKK ACKGINLIDD IKYYFDEKGI MRTGLISFEN NNYYFNENGE MQFGYINIED     2280
KMFYFGEDGV MQIGVFNTPD GFKYFAHQNT LDENFEGESI NYTGWLDLDE KRYYFTDEYI     2340
AATGSVIIDG EEYYFDPDTA QLVISE                                         2366

SEQ ID NO: 9            moltype = DNA   length = 32
FEATURE                 Location/Qualifiers
misc_feature            1..32
                        note = forward primer
source                  1..32
                        mol_type = other DNA
                        organism = synthetic construct
SEQUENCE: 9
caccactagt atgaacttag taactggatg gc                                       32

SEQ ID NO: 10           moltype = DNA   length = 27
FEATURE                 Location/Qualifiers
misc_feature            1..27
                        note = reverse primer
source                  1..27
                        mol_type = other DNA
                        organism = synthetic construct
SEQUENCE: 10
ctcgagttag ccatatatcc cagggc                                              27

SEQ ID NO: 11           moltype = DNA   length = 34
FEATURE                 Location/Qualifiers
misc_feature            1..34
                        note = forward primer
source                  1..34
                        mol_type = other DNA
                        organism = synthetic construct
SEQUENCE: 11
caccatgcat atgagtttag ttaatagaaa acag                                     34

SEQ ID NO: 12           moltype = DNA   length = 33
FEATURE                 Location/Qualifiers
misc_feature            1..33
                        note = reverse primer
source                  1..33
                        mol_type = other DNA
                        organism = synthetic construct
SEQUENCE: 12
ggcctcgagc tattcactaa tcactaattg agc                                      33

SEQ ID NO: 13           moltype = DNA   length = 44
FEATURE                 Location/Qualifiers
misc_feature            1..44
                        note = forward primer
source                  1..44
                        mol_type = other DNA
                        organism = synthetic construct
SEQUENCE: 13
agatctatgc atgagctcct cgagcccaaa acgaaaggct cagc                          44

SEQ ID NO: 14           moltype = DNA   length = 36
FEATURE                 Location/Qualifiers
misc_feature            1..36
                        note = reverse primer
source                  1..36
                        mol_type = other DNA
                        organism = synthetic construct
SEQUENCE: 14
cggtccgggg ccatatatcc caggggcttt tactcc                                   36

SEQ ID NO: 15           moltype = DNA   length = 34
FEATURE                 Location/Qualifiers
misc_feature            1..34
                        note = forward primer
source                  1..34
                        mol_type = other DNA
                        organism = synthetic construct
SEQUENCE: 15
caccccattg atggtaacag gagtatttaa agga                                     34

SEQ ID NO: 16           moltype = DNA   length = 32
FEATURE                 Location/Qualifiers
```

| misc_feature | 1..32 |
| | note = reverse primer |
| source | 1..32 |
| | mol_type = other DNA |
| | organism = synthetic construct |

SEQUENCE: 16

```
ctcgagctat tcactaatca ctaattgagc tg                                           32
```

| SEQ ID NO: 17 | moltype = DNA   length = 4482 |
| FEATURE | Location/Qualifiers |
| misc_feature | 1..4482 |
| | note = C-TADCTB fusion DNA |
| source | 1..4482 |
| | mol_type = other DNA |
| | organism = synthetic construct |

SEQUENCE: 17

```
atggtaacag gagtatttaa aggacctaat ggatttgagt attttgcacc tgctaatact   60
cacaataata acatagaagg tcaggctata gtttaccaga acaaattctt aactttgaat  120
ggcaaaaaat attattttga taatgactca aaagcagtta ctggatggca aaccattgat  180
ggtaaaaaat attactttaa tcttaacact gctgaagcag ctactggatg caaactatt   240
gatggtaaaa aatattactt taatcttaac actgctgaag cagctactgg atggcaaact  300
attgatggta aaaaatatta cttttaatact aacacttca tagcctcaac tggttataca  360
agtattaatg gtaaacattt ttattttaat actgatggta ttatgcagat aggagtgttt  420
aaaggaccta atggatttga atactttgca cctgctaata cggatgctaa caacatagaa  480
ggtcaagcta tactttacca aaataaattc ttaactttga atggtaaaaa atattacttt  540
ggtagtgact caaaagcagt taccggactg cgaactgtta atggtaaaaa atattacttt  600
aatactaaca ctgctgttgc agttactgga tggcaaacta ttaatggtaa aaaatactac  660
tttaatacta acacttctat agcttcaact ggttatacaa ttattagtgg taaacatttt  720
tatttttaata ctgatggtat tatgcagata ggagtgttta aggacctga tggatttgaa  780
tactttgcac ctgctaatac agatgctaac aatatagaag tcaagctat acgttatcaa  840
aatagattcc tatatttaca tgacaatata tattattttg gtaataattc aaaagcggcc  900
actggttggg taactattga tggtaataga attacttcg agcctaatac agctatgggt  960
gcgaatggtt ataaaactat tgataataaa aattttact ttagaaatgg tttacctcag 1020
ataggagtgt ttaaagggtc taatggattt gaatactttg cacctgctaa tacggatgct 1080
aacaatatag aaggtcaagc tatacgttat caaaatagat tcctacatttt acttggaaaa 1140
atatattact ttggtaataa ttcaaaagca gttactggat ggcaaactat taatggtaaa 1200
gtatattact ttatgcctga tactgctatg gctgcagctg gtggactttt cgagattgat 1260
ggtgttatat atttctttgg tgttgatgga gtaaaagccc ctgggatata tggcagatct 1320
atgcataatt tgataactgg atttgtgact gtaggcagta ataaatacta ctttaatcca 1380
attaatggtg gagctgcttc aattggagag acaataattg atgacaaaaa ttattattc 1440
aaccaaagtg gagtgttaca acaggtgta tttagtacag aagatggatt taaatattt 1500
gccccagcta atacacttga tgaaaaccta gaaggagaag caattgattt tactggaaaa 1560
ttaattattg acgaaaatat ttattatttt gatgataatt atagaggagc tgtagaatgg 1620
aaagaattag atggtgaaat gcactatttt agcccagaa caggtaaagc ttttaaaggt 1680
ctaaatcaaa taggtgatta taatactat ttcaattctg atggagttat gcaaaaagga 1740
tttgttagta taaatgataa taacactat tttgatgatt ctggtgttat gaagtaggt 1800
tacactgaaa tagatggcaa gcatttctac tttgctgaaa gcaaatagga 1860
gtatttaata cagaagatgg atttaaatat tttgctcatc ataatgaaga tttaggaaat 1920
gaagaaggtg aagaaatctc atattctggt atattaaatt tcaataataa aatttactat 1980
tttgatgatt catttacagc tgtagttgga tggaaagatt tagaggatgg ttcaaagtat 2040
tattttgatg aagatacagc agaagcatat agggtttgt cattaataaa tgatggtcaa 2100
tattattttt a atgatgatgg aattatgcaa gttggatttg tcactataa tgataaagtc 2160
ttctacttct ctgactctgg aattatagaa tctggagtac aaaacataga tgacaattat 2220
ttctatatag atgataatgg tatagtcaa attggtgtat tgatcttc agatggatat 2280
aaatattttg cacctgtaa tactgtaaat gataataatt acggacaagc agttgaatat 2340
agtggtttag ttagagttgg ggaagatgta tattattttg agaaacata tacaattgag 2400
actggatgga tatgatgatat ggaaatgaa agtgataaat attatttca atccgaaact 2460
aaaaagcat gcaaaggtat taattaatt gatgatataa aatattattt tgatgagaag 2520
ggcataatga aacgggtct tatatcattt gaaaataata attattactt taatgagaat 2580
ggtgaaatgc aattttggtta tataaatata gaagtaaga tgttctatttt tggtagaat 2640
ggtgtcatgc agattggagt atttaataca ccagatggat ttaaaacttt tgcacatcaa 2700
aatactttgg atgagaattt tgagggagaa tcaatataact atactggttg ttagatttta 2760
gatgaaaaga gatattattt tacagatgaa tatattgcag caactggtc agttattatt 2820
gatggtgagg agtattattt tgatcctgat acagctccaat agtgattag tgaactgga 2880
ggattaatat atattaatga ttcattatat tattaaaac accagtaaa taattgata 2940
actgatttg tgactgtagg cgatgataaa tactacttta atccaattaa tggtggagct 3000
gcttcaattg gagagacaat aattgatgac aaaaatttat atttcaacca aagtggagtg 3060
ttaacaacag gtgtattag tacagaagag gatttgcccc agctaataca 3120
cttgatgaaa acctagaagg agaagcaatt gattttactg gaaaattaat tattgacgaa 3180
aatatttatt attttgatga taattataga ggagctgtag aatggaaaga attagatggt 3240
gaaatgcact attttagccc agaaacaggt aaagctttta aaggtctaaa tcaaataggt 3300
gattataat actatttcaa ttctgatgga gttatgcaaa aaggatttgt tagtataaat 3360
gataaaac actatttga tgattctggt gttatgaag aggttacac tgaaatagat 3420
ggcaagcatt tctacttgc tgaaaacggaa gcaaatagga gtagtataatg 3480
gatggattta atattttgc tcatcataat gaagatttag aaatgaaga aggtgaagaa 3540
atctcatatt ctggtatatt aaattcaat aataaaattt actttgat attcatttt 3600
acagctgtat tggatggaa agatttagag atggttcaa gtattatttt tgatgaagat 3660
acagcagaag catatataag tttgtcatta ataatgatg tcaatatta ttttaatgat 3720
gatggaatta tgcaagttgg atttgtcact ataaatgata agtcttcta cttctctgac 3780
```

-continued

```
tctggaatta tagaatctgg agtacaaaac atagatgaca attatttcta tatagatgat  3840
aatggtatag ttcaaattgg tgtatttgat acttcagatg gatataaata ttttgcacct  3900
gctaatactg taaatgataa tatttacgga caagcagttg aatatagtgg tttagttaga  3960
gttgggaag atgtatatta ttttggaaa acatatacaa ttgagactgg atggatatat   4020
gatatggaaa atgaaagtga taaatattat ttcaatccaa aaactaaaaa agcatgcaaa  4080
ggtattaatt taattgatga tataaaaat tattttgatg agaagggcat aatgagaacg   4140
ggtcttatat catttgaaaa taataattat tactttaatg agaatggtga aatgcaattt  4200
ggttatataa atatagaaga taagatgttc tattttggtg aagatggtgt catgcagatt  4260
ggagtattta atacaccaga tggatttaaa tactttgcac atcaaaatac tttggatgag  4320
aattttgagg gagaatcaat aaactatact ggttggttag atttagatga aagagatat   4380
tattttacag atgaatatat tgcagcaact ggttcagtta ttattgatgg tgaggagtat  4440
tattttgatc ctgatacagc tcaattagtg attagtgaat ag                    4482
```

| | | |
|---|---|---|
| SEQ ID NO: 18 | moltype = AA   length = 1493 | |
| FEATURE | Location/Qualifiers | |
| REGION | 1..1493 | |
| | note = C-TADCTB fusion protein | |
| source | 1..1493 | |
| | mol_type = protein | |
| | organism = synthetic construct | |

SEQUENCE: 18
```
MVTGVFKGPN GFEYFAPANT HNNNIEGQAI VYQNKFLTLN GKKYYFDNDS KAVTGWQTID   60
GKKYYFNLNT AEAATGWQTI DGKKYYFNLN TAEAATGWQT IDGKKYYFNT NTFIASTGYT  120
SINGKHFYFN TDGIMQIGVF KGPNGFEYFA PANTDANNIE GQAILYQNKF LTLNGKKYYF  180
GSDSKAVTGL RTIDGKKYYF NTNTAVAVTG WQTINGKKYY FNTNTSIAST GYTIISGKHF  240
YFNTDGIMQI GVFKGPDGFE YFAPANTDAN NIEGQAIRYQ NRFLYLHDNI YYFGNNSKAA  300
TGWVTIDGNR YYFEPNTAMG ANGYKTIDNK NFYFRNGLPQ IGVFKGSNGF EYFAPANTDA  360
NNNIEGQAIRY QNRFLHLLGK IYYFGNNSKA VTGWQTINGK VYYFMPDTAM AAAGGLFEID  420
GVIYFFGVDG VKAPGIYGRS MHNLITGFVT VGDDKYYFNP INGGAASIGE TIIDDKNYYF  480
NQSGVLQTGV FSTEDGFKYF APANTLDENL EGEAIDFTGK LIIDENIYYF DDNYRGAVEW  540
KELDGEMHYF SPETGKAFKG LNQIGDYKYY FNSDGVMQKG FVSINDNKHY FDDSGVMKVG  600
YTEIDGKHFY FAENGEMQIG VFNTEDGFKY FAHHNEDLGN EEGEEISYSG ILNFNNKIYY  660
FDDSFTAVVG WKDLEDGSKY YFDEDTAEAY IGLSLINDGQ YYFNDDGIMQ VGFVTINDKV  720
FYFSDSGIIE SGVQNIDDNY FYIDDNGIVQ IGVFDTSDGY KYFAPANTVN DNIYGQAVEY  780
SGLVRVGEDV YYFGETYTIE TGWIYDMENE SDKYYFNPET KKACKGINLI DDIKYYFDEK  840
GIMRTGLISF ENNNYYFNEN GEMQFGYINI EDKMFYFGED GVMQIGVFNT PDGFKYFAHQ  900
NTLDENFEGE SINYTGWLDL DEKRYYFTDE YIAATGSVII DGEEYYFDPD TAQLVISELE  960
GLIYINDSLY YFKPPVNNLI TGFVTVGDDK YYFNPINGGA ASIGETIIDD KNYYFNQSGV 1020
LQTGVFSTED GFKYFAPANT LDENLEGEAI DFTGKLIIDE NIYYFDDNYR GAVEWKELDG 1080
EMHYFSPETG KAFKGLNQIG DYKYYFNSDG VMQKGFVSIN DNKHYFDDSG VMKVGYTEID 1140
GKHFYFAENG EMQIGVFNTE DGFKYFAHHN EDLGNEEGEE ISYSGILNFN NKIYYFDDSF 1200
TAVVGWKDLE DGSKYYFDED TAEAYIGLSL INDGQYYFND DGIMQVGFVT INDKVFYFSD 1260
SGIIESGVQN IDDNYFYIDD NGIVQIGVFD TSDGYKYFAP ANTVNDNIYG QAVEYSGLVR 1320
VGEDVYYFGE TYTIETGWIY DMENESDKYY FNPETKKACK GINLIDDIKY YFDEKGIMRT 1380
GLISFENNNY YFNENGEMQF GYINIEDKMF YFGEDGVMQI GVFNTPDGFK YFAHQNTLDE 1440
NFEGESINYT GWLDLDEKRY YFTDEYIAAT GSVIIDGEEY YFDPDTAQLV ISE         1493
```

| | | |
|---|---|---|
| SEQ ID NO: 19 | moltype = DNA   length = 3552 | |
| FEATURE | Location/Qualifiers | |
| misc_feature | 1..3552 | |
| | note = C-TANCTB fusion DNA | |
| source | 1..3552 | |
| | mol_type = other DNA | |
| | organism = synthetic construct | |

SEQUENCE: 19
```
atggtaacag gagtatttaa aggacctaat ggatttgagt attttgcacc tgctaatact   60
cacaataata acatagaagg tcaggctata gttaccagaa acaaattctt aactttgaat  120
ggcaaaaaat attatttga taatgactca aaagcagtta ctggatggca aaccattgat  180
ggtaaaaaat attactttaa tcttaacact gctgaagcag ctactggatg gcaaactatt  240
gatggtaaaa aatattactt taatcttaac actgctgaag cagctactga atggcaaact  300
attgatggta aaaaatatta ctttaatact aacactttca tagcctcaac tggttataca  360
agtattaatg gtaaacattt ttattttaat actgatggta ttatgcagat aggagtgttt  420
aaaggaccta atggatttga atactttgca cctgctaata cggatgctaa caacatagaa  480
ggtcaagcta tactttacca aaataaattc ttaactttga atggtaaaaa atattctttt  540
ggtagtgact caaaagcagt taccggactg cgaactattg atggtaaaaa atattactt   600
aatactaaca ctgctgttgc agttactgga tggcaaacta ttaatggtaa aaaatactac  660
tttaatacta cacttctat agcttcaact ggttatacaa ttattagtgg taaacatttt  720
tattttaata ctgatggtat tatgcagata ggagtgttta aaggacctga tggatttgaa  780
tactttgcac ctgctaatac agatgctaac aatatagaag gtcaagctat acgttatcaa  840
aatagattcc tatatttaca tgacaatata tattattttg gtaataattc aaaagcggct  900
actggttggg taactattga tggtaataga tattacttcg agcctaatac agctatgggt  960
gcgaatggtt ataaaactat tgataataaa aattttact ttagaaatgg tttacctcag  1020
ataggagtgt ttaaagggtc taatggattt gaatactttg cacctgctaa tacggatgct 1080
aacaatatag aaggtcaagc tatacgttat caaaatagat tcctacattt acttggaaaa 1140
atatattact ttggtaataa ttcaaaagca gttactggat ggcaaactat taatggtaaa 1200
gtatattact ttatgcctga tactgctatg gctgcagctg gtggactttt cgagattgat 1260
ggtgttatat atttctttgg tgttgatgga gtaaaagccc ctgggatata tggcagatct 1320
atgcataatt tgataactgg atttgtgact gtaggcgatg ataaatacta ctttaatcca 1380
attaatggtg gagctgcttc aattggagag acaataattg atgacaaaaa ttattatttc 1440
```

```
aaccaaagtg gagtgttaca aacaggtgta tttagtacag aagatggatt taaatatttt   1500
gccccagcta atacacttga tgaaaaccta gaaggagaag caattgattt tactggaaaa   1560
ttaattattg acgaaaatat ttattatttt gatgataatt atagaggagc tgtagaatgg   1620
aaagaattag atggtgaaat gcactatttt agcccagaaa caggtaaagc ttttaaaggt   1680
ctaaatcaaa taggtgatta taaatactat ttcaattctg atggagttat gcaaaaagga   1740
tttgttagta taaatgataa taaacactat tttgatgatt ctggtgttat gaaagtaggg   1800
tacactgaaa tagatggcaa gcatttctac tttgctgaaa acggagaaat gcaaatagga   1860
gtatttaata cagaagatgg atttaaatat tttgctcatc ataatgaaga tttaggaaat   1920
gaagaaggtg aagaaatctc atattctggt atattaaatt tcaataataa aatttactat   1980
tttgatgatt catttacagc tgtagttgga tggaaagatt tagaggatgg ttcaaagtat   2040
tatttgatg aagatacagc agaagcatat ataggtttgt cattaataaa tgatggtcaa   2100
tattatttta atgatgatgg aattatgcaa gttggatttg tcactataaa tgataaagtc   2160
ttctacttct ctgactctgg aattatagaa tctggagtac aaaacataga tgacaattac   2220
ttctatatag atgataatgg tatagttcaa attggtgtat ttgatacttc agatggatat   2280
aaatattttg cacctgctaa tactgtaaat gataatattt acggacaagc agttgaatat   2340
agtgggtttag ttagagttgg ggaagatgta tattattttg gagaaacata taatttgag   2400
actggatgga tatatgatat ggaaatgaa agtgataaat attatttcaa tccagaaact   2460
aaaaaagcat gcaaaggtat taatttaatt gatgatataa aattattt tgtgtgagaag   2520
ggcataatga gaacgggtct tatatcattt gaaaataata attattactt taatgagaat   2580
ggtgaaatgc aatttggtta tataaatata gaagataaga tgttctattt tggtgaagat   2640
ggtgtcatgc agattggagt atttaataca ccagatggat taaaatactt tgcacatcaa   2700
aatactttgg atgagaattt tgagggagaa tcaataaact atactggttg gttagattta   2760
gatgaaaaga gatattattt tacagatgaa tatattgcag caactggttc agttattatt   2820
gatggtgagg agtattatt tgatcctgat acagctcaat tagtgattag tgaactcgag   2880
ggattaatat atattaatga ttcattatat tattttaaac caccagtaaa taatttgata   2940
actggatttg tgactgtagg cgatgataaa tactacttta atccaattaa tggtggagct   3000
gcttcaattg gagagacaat aattgatgac aaaaattatt attcaacca aagtggagtg   3060
ttacaaacag gtgtatttag tacagaagat ggatttaaat attttgcccc agctaataca   3120
cttgatgaaa acctagaagg agaagcaatt gattttactg gaaaattaat tattgacgaa   3180
aatatttatt attttgatga taattataga ggagctgtag aatggaaaga attagatgga   3240
gaaatgcact attttagccc agaaacaggt aaagcttta aaggtctaaa tcaaataggt   3300
gattataaat actatttcaa ttctgatgga gttatgcaaa aaggatttgt tagtataaat   3360
gataataaac actatttga tgattctggt gttatgaaag taggttacac tgaaatagat   3420
ggcaagcatt tctactttgc tgaaacgga gaaatgcaaa taggagtatt taatacagaa   3480
gatggattta aatattttgc tcatcataat gaagatttag gaaatgaaga aggtgaagaa   3540
atctcatatt ct                                                      3552

SEQ ID NO: 20           moltype = AA   length = 1184
FEATURE                 Location/Qualifiers
REGION                  1..1184
                        note = C-TANCTB fusion protein
source                  1..1184
                        mol_type = protein
                        organism = synthetic construct
SEQUENCE: 20
MVTGVFKGPN GFEYFAPANT HNNNIEGQAI VYQNKFLTLN GKKYYFDNDS KAVTGWQTID     60
GKKYYFNLNT AEAATGWQTI DGKKYYFNLN TAEAATGWQT IDGKKYYFNT NTFIASTGYT    120
SINGKHFYFN TDGIMQIGVF KGPNGFEYFA PANTDANNIE GQAILYQNKF LTLNGKKYYF    180
GSDSKAVTGL RTIDGKKYYF NTNTAVAVTG WQTINGKKYY FNTNTSIAST GYTIISGKHF    240
YFNTDGIMQI GVFKGPDGFE YFAPANTDAN NIEGQAIRYQ NRFLYLHDNI YYFGNNSKAA    300
TGWVTIDGNR YYFEPNTAMG ANGYKTIDNK NFYFRNGLPQ IGVFKGSNGF EYFAPANTDA    360
NNIEGQAIRY QNRFLHLLGK IYYFGNNSKA VTGWQTINGK VYYFMPDTAM AAAGGLFEID    420
GVIYFFGVDG VKAPGIYGRS MHNLITGFVT GDDKYYFNP INGGAASIGE TIIDDKNYYF    480
NQSGVLQTGV FSTEDGFKYF APANTLDENL EGEAIDFTGK LIIDENIYYF DDNYRGAVEW    540
KELDGEMHYF SPETGKAFKG LNQIGDYKYY FNSDGVMQKG FVSINDNKHY FDDSGVMKVG    600
YTEIDGKHFY FAENGEMQIG VFNTEDGFKY FAHHNEDLGN EEGEEISYSG ILNFNNKIYY    660
FDDSFTAVVG WKDLEDGSKY YFDEDTAEAY IGLSLINDGS YFNDDGIMQ VGFVTINDKV    720
FYFSDSGIIE SGVQNIDDNY FYIDDNGIVQ IGVFDTSDGY KYFAPANTVN DNIYGQAVEY    780
SGLVRVGEDV YYFGETYTIE TGWIYDMENE SDKYYFNPET KKACKGINLI DDIKYYFDEK    840
GIMRTGLISF ENNNYYFNEN GEMQFGYINI EDKMFYFGED GVMQIGVFNT PDGFKYFAHQ    900
NTLDENFEGE SINYTGWLDL DEKRYYFTDE YIAATGSVII DGEEYYFDPD TAQLVISELE    960
GLIYINDSLY YFKPPVNNLI TGFVTVGDDK YYFNPINGGA ASIGETIIDD KNYYFNQSGV   1020
LQTGVFSTED GFKYFAPANT LDENLEGEAI DFTGKLIIDE NIYYFDDNYR GAVEWKELDG   1080
EMHYFSPETG KAFKGLNQIG DYKYYFNSDG VMQKGFVSIN DNKHYFDDSG VMKVGYTEID   1140
GKHFYFAENG EMQIGVFNTE DGFKYFAHHN EDLGNEEGEE ISYS                    1184

SEQ ID NO: 21           moltype = AA   length = 11
FEATURE                 Location/Qualifiers
REGION                  1..11
                        note = Synthetic Polypeptide
source                  1..11
                        mol_type = protein
                        organism = synthetic construct
SEQUENCE: 21
KLKLLLLLKL K                                                         11

SEQ ID NO: 22           moltype = AA   length = 4
FEATURE                 Location/Qualifiers
```

```
REGION              1..4
                    note = Synthetic Polypeptide
source              1..4
                    mol_type = protein
                    organism = synthetic construct
SEQUENCE: 22
FEYF                                                              4

SEQ ID NO: 23       moltype = AA  length = 4
FEATURE             Location/Qualifiers
REGION              1..4
                    note = Synthetic Polypeptide
source              1..4
                    mol_type = protein
                    organism = synthetic construct
SEQUENCE: 23
FKYF                                                              4

SEQ ID NO: 24       moltype = AA  length = 4
FEATURE             Location/Qualifiers
REGION              1..4
                    note = Synthetic Polypeptide
source              1..4
                    mol_type = protein
                    organism = synthetic construct
SEQUENCE: 24
YKYF                                                              4
```

The invention claimed is:

1. A method for producing a recombinant polypeptide derived from *Clostridium difficile* (*C. difficile*) toxins A and B, the method comprising
   i) producing a recombinant nucleic acid encoding said polypeptide,
   ii) introducing a recombinant nucleic acid encoding said polypeptide into a host cell, and
   iii) culturing the host cell under conditions that allow expression of said polypeptide,
   wherein the polypeptide comprises a first C-terminal portion from *C. difficile* toxin A and a second C-terminal portion from *C. difficile* toxin B, and
   wherein the second C-terminal portion from *C. difficile* toxin B comprises amino acids 1988-2366 corresponding to SEQ ID NO: 8 and does not comprise amino acids 1834-1967 corresponding to SEQ ID NO: 8.

2. The method of claim 1, wherein the first C-terminal portion from *C. difficile* toxin A comprises amino acids 2121-2686 corresponding to SEQ ID NO: 6.

3. The method of claim 1, wherein the first C-terminal portion from *C. difficile* toxin A comprises amino acids 2276-2710 corresponding to SEQ ID NO: 6.

4. The method of claim 1, wherein the first C-terminal portion from *C. difficile* toxin A comprises amino acids 2276-2686 corresponding to SEQ ID NO: 6.

5. The method of claim 1, wherein the first C-terminal portion from *C. difficile* toxin A does not comprise amino acids 2687-2710 corresponding to SEQ ID NO: 6.

6. The method of claim 1, wherein the polypeptide comprises at least 19 repeating units derived from the C-terminal domain of *C. difficile* toxin A.

7. The method of claim 1, wherein the polypeptide comprises fewer than 23 repeating units derived from the C-terminal domain of *C. difficile* toxin B.

8. The method of claim 1, wherein the polypeptide is capable of inducing neutralizing antibodies against both *C. difficile* toxins A and B.

9. The method of claim 1, wherein the polypeptide is useful for the treatment and/or prevention of *C. difficile* associated disease (CDAD) or infection.

10. The method of claim 1, wherein the host cell is *Escherichia coli* (*E. coli*).

11. A method for producing a pharmaceutical composition comprising a recombinant polypeptide derived from *Clostridium difficile* (*C. difficile*) toxins A and B, the method comprising combining the recombinant polypeptide and a pharmaceutically acceptable carrier or excipient,
    wherein the polypeptide comprises a first C-terminal portion from *C. difficile* toxin A and a second C-terminal portion from *C. difficile* toxin B, and
    wherein the second C-terminal portion from *C. difficile* toxin B comprises amino acids 1988-2366 corresponding to SEQ ID NO: 8 and does not comprise amino acids 1834-1967 corresponding to SEQ ID NO: 8.

12. The method of claim 11, wherein the polypeptide comprises the first C-terminal portion from *C. difficile* toxin A comprising amino acids 2121-2686 corresponding to SEQ ID NO: 6.

13. The method of claim 11, wherein the polypeptide comprises the first C-terminal portion from *C. difficile* toxin A comprising amino acids 2276-2710 corresponding to SEQ ID NO: 6.

14. The method of claim 11, wherein the polypeptide comprises the first C-terminal portion from *C. difficile* toxin A comprising amino acids 2276-2686 corresponding to SEQ ID NO: 6.

15. The method of claim 11, wherein the polypeptide comprising the first C-terminal portion from *C. difficile* toxin A does not comprise amino acids 2687-2710 corresponding to SEQ ID NO: 6.

16. The method of claim 11, wherein the polypeptide comprises at least 19 repeating units derived from the C-terminal domain of toxin A of *C. difficile*.

17. The method of claim 11, wherein the polypeptide comprises fewer than 23 repeating units of the C-terminal domain of toxin B of *C. difficile*.

18. The method of claim 11, wherein the composition is capable of inducing neutralizing antibodies against *C. difficile* toxins A and B.

19. The method of claim 11, wherein the composition is useful for the treatment and/or prevention of *C. difficile* associated disease (CDAD) or infection.

* * * * *